United States Patent
Buerckstuemmer

(10) Patent No.: US 10,557,151 B2
(45) Date of Patent: Feb. 11, 2020

(54) SOMATIC HUMAN CELL LINE MUTATIONS

(71) Applicant: HORIZON GENOMICS GMBH, Vienna (AT)

(72) Inventor: Tilmann Buerckstuemmer, Vienna (AT)

(73) Assignee: Horizon Discovery Limited, Cambridge (GB)

( * ) Notice: Subject to any disclaimer, the term of this patent is extended or adjusted under 35 U.S.C. 154(b) by 380 days.

(21) Appl. No.: 15/100,105

(22) PCT Filed: Nov. 28, 2014

(86) PCT No.: PCT/EP2014/076028
§ 371 (c)(1),
(2) Date: May 27, 2016

(87) PCT Pub. No.: WO2015/079056
PCT Pub. Date: Jun. 4, 2015

(65) Prior Publication Data

US 2017/0009256 A1    Jan. 12, 2017

(30) Foreign Application Priority Data

| Nov. 28, 2013 | (EP) | 13194939 |
| Nov. 28, 2013 | (EP) | 13194940 |
| Aug. 4, 2014 | (WO) | PCT/EP2014/066732 |
| Aug. 19, 2014 | (EP) | 14181367 |
| Nov. 5, 2014 | (EP) | 14191914 |

(51) Int. Cl.
*C12N 15/90* (2006.01)
*C12N 5/071* (2010.01)
*C12Q 1/6813* (2018.01)
*C12Q 1/68* (2018.01)

(52) U.S. Cl.
CPC ......... *C12N 15/907* (2013.01); *C12N 5/0602* (2013.01); *C12Q 1/6813* (2013.01)

(58) Field of Classification Search
CPC .. C12N 15/902; C12N 15/907; C12N 5/0602; C12Q 1/6813
See application file for complete search history.

(56) References Cited

U.S. PATENT DOCUMENTS

| 2012/0190011 A1 | 7/2012 | Brummelkamp et al. |
| 2015/0232881 A1* | 8/2015 | Glucksmann ........ C12N 15/902 514/44 R |

FOREIGN PATENT DOCUMENTS

| WO | WO 2011/006145 A2 | 1/2011 |
| WO | WO 2015/079057 A2 | 6/2015 |

OTHER PUBLICATIONS

Tilmann Bürckstümmer et al.: "A reversible gene trap collection empowers haploid genetics in human cells", Nature Methods, vol. 10, No. 10, Aug. 25, 2013 (Aug. 25, 2013), pp. 965-971.

Ran F. Ann et al.: "Genome engineering using the CRISPR-Cas9 system", Nature Protocols, Nature Publishing Group, GB, vol. 8, No. 11, Nov. 1, 2013 (Nov. 1, 2013), pp. 2281-2308.

Amy Donner: "Trapping human genes", Science-Business Exchange, vol. 6, No. 37, Sep. 26, 2013 (Sep. 26, 2013).

Wei C. et al.: "TALEN or Cas9—rapid, efficient and specific choices for genome modifications", Journal of Genetics and Genomics, Elsevier BV, NL, vol. 40, No. 6, Jun. 20, 2013 (Jun. 20, 2013), pp. 281-289.

Jan E. Carette et al.: "Ebola virus entry requires the cholesterol transporter Niemann-Pick C1", Nature, vol. 477, No. 7364, Aug. 24, 2011 (Aug. 24, 2011), pp. 340-343.

Seung Woo Cho et al.: "Targeted genome engineering in human cells with the Cas9 RNA-guided endonuclease", Nature Biotechnology, Nature Publishing Group, New Yor, NY, US, vol. 31, No. 3, Mar. 1, 2013 (Mar. 1, 2013), pp. 230-232.

L. Cong et al.: "Multiplex Genome Engineering Using CRISPR-Cas Systems", Science, vol. 339, No. 6121, Feb. 15, 2013 (Feb. 15, 2013), pp. 819-823.

Prashant Mali et al.: "Cas9 as a versatile tool for engineering biology", Nature Methods, Nature Publishing Group, GB, vol. 10, No. 10, Oct. 1, 2013 (Oct. 1, 2013), pp. 957-963.

"PrecisionX Cas9 SmartNuclease™ Vector System", Aug. 29, 2013 (Aug. 29, 2013), pp. 1-17.

(Continued)

*Primary Examiner* — Antonio Galisteo Gonzalez
(74) *Attorney, Agent, or Firm* — Bookoff McAndrews, PLLC

(57) ABSTRACT

The invention provides for a method of producing a mutant somatic human cell line of cells comprising a genomic mutation of interest (MOI) at a predefined genomic site of interest (GOI) in close proximity to a genomic target site, which comprises: a) providing a guide RNA (gRNA) comprising a tracrRNA in conjunction with crRNA including an oligonucleotide sequence that hybridizes with the target site; b) providing an RNA-guided endonuclease which catalyzes the DNA break at the target site upon hybridizing with the gRNA; c) introducing the gRNA into the cells in the presence of the endonuclease to obtain a repertoire of cells comprising a variety of genomic mutations at the target site; d) selecting a cell from said repertoire which comprises a MOI; wherein the cell is haploid for the genomic locus of the target site; and e) expanding the cell to obtain the mutant cell line. The invention further provides for a mutant human somatic cell line obtainable by such method; and libraries of mutant human somatic cell lines of isogenic cells with a variety of genomic mutations at different predefined genomic target sites.

Figure 8:
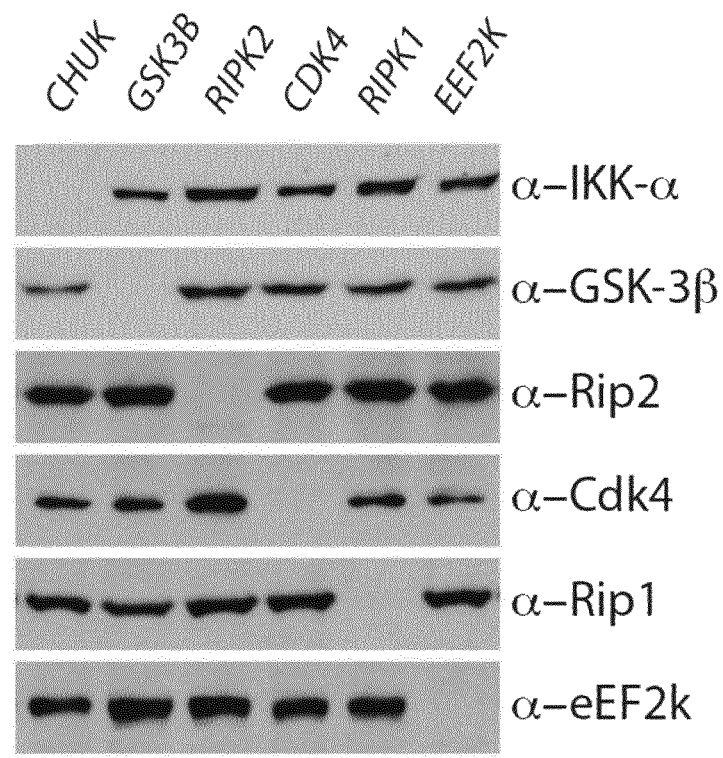

23 Claims, 35 Drawing Sheets
Specification includes a Sequence Listing.

(56) References Cited

OTHER PUBLICATIONS

Anonymous: "HAP1 knockout cell lines", Jan. 1, 2014 (Jan. 1, 2014).
P. Essletzbichler et al.: "Megabase-scale deletion using CRISPR/Cas9 to generate a fully haploid human cell line", Genome Research, vol. 24, No. 12, Nov. 4, 2014 (Nov. 4, 2014), pp. 2059-2065.
Takuro Horii et al.: "Genome engineering of mammalian haploid embryonic stem cells using the Cas9/RNA system", PeerJ, Dec. 23, 2013 (Dec. 23, 2013), p. e230.
A. Xiao et al.: "Chromosomal deletions and inversions mediated by TALENs and CRISPR/Cas in zebrafish", Nucleic Acids Research, vol. 41, No. 14, Jun. 6, 2013 (Jun. 6, 2013), pp. e141-e141.
Jan E Carette et al.: "Global gene disruption in human cells to assign genes to phenotypes by deep sequencing", Nature Biotechnology, vol. 29, No. 6, May 29, 2011 (May 29, 2011), pp. 542-546.
International Search Report for International Application No. PCT/EP2014/076028 dated Mar. 13, 2015, (5 pages).
International Search Report for International Application No. PCT/EP2014/076029 dated Jul. 13, 2015 (5 pages).
Carette, J. et al., "Haploid Genetic Screens in Human Cells Identify Host Factors Used by Pathogens," *Science*, vol. 326, pp. 1231-1235 (2009).

\* cited by examiner

Fig. 1:

1.A)

***Streptococcus Pyogenes* CAS9, NC_002737, SEQ ID 1:**

MDKKYSIGLDIGTNSVGWAVITDEYKVPSKKFKVLGNTDRHSIKKNLIGALLFDSGETAEATRLKRTARRRYTRRKNRIC
YLQEIFSNEMAKVDDSFFHRLEESFLVEEDKKHERHPIFGNIVDEVAYHEKYPTIYHLRKKLVDSTDKADLRLIYLALAHM
IKFRGHFLIEGDLNPDNSDVDKLFIQLVQTYNQLFEENPINASGVDAKAILSARLSKSRRLENLIAQLPGEKKNGLFGNLI
ALSLGLTPNFKSNFDLAEDAKLQLSKDTYDDDLDNLLAQIGDQYADLFLAAKNLSDAILLSDILRVNTEITKAPLSASMIK
RYDEHHQDLTLLKALVRQQLPEKYKEIFFDQSKNGYAGYIDGGASQEEFYKFIKPILEKMDGTEELLVKLNREDLLRKQR
TFDNGSIPHQIHLGELHAILRRQEDFYPFLKDNREKIEKILTFRIPYYVGPLARGNSRFAWMTRKSEETITPWNFEEVVD
KGASAQSFIERMTNFDKNLPNEKVLPKHSLLYEYFTVYNELTKVKYVTEGMRKPAFLSGEQKKAIVDLLFKTNRKVTVK
QLKEDYFKKIECFDSVEISGVEDRFNASLGTYHDLLKIIKDKDFLDNEENEDILEDIVLTLTLFEDREMIEERLKTYAHLFDD
KVMKQLKRRRYTGWGRLSRKLINGIRDKQSGKTILDFLKSDGFANRNFMQLIHDDSLTFKEDIQKAQVSGQGDSLHE
HIANLAGSPAIKKGILQTVKVVDELVKVMGRHKPENIVIEMARENQTTQKGQKNSRERMKRIEEGIKELGSQILKEHPV
ENTQLQNEKLYLYYLQNGRDMYVDQELDINRLSDYDVDHIVPQSFLKDDSIDNKVLTRSDKNRGKSDNVPSEEVVKK
MKNYWRQLLNAKLITQRKFDNLTKAERGGLSELDKAGFIKRQLVETRQITKHVAQILDSRMNTKYDENDKLIREVKVIT
LKSKLVSDFRKDFQFYKVREINNYHHAHDAYLNAVVGTALIKKYPKLESEFVYGDYKVYDVRKMIAKSEQEIGKATAKYF
FYSNIMNFFKTEITLANGEIRKRPLIETNGETGEIVWDKGRDFATVRKVLSMPQVNIVKKTEVQTGGFSKESILPKRNSD
KLIARKKDWDPKKYGGFDSPTVAYSVLVVAKVEKGKSKKLKSVKELLGITIMERSSFEKNPIDFLEAKGYKEVKKDLIIKLP
KYSLFELENGRKRMLASAGELQKGNELALPSKYVNFLYLASHYEKLKGSPEDNEQKQLFVEQHKHYLDEIIEQISEFSKR
VILADANLDKVLSAYNKHRDKPIREQAENIIHLFTLTNLGAPAAFKYFDTTIDRKRYTSTKEVLDATLIHQSITGLYETRIDL
SQLGGD

Protospacer Adjacent Motif (PAM), SEQ ID 2: NGG, wherein N= any of T, C, A or G

Chimeric guide RNA, SEQ ID 3: 20 variable bases (N= any of U, C, A or G) followed by the constant part of guide RNA (SEQ ID 4), including the constant part of crRNA, a linker and the tracrRNA; the 3' terminal part of SEQ ID 4 is variable.

NNNNNNNNNNNNNNNNNNNNGUUUUAGAGCUAGAAAUAGCAAGUUAAAAUAAGGCUAGUCCGUUAUCA
ACUUGAAAAAGUGGCACCGAGUCGGUGC

1.B)

***Streptococcus Pyogenes* CAS9, NC_002737 with N-terminal Nuclear Localization Signal, SEQ ID 5:**

N-terminal extension: *italic*

Nuclear Localization Signal: bold; *PKKKRKV* (SEQ ID 6)

*MPKKKRKVGS*MDKKYSIGLDIGTNSVGWAVITDEYKVPSKKFKVLGNTDRHSIKKNLIGALLFDSGETAEATRLKRTAR
RRYTRRKNRICYLQEIFSNEMAKVDDSFFHRLEESFLVEEDKKHERHPIFGNIVDEVAYHEKYPTIYHLRKKLVDSTDKAD
LRLIYLALAHMIKFRGHFLIEGDLNPDNSDVDKLFIQLVQTYNQLFEENPINASGVDAKAILSARLSKSRRLENLIAQLPG
EKKNGLFGNLIALSLGLTPNFKSNFDLAEDAKLQLSKDTYDDDLDNLLAQIGDQYADLFLAAKNLSDAILLSDILRVNTEI
TKAPLSASMIKRYDEHHQDLTLLKALVRQQLPEKYKEIFFDQSKNGYAGYIDGGASQEEFYKFIKPILEKMDGTEELLVKL
NREDLLRKQRTFDNGSIPHQIHLGELHAILRRQEDFYPFLKDNREKIEKILTFRIPYYVGPLARGNSRFAWMTRKSEETIT
PWNFEEVVDKGASAQSFIERMTNFDKNLPNEKVLPKHSLLYEYFTVYNELTKVKYVTEGMRKPAFLSGEQKKAIVDLLF
KTNRKVTVKQLKEDYFKKIECFDSVEISGVEDRFNASLGTYHDLLKIIKDKDFLDNEENEDILEDIVLTLTLFEDREMIEERL
KTYAHLFDDKVMKQLKRRRYTGWGRLSRKLINGIRDKQSGKTILDFLKSDGFANRNFMQLIHDDSLTFKEDIQKAQVS
GQGDSLHEHIANLAGSPAIKKGILQTVKVVDELVKVMGRHKPENIVIEMARENQTTQKGQKNSRERMKRIEEGIKELG
SQILKEHPVENTQLQNEKLYLYYLQNGRDMYVDQELDINRLSDYDVDHIVPQSFLKDDSIDNKVLTRSDKNRGKSDNV
PSEEVVKKMKNYWRQLLNAKLITQRKFDNLTKAERGGLSELDKAGFIKRQLVETRQITKHVAQILDSRMNTKYDENDK
LIREVKVITLKSKLVSDFRKDFQFYKVREINNYHHAHDAYLNAVVGTALIKKYPKLESEFVYGDYKVYDVRKMIAKSEQEI
GKATAKYFFYSNIMNFFKTEITLANGEIRKRPLIETNGETGEIVWDKGRDFATVRKVLSMPQVNIVKKTEVQTGGFSKE
SILPKRNSDKLIARKKDWDPKKYGGFDSPTVAYSVLVVAKVEKGKSKKLKSVKELLGITIMERSSFEKNPIDFLEAKGYKE
VKKDLIIKLPKYSLFELENGRKRMLASAGELQKGNELALPSKYVNFLYLASHYEKLKGSPEDNEQKQLFVEQHKHYLDEII
EQISEFSKRVILADANLDKVLSAYNKHRDKPIREQAENIIHLFTLTNLGAPAAFKYFDTTIDRKRYTSTKEVLDATLIHQSIT
GLYETRIDLSQLGGD

1.C)

***Streptococcus Pyogenes* CAS9, NC_002737 with C-terminal Nuclear Localization Signal, SEQ ID 7:**

C-terminal extension: *italic*

Nuclear Localization Signal: bold

MDKKYSIGLDIGTNSVGWAVITDEYKVPSKKFKVLGNTDRHSIKKNLIGALLFDSGETAEATRLKRTARRRYTRRKNRIC
YLQEIFSNEMAKVDDSFFHRLEESFLVEEDKKHERHPIFGNIVDEVAYHEKYPTIYHLRKKLVDSTDKADLRLIYLALAHM
IKFRGHFLIEGDLNPDNSDVDKLFIQLVQTYNQLFEENPINASGVDAKAILSARLSKSRRLENLIAQLPGEKKNGLFGNLI
ALSLGLTPNFKSNFDLAEDAKLQLSKDTYDDDLDNLLAQIGDQYADLFLAAKNLSDAILLSDILRVNTEITKAPLSASMIK
RYDEHHQDLTLLKALVRQQLPEKYKEIFFDQSKNGYAGYIDGGASQEEFYKFIKPILEKMDGTEELLVKLNREDLLRKQR
TFDNGSIPHQIHLGELHAILRRQEDFYPFLKDNREKIEKILTFRIPYYVGPLARGNSRFAWMTRKSEETITPWNFEEVVD
KGASAQSFIERMTNFDKNLPNEKVLPKHSLLYEYFTVYNELTKVKYVTEGMRKPAFLSGEQKKAIVDLLFKTNRKVTVK
QLKEDYFKKIECFDSVEISGVEDRFNASLGTYHDLLKIIKDKDFLDNEENEDILEDIVLTLTLFEDREMIEERLKTYAHLFDD
KVMKQLKRRRYTGWGRLSRKLINGIRDKQSGKTILDFLKSDGFANRNFMQLIHDDSLTFKEDIQKAQVSGQGDSLHE
HIANLAGSPAIKKGILQTVKVVDELVKVMGRHKPENIVIEMARENQTTQKGQKNSRERMKRIEEGIKELGSQILKEHPV
ENTQLQNEKLYLYYLQNGRDMYVDQELDINRLSDYDVDHIVPQSFLKDDSIDNKVLTRSDKNRGKSDNVPSEEVVKK
MKNYWRQLLNAKLITQRKFDNLTKAERGGLSELDKAGFIKRQLVETRQITKHVAQILDSRMNTKYDENDKLIREVKVIT
LKSKLVSDFRKDFQFYKVREINNYHHAHDAYLNAVVGTALIKKYPKLESEFVYGDYKVYDVRKMIAKSEQEIGKATAKYF
FYSNIMNFFKTEITLANGEIRKRPLIETNGETGEIVWDKGRDFATVRKVLSMPQVNIVKKTEVQTGGFSKESILPKRNSD
KLIARKKDWDPKKYGGFDSPTVAYSVLVVAKVEKGKSKKLKSVKELLGITIMERSSFEKNPIDFLEAKGYKEVKKDLIIKLP
KYSLFELENGRKRMLASAGELQKGNELALPSKYVNFLYLASHYEKLKGSPEDNEQKQLFVEQHKHYLDEIIEQISEFSKR
VILADANLDKVLSAYNKHRDKPIREQAENIIHLFTLTNLGAPAAFKYFDTTIDRKRYTSTKEVLDATLIHQSITGLYETRIDL
SQLGGD*GS*PKKKRKV

1.D)

*Streptococcus Pyogenes* CAS9, NC_002737 with N- and C-terminal Nuclear Localization Signal, SEQ ID 8:

terminal extension: *italic*

Nuclear Localization Signal: bold

*MPKKKRKVGS*MDKKYSIGLDIGTNSVGWAVITDEYKVPSKKFKVLGNTDRHSIKKNLIGALLFDSGETAEATRLKRTAR
RRYTRRKNRICYLQEIFSNEMAKVDDSFFHRLEESFLVEEDKKHERHPIFGNIVDEVAYHEKYPTIYHLRKKLVDSTDKAD
LRLIYLALAHMIKFRGHFLIEGDLNPDNSDVDKLFIQLVQTYNQLFEENPINASGVDAKAILSARLSKSRRLENLIAQLPG
EKKNGLFGNLIALSLGLTPNFKSNFDLAEDAKLQLSKDTYDDDLDNLLAQIGDQYADLFLAAKNLSDAILLSDILRVNTEI
TKAPLSASMIKRYDEHHQDLTLLKALVRQQLPEKYKEIFFDQSKNGYAGYIDGGASQEEFYKFIKPILEKMDGTEELLVKL
NREDLLRKQRTFDNGSIPHQIHLGELHAILRRQEDFYPFLKDNREKIEKILTFRIPYYVGPLARGNSRFAWMTRKSEETIT
PWNFEEVVDKGASAQSFIERMTNFDKNLPNEKVLPKHSLLYEYFTVYNELTKVKYVTEGMRKPAFLSGEQKKAIVDLLF
KTNRKVTVKQLKEDYFKKIECFDSVEISGVEDRFNASLGTYHDLLKIIKDKDFLDNEENEDILEDIVLTLTLFEDREMIEERL
KTYAHLFDDKVMKQLKRRRYTGWGRLSRKLINGIRDKQSGKTILDFLKSDGFANRNFMQLIHDDSLTFKEDIQKAQVS
GQGDSLHEHIANLAGSPAIKKGILQTVKVVDELVKVMGRHKPENIVIEMARENQTTQKGQKNSRERMKRIEEGIKELG
SQILKEHPVENTQLQNEKLYLYYLQNGRDMYVDQELDINRLSDYDVDHIVPQSFLKDDSIDNKVLTRSDKNRGKSDNV
PSEEVVKKMKNYWRQLLNAKLITQRKFDNLTKAERGGLSELDKAGFIKRQLVETRQITKHVAQILDSRMNTKYDENDK
LIREVKVITLKSKLVSDFRKDFQFYKVREINNYHHAHDAYLNAVVGTALIKKYPKLESEFVYGDYKVYDVRKMIAKSEQEI
GKATAKYFFYSNIMNFFKTEITLANGEIRKRPLIETNGETGEIVWDKGRDFATVRKVLSMPQVNIVKKTEVQTGGFSKE
SILPKRNSDKLIARKKDWDPKKYGGFDSPTVAYSVLVVAKVEKGKSKKLKSVKELLGITIMERSSFEKNPIDFLEAKGYKE
VKKDLIIKLPKYSLFELENGRKRMLASAGELQKGNELALPSKYVNFLYLASHYEKLKGSPEDNEQKQLFVEQHKHYLDEII
EQISEFSKRVILADANLDKVLSAYNKHRDKPIREQAENIIHLFTLTNLGAPAAFKYFDTTIDRKRYTSTKEVLDATLIHQSIT
GLYETRIDLSQLGGD*GSPKKKRKV*

1.E)

*Streptococcus Pyogenes* CAS9, NC_002737 with N-terminal Nuclear Localization Signal from SV40 Large T Antigen and C-terminal Nuclear Localization Signal from Nucleoplasmin
SEQ ID 9:

terminal extensions: *italic*

Nuclear Localization Signal: bold

*MDYKDHDGDYKDHDIDYKDDDDKMA**PKKKRKV**GIHGVPAA*DKKYSIGLDIGTNSVGWAVITDEYKVPSKKFKVLGN
TDRHSIKKNLIGALLFDSGETAEATRLKRTARRRYTRRKNRICYLQEIFSNEMAKVDDSFFHRLEESFLVEEDKKHERHPI
FGNIVDEVAYHEKYPTIYHLRKKLVDSTDKADLRLIYLALAHMIKFRGHFLIEGDLNPDNSDVDKLFIQLVQTYNQLFEE
NPINASGVDAKAILSARLSKSRRLENLIAQLPGEKKNGLFGNLIALSLGLTPNFKSNFDLAEDAKLQLSKDTYDDDLDNLL
AQIGDQYADLFLAAKNLSDAILLSDILRVNTEITKAPLSASMIKRYDEHHQDLTLLKALVRQQLPEKYKEIFFDQSKNGYA
GYIDGGASQEEFYKFIKPILEKMDGTEELLVKLNREDLLRKQRTFDNGSIPHQIHLGELHAILRRQEDFYPFLKDNREKIE
KILTFRIPYYVGPLARGNSRFAWMTRKSEETITPWNFEEVVDKGASAQSFIERMTNFDKNLPNEKVLPKHSLLYEYFTV
YNELTKVKYVTEGMRKPAFLSGEQKKAIVDLLFKTNRKVTVKQLKEDYFKKIECFDSVEISGVEDRFNASLGTYHDLLKII
KDKDFLDNEENEDILEDIVLTLTLFEDREMIEERLKTYAHLFDDKVMKQLKRRRYTGWGRLSRKLINGIRDKQSGKTILD
FLKSDGFANRNFMQLIHDDSLTFKEDIQKAQVSGQGDSLHEHIANLAGSPAIKKGILQTVKVVDELVKVMGRHKPENI
VIEMARENQTTQKGQKNSRERMKRIEEGIKELGSQILKEHPVENTQLQNEKLYLYYLQNGRDMYVDQELDINRLSDYD
VDHIVPQSFLKDDSIDNKVLTRSDKNRGKSDNVPSEEVVKKMKNYWRQLLNAKLITQRKFDNLTKAERGGLSELDKA
GFIKRQLVETRQITKHVAQILDSRMNTKYDENDKLIREVKVITLKSKLVSDFRKDFQFYKVREINNYHHAHDAYLNAVV
GTALIKKYPKLESEFVYGDYKVYDVRKMIAKSEQEIGKATAKYFFYSNIMNFFKTEITLANGEIRKRPLIETNGETGEIVW
DKGRDFATVRKVLSMPQVNIVKKTEVQTGGFSKESILPKRNSDKLIARKKDWDPKKYGGFDSPTVAYSVLVVAKVEKG
KSKKLKSVKELLGITIMERSSFEKNPIDFLEAKGYKEVKKDLIIKLPKYSLFELENGRKRMLASAGELQKGNELALPSKYVN
FLYLASHYEKLKGSPEDNEQKQLFVEQHKHYLDEIIEQISEFSKRVILADANLDKVLSAYNKHRDKPIREQAENIIHLFTLT
NLGAPAAFKYFDTTIDRKRYTSTKEVLDATLIHQSITGLYETRIDLSQLGGD*KRPAATKKAGQAKKKK*

Fig. 2:

2.A)

***Streptococcus Thermophilus* CAS9, YP_820161, SEQ ID 10:**

MSDLVLGLDIGIGSVGVGILNKVTGEIIHKNSRIFPAAQAENNLVRRTNRQGRRLARRKKHRRVRLNRLFEESGLITDFT
KISINLNPYQLRVKGLTDELSNEELFIALKNMVKHRGISYLDDASDDGNSSVGDYAQIVKENSKQLETKTPGQIQLERYQ
TYGQLRGDFTVEKDGKKHRLINVFPTSAYRSEALRILQTQQEFNPQITDEFINRYLEILTGKRKYYHGPGNEKSRTDYGR
YRTSGETLDNIFGILIGKCTFYPDEFRAAKASYTAQEFNLLNDLNNLTVPTETKKLSKEQKNQIINYVKNEKAMGPAKLFK
YIAKLLSCDVADIKGYRIDKSGKAEIHTFEAYRKMKTLETLDIEQMDRETLDKLAYVLTLNTEREGIQEALEHEFADGSFS
QKQVDELVQFRKANSSIFGKGWHNFSVKLMMELIPELYETSEEQMTILTRLGKQKTTSSSNKTKYIDEKLLTEEIYNPVV
AKSVRQAIKIVNAAIKEYGDFDNIVIEMARETNEDDEKKAIQKIQKANKDEKDAAMLKAANQYNGKAELPHSVFHGH
KQLATKIRLWHQQGERCLYTGKTISIHDLINNSNQFEVDHILPLSITFDDSLANKVLVYATANQEKGQRTPYQALDSMD
DAWSFRELKAFVRESKTLSNKKKEYLLTEEDISKFDVRKKFIERNLVDTRYASRVVLNALQEHFRAHKIDTKVSVVRGQF
TSQLRRHWGIEKTRDTYHHHAVDALIIAASSQLNLWKKQKNTLVSYSEDQLLDIETGELISDDEYKESVFKAPYQHFVD
TLKSKEFEDSILFSYQVDSKFNRKISDATIYATRQAKVGKDKADETYVLGKIKDIYTQDGYDAFMKIYKKDKSKFLMYRH
DPQTFEKVIEPILENYPNKQINDKGKEVPCNPFLKYKEEHGYIRKYSKKGNGPEIKSLKYYDSKLGNHIDITPKDSNNKVV
LQSVSPWRADVYFNKTTGKYEILGLKYADLQFDKGTGTYKISQEKYNDIKKKEGVDSDSEFKFTLYKNDLLLVKDTETKE
QQLFRFLSRTMPKQKHYVELKPYDKQKFEGGEALIKVLGNVANSGQCKKGLGKSNISIYKVRTDVLGNQHIIKNEGDK
PKLDF

Protospacer Adjacent Motif (PAM), SEQ ID 11: NN(A/G)G(A/G)A, wherein N= any of T, C, A or G (e.g. NNAGAA(A/T), SEQ ID 12)

Chimeric guide RNA, SEQ ID 13: 20 variable bases (N= any of U, C, A or G) followed by the constant part of guide RNA (SEQ ID 14), including the constant part of crRNA, a linker and the tracrRNA; the 3' terminal part of SEQ ID 14 is variable:

NNNNNNNNNNNNNNNNNNNNGUUUUUGUACUCUCAAGAUUUAAGUAACUGUACAACGAAACUUACACA
GUUACUUAAAUCUUGCAGAAGCUACAAAGAUAAGGCUUCAUGCCGAAAUCAACACCCUGUCAUUUUAUGG
CAGGGUGUUUUUUU

2.B)

_Streptococcus Thermophilus_ CAS9, YP_820161, fused to 3x C-terminal NLS, SEQ ID 15:

terminal extension: _italic_

Nuclear Localization Signal (NLS): bold

MSDLVLGLDIGIGSVGVGILNKVTGEIIHKNSRIFPAAQAENNLVRRTNRQGRRLARRKKHRRVRLNRLFEESGLITDFT
KISINLNPYQLRVKGLTDELSNEELFIALKNMVKHRGISYLDDASDDGNSSVGDYAQIVKENSKQLETKTPGQIQLERYQ
TYGQLRGDFTVEKDGKKHRLINVFPTSAYRSEALRILQTQQEFNPQITDEFINRYLEILTGKRKYYHGPGNEKSRTDYGR
YRTSGETLDNIFGILIGKCTFYPDEFRAAKASYTAQEFNLLNDLNNLTVPTETKKLSKEQKNQIINYVKNEKAMGPAKLFK
YIAKLLSCDVADIKGYRIDKSGKAEIHTFEAYRKMKTLETLDIEQMDRETLDKLAYVLTLNTEREGIQEALEHEFADGSFS
QKQVDELVQFRKANSSIFGKGWHNFSVKLMMELIPELYETSEEQMTILTRLGKQKTTSSSNKTKYIDEKLLTEEIYNPVV
AKSVRQAIKIVNAAIKEYGDFDNIVIEMARETNEDDEKKAIQKIQKANKDEKDAAMLKAANQYNGKAELPHSVFHGH
KQLATKIRLWHQQGERCLYTGKTISIHDLINNSNQFEVDHILPLSITFDDSLANKVLVYATANQEKGQRTPYQALDSMD
DAWSFRELKAFVRESKTLSNKKKEYLLTEEDISKFDVRKKFIERNLVDTRYASRVVLNALQEHFRAHKIDTKVSVVRGQF
TSQLRRHWGIEKTRDTYHHHAVDALIIAASSQLNLWKKQKNTLVSYSEDQLLDIETGELISDDEYKESVFKAPYQHFVD
TLKSKEFEDSILFSYQVDSKFNRKISDATIYATRQAKVGKDKADETYVLGKIKDIYTQDGYDAFMKIYKKDKSKFLMYRH
DPQTFEKVIEPILENYPNKQINDKGKEVPCNPFLKYKEEHGYIRKYSKKGNGPEIKSLKYYDSKLGNHIDITPKDSNNKVV
LQSVSPWRADVYFNKTTGKYEILGLKYADLQFDKGTGTYKISQEKYNDIKKKEGVDSDSEFKFTLYKNDLLLVKDTETKE
QQLFRFLSRTMPKQKHYVELKPYDKQKFEGGEALIKVLGNVANSGQCKKGLGKSNISIYKVRTDVLGNQHIIKNEGDK
PKLDF_AAA__D__PKKKRKVDPKKKRKVDPKKKRKV__DTAA_

Fig. 3:

3.A)

*Neisseria Meningitis* CAS9, YP_002342100, SEQ ID 16:

MAAFKPNPINYILGLDIGIASVGWAMVEIDEDENPICLIDLGVRVFERAEVPKTGDSLAMARRLARSVRRLTRRRAHRL
LRARRLLKREGVLQAADFDENGLIKSLPNTPWQLRAAALDRKLTPLEWSAVLLHLIKHRGYLSQRKNEGETADKELGAL
LKGVADNAHALQTGDFRTPAELALNKFEKESGHIRNQRGDYSHTFSRKDLQAELILLFEKQKEFGNPHVSGGLKEGIET
LLMTQRPALSGDAVQKMLGHCTFEPAEPKAAKNTYTAERFIWLTKLNNLRILEQGSERPLTDTERATLMDEPYRKSKL
TYAQARKLLGLEDTAFFKGLRYGKDNAEASTLMEMKAYHAISRALEKEGLKDKKSPLNLSPELQDEIGTAFSLFKTDEDI
TGRLKDRIQPEILEALLKHISFDKFVQISLKALRRIVPLMEQGKRYDEACAEIYGDHYGKKNTEEKIYLPPIPADEIRNPVVL
RALSQARKVINGVVRRYGSPARIHIETAREVGKSFKDRKEIEKRQEENRKDREKAAAKFREYFPNFVGEPKSKDILKLRLY
EQQHGKCLYSGKEINLGRLNEKGYVEIDHALPFSRTWDDSFNNKVLVLGSENQNKGNQTPYEYFNGKDNSREWQEF
KARVETSRFPRSKKQRILLQKFDEDGFKERNLNDTRYVNRFLCFVADRMRLTGKGKKRVFASNGQITNLLRGFWGLRK
VRAENDRHHALDAVVVACSTVAMQQKITRFVRYKEMNAFDGKTIDKETGEVLHQKTHFPQPWEFFAQEVMIRVFG
KPDGKPEFEEADTPEKLRTLLAEKLSSRPEAVHEYVTPLFVSRAPNRKMSGQGHMETVKSAKRLDEGVSVLRVPLTQLK
LKDLEKMVNREREPKLYEALKARLEAHKDDPAKAFAEPFYKYDKAGNRTQQVKAVRVEQVQKTGVWVRNHNGIAD
NATMVRVDVFEKGDKYYLVPIYSWQVAKGILPDRAVVQGKDEEDWQLIDDSFNFKFSLHPNDLVEVITKKARMFGYF
ASCHRGTGNINIRIHDLDHKIGKNGILEGIGVKTALSFQKYQIDELGKEIRPCRLKKRPPVR

Protospacer Adjacent Motif (PAM), NNNNGANN (SEQ ID 17), or NNNNGTTN (SEQ ID 60) or NNNNGNNT (SEQ ID 61), wherein N= any of T, C, A or G (e.g. NNNNGATT, wherein N= any of T, C, A or G (SEQ ID 18))

Chimeric guide RNA, SEQ ID 19: 24 variable bases (N= any of U, C, A or G) followed by the constant part of guide RNA (SEQ ID 20), including the constant part of crRNA, a linker and the tracrRNA; the 3' terminal part of SEQ ID 20 is variable:

NNNNNNNNNNNNNNNNNNNNNNNNGUUGUAGCUCCCUUUCUCAUUUGGGAAACGAAAUGAGAACCGUU
GCUACAAUAAGGCCGUCUGAAAAGAUGUGCCGCAACGCUCUGCCCCUUAAAGCUUCUGCUUUAAGGGGCA
UCGUUUA

3.B)

***Neisseria Meningitis* CAS9, YP_002342100, fused to 3x C-terminal NLS, SEQ ID 21:**

terminal extension: *italic*

Nuclear Localization Signal (NLS): bold

MAAFKPNPINYILGLDIGIASVGWAMVEIDEDENPICLIDLGVRVFERAEVPKTGDSLAMARRLARSVRRLTRRRAHRL
LRARRLLKREGVLQAADFDENGLIKSLPNTPWQLRAAALDRKLTPLEWSAVLLHLIKHRGYLSQRKNEGETADKELGAL
LKGVADNAHALQTGDFRTPAELALNKFEKESGHIRNQRGDYSHTFSRKDLQAELILLFEKQKEFGNPHVSGGLKEGIET
LLMTQRPALSGDAVQKMLGHCTFEPAEPKAAKNTYTAERFIWLTKLNNLRILEQGSERPLTDTERATLMDEPYRKSKL
TYAQARKLLGLEDTAFFKGLRYGKDNAEASTLMEMKAYHAISRALEKEGLKDKKSPLNLSPELQDEIGTAFSLFKTDEDI
TGRLKDRIQPEILEALLKHISFDKFVQISLKALRRIVPLMEQGKRYDEACAEIYGDHYGKKNTEEKIYLPPIPADEIRNPVVL
RALSQARKVINGVVRRYGSPARIHIETAREVGKSFKDRKEIEKRQEENRKDREKAAAKFREYFPNFVGEPKSKDILKLRLY
EQQHGKCLYSGKEINLGRLNEKGYVEIDHALPFSRTWDDSFNNKVLVLGSENQNKGNQTPYEYFNGKDNSREWQEF
KARVETSRFPRSKKQRILLQKFDEDGFKERNLNDTRYVNRFLCQFVADRMRLTGKGKKRVFASNGQITNLLRGFWGLR
KVRAENDRHHALDAVVVACSTVAMQQKITRFVRYKEMNAFDGKTIDKETGEVLHQKTHFPQPWEFFAQEVMIRVF
GKPDGKPEFEEADTPEKLRTLLAEKLSSRPEAVHEYVTPLFVSRAPNRKMSGQGHMETVKSAKRLDEGVSVLRVPLTQ
LKLKDLEKMVNREREPKLYEALKARLEAHKDDPAKAFAEPFYKYDKAGNRTQQVKAVRVEQVQKTGVWVRNHNGIA
DNATMVRVDVFEKGDKYYLVPIYSWQVAKGILPDRAVVQGKDEEDWQLIDDSFNFKFSLHPNDLVEVITKKARMFG
YFASCHRGTGNINIRIHDLDHKIGKNGILEGIGVKTALSFQKYQIDELGKEIRPCRLKKRPPVR*AAAD***PKKKRKVDPKKK
RKVDPKKKRKV***DTAA*

Fig. 4:

4.A)

*Treponema Denticola* Cas9, NP_970941, SEQ ID 22:

MKKEIKDYFLGLDVGTGSVGWAVTDTDYKLLKANRKDLWGMRCFETAETAEVRRLHRGARRRIERRKKRIKLLQELFS
QEIAKTDEGFFQRMKESPFYAEDKTILQENTLFNDKDFADKTYHKAYPTINHLIKAWIENKVKPDPRLLYLACHNIIKKR
GHFLFEGDFDSENQFDTSIQALFEYLREDMEVDIDADSQKVKEILKDSSLKNSEKQSRLNKILGLKPSDKQKKAITNLISG
NKINFADLYDNPDLKDAEKNSISFSKDDFDALSDDLASILGDSFELLLKAKAVYNCSVLSKVIGDEQYLSFAKVKIYEKHKT
DLTKLKNVIKKHFPKDYKKVFGYNKNEKNNNNYSGYVGVCKTKSKKLIINNSVNQEDFYKFLKTILSAKSEIKEVNDILTEI
ETGTFLPKQISKSNAEIPYQLRKMELEKILSNAEKHFSFLKQKDEKGLSHSEKIIMLLTFKIPYYIGPINDNHKKFFPDRCW
VVKKEKSPSGKTTPWNFFDHIDKEKTAEAFITSRTNFCTYLVGESVLPKSSLLYSEYTVLNEINNLQIIIDGKNICDIKLKQK
IYEDLFKKYKKITQKQISTFIKHEGICNKTDEVIILGIDKECTSSLKSYIELKNIFGKQVDEISTKNMLEEIIRWATIYDEGEGK
TILKTKIKAEYGKYCSDEQIKKILNLKFSGWGRLSRKFLETVTSEMPGFSEPVNIITAMRETQNNLMELLSSEFTFTENIKK
INSGFEDAEKQFSYDGLVKPLFLSPSVKKMLWQTLKLVKEISHITQAPPKKIFIEMAKGAELEPARTKTRLKILQDLYNNC
KNDADAFSSEIKDLSGKIENEDNLRLRSDKLYLYYTQLGKCMYCGKPIEIGHVFDTSNYDIDHIYPQSKIKDDSISNRVLV
CSSCNKNKEDKYPLKSEIQSKQRGFWNFLQRNNFISLEKLNRLTRATPISDDETAKFIARQLVETRQATKVAAKVLEKM
FPETKIVYSKAETVSMFRNKFDIVKCREINDFHHAHDAYLNIVVGNVYNTKFTNNPWNFIKEKRDNPKIADTYNYYKVF
DYDVKRNNITAWEKGKTIITVKDMLKRNTPIYTRQAACKKGELFNQTIMKKGLGQHPLKKEGPFSNISKYGGYNKVSA
AYYTLIEYEEKGNKIRSLETIPLYLVKDIQKDQDVLKSYLTDLLGKKEFKILVPKIKINSLLKINGFPCHITGKTNDSFLLRPAV
QFCCSNNEVLYFKKIIRFSEIRSQREKIGKTISPYEDLSFRSYIKENLWKKTKNDEIGEKEFYDLLQKKNLEIYDMLLTKHKD
TIYKKRPNSATIDILVKGKEKFKSLIIENQFEVILEILKLFSATRNVSDLQHIGGSKYSGVAKIGNKISSLDNCILIYQSITGIFE
KRIDLLKV

Protospacer Adjacent Motif (PAM), SEQ ID 23: NAAAAN, wherein N= any of T, C, A or G

4.B)

*Treponema Denticola* Cas9, NP_970941, with 3x C-terminal NLS, SEQ ID 24:

terminal extension: *italic*

Nuclear Localization Signal (NLS): bold

MKKEIKDYFLGLDVGTGSVGWAVTDTDYKLLKANRKDLWGMRCFETAETAEVRRLHRGARRRIERRKKRIKLLQELFS
QEIAKTDEGFFQRMKESPFYAEDKTILQENTLFNDKDFADKTYHKAYPTINHLIKAWIENKVKPDPRLLYLACHNIIKKR
GHFLFEGDFDSENQFDTSIQALFEYLREDMEVDIDADSQKVKEILKDSSLKNSEKQSRLNKILGLKPSDKQKKAITNLISG
NKINFADLYDNPDLKDAEKNSISFSKDDFDALSDDLASILGDSFELLLKAKAVYNCSVLSKVIGDEQYLSFAKVKIYEKHKT
DLTKLKNVIKKHFPKDYKKVFGYNKNEKNNNNYSGYVGVCKTKSKKLIINNSVNQEDFYKFLKTILSAKSEIKEVNDILTEI
ETGTFLPKQISKSNAEIPYQLRKMELEKILSNAEKHFSFLKQKDEKGLSHSEKIIMLLTFKIPYYIGPINDNHKKFFPDRCW
VVKKEKSPSGKTTPWNFFDHIDKEKTAEAFITSRTNFCTYLVGESVLPKSSLLYSEYTVLNEINNLQIIIDGKNICDIKLKQK
IYEDLFKKYKKITQKQISTFIKHEGICNKTDEVIILGIDKECTSSLKSYIELKNIFGKQVDEISTKNMLEEIIRWATIYDEGEGK
TILKTKIKAEYGKYCSDEQIKKILNLKFSGWGRLSRKFLETVTSEMPGFSEPVNIITAMRETQNNLMELLSSEFTFTENIKK
INSGFEDAEKQFSYDGLVKPLFLSPSVKKMLWQTLKLVKEISHITQAPPKKIFIEMAKGAELEPARTKTRLKILQDLYNNC
KNDADAFSSEIKDLSGKIENEDNLRLRSDKLYLYYTQLGKCMYCGKPIEIGHVFDTSNYDIDHIYPQSKIKDDSISNRVLV
CSSCNKNKEDKYPLKSEIQSKQRGFWNFLQRNNFISLEKLNRLTRATPISDDETAKFIARQLVETRQATKVAAKVLEKM
FPETKIVYSKAETVSMFRNKFDIVKCREINDFHHAHDAYLNIVVGNVYNTKFTNNPWNFIKEKRDNPKIADTYNYYKVF
DYDVKRNNITAWEKGKTIITVKDMLKRNTPIYTRQAACKKGELFNQTIMKKGLGQHPLKKEGPFSNISKYGGYNKVSA
AYYTLIEYEEKGNKIRSLETIPLYLVKDIQKDQDVLKSYLTDLLGKKEFKILVPKIKINSLLKINGFPCHITGKTNDSFLLRPAV
QFCCSNNEVLYFKKIIRFSEIRSQREKIGKTISPYEDLSFRSYIKENLWKKTKNDEIGEKEFYDLLQKKNLEIYDMLLTKHKD
TIYKKRPNSATIDILVKGKEKFKSLIIENQFEVILEILKLFSATRNVSDLQHIGGSKYSGVAKIGNKISSLDNCILIYQSITGIFE
KRIDLLKV*AAAD*PKKKRKVDPKKKRKVDPKKKRKV*DTAA*

Protospacer Adjacent Motif (PAM), SEQ ID 23: NAAAAN, wherein N= any of T, C, A or G

Fig. 5

Guide RNAs parent sequences and variants crRNA sequences underlined, crRNA variable part in bold

N=any of U, C, A or G tracrRNA sequences in *italic* other: linker (GAAA, SEQ ID 48)

**gRNA functional with *Streptococcus Pyogenes* CAS9**

SP_chimera_truncated (SEQ ID 25)

<u>NNNNNNNNNNNNNNNNNNNNGUUUUAGAGCUAG</u>*AAAUAGCAAGUUAAAAUAAGGCUAGUCCGUUAUC AACUUGAAAAAGUGGCACCGAGUCGGUGCUUUUUU*

SP_chimera_full (SEQ ID 26)

<u>NNNNNNNNNNNNNNNNNNNNGUUUUAGAGCUA</u>*UGCUGUUUUGAAUGGUCCCAAAACGAAAUUGUUGG AACCAUUCAAAACAGCAUAGCAAGUUAAAAUAAGGCUAGUCCGUUAUCAACUUGAAAAAGUGGCACCGAGU CGGUGCUUUUUU*

Fig. 5 (continued)

gRNA functional with *Streptococcus Thermophilus* CAS9

ST_chimera_truncated (SEQ ID 27)
NNNNNNNNNNNNNNNNNNNNGUUUUUGUACUCUCAGAAAUGCAGAAGCUACAAAGAUAAGGCUUCAUG
CCGAAAUCAACACCCUGUCAUUUUAUGGCAGGGUGUU ST_chimera_full (SEQ ID 28)
NNNNNNNNNNNNNNNNNNNNGUUUUUGUACUCUCAAGAUUUAAGUAACUGUACAACGAAACUUACACA
GUUACUUAAAUCUUGCAGAAGCUACAAAGAUAAGGCUUCAUGCCGAAAUCAACACCCUGUCAUUUUAUGG
CAGGGUGUU ST_gRNA_mutant 1 (SEQ ID 29)
NNNNNNNNNNNNNNNNNNNNGUUUUUGUACUCUCAGAAAUGCAGAAGCUACAAAGAUAAGGCUUCAUG
CCGAAAUCAACACCCUGUCAUUUUAUGGCAGGGUGUUUUUUU ST_gRNA_mutant 2 (SEQ ID 30)
NNNNNNNNNNNNNNNNNNNNGUUUUAGUACUCUCAGAAAUGCAGAAGCUUCAAAGAUAAGGCUUCAUG
CCGAAAUCAACACCCUGUCAUUUUAUGGCAGGGUGUUUUUUU ST_gRNA_mutant 3 (SEQ ID 31)
NNNNNNNNNNNNNNNNNNNNGUUUGUGUACUCUCAGAAAUGCAGAAGCUACAAAGAUAAGGCUUCAUG
CCGAAAUCAACACCCUGUCAUUUUAUGGCAGGGUGUUUUUUU ST_gRNA_mutant 4 (SEQ ID 32)
NNNNNNNNNNNNNNNNNNNNGUUUAUGUACUCUCAGAAAUGCAGAAGCUACAAAGAUAAGGCUUCAUG
CCGAAAUCAACACCCUGUCAUUUUAUGGCAGGGUGUUUUUUU ST_gRNA_mutant 5 (SEQ ID 33)
NNNNNNNNNNNNNNNNNNNNGUUUUUGUACUCUGAAAAGAAGCUACAAAGAUAAGGCUUCAUGCCGAA
AUCAACACCCUGUCAUUUUAUGGCAGGGUGUUUUUUU

Fig. 5 (continued)

ST_gRNA_mutant 6 (SEQ ID 34)

NNNNNNNNNNNNNNNNNNNNGUUUAGUACUCUGAAAAGAAGCUUCAAAGAUAAGGCUUCAUGCCGAAAUCAACACCCUGUCAUUUUAUGGCAGGGUGUUUUUUU

ST_gRNA_mutant 7 (SEQ ID 35)

NNNNNNNNNNNNNNNNNNNNGUUUGUGUACUCUGAAAAGAAGCUACAAAGAUAAGGCUUCAUGCCGAAAUCAACACCCUGUCAUUUUAUGGCAGGGUGUUUUUUU

ST_gRNA_mutant 8 (SEQ ID 36)

NNNNNNNNNNNNNNNNNNNNGUUUAUGUACUCUGAAAAGAAGCUACAAAGAUAAGGCUUCAUGCCGAAAUCAACACCCUGUCAUUUUAUGGCAGGGUGUUUUUUU

ST_gRNA_mutant 9 (SEQ ID 37)

NNNNNNNNNNNNNNNNNNNNGUUUUGUACUCUCAAGAUUUAAGUAACUGUACAACGAAACUUACACAGUUACUUAAAUCUUGCAGAAGCUACAAAGAUAAGGCUUCAUGCCGAAAUCAACACCCUGUCAUUUUAUGGCAGGGUGUUUUUU

ST_gRNA_mutant 10 (SEQ ID 38)

NNNNNNNNNNNNNNNNNNNNGUUUAGUACUCUCAAGAUUUAAGUAACUGUACAACGAAACUUACACAGUUACUUAAAUCUUGCAGAAGCUUCAAAGAUAAGGCUUCAUGCCGAAAUCAACACCCUGUCAUUUUAUGGCAGGGUGUUUUUU

ST_gRNA_mutant 11 (SEQ ID 39)

NNNNNNNNNNNNNNNNNNNNGUUUGUGUACUCUCAAGAUUUAAGUAACUGUACAACGAAACUUACACAGUUACUUAAAUCUUGCAGAAGCUACAAAGAUAAGGCUUCAUGCCGAAAUCAACACCCUGUCAUUUUAUGGCAGGGUGUUUUUU

ST_gRNA_mutant 12 (SEQ ID 40)

NNNNNNNNNNNNNNNNNNNNGUUUAUGUACUCUCAAGAUUUAAGUAACUGUACAACGAAACUUACACAGUUACUUAAAUCUUGCAGAAGCUACAAAGAUAAGGCUUCAUGCCGAAAUCAACACCCUGUCAUUUUAUGGCAGGGUGUUUUUU

Fig. 5 (continued)

**gRNA functional with *Neisseria Meningitis* CAS9**

NM_chimera_truncated (SEQ ID 41)

NNNNNNNNNNNNNNNNNNNNNGUUGUAGCUCCCUUUCUCGAAAGAGAACCGUUGCUACAAUAAGGCCGU*CUGAAAAGAUGUGCCGCAACGCUCUGCCCCUUAAAGCUUCUGCUUUAAGGGGC*

NM_chimera_full (SEQ ID 42)

NNNNNNNNNNNNNNNNNNNNNGUUGUAGCUCCCUUUCUCAUUUCGCAGUGCUACAAUGAAAA*UUGUCGCACUGCGAAAUGAGAACCGUUGCUACAAUAAGGCCGUCUGAAAAGAUGUGCCGCAACGCUCUGCCCCUUAAAGCUUCUGCUUUAAGGGGC*

NM_gRNA_mutant 1 (SEQ ID 43)

NNNNNNNNNNNNNNNNNNNNNGUUGUAGCUCCCUUUCUCGAAAGAGAACCGUUGCUACAAUAAGGCCGUCUGAAAAGAUGUGCCGCAACGCUCUGCCCCUUAAAGCUUCUGCUUUAACGGGCUUUUUUU

NM_gRNA_mutant 2 (SEQ ID 44)

NNNNNNNNNNNNNNNNNNNNNGUUGUAGCUCCCUUUCGAAAGAACCGUUGCUACAAUAAGGCCGUCUGAAAGAUGUGCCGCAACGCUCUGCCCCUUAAAGCUUCUGCUUUAACGGGCUUUUUUU

NM_gRNA_mutant 3 (SEQ ID 45)

NNNNNNNNNNNNNNNNNNNNNGUUGUAGCUCCCGAAACGUUGCUACAAUAAGGCCGUCUGAAAAGAUGUGCCGCAACGCUCUGCCCCUUAAAGCUUCUGCUUUAACGGGCUUUUUUU

NM_gRNA_mutant 4 (SEQ ID 46)

NNNNNNNNNNNNNNNNNNNNNGUUGUAGCUCCCUUUCUCAUUUCGCAGUGCUACAAUGAAAAUUGUCGCACUGCGAAAUGAGAACCGUUGCUACAAUAAGGCCGUCUGAAAAGAUGUGCCGCAACGCUCUGCCCCUUAAAGCUUCUGCUUUAAGGGGCUUUUUUU

NM_sgRNA (SEQ ID 47)

NNNNNNNNNNNNNNNNNNNNNGUUGUAGCUCCCUUUCUCAUUUCGGAAACGAAAUGAGAACCGUUGCUACAAUAAGGCCGUCUGAAAAGAUGUGCCGCAACGCUCUGCCCCUUAAAGCUUCUGCUUUAAGGGGCAUCGUUUA

Fig. 6

NNNNNNNNNNNNNNNNNNNNGUUUUAGAGCUAGAAAUAGCAAGUUAAAAUAAGGCUAGUCCGUUAUCAACUUGAAAAGUGGCACCGAGUCGGUGCUUUUUU

SEQ ID 53: Guide RNA structure for *Streptococcus pyogenes* Cas9. The crRNA sequence (underlined) contains a variable part (20 variable bases designated "N", wherein N= any of U, C, A, or G) and a constant part (GUUUUAGAGCUA, SEQ ID 54). A linker region is indicated in bold. The tracrRNA sequence is shown in italic.

Fig. 7

CHUK, clone 3-11 (SEQ ID 74, SEQ ID 75)

```
Wt      CTGCGGCCGGGCGCGGGCGGGCCCTGGGAGATGCGGGAGCGGCTGGGCACCGGCGGCTTCGGGAACGTCTGTCTGTACCAGCATCGGGT
        |||||||||||||||||||||||||||||||||||||||||                         ||||||||||||||||||||||||
Clone   CTGCGGCCGGGCGCGGGCGGGCCCTGGGAGATGCGGGA-------------------------ACGTCTGTCTGTACCAGCATCGGGT
```

GSK3B, clone 7-24 (SEQ ID 76, SEQ ID 77)

```
Wt      GGTGATTCGCGAAGAGAGTGATCATGTCAGGGCGGCCCAGAACCACCTCCTTTGCGGAGAGCTGCAAGCCGGTGCAGCAGCCTTCAGC
        ||||||||||||||||||||||||||||||||||||||||||||||||||||||||||||        ||||||||||||||||||||
Clone   GGTGATTCGCGAAGAGAGTGATCATGTCAGGGCGGCCCAGAACCACCTCCTTTGCGGA--------AGCCGGTGCAGCAGCCTTCAGC
```

RIPK2, clone 28-5 (SEQ ID 78, SEQ ID 79)

```
Wt      TGCGCTACCTGAGCCGCGGCGCCTCTGGCACTGTGTCGTCCGCCCGCCACGCAGACTGGCGCGTCCAGGTGGCCGTGAAGCACCTG
        ||||||||||||||||||||||||||||||||||||||||||||||||||||     |||||||||||||||||||||||||||
Clone   TGCGCTACCTGAGCCGCGGCGCCTCTGGCACTGTGTCGTCCGCCCGCCACGCA-----GCGCGTCCAGGTGGCCGTGAAGCACCTG
```

CDK4, clone 44-20 (SEQ ID 80, SEQ ID 81)

```
Wt      GTGGCCCTCAAGAGTGTGAGAGTCCCCAATGGAGGAGGAGGTGGAGGAGGCCTTCCCATCAGCACAGTTCGTGAGGTGGCTTTACTGAGG
        ||||||||||||||||||||||||||||||||||||||||||||||||||||||||||||||||||        ||||||||||||||||
Clone   GTGGCCCTCAAGAGTGTGAGAGTCCCCAATGGAGGAGGAGGTGGAGGAGGCCTTCCCATCAGCACAGT----GAGGTGGCTTTACTGAGG
```

RIPK1, clone 60-15 (SEQ ID 82, SEQ ID 83)

```
Wt      CATAGACTTAATATCACTTGTTTTAGATGAGTACTCCGCTTTCTGTAAAAGGAAGGATAATTTTGGAAATCATTGAAGGAATGTGCTA
        |||||||||||||||||||||||||||||.||||||||||||||||||             ||||||||||||||||||||||||||
Clone   CATAGACTTAATATCACTTGTTTTANATGAGTACTCCGCTTTCTGT--------------TTTTGGAAATCATTGAAGGAATGTGCTA
```

EEF2K, clone 85-14 (SEQ ID 84, SEQ ID 85)

```
Wt      GGTTACTTCATCTGCCCCATCACGGATGACCCAAGCTCGAACCAGAATGTCAATTCCAAGGTTAATAAGTACTACAGCAACCTAACAAA
        |||||||||||||||||||||||||||           ||||||||||||||||||||||||||||||||||||||||||||||||||
Clone   GGTTACTTCATCTGCCCCATCACGGAT-----------GAACCAGAATGTCAATTCCAAGGTTAATAAGTACTACAGCAACCTAACAAA
```

Fig. 9

EGFR local sequence (SEQ ID 55)

TGGCTTAAAAACCCTGAACGACATTCCTTTGCACCAGCTTGGTGAGGAGGGCATGGTCCCCGCCACCCCCCACCC

CCACTTTGCAGATAAACCACATGCAGGAAGGTCAGCCTGGCAAGTCCAGTAAGTTCAAGCCCAGGTCTCAACTG

GGCAGCAGAGCTCCTGCTCTTCTTTGTCCTCATATACGAGCACCTCTGGACTTAAAACTTGAGGAACTGGATGGA

GAAAAGTTAATGGTCAGCAGCGGGTTACATCTTCTTTCATGCGCCTTTCCATTCTTTGGATCAGTAGTCACTAACG

TTCGCCAGCCATAAGTCCTCGACGTGGAGAGGCTCAGAGCCTGGCATGAACATGACCCTGAATTCGGATGCAGA

GCTTCTTCCCATGATGATCTGTCCCTCACAGCAGGGTCTTCTCTGTTTCAGGGCATGAACTACTTGGAGGACCGTC

GCT_TGG_TGCACCGCGACCTGGCAG_CCA_GGAACGTACTGGTGAAAACACCGCAGCATGTCAAGATCACAGATTTT

GGG<u>CT</u>GGCCAAACTGCTGGGTGCGGAAGAGAAAGAATACCATGCAGAAGGAGGCAAAGTAAGGAGGTGGCTT

TAGGTCAGCCAGCATTTTCCTGACACCAGGGACCAGGCTGCCTTCCCACTAGCTGTATTGTTTAACACATGCAGG

GGAGGATGCTCTCCAGACATTCTGGGTGAGCTCGCAGCAGCTGCTGCTGGCAGCTGGGTCCAGCCAGGGTCTCC

TGGTAGTGTGAGCCAGAGCTGCTTTGGGAACAGTACTTGCTGGGACAGTGAATGAGGATGTTATCCCCAGGTGA

TCATTAGCAAATGTTAGGTTTCAGTCTCTCCCTGCAGGATATATAAGTCCCCTTCAATAGCGCAATTGGGAAAGGT

CACAGCTGCCTTGGTGGTCCACTGCTGTCAAGGACACCTAAGGAACAGGAAAGGCCC

Fig. 10

HR template used for introduction of L858R in the EGFR gene (SEQ ID 56)
TGGCTTAAAAACCCTGAACGACATTCCTTTGCACCAGCTTGGTGAGGAGGGCATGGTCCCCGCCACCCCCCACCC
CCACTTTGCAGATAAACCACATGCAGGAAGGTCAGCCTGGCAAGTCCAGTAAGTTCAAGCCCAGGTCTCAACTG
GGCAGCAGAGCTCCTGCTCTTCTTTGTCCTCATATACGAGCACCTCTGGACTTAAAACTTGAGGAACTGGATGGA
GAAAAGTTAATGGTCAGCAGCGGGTTACATCTTCTTTCATGCGCCTTTCCATTCTTTGGATCAGTAGTCACTAACG
TTCGCCAGCCATAAGTCCTCGACGTGGAGAGGCTCAGAGCCTGGCATGAACATGACCCTGAATTCGGATGCAGA
GCTTCTTCCCATGATGATCTGTCCCTCACAGCAGGGTCTTCTCTGTTTCAGGGCATGAA**CTACTTGGAGGACCGTC
GCT***TGG*TGCACCGCGACCTGGCAG*CCA*GGAACGT<u>ACTAGT</u>GAAAACACCGCAGCATGTCAAGATCACAGATTTT
GGG<u>C</u>GGGCCAAACTGCTGGGTGCGGAAGAGAAAGAATACCATGCAGAAGGAGGCAAAGTAAGGAGGTGGCTT
TAGGTCAGCCAGCATTTTCCTGACACCAGGGACCAGGCTGCCTTCCCACTAGCTGTATTGTTTAACACATGCAGG
GGAGGATGCTCTCCAGACATTCTGGGTGAGCTCGCAGCAGCTGCTGCTGGCAGCTGGGTCCAGCCAGGGTCTCC
TGGTAGTGTGAGCCAGAGCTGCTTTGGGAACAGTACTTGCTGGGACAGTGAATGAGGATGTTATCCCCAGGTGA
TCATTAGCAAATGTTAGGTTTCAGTCTCTCCCTGCAGGATATATAAGTCCCCTTCAATAGCGCAATTGGGAAAGGT
CACAGCTGCCTTGGTGGTCCACTGCTGTCAAGGACACCTAAGGAACAGGAAAGGCCC

Fig. 11

Single stranded oligonucleotide used as HR template (SEQ ID 57)
GTACTGGTGAAAACACCGCAGCATGTCAAGATCACAGATTTTGGG<u>C</u>GGGCC<u>AAGCTT</u>CTGGGTGCGGAAGAGA
AAGAATACCATGCAGAAGGA

Fig. 14

Clone 3-5, guide RNA 1 + plasmid (SEQ ID 58)

CTCGACGTGGAGAGGCTCAGAGCCTGGCATGAACATGACCCTGAATTCGGATGCAGAGCTTCTTCCCATGATGA
TCTGTCCCTCACAGCAGGGTCTTCTCTGTTTCAGGGCATGAACTACTTGGAGGACCGT*CA*CGCTTGGTGCACCGC
GACCTGGCAGCCAGGAACGT<u>ACTAGT</u>GAAAACACCGCAGCATGTCAAGATCACAGATTTTGGG<u>CGG</u>GCCAAACT
GCTGGGTGCGGAAGAGAAAGAATACCATGCAGAAGGAGGCAAAGTAAGGAGGTGGCTTTAGGTCAGCCAGCA
TTTTCCTGACACCAGGGACCAGGCTGCCTTCCCACTAGCTGTATTGTTTAACACATGCAGGGGAGGATGCTCTCC
AGACATTCTGGGTGAGCTCGCAGCAGCTGCTGCTGGCAGCTGGGTCCAGCCAGGGTCTCCTGGTAGTGTGAGCC
AGAGCTGCTTTGGGAAC*G*GTACTTGCTGGGACAGTGAATGAGGATGTTATCCCCAGGTGATCATTAGCAAATGT
TAGGTTTCAGTCTCTCCCTGCAGGATATATAAGTCCCCTTCAATAGCGCAATTGGGAAAGGTCACAGCTGCCTTG
GTGGTCCACTGCTGTCAAGGACACCTAAGGAACAGGAAAGGCCCCATGCGGACCCGAGCTCCCAGGGCTGTCTG
TGGCTCGTGGCTGGGACAGGCAGCAATGGAGTCCTTCTCTCCACNCCCNNGGCTCACATGAANNAGATGTAACC
CGCTGCTGACCATTAACTTTTTCTCCATCCAGTTCCTCAAGTTTTAAGTCCAGAGGTGCTCGTATATGA

Clone 7-12, guide RNA 2 + PCR product (SEQ ID 59)

GTGGAGAGGCTCAGAGCCTGGCATGAACATGACCCTGAATTCGGATGCAGAGCTTCTTCCCATGATGATCTGTCC
CTCACAGCAGGGTCTTCTCTGTTTCAGGGCATGAACTACTTGGAGGACCGTCGCTTGGTGCACCGCGACCTGGCA
GCCAGG*A*AACGT<u>ACTAGT</u>GAAAACACCGCAGCATGTCAAGATCACAGATTTTGGG<u>CGG</u>GCCAAACTGCTGGGT
GCGGAAGAGAAAGAATACCATGCAGAAGGAGGCAAAGTAAGGAGGTGGCTTTAGGTCAGCCAGCATTTTCCTG
ACACCAGGGACCAGGCTGCCTTCCCACTAGCTGTATTGTTTAACACATGCAGGGGAGGATGCTCTCCAGACATTC
TGGGTGAGCTCGCAGCAGCTGCTGCTGGCAGCTGGGTCCAGCCAGGGTCTCCTGGTAGTGTGAGCCAGAGCTG
CTTTGGGAAC*G*GTACTTGCTGGGACAGTGAATGAGGATGTTATCCCCAGGTGATCATTAGCAAATGTTAGGTTTC
AGTCTCTCCCTGCAGGATATATAAGTCCCCTTCAATAGCGCAATTGGGAAAGGTCACAGCTGCCTTGGTGGTCCA
CTGCTGTCAAGGACACCTAAGGAACAGGAAAGGCCCCATGCGGACCCGAGCTCCCAGGGCTGTCTGTGGCTCGT
GGCTGGGACAGGCAGCAATGGAGTCCTTCTCTCCCTCN

Fig. 14 continued

Clone 8-5, guide RNA 2 + plasmid (SEQ ID 62)

TGGAGAGGCTCAGAGCCTGGCATGAACATGACCCTGAATTCGGATGCAGAGCTTCTTCCCATGATGATCTGTCCC
TCACAGCAGGGTCTTCTCTGTTTCAGGGCATGAACTACTTGGAGGACCGTCGCTTGGTGCACCGCGACCTGGCAG
CCAGGAACGTACTAGTGAAAACACCGCAGCATGTCAAGATCACAGATTTTGGGC<u>GGG</u>CCAAACTGCTGGGTGC
GGAAGAGAAAGAATACCATGCAGAAGGAGGCAAAGTAAGGAGGTGGCTTTAGGTCAGCCAGCATTTTCCTGAC
ACCAGGGACCAGGCTGCCTTCCCACTAGCTGTATTGTTTAACACATGCAGGGGAGGATGCTCTCCAGACATTCTG
GGTGAGCTCGCAGCAGCTGCTGCTGGCAGCTGGGTCCAGCCAGGGTCTCCTGGTAGTGTGAGCCAGAGCTGCTT
TGGGAACAGTACTTGCTGGGACAGTGAATGAGGATGTTATCCCCAGGTGATCATTAGCAAATGTTAGGTTTCAG
TCTCTCCCTGCAGGATATATAAGTCCCCTTCAATAGCGCAATTGGGAAAGGTCACAGCTGCCTTGGTGGTCCACT
GCTGTCAAGGACACCTAAGGAACAGGAAAGGCCCCATGCGGACCCGAGCTCCCAGGGCTGTCTGTGGCTCGTG
GCTGGGACAGGCAGCAATGGAGTCCTTCTCTCCANNCCNNNGNCTTCAATGAAANAAANATGTAACCCCNCTG
CTGACCNTTAACTTTTTCTCCATCCAGTTCCTCAAGTTTTAAGTCCA

Clone 8-10, guide RNA 2 + plasmid (SEQ ID 63)

GTGGAGAGGCTCAGAGCCTGGCATGAACATGACCCTGAATTCGGATGCAGAGCTTCTTCCCATGATGATCTGTCC
CTCACAGCAGGGTCTTCTCTGTTTCAGGGCATGAACTACTTGGAGGACCGTCGCTTGGTGCACCGCGACCTGGCA
GCCAGGAACGTACTAGTGAAAACACCGCAGCATGTCAAGATCACAGATTTTGGG<u>CGG</u>GCCAAACTGCTGGGTG
CGGAAGAGAAAGAATACCATGCAGAAGGAGGCAAAGTAAGGAGGTGGCTTTAGGTCAGCCAGCATTTTCCTGA
CACCAGGGACCAGGCTGCCTTCCCACTAGCTGTATTGTTTAACACATGCAGGGGAGGATGCTCTCCAGACATTCT
GGGTGAGCTCGCAGCAGCTGCTGCTGGCAGCTGGGTCCAGCCAGGGTCTCCTGGTAGTGTGAGCCAGAGCTGC
TTTGGGAAC*GG*TACTTGCTGGGACAGTGAATGAGGATGTTATCCCCAGGTGATCATTAGCAAATGTTAGGTTTCA
GTCTCTCCCTGCAGGATATATAAGTCCCCTTCAATAGCGCAATTGGGAAAGGTCACAGCTGCCTTGGTGGTCCAC
TGCTGTCAAGGACACCTAAGGAACAGGAAAGGCCCCATGCGGACCCGAGCTCCCAGGGCTGTCTGTGGCTCGTG
GCTGGGACAGGCAGCAATGGAGTCCTTCTCTCCCACNNNCTGGGCTTCACATGAAAGAAGATGTAACCCGCTGC
TGACCATTAACTTTTCTCCATCCAGTTCCTCAAGTTTTAAGTCCAGA

Fig. 15

EGFR T790M donor template (SEQ ID 64)

CCGGACCCCACACAGATTCCTACAGGCCCTCATGATATTTTAAAACACAGCATCCTCAACCTTGAGGCGGAGGTC
TTCATAACAAAGATACTATCAGTTCCCAAACTCAGAGATCAGGTGACTCCGACTCCTCCTTTATCCAATGTGCTCC
TCATGGCCACTGTTGCCTGGGCCTCTCTGTCATGGGGAATCCCCAGATGCACCCAGGAGGGGCCCTCTCCCACTG
CATCTGTCACTTCACAGCCCTGCGTAAACGTCCCTGTGCTAGGTCTTTTGCAGGCACAGCTTTTCCTCCATGAGTA
CGTATTTTGAAACTCAAGATCGCATTCATGCGTCTTCACCTGGAAGGGGTCCATGTGCCCCTCCTTCTGGCCACCA
TGCGAAGCCACACTGACGTGCCTCTCCCTCCCTCCAGGA<u>AGCCTACGTGATGGCCAGCGTA</u>GACAACC*<u>CTCACGT
GTGCCGCCTGCTGGGC</u>*AT<u>AT</u>GCCTCACCTCCACCGTGCAGCTCATC<u>ATG</u>CAGCTCATGCCCTTCGGCTGCCTCCTG
GACTATGTCCGGGAACACAAAGACAATATTGGCTCCCAGTACCTGCTCAACTGGTGTGTGCAGATCGCAAAGGT
AATCAGGGAAGGGAGATACGGGGAGGGGAGATAAGGAGCCAGGATCCTCACATGCGGTCTGCGCTCCTGGGA
TAGCAAGAGTTTGCCATGGGGATATGTGTGTGCGTGCATGCAGCACACACACATTCCTTTATTTTGGATTCAATC
AAGTTGATCTTCTTGTGCACAAATCAGTGCCTGTCCCATCTGCATGTGGAAACTCTCATCAATCAGCTACCTTTGA
AGAATTTTCTCTTTATTGAGTGCTCAGTGTGGTCTGATGTCTCTGTTCTTATTTCTCTGGAATTCTTTGTGAATACT
GTGGTGATTTGTAGTGGAGAAGGAATATTGCTTCCCCCATTCAGGACTTGATAACAAGGTAAGCAAGCCAGGCC
AAGGCCAGGAGGACCCAGGTGAT

JAK2 V617F donor template (SEQ ID 65)

TATCCTGACACAGATGTCGTGATATTTTATCTGCACATTCTTAATTCTTTAGCAAGTGTTATTTAAAGGCTACATCC
ATCTACCTCAGTTTCCTATATCTATCTCTGACATCTACCTCTAGTTGTACTTCTGTCCTCTATTTCAGGTGTTATGGG
TCAAGCCTGTTTGACTGGCATTATTCATGATTCCTGTACCACTCTTGCTCTCTCTCACTTTGATCTCCATATTCCAGG
CTTACACAGGGGTTTCCTCAGAACGTTGATGGCAGTTGCAGGTCCATATAAAGGGACCAAAGCACATTGTATCCT
CATCTATAGTCATGCTGAAAGTAGGAGAAAGTGCATCTTTATTATGGCAGAGAGAATTTTCTGAACTATTTATGG
ACAACAGTCAAACAACAATTCTTTGTACTTTTTTTTTTCCTTAGTCTTTCTTTGAAGCAGCAAGTATGATGAGCAAG
CTTTCTCACAAGCATTTGGTTTTAAATTATGGAGTATGT<u>TTC</u>TGTGGAG*<u>ACGAGAGTAAGTAAAACTACAGA</u>*CTTT
CTAATG*<u>CTTTTCTCAGAGCATCTGTTTTT</u>*GTTTATATAGA<u>GAATTC</u>AGTTTCAGGATCACAGCTAGGTGTCAGTGT
AAACTATAATTTAACAGGAGTTAAGTATTTTTGAAACTGAAAACACTGTAGGACTATTCAGTTATATCTTGTGAAA
AAGGAAAGCAATGAAGTTAAAAGTAGAAGGTTACAATGCCCAAACAATAGAGTATTATAGTAAACAAATGTCTA
TAAAACATTTTGTGTTCATGATAGCAAAAGAGATTATGGCAGGTTCAACATAACATTGGAATAACTGGCCTTTTC
AGTACAAACTTATCTGGAATTATGAAGACAAAGCATATAAATGATACACTTAATTTTTAATGGAACTGACAGAAA
TGATTATGTTGATATGATACTAGATATATTTTTTGGCTAAATTTAGGTGTTCACAGAAACTACTAAAAGTATAAAT
CGTACCCCATGC

Fig. 15 continued

KIT D816V donor template (SEQ ID 66)

AAGGACATTCAAAGAGATGCATGCAAAATGAATTTTCAGTTTAAACAATATGATATGACTATTTCTTATGTATTTC
CCTATGAATGAAAGCAGTCCTGAGAAGAAAACAGCATTTATTAGAATTGCTTTTAAAAGAGATTATAATAATTAG
ACTCTTGATTATGTGAACATCATTCAAGGCGTACTTTTGATTTTTATTTTTGGTGTACTGAATACTTTAAAACAAAA
GTATTGGATTTTTTATAATATAAGCAACACTATAGTATTAAAAAGTTAGTTTTCACTCTTTACAAGTTAAAATGAAT
TTAAATGGTTTTCTTTTCTCCTCCAACCTAATAGTGTATTCACAGAGACTTGGCAGCCAGAA*ATATCCTCCTTACTC*
*ATGGTCGA*ATCACAAAGATCTGTGATTTTGGTCTAG*CAAGAGTCATCAAGAATGATTCT*AATTATGTGGTTAAAG
GAAACGTGAGTACCCATTCTCTGCTTGACAGTCCTGCAAAGGATTTTTAGTTTCAACTTTCGATAAAAATTGTTTC
CTGTGATTTTCATAATGTAAATCCTGTCTAGGGATATCACACATTTTAGCAGTCAAATTAAGTATACTTCAGCAAA
ATTTGCATGGTATGCTGAACATTACTACAACTAACATTCAATAATAGAAGTCCTAATTCTAATTGTGTAATTTTGG
GGCATGTGAAGGAAACAGAAATAGCCTTAATTTTCATTATAGCCTGAGAATAGCAATGAACTTGATTTTGCTCAA
GTGTAACAAATGTAGGTCATTGAAGGTCACAGCAGGAGAAATTTTGGGGGGATTGGCATGCCGTGTGAAAAAT
ATTAAAATCTAAGATCATATTCAGAGTTAGCCATATAGAATGTTGGATCCTAGAATACACGGAGAGCTATTAAAT
AGGTTCATAAGTAATA

Fig. 16:

JAK2 V617F: >JAK2_V617F_c778 (SEQ ID 67)

CTATCTCTGANATCTACCTCTAGTTGTACTTCTGTCCTCTATTTCAGGTGTTATGGGTCAAGCCTGTTTGACTGGCA
TTATTCATGATTCCTGTACCACTCTTGCTCTCTCTCACTTTGATCTCCATATTCCAGGCTTACACAGGGGTTTCCTCA
GAACGTTGATGGCAGTTGCAGGTCCATATAAAGGGACCAAAGCACATTGTATCCTCATCTATAGTCATGCTGAAA
GTAGGAGAAAGTGCATCTTTATTATGGCAGAGAGAATTTTCTGAACTATTTATGGACAACAGTCAAACAACAATT
CTTTGTACTTTTTTTTTCCTTAGTCTTTCTTTGAAGCAGCAAGTATGATGAGCAAGCTTTCTCACAAGCATTTGGTT
TTAAATTATGGAGTATGTTTCTGTGGAGACGAGAGTAAGTAAAACTACAGACTTTCTAATGCTTTTCTCARAGCAT
CTGTTTTTGTTTATATAGAAAATTCAGTTTCAGGATCACAGCTAGGTGTCAGTGTAAACTATAATTTAACAGGAGT
TAAGTATTTTTGAAACTGAAAACACTGTAGGACTATTCAGTTATATCTTGTGAAAAAGGAAAGCAATGAAGTTAA
AAGTAGAAGGTTACAATGCCCAAACAATAGAGTATTATAGTAAACAAATGTCTATAAAACATTTTGTGTTCATGA
TAGCAAAAGAGATTATGGCAGGTTCAACATAACATTGGAATAACTGGCCTTTTCAGTACAAACTTATCTGGAATT
ATGAAGACAAAGCATATAAATGATACACTTAATTTTTAATGGAACTGACAGAAATGATTATGTTGATATGATACT
AGATATATTTTTTGGCTAAATTTAGGTGTTCACAGAAACTACTAAAAGTATAAATCGTACCCCATGCTTTAATACT
ATACAG

KIT D816V: >KIT_D816V_c760 (SEQ ID 68)

CTGAGAAGAAAACAGCATTTATTAGAATTGCTTTTAAAAGAGATTATAATAATTAGACTCTTGATTATGTGAACAT
CATTCAAGGCGTACTTTTGATTTTTATTTTTGGTGTACTGAATACTTTAAAACAAAAGTATTGGATTTTTTATAATA
TAAGCAACACTATAGTATTAAAAAGTTAGTTTTCACTCTTTACRAGTTAAAATGAATTTAAATGGTTTTCTTTTCTC
CTCCAACCTARTAGTGTATTCACAGAGACTTGGCAGCCAGAAATATCCTCCTTACTCATGGTCGAATCACARAGAT
CTGTGATTTTGGTCTAGCAAGAGTCATCAAGAATGATTCTAATTATGTGGTTAAAGGAAACGTGAGTACCCATTC
TCTGCTTGACAGTCCTGCAAAGGATTTTTAGTTTCAACTTTCGATAAAAATTGTTTCCTGTGATTTTCATAATGTAA
ATCCTGTCTAGGGATATCACACATTTTAGCAGTCAAATTAAGTATACTTCAGCAAAATTTGCATGGTATGCTGAAC
ATTACTACAACTAACATTCAATAATAGAAGTCCTAATTCTAATTGTGTAATTTTGGGGCATGTGAAGGAAACAGA
AATAGCCTTAATTTTCATTATAGCCNTGAGAATAGCAATGAACTTTGATTTTTGCTCAAAGTGTAACAAAATGTAA
GGTCATTTGAAAGGTCACAAGCAGGGAGAAAATTK

Fig. 16 continued

KIT D816V: >KIT_ D816V_c780 (SEQ ID 69)
AAAGCAGTCCTGAGAAGAAAACAGCATTTATTAGAATTGCTTTTAAAAGAGATTATAATAATTAGACTCTTGATT
ATGTGAACATCATTCAAGGCGTACTTTTGATTTTTATTTTTGGTGTACTGAATACTTTAAAACAAAAGTATTGGATT
TTKTATAATATAAGCAACACTATAGTATTAAAAAGTTAGTTTTCACTCTTTACRAGTTAAAATGAATTTAAATGGTT
TTCTTTTCTCCTCCAACCTARTAGTGTATTCACAGAGACTTGGCAGCCAGAAATATCCTCCTTACTCATGGTCGAAT
CACANAGATCTGTGATTTTGGTCTAGCAAGA<u>GTC</u>ATC<u>AAGAATGATTCT</u>AATTATGTGGTTAAAGGAAACGTGAG
TACCCATTCTCTGCTTGACAGTCCTGCAAAGGATTTTTAGTTTCAACTTTCGATAAAAATTGTTTCCTGTGATTTTC
ATAATGTAAATCCTGTCTAGGGATATCACACATTTTAGCAGTCAAATTAAGTATACTTCAGCAAAATTTGCATGGT
ATGCTGAACATTACTACAACTAACATTCAATAATAGAAGTCCTAATTCTAATTGTGTAATTTTGGGGCATGTGAAG
GAAACAGAAATAGCCTTAATTTTCATTATAGCCTGAGAATAGCAATGAACTTGATTTTTGCTCAAGTGTAACAAAT
GTAGGTCATTTGAAGGTCACAGCAGGGAG

KIT D816V: >KIT_ D816V_c759 (SEQ ID 70)
GCATGCAAAATGAATTTCAGTTTAAACAATATGATATGACTATTCTTATGTATTTCCCTATGAATGAAAGCAGTCC
TGAGAAGAAAACAGCATTTATTAGAATTGCTTTTAAAAGAGATTATAATAATTAGACTCTTGATTATGTGAACATC
ATTCAAGGCGTACTTTTGATTTTTATTTTTGGTGTACTGAATACTTTAAAACAAAAGTATTGGATTTTTTATAATAT
AAGCAACACTATAGTATTAAAAAGTTAGTTTTCACTCTTTACAAGTTAAAATGAATTTAAATGGTTTTCTTTTCTCC
TCCAACCTAATAGTGTATTCACAGAGACTTGGCAGCCAGAAATATCCTCCTTACTCATGGTCGAATCACAAAGATC
TGTGATTTTGGTCTAGCAAGA<u>GTC</u>ATC<u>AAGAATGATTCT</u>AATTATGTGGTTAAAGGAAACGTGAGTACCCATTCT
CTGCTTGACAGTCCTGCAAAGGATTTTTAGTTTCAACTTTCGATAAAAATTGTTTCCTGTGATTTTCATAATGTAAA
TCCTGTCTAGGGATATCACACATTTTAGCAGTCAAATTAAGTATACTTCAGCAAAATTTGCATGGTATGCTGAACA
TTACTACAACTAACATTCAATAATAGAAGTCCTAATTCTAATTGTGTAATTTTGGGGCATGTGAAGGAAACAGAA
ATAGCCTTAATTTTCATTATAGCCTGAGAATAGCAATGAACTTGATTTTGCTCAAGTGTAACAAATGTAGGTCATT
GAAGGTCACAGCAGGAGAAATTTTGGGGGGATTGGCATGCCGTGTGAAAAATATTAAAATCTAA

Fig. 16 continued

KIT D816V: >KIT_ D816V_c769 (SEQ ID 71)

AAGAAAACAGCATTTATTAGAATTGCTTTTAAAAGAGATTATAATAATTAGACTCTTGATTATGTGAACATCATTC
AAGGCGTACTTTTGATTTTTATTTTTGGTGTACTGAATACTTTAAAACAAAAGTATTGGATTTTTTATAATATAAGC
AACACTATAGTATTAAAAAGTTAGTTTTCACTCTTTACAAGTTAAAATGAATTTAAATGGTTTTCTTTTCTCCTCCA
ACCTARTAGTGTATTCACAGAGACTTGGCAGCCAGAAATATCCTCCTTACTCATGGTCGGATCACARAGATTTGTG
ATTTTGGTCTAGCAAGAGTCATCAAGAATGATTCTAATTATGTGGTTAAAGGAAACGTGAGTACCCATTCTCTGCT
TGACAGTCCTGCAAAGGATTTTTAGTTTCAACTTTCGATAAAAATTGTTTCCTGTGATTTTCATAATGTAAATCCTG
TCTAGGGATATCACACATTTTAGCAGTCAAATTAAGTATACTTCAGCAAAATTTGCATGGTATGCTGAACATTACT
ACAACTAACATTCAATAATAGAAGTCCTAATTCTAATTGTGTAATTTTGGGGCATGTGAAGGAAACAGAAATAGC
CTTAATTTTCATTATAGCCTGAGAATAGCAATGAACTTGATTTTGCTCAAGTGTAACAAATGTAGGTCATTGAAGG
TCACAGCAGGAGAAATTTTGGGGGGATTGG

EGFR T790M: >EGFR_T790M_c772 (Donor template: plasmid) (SEQ ID 72)

CCGACTCCTCCTTTATCCAATGTGCTCCTCATGGCCACTGTTGCCTGGGCCTCTCTGTCATGGGGAATCCCCAGAT
GCACCCAGGAGGGGCCCCCTCCCACTGCATCTGTCACTTCACAGCCCTGCGTAAACGTCCCTGTGCTAGGTCTTTT
GCAGGCACAGCTTTTCCTCCATGAGTACGTATTTTGAAACTCAAGATCGCATTCATGCGTCTTCACCTGGAAGGG
GTCCATGTGCCCCTCCTTCTGGCCACCATGCGAAGCCACACTGACGTGCCTCTCCCTCCCTCCAGGAAGCCTACGT
GATGGCCAGCGTAGACAACCCTCACGTGTGCCGCCTGCTGGGCATATGCCTCACCTCCACCGTGCAGCTCATCAT
GCAGCTCATGCCCTTCGGCTGCCTCCTGGACTATGTCCGGGAACACAAAGACAATATTGGCTCCCAGTACCTGCT
CAACTGGTGTGTGCAGATCGCAAAGGTAATCAGGGAAGGGAGATACGGGGAGGGGAGATAAGGAGCCAGGAT
CCTCACATGCGGTCTGCGCTCCTGGGATAGCAAGAGTTTGCCATGGGGATATGTGTGTGCGTGCATGCAGCACA
CACACATTCCTTTATTTTGGATTCAATCAAGTTGATCTTCTTGTGCACAAATCAGTGCCTGTCCCATCTGCATGTGG
AAACTCTCATCAATCAGCTACCTTTGAAGAATTTTCTCTTTATTGAGTGCTCAGTGTGGTCTGATGTCTCTGTTCTT
ATTTCTCTGGAATTCT

Fig. 16 continued

EGFR T790M: > EGFR_T790M_c763 (Donor template: PCR product) (SEQ ID 73)
GACTCCTCCTTTATCCAATGTGCTCCTCATGGCCACTGTTGCCTGGGCCTCTCTGTCATGGGGAATCCCCAGATGC
ACCCAGGAGGGGCCCTCTCCCACTGCATCTGTCACTTCACAGCCCTGCGTAAACGTCCCTGTGCTAGGTCTTTTGC
AGGCACAGCTTTTCCTCCATGAGTACGTATTTTGAAACTCAAGATCGCATKCATGCGTCTTCACCTGGAAGGGGT
CCATGTGCCCCTCCTTCTGGCCACCATGCGAAGCCACACTGACGTGCCTCTCCCTCCCTCCAGGA<u>AGCCTACGTGA
TGGCCAGCG</u>TAGACAACCCTC<u>ACGTGTGCCGCCTGCTGGGC</u>ATATGCCTCACCTCCACCGTGCAGCTCATCATGC
AGCTCATGCCCTTCGGCTGCCTCCTGGACTATGTCCGGGAACACAAAGACAATATTGGCTCCCAGTACCTGCTCA
ACTGGWGTGTGCAGATCGCAAAGGTAATCAGGGAAGGGAGATACGGGGAGGGGAGATAAGGAGCCAGGATC
CTCACATGCGGTCTGCGCTCCTGGGATAGCAAGAGTTTGCCATGGGGATATGTGTGTGCGTGCATGCAGCACAC
ACACATTCCTTTATTTTGGATTCAATCAAGTTGATCTTCTTGTGCACAAATCAGTGCCTGTCCCATCTGCATGTGGA
AACTCTCATCAATCAGCTACCTTTGAAGAATTTTCTCTTTATTGAGTGCTCAGTGTGGTCTGATGTCTCTGTNCTAT
TTCTCTGGAATTCTT

Fig. 17

OTUB1, clone 506-10 (SEQ ID 86, SEQ ID 87)

```
Wt      TGTTAACTGTCTGGCCTATGATGAAGCCATCATGGCTCAGCAGGACCGAATTCAGCAAGAGGTGAGGGGCTGCAGTGGGCGAGGGAGG
        |||||||||||||||||||||||||||||             |||||||||||||||||||||||||||||||||||||||||||||
Clone   TGTTAACTGTCTGGCCTATGATGAAGCCA-------TCAGCAGGACCGAATTCAGCAAGAGGTGAGGGGCTGCAGTGGGCGAGGGAGG
```

BRDT, clone 1321-08 (SEQ ID 88, SEQ ID 89)

```
Wt      GCATGGCCCTTTTATAATCCTGTTGACGTTAATGCTTTGGGACTCCATAACTACTATGACGTTGTCAAAAATCCGATGG
        ||.|||||||||||||||||||  ||||||||||||||||||||||||||||||||||||||||||||||||||||||
Clone   GCNTGGCCCTTTTATAATCCTG--GACGTTAATGCTTTGGGACTCCATAACTACTATGACGTTGTCAAAAATCCGATGG
```

DDIT4, clone 1351-01 (SEQ ID 90, SEQ ID 91)

```
Wt      CCTGGGGGTCGGCGACCCGGGAGGAGGGGTTTGACCGCTCCACGAGCCTGGAGAGCTCGGACTGCGAGTCCCTGGACAGCAGCAAC
        |||||||||||||||||||||||||||||||||||||||||||       |||||||||||||||||||||||||||||||||||
Clone   CCTGGGGGTCGGCGACCCGGGAGGAGGGGTTTGACCGCTCCAC-------GAGAGCTCGGACTGCGAGTCCCTGGACAGCAGCAAC
```

DDIT4L, clone 1352-10 (SEQ ID 92, SEQ ID 93)

```
Wt      AAAAAGAAAACTCCATTTCTTACAGATTTTGACTACTGGGATTATGTTGTTCCTGAACCCAACCTCAACGAGGTAATATTTGAGGAAT
        ||||||||||||||||||||||||||||||||||||||||||||||||||||||          |||||||||||||||||||||||
Clone   AAAAAGAAAACTCCATTTCTTACAGATTTTGACTACTGGGATTATGTTGTTCCTGAA----------ACGAGGTAATATTTGAGGAAT
```

EIF4EBP1, clone 1353-02 (SEQ ID 94, SEQ ID 95)

```
Wt      CTCCCGCCCGGGGACTACAGCACGACCCCCGGCGGCACGCTCTTCAGCACCACCCCGGGAGGTAGGCGCGGGCTTGGCGACGCCGCTTG
        |||||||||||||||||||||||||||              ||||||||||||||||||||||||||||||||||||||||||||||
Clone   CTCCCGCCCGGGGACTACAGCACGA---------------CTCTTCAGCACCACCCCGGGAGGTAGGCGCGGGCTTGGCGACGCCGCTTG
```

Fig. 18
(A) 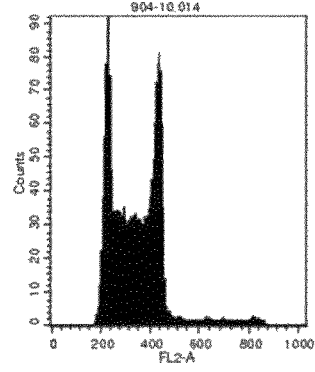
(B) 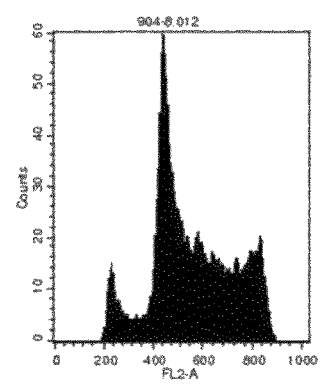
(C) 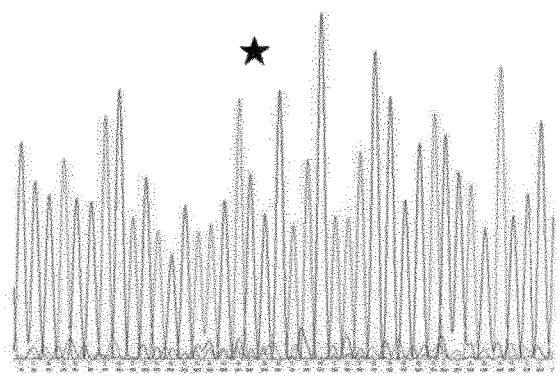
(D) 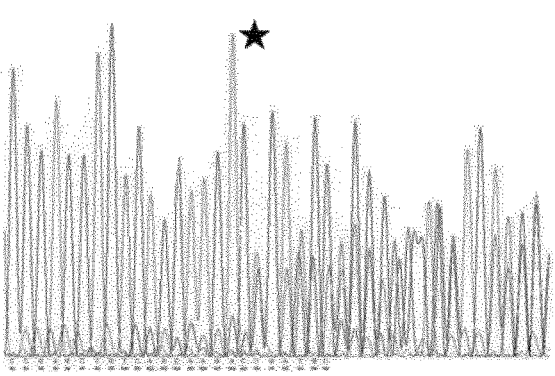

Fig. 21
(A)
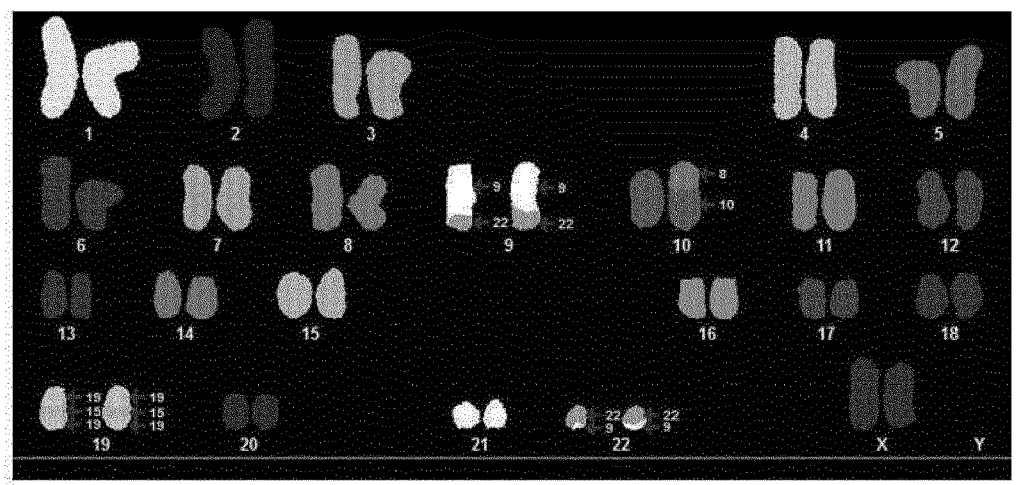
(B)
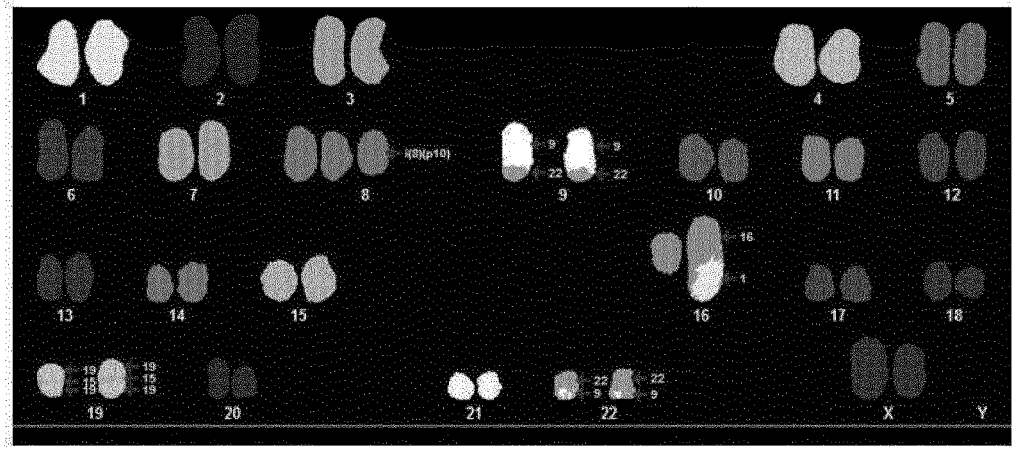
(C)
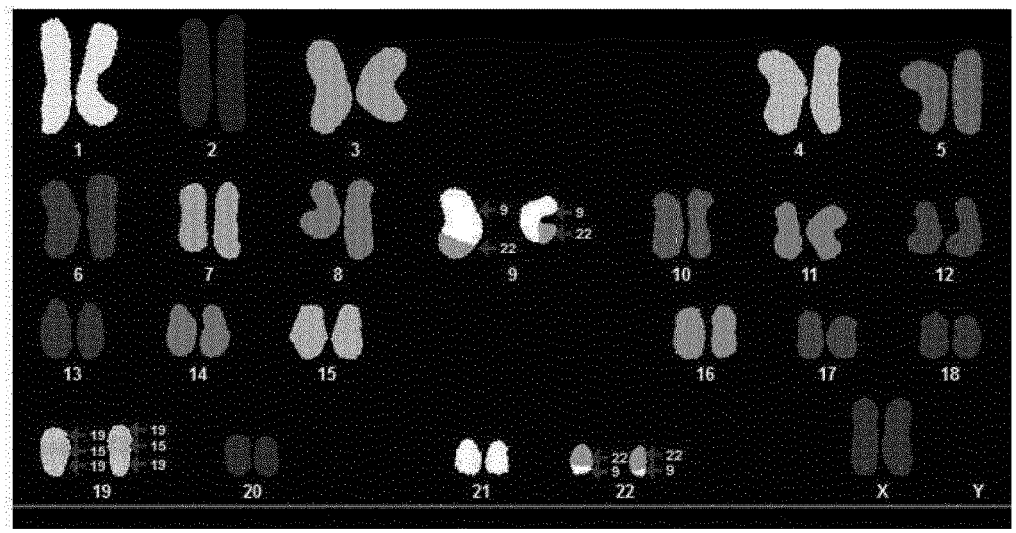

SOMATIC HUMAN CELL LINE MUTATIONS

CROSS-REFERENCE TO RELATED APPLICATIONS

This application is a U.S. national stage filing under 35 U.S.C. § 371 of International Application No. PCT/EP2014/076028, filed on Nov. 28, 2014, incorporated by reference herein in its entirety, which claims the benefit of priority to European Patent Application No. 14191914.2, filed on Nov. 5, 2014, European Patent Application No. 14181367.5, filed on Aug. 19, 2014, International Application No. PCT/EP2014/066732, filed on Aug. 4, 2014, European Patent Application No. 13194940.6, filed on Nov. 28, 2013, and European Patent Application No. 13194939.8, filed on Nov. 28, 2013.

SEQUENCE LISTING

This application contains a sequence listing, submitted electronically in ASCII format under the filename 00012-0015-00000_Sequence_Listing.txt, which is incorporated by reference herein in its entirety. The ASCII copy of the sequence listing was created on May 27, 2016, and is 178,363 bytes in size.

The invention refers to mutant somatic human cell lines of cells comprising a genomic mutation at a predefined genomic target site, and methods or tools for producing the same.

BACKGROUND

Bacteria have a need to maintain their genomic integrity and defend against invading viruses and plasmids. Recently, genomic loci with clustered, regularly interspaced, short palindromic repeats (CRISPRs) were found in bacteria and were shown to mediate adaptive immunity to invading pathogens [1]: Bacteria can capture short nucleic acid sequences from invading pathogens and integrate them in the CRISPR loci. Small RNAs, produced by transcription of the CRISPR loci, can guide a set of bacterial endonucleases to cleave the genomes of invading pathogens.

The minimal requirements for one bacterial endonuclease, CAS9 from *Streptococcus pyogenes*, were characterized by purifying the enzyme and reconstituting the cleavage reaction in vitro [2]. Surprisingly, CAS9 itself is sufficient for endonuclease cleavage and no further polypeptides are required for the cleavage reaction. In addition, CAS9 requires two RNA cofactors: a constant tracrRNA and a crRNA bearing both constant and variable parts. Importantly, the variable part of the crRNA can be used to reprogram the cleavage specificity of CAS9, thereby enabling the targeting of CAS9 to genomic loci of interest. Cleavage specificity is limited by the protospacer adjacent motif (PAM) that is specific to CAS9 and lies adjacent to the cleavage site. In an attempt to simplify the system, crRNA and tracrRNA were fused to give rise to one chimeric RNA molecule referred to as the guide RNA.

Following this publication, several laboratories showed that this system can be used in cells from different species including humans [3,4], zebrafish [5], fruit flies [6] and yeast [7]. Once a certain locus is specified by the crRNA, CAS9 induces DNA double-strand breaks with remarkable efficiency at that particular locus and triggers cellular DNA damage repair mechanisms: In the presence of a homology template, homology-directed repair (HDR) allows the precise engineering of the locus of interest, enabling for instance the introduction of tags or point mutations. In the absence of a homology template, non-homologous end joining (NHEJ) is the predominant repair mechanism. As NHEJ is error-prone, it often creates small insertions or deletions. If the CAS9 cleavage site is located in an exon of a human gene, NHEJ often gives rise to frameshift mutations, thereby disrupting the gene of interest and generating a gene knockout.

The endonuclease CAS9 has two domains with endonuclease activity, a RuvCI domain and an HNH domain. Point mutations in either of the two domains generate a CAS9 nickase that cleaves only one of the two DNA strands, giving rise to nicked DNA [2]. This is of particular interest because nicked DNA is a suitable template for HDR, but not NHEJ [4]. So by using the CAS9 nickase, one can enhance HDR efficiency considerably. In addition, the introduction of two DNA nicks in close proximity can enhance cleavage specificity considerably [8].

Of note, CAS9 can not only be used to induce cleavage of a particular genomic locus, but it can be used as a universal targeting tool. For that purpose, catalytically inactive mutants of CAS9 turned out to be useful. For instance, fusion of inactive CAS9 to transcriptional activator domains enables the targeted activation of transcription [9]. Using this approach, a plethora of applications of CAS9 is conceivable in which CAS9 serves as targetable genome tether.

Finally, variants of CAS9 have been identified in several other bacterial species including *Streptococcus thermophiles, Neisseria meningitis* and *Treponema denticola* [10, 11]. Importantly, all CAS9 variants described so far differ with regard to their PAM, thereby enlarging the repertoire of accessible cleavage sites and enabling the simultaneous targeting of several sites by orthogonal CAS9 proteins.

US 2010/0076057 A1 discloses the targeted DNA interference with crRNA and CRISPR-associated (cas) proteins, in particular for horizontal gene transfer based on the use of CRISPR sequences.

The RNA-directed DNA cleavage by the CAS9-crRNA complex is described by WO 2013/141680 A1 and WO 2013/142578 A1.

The CRISPR/Cas technology has been used to engineer gene knockouts in various mammalian cell types including diploid human cell lines (e.g. 293T cells) [15].

A near-haploid human cell line KBM-7 was reportedly used to inactivate single human genes using a retroviral gene trapping approach, thereby producing a collection of mutant KBM-7 cell lines carrying single gene trap insertions. Difficulties in producing a human library containing a knockout clone for each human gene have been described [16]. Such collections would be significantly distinct from the KBM-7 gene trap collections, in which the impact of the gene trap on gene expression is often incomplete and heavily dependent on the genomic locus of interest. TALENs (transcription activator-like effector nucleases) and CRISPR/Cas9 were used for genome engineering in a variety of cell types, including human cells [17].

Human knockout cells are invaluable tools that allow for the systematic investigation of human gene function in vitro. A collection of all human gene knockouts may be used, e.g. for reverse genetic studies or for the discovery of novel drug targets.

A prior art collection of human mutant cells was produced using gene-trap mutagenesis in near-haploid human cells. Every cell line carries a gene-trap insertion at a particular genomic locus, leading to the inactivation of that particular gene. In that regard, haploid gene trap mutants resemble conventional gene knockouts. Yet, gene traps cannot be targeted to a particular locus of interest and thus, the gene trap integration site is determined by the integration pattern of the retroviral vector used for the delivery of the gene trap. [12].

It is the object of the present invention to provide for an efficient method of producing somatic human cell lines with predefined mutations.

SUMMARY OF THE INVENTION

The object is solved by the subject matter as claimed.

According to the invention, there is provided a method of producing a mutant somatic human cell line of cells comprising a genomic mutation of interest (MOI) at a predefined genomic target site, which comprises:

a) providing a guide RNA (gRNA) comprising a tracrRNA in conjunction with crRNA including an oligonucleotide sequence that hybridizes with the target site;

b) providing an RNA-guided endonuclease which catalyzes the DNA break at the target site upon hybridizing with the gRNA;

c) introducing the gRNA into the cells in the presence of the endonuclease to obtain a repertoire of cells comprising a variety of genomic mutations at the target site;

d) selecting a cell from said repertoire which comprises a MOI; wherein the cell is haploid for the genomic locus of the target site; and e) expanding the cell to obtain the mutant cell line.

The MOI is specifically at least one of
(i) a mutation knocking out the function of a gene;
(ii) a mutation introducing at least one of a deletion, substitution, or insertion of one or more nucleotides; and/or
(iii) a mutation introducing an exchange sequence of a homology template.

Such MOI may specifically include frameshift mutations that disrupt gene function or gene expression (gene knock-outs), defined point mutations (knock-ins), insertions of foreign DNA sequences that are non-naturally present (e.g. tags such as GFP or the TAP tag) or deletions of sequences that are naturally present (e.g. deletions of entire genes, exons or regulatory elements).

The mutation knocking out the function of a gene may e.g. down-modulate DNA expression, delete at least part of the gene and/or disrupt the open reading frame of the gene.

The mutation introducing an exchange sequence of a homology template is optionally obtained by providing a homology template which is a human DNA fragment or a plasmid containing such fragment comprising a recombining sequence of at least 20 bp having a sequence homology of at least 90% to the GOI and capable of homologous recombination with the GOI, and an exchange sequence comprising a human nucleotide sequence that differs from the GOI in at least one point mutation. When introducing the gRNA into the cells in the presence of the endonuclease the homology template can further be introduced into the cells.

By using an exchange sequence, a mutation may be knocked-in at a predetermined position. The mutation which is a knock-in mutation, may e.g. comprise the knock-in of individual point mutations or SNPs.

Specifically, the cell may comprise the exchange sequence in total or in part, e.g. such that the part of the exchange sequence is introduced into the cell which comprises at least one point mutation and optionally further mutations that may be present within the exchange sequence as compared to the GOI.

Specifically, the homology template is co-transfected with at least one of the tracrRNA and crRNA, or the gRNA. The homology template may suitably be co-transfected with the gRNA and a DNA encoding the endonuclease.

Specifically, one, two or more gRNAs, e.g. a gRNA library, may be used.

Specifically, the gRNA may e.g. be introduced into the cells by one or more expression constructs to enable the expression of the gRNA or one or more of its components by the cells.

The guide RNA may be provided as a binary complex of tracrRNA and a crRNA, and optional further linker sequences, each provided as separate components that associate ex vivo or within a cell. Preferably, the guide RNA is provided as a chimeric or recombination product which comprises the components tracrRNA and crRNA linked to each other, e.g. by a linkage where the crRNA is linked to the 5' end of the tracrRNA directly, with or without a linker sequence, e.g. a sequence of SEQ ID 48.

The crRNA typically comprises a constant part, which is the 3' part that provides for the association or linkage with the tracrRNA. The crRNA further comprises a variable part, designed to hybridize with a specific target site, which variable part is typically incorporated in the 5' part or 5' end of the crRNA and gRNA, respectively.

According to a specific aspect, a component consisting of the RNA-guided endonuclease in conjunction with the tracrRNA may be used. Such component is preferably used in combination with the target-specific RNA (crRNA).

The guide RNA and the RNA-guided endonuclease may be conveniently provided as a ternary complex of the endonuclease with the tracrRNA and the crRNA, each provided as separate components that associate ex vivo or within a cell. Preferably, there is provided a binary complex of the endonuclease with the guide RNA, each provided as separate components that associate ex vivo or within a cell. In such complex with the endonuclease, the guide RNA preferably comprises the tracrRNA and the crRNA linked to each other, thus is a chimeric RNA product.

Preferably functional pairs of tracrRNA or gRNA paired with an RNA-guided endonuclease are used, e.g. a functional pair of the constant part of the gRNA and the endonuclease, specifically functional pairs in a complex or as separate components. Specifically, the functional pairs are of a suitable type II CRISPR systems, such as a CRISPR system of bacterial origin.

Functional pairs of the tracrRNA/gRNA and the matching endonuclease are preferably used with one or more different crRNA components, e.g. with a series of crRNA oligonucleotides that target different genomic target sites.

Specifically, the cell is a haploid or near-haploid to produce the mutated cell, preferably an adherent cell. Specifically, the cell is a karyotypically stable human cell line.

The haploid (or near-haploid) mutated cell may be expanded to obtain a haploid cell line, or else be subject to further processing, e.g. including diploidization (duplication of chromosomes to obtain sister chromosomes), to obtain a diploid (or near-diploid) or diploidized mutated cell line.

Specifically, the cell is capable of cellular repair mechanism, e.g. non-homologous end joining or homology-directed repair, which is optionally following a DNA break. Specifically, the genomic mutation within the haploid cell is obtained by cellular repair mechanisms induced by DNA break.

For example, a genomic mutation could be obtained by HDR in the presence of a donor template, or by NHEJ if one wants to obtain frameshift mutants.

Specifically, a MOI may be obtained by any of the following methods:
1. Mutations are introduced by CRISPR/Cas-mediated breakage of DNA. To this end, at least one guide RNA and a Cas9 nickase can be used to introduce a single-strand break. However, more than one guide RNA (two in a specific embodiment: paired nicking) can be used, and Cas9 wild-type or nickase can be used.
2. Following cleavage, the cells will repair the DNA damage either by NHEJ or homology-directed repair (HDR), or other mechanisms. There are further possible repair pathways, e.g. including base-excision repair, mismatch repair or single strand annealing.
3. Mutations include:
   a. Small insertions of deletions (indels). If an exon is targeted, such mutations disrupt the frameshift (frameshift mutations) and the resulting cell line would qualify as a gene knockout. Such mutations are e.g. obtained by
      i. Single guide and Cas9 wt, followed by NHEJ;
      ii. Paired guides and Cas9 nickase, followed by NHEJ;
   b. Single nucleotide substitutions or point mutations. Such mutations are e.g. obtained by
      i. Single guide, Cas9 wt and donor template, followed by HDR;
      ii. Paired guides, Cas9 nickase and donor template, followed by HDR;
   c. Deletions of sequences that are naturally present. Such mutations are e.g. obtained by
      i. Paired guides (deleted sequence lies between the two guide RNAs) and Cas9 wt, followed by spontaneous end joining (NHEJ);
   d. Insertion of sequences that are naturally present (e.g. as genes or exons) or non-naturally present (e.g. GFP, Myc tag). Such mutations are e.g. obtained by
      i. Single guide, Cas9 wt and donor template, followed by HDR;
      ii. Paired guides, Cas9 nickase and donor template, followed by HDR;

For example, specific repair mechanisms integrating a nucleotide sequence include any of the following:
1. NHEJ-Mediated Integration While the integration of a foreign exchange sequence (e.g. GFP) is usually achieved by homology-directed repair, it can also be obtained by non-homologous end joining. To this end, one can use a plasmid containing the exchange sequence, flanked by a guide RNA recognition site that is not present in the human genome. If such a plasmid is co-transfected with Cas9, a guide RNA that targets the human genome and a guide RNA that targets the recognition sites present in the plasmid, the exchange sequence will get liberated in cells expressing Cas9. Following liberation, it can be integrated in the human genome in a targeted fashion. The resulting cell line will carry a single integration of the exchange sequence, proximal to the site that was targeted in the human genome.

2. DNA Repair Mechanisms

DNA double-strand breaks, induced by Cas9, are repaired by NHEJ or HDR. While NHEJ is well understood, the mechanisms governing HDR are less well characterized. Though HDR is synonymously used with homologous recombination, it can be more complex and other repair pathways may additionally contribute. For instance, it has been shown that the mismatch repair pathway suppresses HDR and consequently, MSH2 or PMS2 knockout cells display higher rates of HDR. In addition, the contribution of other repair pathways may depend on the nature and the length of the donor template. For instance, when short oligonucleotides are used as donors, it has been speculated that incorporation is aided by DNA replication factors, similar to Okazaki fragments. With longer donors, factors involved in homologous recombination may contribute more.

Specifically, the method employs
a) an expression plasmid incorporating a nucleic acid sequence to express the gRNA used to transform the cells and to obtain a repertoire of transformant cells comprising the variety of genomic mutations at the target site, e.g. proximal to the target site; and
b) a transformant cell from said repertoire is selected that comprises the MOI.

According to a specific aspect, the cell is a near-haploid or fully haploid cell, preferably an adherent cell line, preferably the HAP1 cell line or the HAP2 cell line deposited under DSM ACC3220 (herein also referred to as eHAP), or a functional variant of any of the foregoing, specifically functional variants with a similar gene expression profile. Specifically, the functional variants are characterized by substantially the same gene expression profile, i.e., the functional variant comprises a genome, wherein the level of expression of the genes is substantially the same, e.g. the gene expression level of less than 1000 genes would differ, preferably less than 750, or less than 500, or less than 300 genes.

The cell line designated HAP2 is a fully haploid human cell line, which is provided as biological material deposited at the DSMZ—Deutsche Sammlung von Mikroorganismen und Zellkulturen, Mascheroder Weg 1b/Inhoffenstraße 7B, 38124 Braunschweig (DE) under the accession number DSM ACC3220 (deposition date: Nov. 21, 2013; depositor: Haplogen GmbH, Vienna, Austria). The HAP2 cell line and functional variants comprise the complete set of human chromosomes in the monosomic state, even for at least 20 passages. Functional variants are preferably characterized by a similar gene expression pattern.

The cell line of the invention turned out to be karyotypically stable, e.g. karyotypically stable mutants or engineered variants of the deposited material or functional variants thereof. Specifically, the haploid or diploid karyotype is karyotypically stable over at least 10 passages, preferably over at least 20 passages.

Different clones of the cell line may show the same or similar gene expression pattern. For example, independent clones may be produced by mutating a parental clone, which independent clones are karyotypically stable and have substantially the same gene expression profile.

According to a specific aspect, cells of the cell line comprise the complete set of human chromosomes in the monosomic state. Upon duplication of the chromosomes, the cell may comprise the complete set of duplicated chromosomes. In particular, the cell may comprise the complete set of human chromosomes in the disomic state.

Further specific cells which may be used according to the invention as a parental cell may be obtained or derived from a cancer patient, preferably a patient suffering from leukemia, such as Chronic Myelogenous Leukemia or Acute Lymphoblastic Leukemia, or a solid tumor, such as peripheral chondrosarcoma.

According to a further specific aspect, the gRNAs comprises a sequence selected from the group consisting of SEQ ID 3, SEQ ID 13, SEQ ID 19, and any of SEQ ID 24-47, or a functional variant of any of the foregoing which is a co-substrate of the endonuclease.

According to a further specific aspect, the endonuclease is selected from the group consisting of CAS9 enzymes originating from any of *Streptococcus pyogenes, Streptococcus thermophiles, Neisseria Meningitis* or *Treponema Denticola*, and functional variants of any of the foregoing, including Cas9 nickases or artificial enzymes, specifically including recombinant enzymes, e.g. mutant or chimeric enzymes. Specific Cas9 nickases are derived from the Cas9 of *S. pyogenes* and comprise an amino acid mutation at position D10A or H840A resulting in the inactivation of the catalytic activity of one nuclease domain and converting Cas9 to a "nickase" enzyme that makes single-stranded breaks at the target site.

According to a specific embodiment, the method employs at least one of

A the gRNA comprising the nucleotide sequence of any of SEQ ID 3, 25, or 26, or a functional variant of any of the foregoing; and the endonuclease comprising the amino acid sequence of any of SEQ ID 1, 5, 7, 8, or 9, or a functional variant of any of the foregoing; or

B the gRNA comprising the nucleotide sequence of any of SEQ ID 13, 27-40, or a functional variant of any of the foregoing; and the endonuclease comprising the amino acid sequence of SEQ ID 10 or 15, or a functional variant of any of the foregoing; or

C the gRNA comprising the nucleotide sequence of any of SEQ ID 19, 41-47, or a functional variant of any of the foregoing; and the endonuclease comprising the amino acid sequence of SEQ ID 16 or 21, or a functional variant of any of the foregoing.

Specifically, the cell is engineered to express the CAS9 endonuclease and/or the gRNA, or one or more components of the gRNA, or with the gRNA.

According to a further specific aspect, the DNA break is a double strand break or a paired single strand break, proximal to a protospacer associated motif (PAM), preferably 3 bp upstream of the PAM. Exemplary PAM sequences are selected from the group consisting of SEQ ID 2, SEQ ID 11, SEQ ID 12, SEQ ID 17, SEQ ID 18, SEQ ID 23, SEQ ID 60 and SEQ ID 61, or a complementary sequence of any of the foregoing. The paired single strand break is herein sometimes referred to as a specific embodiment of a "double strand" break. The paired nicking (single strand break) is specifically proximal to two PAMs, one PAM for each single strand break.

The complementary DNA sequences are typically recognized for the DNA break of the complementary strand. It is preferred that a suitable PAM sequence is selected which is recognized by the specific endonuclease and the specific CRISPR system.

According to a further specific aspect, the genomic mutation is obtained by cellular repair mechanisms induced by the DNA break, preferably introducing at least one frameshift mutation, insertion, substitution and/or deletion of one or more nucleotides.

According to a further specific aspect, the mutation refers to larger areas of mutations. For example, an exon of the gene or the entire gene is deleted.

The method of the invention specifically employs at least two DNA double-strand breaks (DSB), wherein at least one DSB is performed within a target site proximal to the 5' and at least one DSB is performed within a target site proximal to the 3' end of the chromosomal region. Such DSB may result from two single strand breaks within a target region, which are located at different positions on the target site on each DNA strand, e.g. proximal to each other and in sum would provide for the DSB, or a DSB at the same position of the target site on each DNA strand.

Specifically, in order to delete a genomic region that is naturally present, a double strand DNA break may be induced according to the invention, employing two crRNA molecules hybridizing on both sides lateral to the genomic (chromosomal) region to be excised, e.g. proximal or adjacent to the 5' and 3' end of the genomic region. Upon such DNA break the cellular repair would provide for the joining of the free ends, thereby excising the genomic region.

Such mutation(s) are typically localized within 20 bp upstream and downstream of the DNA double-strand break, specifically within 15 bp or 10 bp upstream and downstream of the DNA break. The mutation(s) specifically provided are located at one or more positions, e.g. at least 1 or 2 point mutations, including single insertions, deletions or substitutions of one or more basepairs, specifically at least 3, 4, 5, up to 10 point mutations.

According to a specific aspect the incorporation of the exchange sequence, (herein also referred to as mutation(s)) are localized within 500 bp upstream and downstream of the DNA break, specifically within 250 bp or 100 bp upstream and downstream of the DNA break and more specifically within 50 bp or 10 bp upstream and downstream of the DNA break.

According to a further specific aspect, at least two different target sites are targeted by different crRNAs or gRNAs, employing the same or different functional pairs of tracrRNA and endonuclease or functional pairs of the constant part of gRNA and endonuclease.

According to the invention, there is further provided a mutant human somatic cell line obtainable by the method of the invention. Such cell line differs from a cell line of the prior art, because of the stable karyotype and characteristic mutations, in particular containing targeted frameshift or knockout mutations, point mutations or knock-in mutations proximal to an PAM sequence, and optionally comprising inactivated PAM sequences, which are characteristic for the CRISPR system Specifically, the MOI is at least a mutation introducing an exchange sequence of a homology template, and homology template is a) an oligonucleotide of 20-200 bp length, specifically 20-100 bp; or b) a PCR product of 20-5000 bp length, specifically 20-1000 bp; or c) any of a) or b) comprised in a donor plasmid.

The exchange sequence may comprise only one point mutation, such as the substitution of one or more nucleotides thereby encoding a different amino acid, or a series of point mutations, e.g. to obtain a pattern of mutations, sometimes referred to as SNPs (Single Nucleotide Polymorphism) wherein a single nucleotide—A, T, C or G—in the genome differs between human beings or paired chromosomes, or the insert of larger constructs, e.g. such that endogenous genes are modified to contain a specific sequence tag (myc tag, His tag, HA tag, V5 tag, TAP tag, LAP tag, GFP, RFP, dsRed, mCherry). The exchange sequence may encompass non-coding or coding regions. Typically, the exchange sequence identifies a specific gene expression pattern or product, or a specific phenotype, including genetic predisposition or disorders, or disease conditions.

Specifically, the exchange sequence is embedded into the recombining sequence, or overlapping with the recombining sequence, or flanked by one or more recombining sequences, preferably comprising the exchange sequence and flanking sequences at the 5'-end and 3'-end capable of homologous recombination with the GOI. Specific examples refer to homology templates, wherein the recombining sequence incorporates the mutation, thus, the exchange sequence is incorporated into the recombining sequence. According to an alternative example, an exchange sequence is used which is larger than the recombining sequence. Thereby a larger segment within the GOI may be exchanged, e.g. to introduce more than one point mutations. Typically, the exchange sequence has a length of 1-1000 bp, typically at least 10 bp, or at least 20 bp, and may be even larger than 1000 bp, up to 5000 bp.

Specifically, the exchange sequence has a sequence homology of at least 90%, or at least 95%, at least 98%, or at least 99% to the GOI, preferably wherein the exchange sequence comprises one or more point mutations, specifically a sequence homology of less than 99.9% or less than 99.5% as compared to the GOI, or a modified DNA region causing a different DNA expression and/or a different phenotype.

Specifically, the homology template comprises a PAM, optionally wherein the PAM is mutated to prevent cleavage and repair of the DNA by non-homologous end joining.

Specifically, the method further comprises the step of cultivating the mutant cell line asexually replicating the chromosomes within the cells, thereby obtaining a population of individual cells, and upon determination of the karyotype of individual cells, selecting a diploid cell, and further expanding the diploid cell to obtain a mutant cell line comprising a diploid karyotype.

The invention further provides for the mutant human somatic cell line obtainable by the method as described herein.

Specifically, there is provided a mutant human somatic near-haploid or fully haploid cell line which comprises a mutational pattern characteristic for RNA-guided endonucleases that lies proximal to a PAM, wherein the mutational pattern comprises a MOI.

Specifically, the cell line is a mutant of a near-haploid or fully haploid cell, preferably an adherent cell line, preferably a mutant of the HAP2 cell line deposited under DSM ACC3220, or a functional variant thereof.

Specifically, the cell line is engineered to express the Cas9 enzyme and/or the gRNA, or at least one component of gRNA.

Specifically, the cell line is engineered to express the CAS9 endonuclease, preferably a CAS9 endonuclease selected from the group consisting of CAS9 enzymes originating from any of Streptococcus pyogenes, Streptococcus thermophiles, Neisseria Meningitis or Treponema Denticola, and functional variants of any of the foregoing, including Cas9 nickases or artificial enzymes.

According to a further aspect, the invention provides for a near-haploid or fully haploid cell, which is engineered to express a Cas9 enzyme and/or a gRNA and/or at least one component of gRNA, preferably wherein an adherent cell line is engineered, preferably the HAP2 cell line deposited under DSM ACC3220, or a functional variant thereof.

Specifically, the cell line is engineered to express both, the Cas9 enzyme and the gRNA (or at least one component of the gRNA), wherein a variety of gRNAs (or the gRNA components) are introduced into the cell, e.g. a library of gRNAs (or a library of the gRNA components), resulting in a repertoire of mutant cells with a variety of MOI at different GOI. Thereby, a library of cell lines can be produced, comprising a repertoire of library members which are cell lines which differ from each other in one or more MOI at the same or different GOI.

According to a specific embodiment, there is provided a repertoire of isogenic cell lines comprising
a) a near-haploid or fully haploid cell, preferably an adherent cell line, preferably the HAP2 cell line deposited under DSM ACC3220, or a functional variant thereof; and
b) a mutant thereof, which is the cell line as described herein, in particular a pair of isogenic cells, or a repertoire containing the native (non-mutated cell line) and one or more mutants thereof, e.g. a library of mutant cell lines.

Specifically, the library is of somatic fully haploid, karyotypically stable human cells comprising a repertoire of isogenic cell variants comprising genomic mutations at different genomic target sites.

The invention further provides for a mutant human somatic diploid cell line which comprises a mutational pattern characteristic for a RNA-guided endonuclease that lies proximal to a PAM, wherein the mutational pattern comprises a homozygous MOI.

Such diploid cell line is specifically understood to comprise duplicated chromosomes, e.g. of near-haploid or fully haploid cells, so to obtain a near-diploid or fully-diploid cell. The duplicated chromosomes are specifically a set of duplicated sister chromosomes, or at least part thereof, wherein the duplicated region comprises homozygous SNPs, and is specifically characterized by the absence of heterozygous SNPs.

Specifically, in the cell line of the invention, the alleles of the sister chromosomes are identical and do not contain heterozygous single nucleotide polymorphisms (SNP). Identical sister chromosomes are specifically characterized by the homozygous SNPs or SNP pattern (or the absence of heterozygous SNPs).

Specifically, a diploid cell comprising two sets of duplicated sister chromosomes is produced from an adherent cell line of a somatic haploid (or near-haploid cell), e.g. by cultivating said cell line in a monolayer cell culture asexually replicating the chromosomes within the cells, thereby obtaining a population of individual cells, specifically adherent cells, and upon determination of the karyotype of individual cells, selecting a diploid cell, and expanding the diploid cell to obtain an adherent cell line comprising a diploid karyotype.

According to a specific aspect, said haploid cell line is cultivated under cellular stress conditions, thereby accelerating conversion to the diploid state.

Specifically, the cellular stress conditions employ at least one of:
a) a temperature stress, preferably by heat or cold shock;
b) a physical stress, preferably by shearing force;
c) continued passaging, preferably by at least 20 or 25 passages;
d) a high cell density, preferably confluence for at least 24 hours;
e) a culture medium composition comprising a suboptimal but tolerable amount of nutrients, metabolites and/or toxins;
f) temporal lowering of oxygen levels to a suboptimal level; and
g) the presence of reactive oxygen species in the culture medium, preferably for at least 2 hours.

Such stress conditions are e.g.:
Heat shock: Exposure of the cells to higher temperatures, specifically any of the temperatures (+/−1° C.): 40° C., 42° C., 44° C., 46° C., 48° C., or 50° C., for a defined period of time (e.g. at least 1 h, 2 h, 4 h, 6 h, 8 h, up to 16 h);

Cold shock: Exposure of the cells to lower temperatures, specifically any of the temperatures (+/−2° C., however, above the freezing temperature): 0° C., 4° C., 8° C., 12° C., 16° C., 20° C., 24° C., 28° C., or 32° C., for a defined period of time (e.g. at least 1 h, 2 h, 4 h, 6 h, 8 h, up to 16 h);

Cell straining and shearing: Exposure of the cells to shearing force, e.g. by treating the adherent cells to obtain the cells in suspension, such as by treatment with trypsin or other enzymes, and aspirating the cells through a needle (e.g. at least 4, 8, 12, 16, or 20 passages through a 20-, 25- or 30-gauge needle), or mixing the suspension by physical means, or employing shearing stress to the cells when adherent to a solid carrier, by physical treatment;

High density of cells: Cells are not trypsinized in time, but are exposed to higher cell density in the cell culture dish, such as to obtain a higher density than monolayer density (e.g. at least for another 6 h, 12 h, 18 h, 24 h, 30 h, 36 h, 42 h, or 48 h at confluence);

Toxins: Treatment of cells with toxic compounds during cell culture (e.g. ricin toxin, shiga toxin or tunicamycin) in a tolerable amount, such as to obtain a level of surviving viable cells of at least 30%, preferably at least 50% or at least 70%;

Hypoxia: Temporal lowering of oxygen levels, specifically any of the amounts (+/−1% v/v): 1%, 2%, 4%, or 8% $O_2$ for a defined period of time, e.g. at least 24 h, 48 h, up to 72 h;

Presence of reactive oxygen species: Treatment of cells with hydrogen peroxide for 6 h, 12 h, 18 h, 24 h Continued passage of adherent cells, under suboptimal or optimal cell culture conditions, e.g. by at least 20, 25, 30 or 35 passages.

Specifically, the mutant cell is homozygous comprising two mutant alleles for the same knock-out, knock-in or substitution of a nucleotide sequence.

Specifically, the cell line is of a nullizygous cell comprising two mutant alleles for the same gene knocking out the function of the gene, specifically by down-modulating DNA expression and/or disrupting the open reading frame of the gene.

Specifically, the cell line is an adherent somatic human cell line of a diploid or near-diploid cell comprising two sets of duplicated sister chromosomes.

Specifically, the cell line is a mutant of the diploid cell line C665 as deposited under DSM ACC3250, or a functional variant thereof.

The cell line designated C665 (also referred to as diploid eHAP) is a diploid human cell line that is considered near-diploid (because it contains duplicated chromosomes of the near-haploid cell line HAP1), and which is provided as biological material deposited under DSM ACC3250 at the DSMZ—Deutsche Sammlung von Mikroorganismen und Zellkulturen, Mascheroder Weg 1b/Inhoffenstraße 7B, 38124 Braunschweig (DE), date of deposit: Oct. 29, 2014; depositor: Haplogen Genomics GmbH, Vienna, Austria).

According to a specific aspect, the invention provides for a repertoire of isogenic cell lines comprising a) the diploid cell line C665 as deposited under DSM ACC3250, or a functional variant thereof; and b) a mutant thereof, which is the cell line of the invention, in particular a pair of isogenic cells, or a repertoire containing the native (non-mutated cell line) and one or more mutants thereof, e.g. a library of mutant cell lines.

The mutant of diploid cells as described herein is specifically produced by mutating the haploid cell followed by diploidization. For example, a mutant of C665 can be produced by mutating the HAP1 cell following diploidization.

Typically, the mutated nucleotide sequence identifies a specific gene expression pattern or product, or a specific phenotype, including genetic predisposition or disorders, or disease conditions.

Any of the haploid (including near-haploid) or diploid (including near-diploid) cell lines as described herein can be subject to genomic DNA extraction, e.g. through methods of DNA extraction well-known in the art, e.g. including cell suspensions using several technology formats, organic extraction, silica spin columns, and magnetic beads.

Therefore, the invention further provides for a DNA preparation comprising the genomic DNA extracted from the cell line as described herein. The genomic DNA extracted from a haploid (e.g. a fully haploid or near-haploid) cell has the unique property of carrying only one copy of each gene, and when it comes to preparing mixtures of genomic DNA, this can have a significant impact on the ability to create more uniform mixtures. Such preparation of genomic DNA can be used as a uniform standard preparation of genomic DNA, e.g. for use as a reference standard for any mutant or native (non-mutant) cell. By using haploid cells or even haploid cells driven to diploid status (diploidized cells, where the genome of haploid cells is duplicated to obtain the diploid status), these difference between alleles are significantly reduced, making for a more uniform standard preparation.

The invention further provides for a polyclonal population of adherent somatic cells, which is composed of cell lines of at least 2 different or independent clones, wherein each of the cell lines is a haploid or diploid cell line as described herein, preferably wherein each of the cell lines is of a mutant cell comprising the same genomic mutation with respect to a predefined GOI, e.g. a homozygous mutation in the case of a diploid cell.

Specifically, the population is a heterogeneous mixture, such as a mixture of isolated clones with the desired karyotype, comprising at least 2, 3, 4, 5, 10, or 20 different clones, e.g. on only one solid carrier or on different carriers or compartments, e.g. wherein each clone is located at spatially distinct positions. Such mix of clones is specifically suitable to provide a stable population in which genetic drift of isolated single clones is compensated by the polyclonal nature of the mix.

Specifically, the population comprises functional variants which are independent clones. The genomic or karyotypic stability of the individual clones of such population can be determined, to select those, which are karyotypically stable as defined herein, and may be further produced as a cell line that can be provided as a commercial product, or further engineered to obtain mutants.

Specifically, a method is provided, wherein a library of mutant human somatic cell lines of isogenic cells with a variety of genomic mutations at different predefined genomic target sites is produced.

Specifically, the method of the invention further provides for producing a library of mutant human somatic cell lines of isogenic cells with a variety of genomic mutations at different predefined genomic target sites. Such library differs from libraries of the prior art, such as libraries obtained by gene trap mutations, because of the stable karyotype and characteristic mutations, in particular containing targeted frameshift or knockout mutations, point mutations or knock-in mutations proximal to an PAM sequence, and optionally comprising inactivated PAM sequences, which are characteristic for the CRISPR system Specifically, the CRISPR/Cas9 characteristic mutation pattern is distinguished from other patterns obtained by prior art mutagenesis. In particular, gene trap mutagenesis refers to the insertion of a splice acceptor-GFP cassette into the host genome. The resulting cell lines significantly differ in sequence, because gene trap mutants still contain the gene trap. In contrast, CRISPR mutants show a characteristic mutational pattern and function. While gene trap mutants show variable degrees of reduction of gene expression, frameshift mutations, introduced by CRISPR/Cas technology, completely abolish gene expression and gene function CRISPR mutations also differ from TALENs, because the CRISPR mutations lie proximal to the PAM. Typically, the CRISPR/Cas mutation induces more deletions, while TALENs induce more insertions.

Therefore, the invention further provides for a library of mutant human somatic cell lines of isogenic cells with a variety of genomic mutations at different predefined genomic target sites, wherein the cells are haploid for the genomic locus of the target sites, obtainable by the method of the invention. Optionally, the cells are subject to diploidization, and the library of cell lines is characterized by the cells comprising duplicated sister chromosomes.

Specifically, the library comprises a repertoire of mutants of a near-haploid or fully haploid cell, preferably mutants of an adherent cell line, preferably the HAP2 cell line deposited under DSM ACC3220, or a functional variant thereof.

Specifically, the library comprises a repertoire of mutants of the diploid cell line C665 as deposited under DSM ACC3250, or a functional variant thereof.

Specifically, the library comprises a repertoire of at least 50 cell lines with mutations at different genomic target sites, preferably at least 100, preferably at least 300, at least 1.000 or at least 10.000.

According to a specific embodiment, each cell line of a cell line repertoire or library is provided in separate containers.

According to a further specific embodiment, the library is comprised in an array including microarrays, wherein each cell line is located at spatially distinct positions, e.g. spots. Therefore, the invention provides for such array comprising the library of the invention.

The library as further described herein may be subject to any screening method. Therefore, the invention further provides for a method of identifying a human somatic cell line comprising a MOI at a predefined GOI by determining the functional characteristics or the phenotype of one or more cell lines of any library as described herein, and selecting a cell line according to its function as an indicator of the MOI or the genotype. For example, such screening involves phenotypic screening as typically used in biological research and drug discovery to identify substances such as small molecules, peptides, or RNAi that alter the phenotype of a cell in a desired manner. Once a substance has been discovered, unbiased genetic screening such as described above can uncover the human genes that are required to produce a phenotype of interest. This is of particular interest for the unbiased identification of drug targetsPanels of isogenic cell lines may allow molecularly-defined cellular models to be systematically profiled, for use as a research tool to compare the effect of a substance on such panel of native and mutant cell lines.

The invention further provides for a library of human expression plasmids, each being capable of transfecting human cells, comprising a variety of nucleic acid sequences to express different crRNAs, gRNAs or components of a gRNA including the variable part of the crRNA, to hybridize with different target sites, wherein the target sites are located proximal to different genes of a human cell.

The invention further provides for a library of oligonucleotides comprising a variety of nucleotide sequences, preferably at a length of 16 to 26 bases, preferably 18, 20, 22, 24, or 26 bases, each hybridizing with a different human genomic target site, including the wild-type sequence or mutants of the target site. A specific embodiment refers to a library of oligonucleotides which are probes to hybridize with or target complementary sequences at the genomic target sites. Such probes may be employed to provide or engineer specific crRNA, for use with any suitable functional pair of tracrRNA or gRNA and the RNA-guided endonuclease. Alternatively, such probes may be employed for determining the specific mutations obtained by the method of the invention.

The invention further provides for isolated DNA templates that correspond to the tracrRNA, crRNA or gRNA, or the constant or variable part of any of the foregoing, or functional variants of any of the foregoing, including truncated variants, and which may be used to express the individual components, the complex or the chimeric product.

FIGURES

FIG. 1: Sequence information of functional pairs of tracrRNA or gRNA and RNA-guided CAS9 endonuclease of *S. pyogenes:*

A)
amino acid sequence of CAS9 (SEQ ID 1)
PAM motif (SEQ ID 2)
gRNA (SEQ ID 3)
constant part of the gRNA, including the constant part of crRNA, a linker and the tracrRNA (SEQ ID 4)

B)
amino acid sequence of CAS9 with an additional NLS sequence located in the N-terminal extension of the amino acid sequence of SEQ ID 1 (SEQ ID 5)
NLS sequence (SEQ ID 6)

C)
amino acid sequence of CAS9 with an additional NLS sequence located in the C-terminal extension of the amino acid sequence of SEQ ID 1 (SEQ ID 7)

D)
amino acid sequence of CAS9 with an additional NLS sequence located in the N-terminal extension, and an additional NLS sequence located in the C-terminal extension of the amino acid sequence of SEQ ID 1 (SEQ ID 8)

E)
amino acid sequence of CAS9 with an additional NLS sequence located in the N-terminal extension, and an additional NLS sequence located in the C-terminal extension of the amino acid sequence of SEQ ID 1 (SEQ ID 9)

FIG. 2: Sequence information of functional pairs of of tracrRNA or gRNA and RNA-guided CAS9 endonuclease of *S. thermophilus:*

A)
amino acid sequence of CAS9 (SEQ ID 10)
PAM motif (SEQ ID 11)

Exemplary PAM motif (SEQ ID 12)
gRNA (SEQ ID 13)
constant part of the gRNA, including the constant part of crRNA, a linker and the tracrRNA (SEQ ID 14)
B)
amino acid sequence of CAS9 with three additional NLS sequences (SEQ ID 6) located in the C-terminal extension of the amino acid sequence of SEQ ID 10 (SEQ ID 15)

FIG. 3: Sequence information of functional pairs of of tracrRNA or gRNA and RNA-guided CAS9 endonuclease of *N. meningitis:*
A)
amino acid sequence of CAS9 (SEQ ID 16)
PAM motif (SEQ ID 17), or (SEQ ID 75), or (SEQ ID 76)
Exemplary PAM motifs (SEQ ID 18)
gRNA (SEQ ID 19)
constant part of the gRNA, including the constant part of crRNA, a linker and the tracrRNA (SEQ ID 20)
B)
amino acid sequence of CAS9 with three additional NLS sequences (SEQ ID 6) located in the C-terminal extension of the amino acid sequence of SEQ ID 16 (SEQ ID 21)

FIG. 4: Sequence information of functional pairs of of tracrRNA or gRNA and RNA-guided CAS9 endonuclease of *T. denticola:*
A)
amino acid sequence of CAS9 (SEQ ID 22)
PAM motif (SEQ ID 23)
B)
amino acid sequence of CAS9 with three additional NLS sequences (SEQ ID 6) located in the C-terminal extension of the amino acid sequence of SEQ ID 22 (SEQ ID 24)

FIG. 5: Functional gRNA sequences, including functional variants of parent sequences (SEQ ID 25-47), linker GAAA (SEQ ID 48).

FIG. 6: Guide RNA structure for *Streptococcus pyogenes* Cas9, as used in Examples 1 and 2.

FIG. 7: Sanger Sequencing results for several clones, obtained in Example 1 (guide RNA target sequences are underlined).

FIG. 8: Results of Western blotting experiment from six clones obtained in Example 1.

FIG. 9: EGFR local sequence (SEQ ID 55). Amino acid encoding Leu858 is highlighted in underscore; guide RNAs highlighted in bold, protospacer-adjacent motifs (PAMs) highlighted in italic.

FIG. 10: HR template used for introduction of L858R in the EGFR gene (SEQ ID 56). Mutation Leu858Arg is highlighted in underscore; guide RNAs highlighted in bold, protospacer-adjacent motifs (PAMs) highlighted in italic, SpeI site highlighted in bold and underscore.

FIG. 11: Single-stranded oligonucleotide used as HR template (SEQ ID 57). Mutation Leu858Arg is highlighted in underscore; guide RNA (partial sequence) is highlighted in bold, Hind III site highlighted in bold and underscore.

Figure 12:
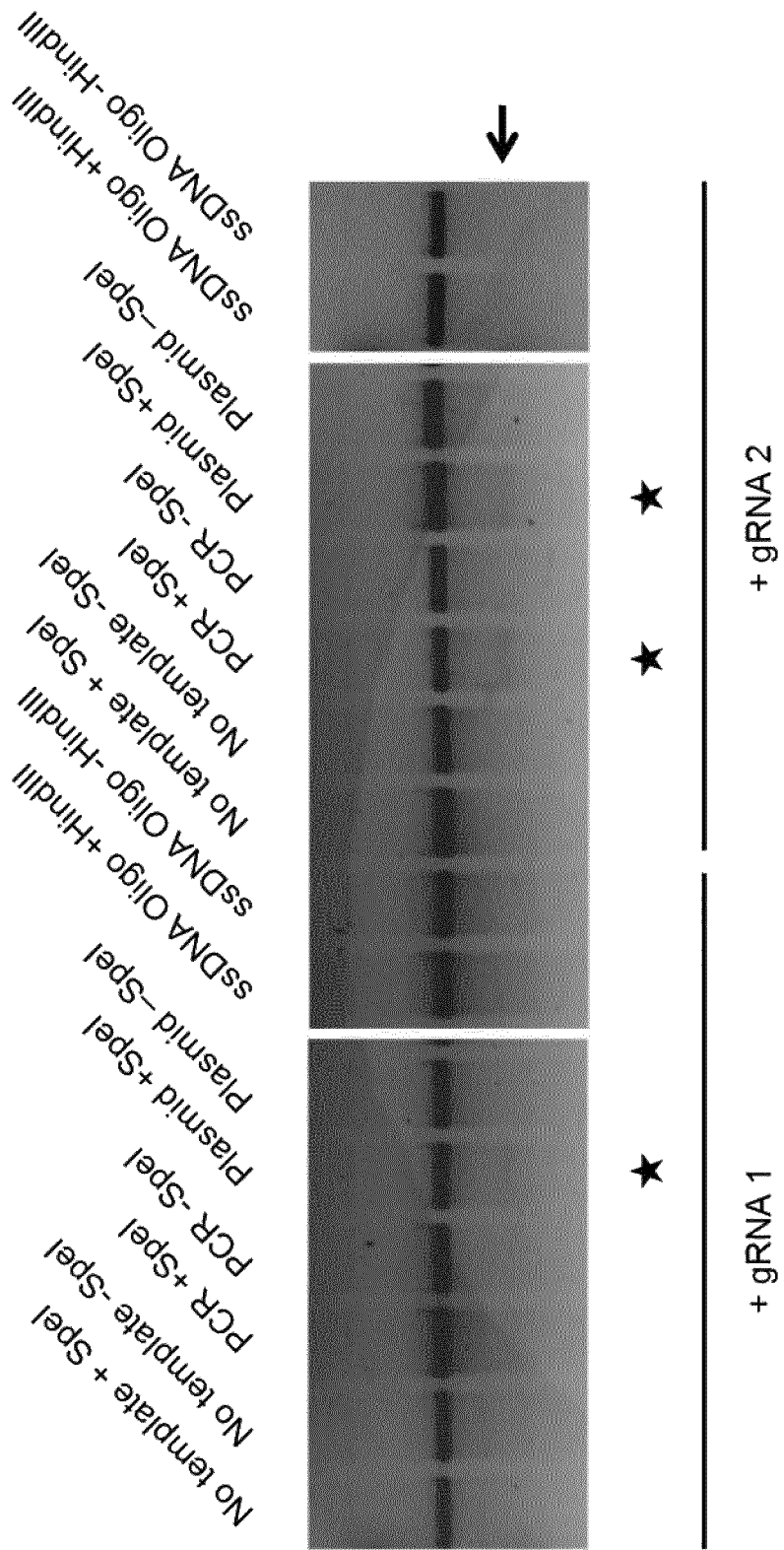

FIG. 12: Restriction digest analysis of PCR products obtained from pools of mutant cells. Following transfection of HAP1 cells with Cas9, guide RNA and homology template as indicated, genomic DNA was isolated and the EGFR locus amplified under investigation by PCR (EGFR fwd TCAGAGAGTCCAAGAAAGCACA (SEQ ID 96), EGFR bwd GAGCCAGTGAAGGGAGAGAA (SEQ ID 97)). PCR products were either digested with SpeI or HindIII (as indicated by "+SpeI" or "+HindIII") or left undigested (as indicated by "−SpeI" or "-Hind III") and analyzed by agarose gel electrophoresis.

Figure 13:
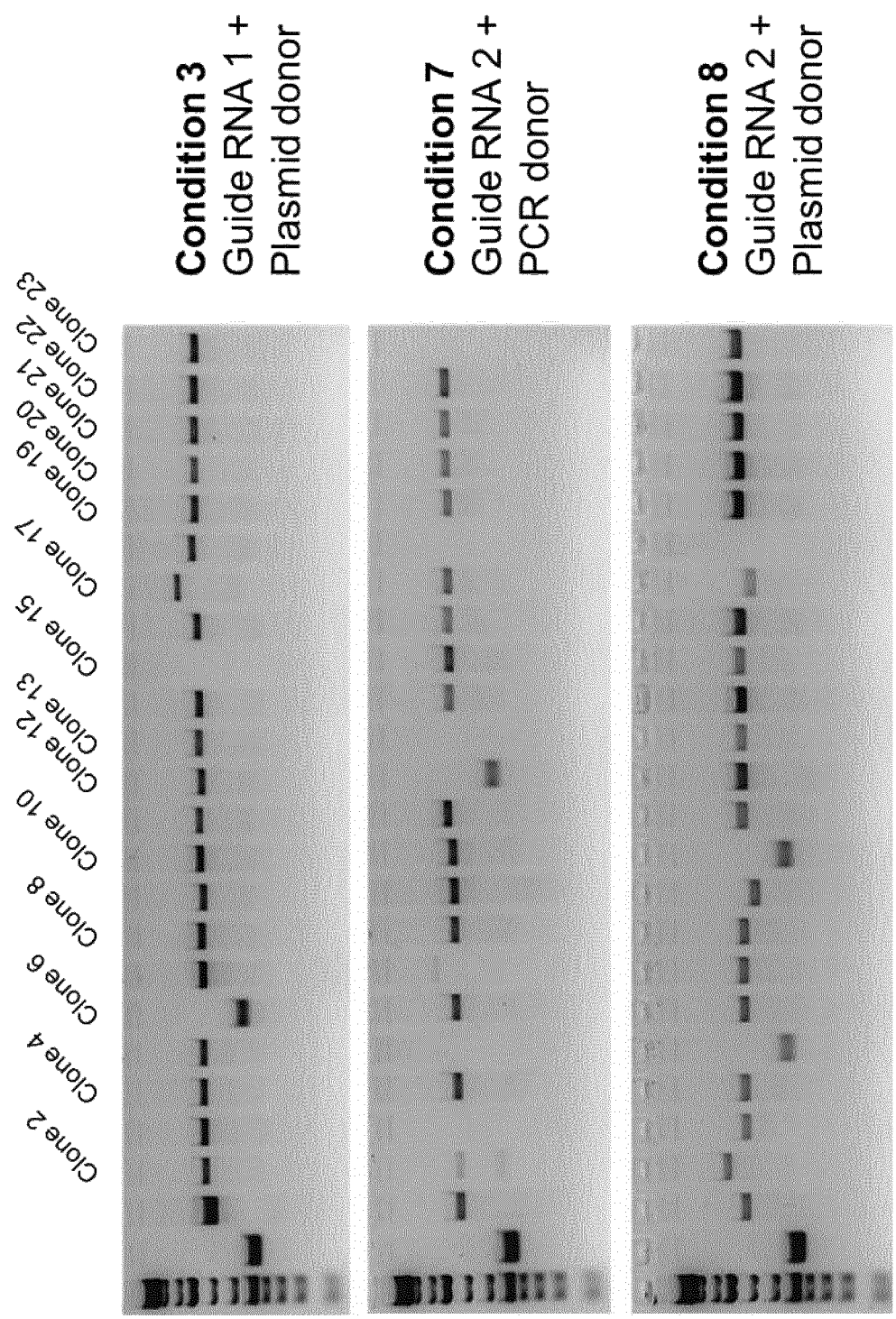

FIG. 13: Restriction digest performed on individual clones. Genomic DNA was isolated from single cell clones. The EGFR locus under investigation was amplified by PCR (EGFR fwd TCAGAGAGTCCAAGAAAGCACA (SEQ ID 96), EGFR bwd GAGCCAGTGAAGGGAGAGAA (SEQ ID 97)). PCR products were digested with SpeI and analyzed by agarose gel electrophoresis.

FIG. 14: Sequencing data obtained from EGFR mutant clones (SEQ ID 58, 59, 62, 63). Restriction digest performed on individual clones. Genomic DNA was isolated from single cell clones. The EGFR locus under investigation was amplified by PCR (EGFR fwd TCAGAGAGTCCAAG GCACA (SEQ ID 96), EGFR bwd GAGCCAGT-GAAGGGAGAGAA (SEQ ID 97)). PCR products were sequenced by Sanger sequencing. The Leu858Arg mutation is highlighted in underscore. The SpeI restriction site is highlighted in bold and underscore. Additional mutations that differ from the reference genome are highlighted in bold and italic.

FIG. 15: Homology donor templates. Mutated nucleotides are shown in bold. The guide RNA sequence and PAM motif are depicted in italics and underlined. The restriction site is underlined and the nucleotide triplet of amino acid that will be mutated is double underlined.

FIG. 16: Sequences from correctly edited clones. The mutated triplet is highlighted in bold. The guide RNA sequence is underlined.

FIG. 17: Sanger Sequencing results for several clones, obtained in Example 2 (guide RNA target sequences are underlined).

FIG. 18: Analysis of haploid or diploid clones by propidium iodide staining and Sanger sequencing. Propidium iodide staining of clones 904-10 (A) and 904-08 (B). Sanger sequencing chromatograms from clone 904-10 (C) and 904-08 (D).

Figure 19:
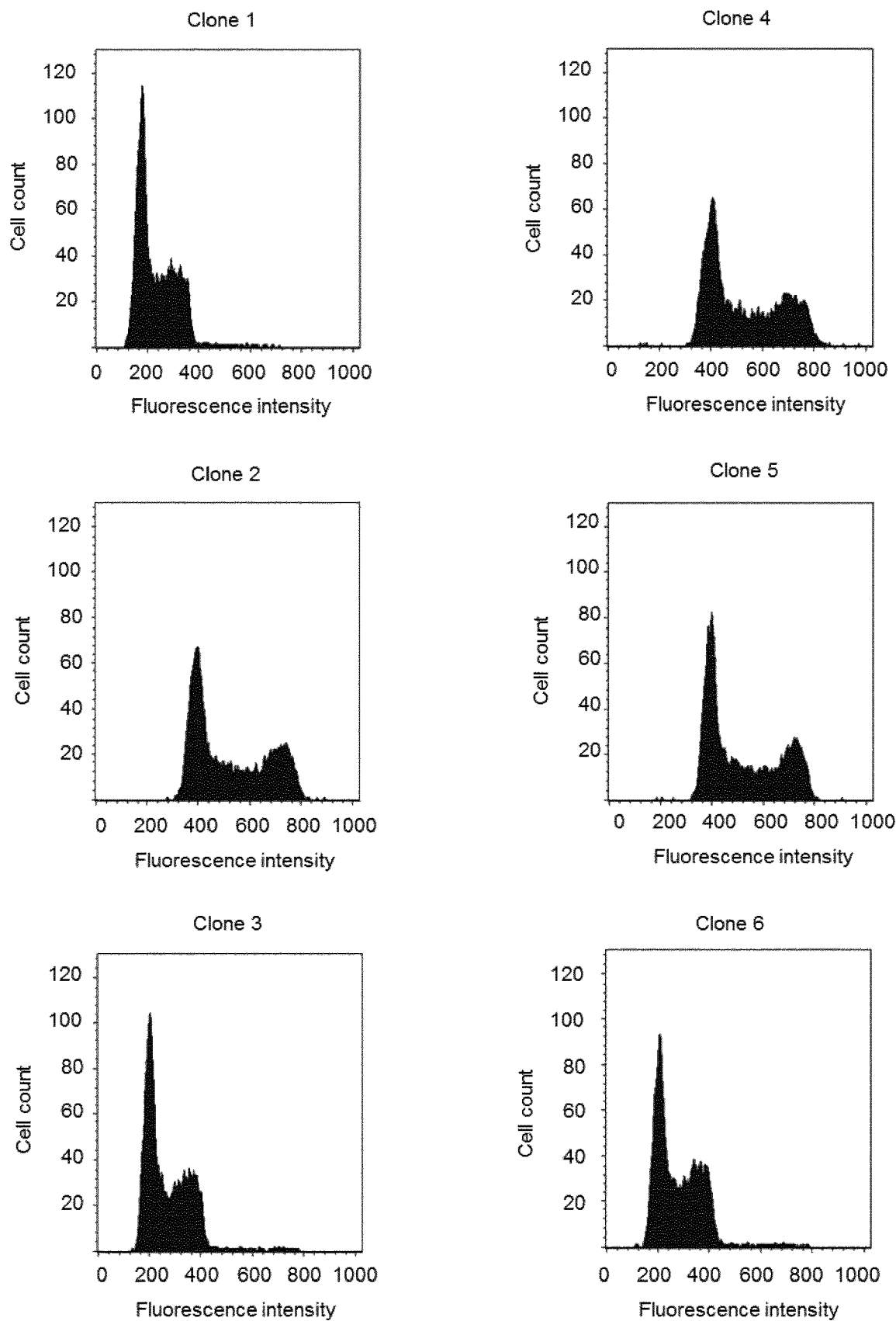

FIG. 19: Single-cell clones isolated from a population of HAP1 can be haploid or diploid. Six clones (designated clones 1-6) were isolated by limiting dilution and analyzed by propidium iodide staining and FACS. Clones 1, 3 and 6 are haploid, whereas clones 2, 4 and 5 are diploid.

Figure 20:
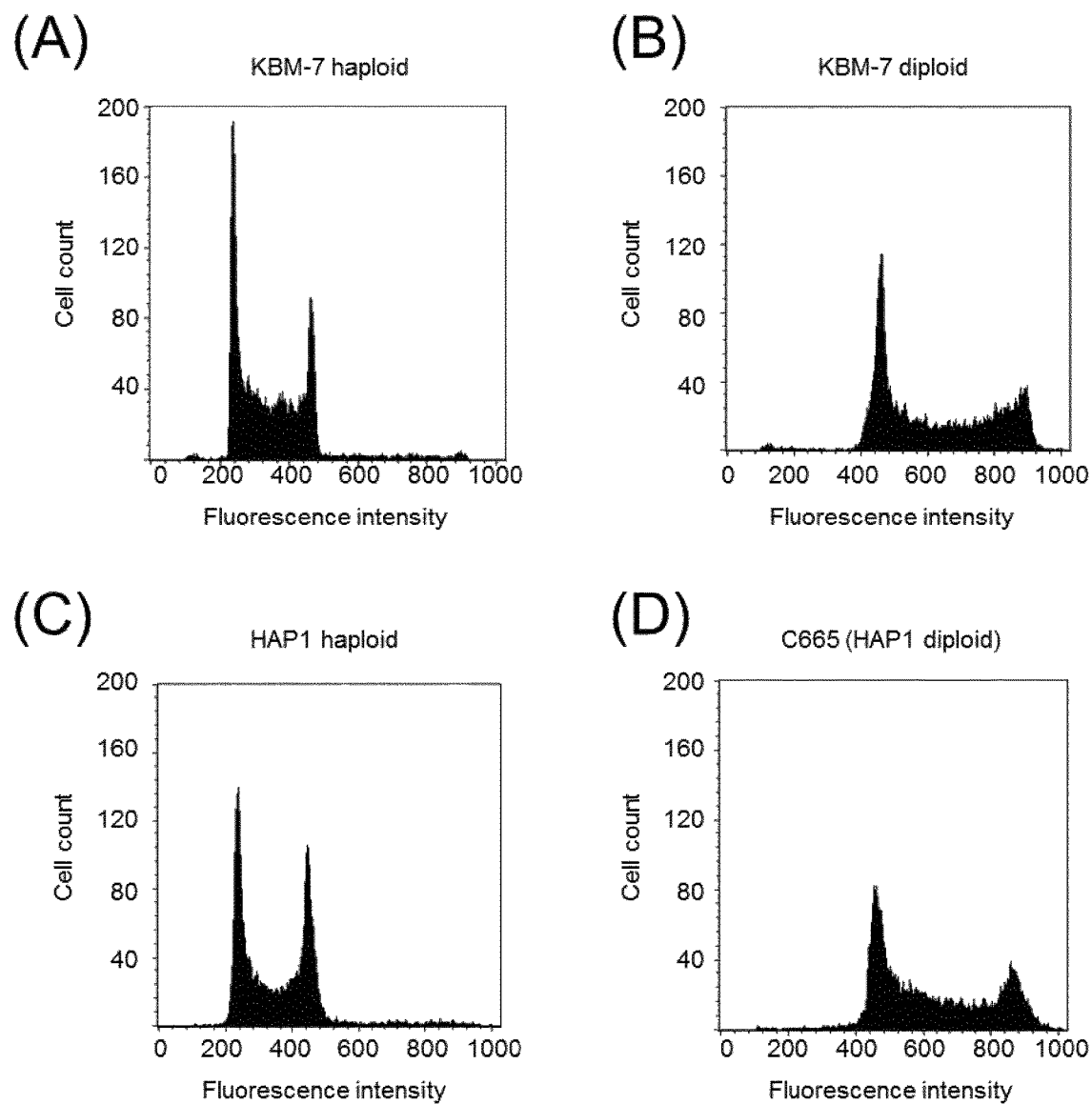

FIG. 20: Haploid and diploid cell lines can be derived from KBM-7 and HAP1 cells. Multiple haploid clones or diploid clones, derived from KBM-7 and HAP1, were pooled to give rise to stable haploid or diploid cell lines. The resulting cell lines were analyzed by propidium iodide staining and FACS. Panels A and B display KBM-7-derived cell lines, panels C and D display HAP1-derived cell lines.

FIG. 21: Spectral karyotyping analysis of cell line C665. Cell line C665 (diploid HAP1 cells) were analyzed by spectral karyotyping. Panels A, B and C represent independent C665 sub-clones that show distinct karyotypes.

DETAILED DESCRIPTION OF THE INVENTION

Specific terms as used throughout the specification have the following meaning.

The term "cell line" as used herein shall mean an established clone of a particular cell type that has acquired the ability to proliferate over a prolonged period of time, specifically including immortal cell lines, cell strains and primary cultures of cells. The term is specifically used for haploid or diploid cell lines, in particular for cell lines of somatic cells. The term specifically encompasses wild-type, e.g. cells which are naturally occurring and can be found in nature or can be isolated from a source in nature and which has not been intentionally modified by man in the laboratory, or mutant cell lines, which comprise a genomic mutation, e.g. at a coding or non-coding site in the genome, as compared to a wild-type cell line. Also, when introducing a mutation of interest at a GOI, the non-mutated nucleotide sequence is herein referred to as wild-type or parent one. Further, a cell is considered wild-type, if no mutation has been introduced into the genome despite the fact that the cell is not naturally-occurring, but artificially produced. Therefore, the term "wild-type" shall not only apply to human cell lines obtained by culturing parent cells that are obtained from a human being, but also to artificial cells which comprise a human genome, either haploid or diploid. The term specifically encompasses human cell lines that are obtained by engineering cells which originate from a human being, specifically cells including alterations of the diploidy or haploidy of the chromosome. Parent cells may further comprise a mutation of individual exons, or genes, in particular introducing site directed mutations.

The cell line may be a eukaryotic and specifically a human cell line, which is understood as a cell line comprising the human genetic code, with or without mutations or otherwise alterations. Therefore, the term shall not only apply to human cell lines derived from parent cells that are obtained from a human being. The term also encompasses human cell lines that are obtained by engineering cells which originate from a human being, specifically cells including alterations of the diploidy or haploidy of the chromosome, or mutation of individual exons, or genes, in particular knocking out the function of a gene and/or introducing site directed mutations.

Isolated clones or a population or mixtures of isolated clones are herein referred to as artificial products, in particular, clones which are not naturally-occurring. Specifically; the diploid cell lines as described herein which comprise duplicated sister chromosomes and homozygous SNPs, are not occurring in nature, because native (naturally-occurring) somatic diploid cells would always comprise heterozygous SNPs.

Mutant cell lines may be recombinant cell lines employing recombination means and methods to obtain a recombinant DNA, thus obtained by recombinantly engineering the cell genome. Such recombinant engineering typically employs artificial constructs like plasmids or oligonucleotides or RNA/DNA or respective fragments, as tools to produce a recombined DNA. Specific mutants may be obtained by mutating a (chromosomal) region, thereby obtaining a genomic mutation at a specific locus of the chromosome. A mutant recombinant DNA may specifically be produced by either random or targeted recombination. Exemplary mutated cells comprise at least one genetic element exogenous to the cell that is integrated into the cell genome. In some aspects, the exogenous genetic element can be integrated at a random location in the cell genome. In other aspects, the genetic element is integrated at a specific site in the genome. For example, the genetic element may be integrated at a specific position such as to provide a change relative to the endogenous sequence.

Further exemplary mutated cells comprise an insertion or deletion of a coding or non-coding sequence, e.g. to produce a phenotype different from the parent cell. Mutated cells may also include cell lines in which individual nucleotides have been substituted.

Alternatively, the cells may be mutagenized by evolutionary mechanisms, e.g. using cells with normal or increased spontaneous mutation rate. Upon recombination or mutagenesis, a suitable mutant cell line may be selected according to its specific genetic sequence, e.g. by determining the specific alteration of the sequence.

It is understood that mutant cell lines may be provided as a product ready-to-use for cultivation, e.g. for research, industrial or analytical use. It is well understood that the human cell lines as specifically described herein are somatic cell lines, thus, the scope of the present invention does not encompass human beings or techniques directly related to human germline manipulation or human cloning.

Specific cell lines as described herein are adherent cell lines, thus, can be cultivated as adherent cells to surfaces or in suspension, e.g. in presence or absence of solid carriers. Cell line culture can be done for instance in dishes, roller bottles or in bioreactors, using batch, fed-batch, continuous systems, hollow fiber, and the like. The adherent cells typically are cultures one a solid surface in the form of a monolayer culture. Anchorage-dependent cell lines growing in monolayers are typically subcultured at regular intervals to maintain them in exponential growth. When the cells are near the end of exponential growth (roughly 70 to 90% confluent), they are usually subcultured, thereby undergoing a passage. The passage from a primary culture to a secondary culture is characterized by a split ratio which represents the proportion of the primary culture in the form of detached cells which is required for seeding a further culture device at a given cell density and thereby providing the secondary culture.

Adherent cells typically anchorage loosely or strongly on a cell support or carrier. Exemplary carriers on which cells would grow are known in the art and preferably are adapted to the purpose of cell cultivation. The carrier is suitably a particulate carrier. Carriers may be made of any suitable material supporting cell growth, such as, dextran, plastic, gelatine, collagen or cellulose, glass or others. Conventional adherent cell culture employs surfaces of tissue culture bottles, vials, well slides or other vessels, or microcarriers involving growing adherent cells as monolayers on the surface of small micron range diameter particles which are usually suspended in culture medium.

In a cell culture of adherent cells, most cells attach firmly to the solid surface. In some cases, cells round up and detach somewhat during mitosis. Following mitosis, they will reattach.

Standard protocols of cultivating adherent cells are known in the art, e.g. of Life Technologies. These include method steps of cell cultivation, cell dissociation, counting cells, determining optimal seeding density and preparing new culture vessels for passaged cells. Adherent cell lines will grow in vitro until they have covered the surface or the medium is depleted of nutrients. At this point the cell lines are typically subcultured in order to prevent the culture from dying. To subculture the cells they need to be brought into suspension, e.g. using a detachment buffer. The degree of adhesion varies from cell line to cell line but in the majority of cases proteases, e.g. trypsin, are used to detach and release the cells from the solid surface. Adhesion of cells to the carrier is promoted by alkaline earth metal salts such as calcium and magnesium salts. Therefore, the detachment buffer suitably does not contain any components which promote cell adhesion and, for example, alkaline earth metal salts such as calcium and magnesium salts are suitably avoided. In principle, cells are detached from a carrier to which they are adhered by a number of well-known enzymatic means. The most common means of detachment is using proteolytic degradation, most typically employing a cysteine or serine endopeptidase, such as trypsin, but also papain, actinidin, bromelain or ficin may be used.

The term "cellular stress conditions" as used herein is understood in the following way. When the cell is under stress, e.g. arising from oxidation, heat, infection, toxic contamination or any other stressful condition, they can mount a variety of responses. Some of these are generic; others are more specific to the stress-inducing agent. Physiological or non-physiological (e.g. physical) stressors would cause the cells to react in various specific ways to stress. Well-established markers for stress include (i) upregulation of heat-shock proteins (such as HSP70 or HSP90), (ii) activation of stress-induced kinases (such as SAPK, CHK1 or CHK2), (iii) activation of caspases (such as CASP3 or CASP7), (iv) upregulation of HIF-1 and other hypoxia-inducible factors in response to hypoxia, (v) activation of the unfolded protein response in response to cellular stress at the endoplasmatic reticulum, (vi) temporary cell cycle arrest in response to high cell density.

Such cellular stress conditions as described herein would enhance the spontaneous diploidization of a haploid genome. The stress conditions can be employed to a culture of adherent cells when attached on the solid surface or upon detachment, before cells are re-attached to a solid surface to further cultivate the cells. Shearing is suitably applied after detachment, treatment with toxins is advantageously applied to adherent cells.

The term "cellular repair mechanism" as used herein is specifically understood as mechanisms to detect and repair the various types of damage that can occur to DNA. A specific DNA damage is single-strand or double-strand breaks, which may be highly deleterious possibly leading to loss or rearrangement of genomic sequences. Double-strand breaks are repaired through non-homologous end joining (NHEJ) or homologous recombination (HR). In NHEJ, additional errors can be introduced during this process leading to specific mutations proximal to the DNA break. Therefore, NHEJ is considered inherently mutagenic as it relies on chance pairings, called microhomologies, between the single-stranded tails of the two DNA fragments to be joined. HR is a repair process that uses a DNA template for correction. It is more precise than NHEJ, yet less efficient. If a suitable exogenous DNA template is provided to the cells, HR offers the possibility to engineer mutations in specific GOIs.

The term "expression" as used herein shall refer to the production of RNA and/or of protein, polypeptide or peptide based on a nucleic acid molecule that is capable of directing transcription. Expression may be transient or may be stable. In the context of the present invention, the term "transcription" relates to a process, wherein the genetic code in a DNA sequence is transcribed into RNA.

"Expression constructs" or "vectors" or "plasmid" refers to nucleic acid molecules containing a desired nucleotide sequence and control sequences in operable linkage, so that hosts transformed or transfected with these sequences are capable of producing the encoded molecules. In order to effect transformation, the expression system may be included in a vector; however, the relevant DNA may also be integrated into the host chromosome. Expression plasmids are herein termed "human expression plasmids" if designed for transforming human cells.

According to the invention, the RNA specifically used in the RNA-guided system may be provided by in vitro transcription wherein RNA is in vitro synthesized in a cell-free system, preferably using appropriate cell extracts or chemical synthesis, or by in vivo transcription wherein RNA is in vivo synthesized in a cell-based system, which particularly includes ex vivo production employing the cells in an environment outside the human body.

Preferably, an expression plasmid is applied for the generation of transcripts obtained by transcription of an appropriate DNA template, which plasmids are herein specifically understood as cloning vectors. Specifically an expression plasmid employed for the purpose of the invention may be used for transient expression of gRNA, or any of the tracrRNA and the crRNA components of a gRNA, and/or the homology template. Specifically, the respective nucleotide sequences may be provided by one or more expression plasmids which are co-transfected.

The term "plasmid" as used herein refers to a macromolecule or complex of molecules comprising a polynucleotide to be delivered to a host cell, either in vitro or in vivo. A plasmid is typically understood as a common type of a vector, being an extra-chromosomal DNA molecule separate from the chromosomal DNA which is capable of replicating independently of the chromosomal DNA. In certain cases, it is circular and double-stranded. Thus, a plasmid specifically includes autonomously replicating nucleotide sequences as well as genome integrating nucleotide sequences. Expression plasmids usually comprise an origin for autonomous replication in the host cells, selectable markers (e.g. an amino acid synthesis gene or a gene conferring resistance to antibiotics such as blasticidin, zeocin, kanamycin, G418 or hygromycin), a number of restriction enzyme cleavage sites, a suitable promoter sequence and a transcription terminator, which components are operably linked together. The promoter for controlling transcription can be any promoter for any RNA polymerase. If transcription occurs ex vivo, one typically uses bacteriophage-derived T7, T3, and SP6 RNA polymerases in conjunction with their cognate promoters. If transcription is meant to occur in human cells, one typically uses the U6 promoter, which is derived from the human U6 snRNA locus, driving the transcription via human RNA polymerase III.

A DNA template for transcription may be obtained by cloning a nucleic acid and introducing it into an appropriate vector for transcription. The DNA may be obtained by reverse transcription of RNA.

The term "RNA" as used herein comprises double-stranded RNA, single-stranded RNA, isolated RNA such as partially or completely purified RNA, essentially pure RNA, synthetic RNA, and recombinantly generated RNA, such as modified RNA which is functionally the same or similar, but differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

The terms "guide RNA", "tracrRNA", and "crRNA" are understood in the following way.

A guide RNA (gRNA, also termed chimeric guide RNA) is a chimeric RNA molecule comprising the tracrRNA, which—together with the constant part of the crRNA—specifically determines the structure of the gRNA necessary to provide a co-substrate to a matching RNA-guided endonuclease, also termed chimeric guide RNA scaffold, which is understood as a constant RNA sequence forming a functional pair with an endonuclease guided by the gRNA. The crRNA comprises a constant part capable of interacting with or linking to the tracrRNA, and a variable part (also termed oligo RNA) which is composed of a short oligonucleotide sequence which is complementary to a DNA target site in the human genome. The constant part of the crRNA is typically located at the 3' part of the molecule, whereas the variable part is typically located at the 5' end of the molecule. The tracrRNA and the crRNA may directly associate though hybridizing parts, or joined with a linker sequence.

gRNA forms a co-substrate to direct RNA-guided endonuclease activity to the genomic target site where the gRNA (through its crRNA component) hybridizes with the target. Thus, the crRNA is understood as containing the part encoding the genome editing information in the form of complementary sequences (allowing GU as well as GC base pairs), and the RNA-guided DNA endonuclease is understood as a nuclease cleaving target DNA at a specific site. For example, CAS9 assembles with the chimeric gRNA in human cells and can induce the formation of a DNA breaks, e.g. a double strand DNA break at a site complementary to the gRNA sequence in genomic DNA. This cleavage activity requires both CAS9 and the complementary binding of the guide RNA through the variable crRNA part.

Therefore the gRNA as described herein is typically a non-coding RNA, specifically hybridizing with a DNA target site and directing the RNA-guided endonuclease to the DNA target site, to induce a DNA break within the region of hybridization. This system provides for invaluable tools for human genome engineering at the cellular level by reprogramming of a CRISPR-CAS system to achieve RNA-guided genome engineering in human cells.

The set of matching RNA-guided endonuclease and tracrRNA or gRNA or constant part of gRNA is herein understood as a functional pair, which may be used with one or more variable parts, i.e. with one or more crRNA or crRNA variable parts, e.g. a 20b, 22b, 24b or 26b RNA-type oligonucleotide, to target one or more predetermined, random or different human genomic target site. For example, a set of CAS endonuclease, e.g. type II, and a matching tracrRNA is used for interference of the crRNA (the oligonucleotide conjugated to the 5' end of the tracrRNA, e.g. employing a linker) with the target nucleic acid sequence through its variable crRNA oligo sequence. Targeting occurs upon hybridization of the crRNA to the complementary target site. Exemplary functional pairs of tracrRNA and endonuclease or functional pairs of gRNA and endonuclease are illustrated in FIGS. 1 to 4. Specific gRNA variants are illustrated in FIG. 5. Functional variants of the endonuclease, tracrRNA or the gRNA are feasible. In particular, gRNA variants may comprise a variable 3' end, e.g. within the region of the 20, or 15, or 10, or 6 terminal bases, such as a truncation, elongation and/or a point mutation of any of the bases in the 3' terminal RNA sequence.

Functional variants of the RNA-guided endonuclease are specifically those of the same type or subtype as obtained from bacterial sources or derived from the amino acid sequences of bacterial origin, including artificial or recombinant enzymes comprising the same or mutated sequences, e.g. comprising one or more mutations and a specific sequence identity to the wild-type sequence.

A functional variant of a CAS endonuclease may be a CAS9 nickase, which is herein understood as a CAS9 mutant comprising specific point mutations, e.g. an exchange of one or more single (non-contiguous) amino acids resulting in the inactivation of one domain with nuclease activity and converting CAS9 to a "nickase" enzyme that makes single-stranded breaks at the target site instead of a double strand break. Such nickase may as well be used for double strand DNA break, e.g. when used with paired guide RNAs to introduce targeted double-strand breaks.

Examples of wild-type enzymes and sequences are provided in FIGS. 1 to 4. Parent CAS9 enzyme sequences may be obtained from the respective coding DNA sequences or the amino acid sequences of bacterial CAS9 of *S. pyogenes, S. thermophiles, N. Meningitis* or *T. denticola*, e.g. comprising or consisting of any of the amino acid sequences of SEQ ID 1, 6, 7, 8, 9, 10, 15, 16, 21, 22, or 24. Functional variants of a parent enzyme may e.g. be analogs, such as wild-type sequences obtained from other species, e.g. other bacterial species of the same genus or family as the parent endonuclease, or mutated wild-type sequences of analogs. When an analog of the endonuclease is used, specifically the analogous tracrRNA or gRNA sequence of the same species or the same family may be used to form a functional pair, e.g. which components are natively paired.

Wild-type tracrRNA or gRNA sequences, in particular the constant part of the gRNA or tracrRNA, which is herein understood to confer a specific co-substrate structure, thus, referred to as structural part of gRNA, may be used to form a functional pair with a functional variant of the endonuclease. Alternatively, functional variants of the tracrRNA or gRNA (in particular the constant part of gRNA) may be used, e.g. which are obtained by mutagenesis of the wild-type sequences used as parent sequences.

The functionally active variant of an RNA, such as a gRNA or a component of gRNA, e.g. the tracrRNA of the invention, is specifically understood to encompass a nucleotide sequence which forms a functional co-substrate to the matching RNA-guided endonuclease, and/or any of the functionally active size variants, including truncated versions or fragments, mutants or hybrid nucleic acid sequences of a wild-type RNA. Functional variants of the RNA molecules as described herein may e.g. be obtained by one or more mutations in the nucleotide sequence of a parent (wild-type) RNA, wherein the mutated RNA is still functional and hybridizes under stringent conditions to a strand complementary to the parent RNA.

It is understood that the term "constant" with respect to a RNA sequence or a part of an RNA sequence, as used herein shall refer to the sequence of the RNA which is determined by the sequence of bacterial origin of a specific species, independent on the variability of the oligonucleotide (being part of the crRNA) which hybridizes with a target DNA. Such constant RNA molecule or part of a gRNA is typically of the same or similar structure for all cells of a specific species, and provides for interaction with the RNA-guided endonuclease of the same species thereby forming a functional pair, independent on type or origin of the genomic target site. It is well understood that such constant molecules or parts of the molecules may still vary from species to species, or be used as a parent molecule to produce mutants, which may be used as functional variants.

The "variable" part of the crRNA as described herein is understood as the part that hybridizes with a specific part of a target DNA, thus is complementary to any specific site. Since the human genomic target sites are located throughout the human genome, a plurality of oligonucleotides may be used for hybridizing the crRNA or gRNA with the target site, either with a predetermined target site or randomly targeting the human genome. Therefore, this part is considered to be variable, according to the specific hybridization target.

Functional variants of crRNA or gRNA or a constant part of the gRNA are feasible when a parent sequence is used as a template or is mutated, e.g. through mutagenesis or directed engineering, such as by engineering fragments or terminal extensions, and/or by one or more point mutations. A parent wild-type tracrRNA sequence or constant part of gRNA may e.g. comprise any of the sequences of FIG. 1 to 5 indicated as gRNA or constant part of gRNA (i.e. the gRNA excluding the crRNA variable part which may or may not include a linker sequence), in particular the tracrRNA and constant part of the crRNA or gRNA of SEQ ID 3, SEQ ID 13, SEQ ID 19, and any of SEQ ID 24-47.

The RNA may comprise specific modifications. For example, a further modification of the RNA used in the present invention may be an extension or truncation of the naturally occurring poly(A) tail or an alteration of the 5'- or 3'-untranslated regions (UTR).

The "functionally active variant" or "functional variant" of a nucleotide or amino acid sequence as used herein specifically means a mutant sequence, e.g. resulting from modification of a parent sequence by insertion, deletion or substitution of one or more nucleotides or amino acids within the sequence or at either or both of the distal ends of the sequence, and which modification does not affect (in particular impair) the activity of this sequence.

Specifically, the functionally active variant of the sequence has substantially the same activity as a parent sequence and is selected from the group consisting of homologs with at least about 60% nucleotide sequence identity, preferably at least 70%, at least 80%, or at least 90% degree of homology or sequence identity to the parent sequence; and/or homologs obtainable by modifying the parent sequence, or the sequence of a size variant used as a template to provide for mutations, e.g. by insertion, deletion or substitution of one or more nucleotides within the sequence or at either or both of the distal ends of the sequence;

sequence variants derived from a parent or wild-type sequence as described herein by extension and/or fragmentation of the parent sequence, e.g. +/−50% or +/−25%, or +/−10% of the length; or analogs derived from species other than *S. pyogenes, S. thermophiles, N. Meningitis* or *T. denticola*.

The functionally active variants as described herein are also understood to encompass hybrids or chimeras of two or more parent sequences, e.g. resulting from combination of sequences that qualify as parent sequence with functional activity.

Suitable variants have "substantially the same activity", which term is herein specifically understood to refer to the activity as indicated by substantially the same or improved efficacy of directed DNA break and/or mutagenesis, e.g. +/−50% or +/−25%, or +/−10%, as determined by the rate of successful DNA break and/or recombination.

Functional variants which have "substantially the same gene expression profile" are characterized by the same or similar expression of each of the genes.

The term "functional variant" with respect to a cell line is specifically understood as a clone which is different from a parent (or comparable) clone. Such functional variant may be independently produced, e.g. by separate or parallel engineering measures, and therefore referred to as independent. Functional variants may as well be subclones of the parent clone.

The functional variants of the HAP2 clone, such as the deposited material referred to herein, are particularly characterized by the complete set of human chromosomes which are fully haploid, and further characterized by the stable haploid karyotype. Preferred functional variants of the HAP2 clone have the same or similar gene expression profile, e.g. as determined by the level of gene expression of a number of individual genes.

Specifically, the present invention refers to the HAP2 cell line deposited under DSM ACC3220, or a functional variant thereof, preferably with a similar gene expression profile.

Specifically, functional variants of a clone or of a cell line (herein also referred to as parent cell line, such as a deposited material as described herein) are characterized by substantially the same gene expression profile, which functional variant comprises a genome, wherein the level of expression of the genes is substantially the same, e.g. the gene expression level of less than 1000 genes would differ, preferably less than 750, or less than 500, or less than 300 genes.

Specifically, the functional variant comprises the human genome, wherein the level of expression of the genes is substantially the same, e.g. the gene expression level of less than 1000 genes would differ, preferably less than 750, or less than 500, or less than 300 genes.

For example, the independently produced clones may have substantially the same gene expression profile, which is different with respect to less than 500 genes only.

Yet, two cell lines cannot be considered functional equivalents of the HAP2 cell line, such as KBM-7, if they vary in the expression level of ~3,000 human genes.

The identity of the level of expression with respect to one gene in individual clones is herein understood as the same or similar level of gene expression (e.g. +/−2-fold difference) for individual genes. Thus, the expression level is considered different for an individual gene, if the level of expression of said gene is at least 2-fold higher (200%) or less than one half (<50%). This is understood as a conservative cut-off of 2, to determine the same or similar level of gene expression when compared to a reference clone.

A less conservative cut-off is 3, or 4, or 5, i.e. indicating a 3-fold difference, or a 4-fold difference, or a 5-fold difference. Thus, the expression level is considered different for an individual gene, if the level of expression of said gene is at least 3-fold higher (300%) or less than one third (<33%); or at least 4-fold higher (400%) or less than one fourth (<25%); or at least 5-fold higher (≥500%) or less than one fifth (<20%).

The term "genomic site of interest" or "GOI" as used herein shall refer to a genetic sequence of interest which is any nucleic acid sequence endogenous to a cell, such as, for example a gene or a non-coding sequence within or adjacent to a gene, in which it is desirable to modify by targeted mutagenesis and/or targeted homologous recombination. The GOI can be present in a chromosome, an episome, an organellar genome such as mitochondrial genome. A GOI can be within the coding sequence of a gene, within transcribed non-coding sequence such as, for example, promoter or leader sequences, or introns, or within non-transcribed sequence, either upstream or downstream of a coding sequence.

The term "homolog" or "homology" indicates that two or more nucleotide or amino acid sequences have the same or conserved pairs at a corresponding position, to a certain degree, up to a degree close to 100%. A homologous sequence of a functionally active variant typically has at least about 60% nucleotide or amino acid sequence identity, preferably at least about 70% identity, more preferably at least about 80% identity, more preferably at least about 90% identity, more preferably at least about 95% identity, more preferably at least about 98% or 99% identity. The term "homologous" may also include analogous sequences.

The term "homology template" as used herein refers to a DNA or a DNA sequence or fragment that at least partially hybridizes to a GOI and may act as a donor to introduce specific inserts or exchange one or more nucleotides within the GOI by homologous recombination or homology-directed repair. Homologous recombination is typically involved in the repair of double-stand breaks which may promote the exchange of genetic information between an endogenous genetic sequence (i.e. a GOI initially present into the cell) and the homology template acting as a donor. Depending of the design of the donor, coding or non-coding regions present on the GOI can be knocked-in (as further described herein) in a rational, precise and efficient manner. The process requires sequence homology between one sequence present on the donor, referred to as homologous or recombining sequence, and the endogenous targeted GOI. Preferably, homologous recombination is performed using two flanking sequences having identity with the endogenous GOI in order to make more precise integration.

Specific homology templates comprise a recombining sequence that is complementary to at least a portion of a single-strand oligonucleotide such that two single-strand oligonucleotides can partially hybridize together. The complementary sequence of the single-strand oligonucleotide can be any length that supports specific and stable hybridization between the two single-strand oligonucleotides under the reaction conditions. The recombining sequence generally authorizes at least a partial double stranded overlap between the homology template and the GOI over at least 10 bp, preferably at least 20 bp.

"Percent (%) identity" with respect to the nucleotide or amino acid sequence is defined as the percentage of nucleotides in a candidate DNA sequence that is identical with the nucleotides in the DNA sequence or the amino acids in a peptide/polypeptide/protein sequence, after aligning the sequence and introducing gaps, if necessary, to achieve the maximum percent sequence identity, and not considering any conservative substitutions as part of the sequence identity. Alignment for purposes of determining percent nucleotide sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared.

A functionally active variant of a parent sequence as described herein may specifically be obtained through mutagenesis methods. The term "mutagenesis" as used in the context of the present invention shall refer to a method of providing mutants of a sequence, e.g. through insertion, deletion and/or substitution of one or more nucleotides or amino acids, so to obtain variants thereof. Mutagenesis may be through random, semi-random or site directed mutation. Typically large randomized gene libraries are produced with a high gene diversity, which may be selected according to a specifically desired genotype or phenotype.

Preferably the functionally active tracrRNA comprises or consists of a nucleotide sequence of at least 50 bases, specifically at least 60 bases, typically up to 90 or 100 bases. According to a specific example, the truncated tracrRNA is typically about 60 bases long, preferably 60-70 bases, e.g. 66 bases long, the full-length tracrRNA is typically 90 bases long. Some of the preferred functionally active variants of the tracrRNA according to the invention are size variants or specifically fragments of a tracrRNA including truncated versions, preferably those including the 3' part of the tracrRNA molecule, e.g. including a truncated 5' part of a nucleotide sequence. For example a nucleotide sequence derived from one of exemplary tracrRNA nucleotide sequences which has a specific length and insertions or a deletion of the 5' terminal region, e.g. an elongation or truncation of the nucleotide sequence at the 5' end, so to obtain a specific length with a range from the 3' end to a varying 5' end, such as with a length of the nucleotide sequence of at least 50 bases, preferably at least 60 bases. The elongated size variant of the invention preferably comprises additional one or more nucleotide(s) at the 5' end of the tracrRNA sequence.

Preferably the functionally active crRNA comprises or consists of a nucleotide sequence of at least 25 bases, specifically at least 30 bases, typically up to 70 or 80 or 90 or 100 bases. According to a specific example, the truncated crRNA is typically about 30 bases long, preferably 30-40 bases, e.g. 32 bases long, the full-length crRNA is typically 50-60 bases long, e.g. 55 bases. Some of the preferred functionally active variants of the crRNA according to the invention are size variants or specifically fragments of a crRNA including truncated versions, preferably those including the 5' part of the crRNA molecule, e.g. including a truncated 3' part of a nucleotide sequence. For example a nucleotide sequence derived from one of exemplary crRNA nucleotide sequences which has a specific length and insertions or a deletion of the 3' terminal region, e.g. an elongation or truncation of the nucleotide sequence at the 3' end, so to obtain a specific length with a range from the 5' end to a varying 3' end, such as with a length of the nucleotide sequence of at least 25 bases, preferably at least 30 bases. The elongated size variant of the invention preferably comprises additional one or more nucleotide(s) at the 3' end of the crRNA sequence.

The functionally active tracrRNA variants may still include a region of complementarity to interact with the constant part of the crRNA. On the other hand, the functionally active crRNA variants may still include a region of complementarity to interact with the trcrRNA. Typically, the 3' part of the crRNA or a functional variant of the crRNA is interacting with the 5' part of the tracrRNA (with or without a linker) through a region of complementarity. Thus, it is preferred that functional variants of the tracrRNA and the crRNA still comprise a region of complementarity which is at least 5 bp, preferably at least 10 bp, specifically located in the 5' part of the tracrRNA and in the 3' part of the crRNA.

Preferably the functionally active RNA-guided endonuclease comprises or consists of an amino acid sequence of 500 to 3000 amino acids, preferably at least 1000 amino acids. Some of the preferred functionally active variants of the endonuclease as used according to the invention are size variants or specifically fragments of a parent enzyme, in particular where the functionally active variants still comprise the active site of the enzyme including a RuvCI domain (containing a catalytic Asp residue) and an HNH domain (containing a catalytic His residue).

A functionally active variant of a crRNA, in particular the variable part of the crRNA, or an oligonucleotide as described for the purpose of the present invention need not be 100% complementary to its target sequence to be specifically hybridizable. An oligonucleotide is specifically hybridizable when binding of the oligonucleotide to the target DNA molecule interferes with the normal function of the target DNA, and there is a sufficient degree of complementarity to avoid non-specific binding of the oligonucleotide to non-target sequences under conditions where specific binding is desired, for example under physiological conditions in the case of in vivo assays or systems. Such binding is referred to as specific hybridization, e.g. hybridization under stringent conditions.

The DNA target site is typically characterized by a protospacer associated motif (PAM), which is a short DNA recognition site located adjacent to the target site in the human DNA sequence and which defines the site of RNA hybridization and the DNA break. Typically, the RNA hybridization is such that the crRNA hybridizes with the DNA sequence upstream the PAM motif, e.g. the DNA sequence joined to the 5' end of the motif. The DNA break is then catalyzed within the region of hybridization, e.g. a DNA break proximal to the PAM motif, in most cases in close proximity to the 5' end of the motif, such as within 10 positions, or within/at 5 positions or within/at 3 positions upstream the PAM motif. Following the DNA break, the cellular repair mechanism provides for rejoining the DNA ends with or without incorporating mutations, typically proximal to the DNA break, e.g. in close proximity to the 5' end or 3' end of the DNA break, such as within 20 positions, or within 10 positions, or within 5 positions or within 3 positions upstream or downstream the DNA break.

A specific genomic target site of interest may be randomly chosen, or predetermined and selected at any position of the human chromosomal genome where a DNA cleavage (single stranded or double stranded DNA break) and optionally recombination and/or mutation is desirable, and where a PAM motif is present or has been introduced, including a target site within coding and non-coding sequences.

Small (random) inserts or deletions of one or more nucleotides may be desirable, e.g. to produce frameshift mutations. In particular, such deletions or insertions or frameshift mutations provide for knockout mutations, which are understood to encompass any mutation within a gene sequence or regulatory sequence directing the function of a gene, e.g. leading to a different gene expression as assessed at the protein level or a different phenotype, e.g. leading to a significant loss of the function of a gene (partial knock-out) or a complete knock-out of the gene. The significant functional loss of a gene specifically provides for a gene expression level or gene function of less than 10%, preferably less than 5%, or no detectable gene expression or function as compared to the parent or reference (e.g. isogenic) cell without the knockout mutation. Specific mutations lead to a different gene expression or a different phenotype. Also, exons or genes or chromosomal parts including a series of genes may be exchanged and marker sites introduced, e.g. restriction sites, or tags.

Therefore, using gRNA, CAS9 can be guided to cleave DNA at any site defined by the guide RNA sequence and including a PAM motif. CAS9 can be expressed and localized to the nucleus of human cells, e.g. employing one or more additional nuclear localization signals (NLS), e.g. at least 1, 2, 3, 4, or 5 repeats of NLS preferably located within N-terminal or C-terminal extensions of the CAS9 amino acid sequence. For example the NLS may be a short peptide sequence of 3 to 15 amino acids, e.g. 5 to 10, such as 7 amino acids, which facilitates the active transport of the complex of RNA-guided endonuclease with the gRNA through the nuclear pores. Putative NLS sequences can be found and derived from the SV40 Large T Antigen or Nucleoplasmin Exemplary NLS sequences are, e.g. PKKKRKV (SEQ ID 6, from SV40 Large T antigen), KRPAATKKAGQAKKKK (SEQ ID 49, from Nucleoplasmin), PAAKRVKLD (SEQ ID 50, from c-Myc), PPRKKRTVV (SEQ ID 51, from HCV NS5A) or PRPPKMARYDN (SEQ ID 52, from human RNA helicase A).

RNA expression systems commonly used for delivery of RNA molecules to the cell may be employed. According to a specific embodiment, the endonuclease is co-expressed together with a tracrRNA and/or crRNA and/or gRNA designed to target a specific human coding or non-coding sequence, e.g. a human gene to impair or knock out the function of the gene. A suitable DNA may be used in an expression construct to express the tracrRNA and/or crRNA and/or gRNA or the functional pair of the tracrRNA or gRNA or the constant part of the gRNA and the RNA-guided endonuclease. Therefore, there is further provided such DNA which is a template DNA, e.g. comprising the sequence encoding the tracrRNA and/or crRNA and/or gRNA and/or the constant part of the gRNA, and optionally a DNA encoding the RNA-guided endonuclease, specifically operably linked to regulatory sequences to express such molecules in vivo or in vitro.

The RNA(s) may be synthesized ex vivo, e.g. in vitro transcribed RNA or synthetic RNA, and delivered to, e.g. (co-)transfected into, a cell by suitable means.

Transfection of RNA or the DNA encoding such RNA may be accomplished by a variety of means known to the art including, e.g., electroporation, microinjection, liposome fusion, lipofection.

According to a specific aspect, transformed or transfected cells transiently express the inserted DNA or RNA for limited periods of time. For instance, the foreign DNA or RNA persists in the nucleus of the cell for several days.

Transfection may as well be stable to produce a stable transfectant, e.g. introducing and optionally integrating foreign DNA or RNA into the transfected cell.

Likewise, the endonuclease may be produced by a cell transformed by a DNA encoding the endonuclease, in particular a codon-optimized DNA, or produced separate from the cell, and delivered to the cell by suitable means, including electroporation. For instance, the endonuclease may be fused to a peptide sequence enabling penetrance of the plasma membrane (such as the cationic peptide derived from HIV-1 Tat or a peptide derived from the antennapedia homeodomain), thereby enabling the direct application of purified protein to cells.

The term "isolated" or "isolation" as used herein with respect to a nucleic acid, e.g. an isolated gRNA an isolated constant part of the gRNA, an isolated tracrRNA or crRNA, or an isolated protein, e.g. an isolated RNA-guided endonuclease, or an isolated functional pair, such as an isolated pair or complex of a gRNA or a tracrRNA associated or bound to the RNA-guided endonuclease, shall refer to such compound that has been sufficiently separated from the environment with which it would naturally be associated, so as to exist in "substantially pure" form. "Isolated" does not necessarily mean the exclusion of artificial or synthetic mixtures with other compounds or materials, or the presence of impurities that do not interfere with the fundamental activity, and that may be present, for example, due to incomplete purification. In particular, isolated nucleic acid molecules of the present invention are also meant to include those chemically synthesized.

Nucleic acids of the invention are specifically provided as "isolated nucleic acid" or as an "isolated nucleic acid sequence". This term, when applied to RNA or DNA, refers to a molecule that is separated from sequences with which it is immediately contiguous in the naturally occurring organism. For example, an "isolated nucleic acid" may comprise a DNA molecule inserted into a vector, such as a plasmid, to express the respective gRNA encoded by such DNA. An "isolated nucleic acid" (either DNA or RNA) may further represent a molecule produced directly by biological or synthetic means and separated from other components present during its production.

An isolated RNA-guided endonuclease is typically provided as a molecule isolated from a natural source, e.g. a bacterial cell culture, or provided as a recombinant molecule obtained from a recombinant host cell culture, or provided as artificial product obtained by a suitable method of synthesis. Such isolation typically involves suitable methods of purification, e.g. to obtained a purity of at least 80%, preferably at least 90% or at least 95%, up to 100% (w/w).

The term "isolated" as used herein with respect to a cell or clone, e.g. isolated by limited dilution optionally followed by cultivating single cells to grow a clone (a single cell clone), shall refer to such cell or clone that has been sufficiently separated from the environment with which it would naturally be associated, so as to exist in "substantially pure" form. The isolated clone would not contain viable cells of a different clone, e.g. derived from an isolated cell with different genomic properties. Typically, different clones or subclones differ in at least one genomic mutation or SNP, thus, can be differentiated from cells of the same clone or subclone by genomic analysis. "Isolated" does not necessarily mean the exclusion of artificial or synthetic mixtures with other clones or materials, or the presence of impurities, in particular cellular components other than viable cells, that do not interfere with the fundamental activity, and that may be present, for example, due to incomplete isolation.

The term "diploid" as used herein shall specifically refer to a cell or cell line including a genome wherein the cell is disomic or diploid for one or more specific or predetermined genomic loci, e.g. the majority of loci, or even the full genome.

The specific diploid cell line as described herein comprises two sets of sister chromosomes, which are at least partly duplicated, or (nearly) fully duplicated, and is understood to contain two copies (chromatids) formed by the asexual replication of a single chromosome, with both copies being present within one cell. One sister chromosome is therefore understood as one-half of the duplicated chromosome. The set of sister chromosomes specifically comprises homologous chromosomes, which are at least substantially identical (near-diploid) or identical (diploid). The pair of chromosomes having the substantially the same gene sequences, are characterized by substantially the same nucleotide sequence, since the sister chromosomes originate from one parent haploid cell only. The term "substantially identical chromosomes" or "substantially the same nucleotide sequence" is specifically understood in relation to duplicated chromosomes, such as to obtain near-diploid cells as further described herein. A duplicated set of sister chromosomes is created during diploidization of the haploid cell as further described herein.

The term "diploid" specifically includes near-diploid cells and fully diploid cells.

The term "near-diploid" as used herein is understood in the following way. A near-diploid cell is a cell in which no more than 5 chromosomes are present in one copy or more than two copies, e.g. four copies (tetrasomic for the specific genomic loci). In some embodiments, a near-diploid human cell has no more than 1, 2, 3, or 4 chromosomes present in more than two copies. Near-diploid cells can be genomically stable maintaining their status several months in culture. An exemplary near-diploid somatic human cell is a chromosomally stable colon cancer cell line HCT116 [20], or an adherent cell line obtained by a method described herein, e.g. upon diploidization of the near-haploid cell line HAP1 cell line, which again is an adherent cell line obtained by engineering the KBM-7 cell line, which has lost the second copy of chromosome 8, and is hence "more haploid" than its KBM-7 parent, but still retains a portion of chromosome 15 and can therefore not be considered fully haploid. Diploidization of a near-haploid cell line will result in the near-diploid cell line as described herein, which e.g. contains only a couple of tetrasomic genomic loci.

A specific example of a near-diploid somatic human cell line is the cell line C665 which is obtained by diploidization of HAP1 according to the method as further described herein.

The term "fully diploid" as used herein shall specifically refer to a cell or cell line including a genome comprising human chromosomes or the sister chromosomes in the disomic state. Specifically, the pair of chromosomes is identical, characterized by the same gene sequences, or characterized by the same nucleotide sequence, since the sister chromosomes originate from one parent haploid cell only. Fully diploid cells are e.g. characterized by the absence of heterozygous SNPs the sister chromosomes of complete set.

The term "haploid" as used herein shall specifically refer to a cell or cell line including a genome wherein the cell is haploid for one or more specific or predetermined genomic loci, e.g. the majority of loci, or even the full genome.

The term specifically includes near-haploid cells and fully haploid cells.

The term "near-haploid" as used herein is understood in the following way. A near-haploid cell is a cell in which no more than 5 chromosomes are present in two or more copies. In some embodiments, a near-haploid human cell has no more than 1, 2, 3, or 4 chromosomes present in two or more copies. Near-haploid cells were found to maintain their status several months in culture. An exemplary near-haploid somatic human cell is haploid for most chromosomes with the exception of chromosome 8, and optionally a portion of chromosome 15, e.g. a cell of the KBM-7 cell line (WO 2011/006145 A2), which is a non-adherent cell line. A further example of a near-haploid cell line is the HAP1 cell line [6]. Further near-haploid cell lines (in particular adherent cells) may be derived from a cancer patient, specifically a patient suffering from a solid tumor, such as peripheral chondrosarcoma, which brings about cells of reduced diploidy. In some cases, further adherent near-haploid cell lines may be derived from a patient suffering from leukemia, such as Chronic Myelogenous Leukemia or Acute Lymphoblastic Leukemia.

The term "fully haploid" as used herein shall specifically refer to a cell or cell line including a genome comprising human chromosomes in the monosomic state.

Haploidy or diploidy may be determined or tested by known methods, e.g. spectral karyotyping, comparative genomic hybridization or comparative propidium iodide staining.

A specific example of a fully haploid somatic human cell line is the HAP2 cell line which is obtained by engineering HAP1 cells through excision of the portion of chromosome 15 that retained its diploidy in the HAP1 cell line, thus, is considered truly or fully haploid. It turned out that the HAP2 cell line comprises the complete set of human chromosomes in the monosomic state. The cell line designated HAP2 is deposited at the DSMZ under the accession number DSM ACC3220.

Haploid or diploid progeny can be derived by subcloning the parental cell line and picking haploid and diploid subclones, respectively. Preferably a cell line as described herein shows a genomic stability over at least 10 passages, preferably at least 15 or at least 20 passages, e.g. while avoiding cellular stress conditions. Genetic stability can be assessed by propidium iodide staining (total DNA content) or by spectral karyotyping (single chromosome resolution).

As used in the present invention, the term "hybridization" or "hybridizing" is intended to mean the process during which two nucleic acid sequences anneal to one another with stable and specific hydrogen bonds so as to form a double strand under appropriate conditions. The hybridization between two complementary sequences or sufficiently complementary sequences depends on the operating conditions that are used, and in particular the stringency. The stringency may be understood to denote the degree of homology; the higher the stringency, the higher percent homology between the sequences. The stringency may be defined in particular by the base composition of the two nucleic sequences, and/or by the degree of mismatching between these two nucleic sequences. By varying the conditions, e.g. salt concentration and temperature, a given nucleic acid sequence may be allowed to hybridize only with its exact complement (high stringency) or with any somewhat related sequences (low stringency). Increasing the temperature or decreasing the salt concentration may tend to increase the selectivity of a hybridization reaction.

As used in the present invention the phrase "hybridizing under stringent hybridizing conditions" is preferably understood to refer to hybridizing under conditions of certain stringency. In a preferred embodiment the crRNA as described herein is hybridizing under "stringent hybridizing conditions" to the genomic target site, wherein homology of the two nucleic acid sequences is at least 70%, preferably at least 80%, preferably at least 90%, i.e. under conditions where hybridization is only possible if the double strand obtained during this hybridization comprises preferably at least 70%, preferably at least 80%, preferably at least 90% of A-T or A-U bonds and C-G bonds.

The stringency may depend on the reaction parameters, such as the concentration and the type of ionic species present in the hybridization solution, the nature and the concentration of denaturing agents and/or the hybridization temperature. The appropriate conditions can be determined by those skilled in the art, e.g. as described in Sambrook et al. (Molecular Cloning: A Laboratory Manual, Cold Spring Harbor, 1989).

The term "karyotypically stable" or "stable karyotype" with respect to a cell is herein understood as a genomically stable cell, which does not significantly change its karyotype for specific genomic loci for a prolonged period of time or for a number of passages. The short and long-term genomic stability is a quality criterion of a stable cell line which can be analyzed by routine methods. The karyotypic stability is particularly determined if the haploid or diploid karyotype for the complete set of human chromosomes has proven in more than 90% of the cells in a cell culture. Such cells would essentially not comprise more than the monosomic DNA content (in the case of a haploid cell), or more than the disomic DNA content (in the case of a diploid cell). The genomic or karyotypic stability is a particular feature of the cell line of the invention, which can be used for engineering a series of isogenic mutant cell lines, which differ in the genes or gene expression only at predefined locations.

The term "library" as used herein, e.g. with respect to mutant cell lines of isogenic cells, or with respect to a library of expression plasmids, or with respect to a library of oligonucleotides, is understood as a repertoire or a variety of library members, e.g. cell lines, expression plasmids or oligonucleotides, which library members distinguish from other library members.

The library of cell lines as described herein specifically comprises a library of strains, e.g. human cell lines that have at least one genotypic and/or phenotypic characteristic. Specific library members may comprise different genomic mutations, such as different knockout mutations to produce a variety of genotypes and optionally a variety of phenotypes. It is preferred that libraries are provided comprising a variety of library members, wherein each library member is lacking a functional ORF or the coding sequence of a different single gene.

The cell line library of the invention preferably comprises at least 50, or at least 100, or at least 300, or at least 1.000, or at least 10.000 library members which are characterized by different mutations, e.g. a knockout of different genes in the cell genome. If the mutants are produced by mutagenesis of a parent cell line, a variety of isogenic cells of the same type of the parent cell line is produced.

Each library member may be individually characterized and marked by a selectable marker or a barcode, to facilitate the selection of a library member in the library. Alternatively, the genetic mutation may be determined directly by a suitable determination method, e.g. employing specific probes hybridizing with the mutated region, to select the cell line comprising the mutation.

It may be desirable to locate the library members in separate containers, to obtain a library of cell collections in containers. According to a specific embodiment, the library is provided in an array, e.g. a cell chip, wherein the array comprises a series of spots on a solid carrier, wherein the series of spots include a suspension of one or more cells from a cell collection. Likewise, the cell library may be indexed to nucleic acid arrays.

Such libraries may be used to select specific library members to study the interaction with a predefined substance, e.g. a chemical or biological, such as an inhibitor or enhancer. Specific applications of such library are (i) the identification of genes involved various biological processes, such as the life cycle of a virus or responses to growth factors or cytokines, (ii) the determination of the specificity of an antibody or (iii) the use of a mutant cell line for the production of a biological (antibody, cytokine).

A further application may be the selection of a suitable host cell, for expressing a recombination product. Cell arrays may be employed to enable highly parallel, high throughput analyses of cell phenotypes that complement efforts for assessing cell growth and morphology, protein expression levels, and imaging of tissues.

The library of expression plasmids as described herein may specifically comprise a variety of expression constructs to transform human or other mammalian somatic host cells for expressing tracrRNA and/or crRNA and/or gRNA and/or gRNA components, e.g. the constant part of the gRNA, or a functional pair with the RNA-guided endonuclease, in particular a functional pair of gRNA and the endonuclease which is eligible to being guided by the gRNA. Therefore, library members are provided comprising a variety of DNA sequences (DNA templates) encoding specific RNA molecules, operably linked to regulatory sequences for RNA expression. A variety of gRNAs suitably differs in the variable crRNA part, but remains constant in the tracrRNA part and the constant crRNA part, to enable the targeting of different human genomic target sites, but interacting with the same RNA-guided endonuclease. Such library conveniently comprises at least 50 or at least 100, preferably at least 200 or at least 300 or at least 400, 500 or even 1.000 or more library members, which are expression plasmids encoding a variety of gRNA, optionally capable of co-expressing the functional pair of gRNA and the RNA-guided endonuclease.

The library of oligonucleotides as described herein may specifically comprise a variety of oligonucleotides to be used as probes or crRNA, to support the production or expression of the respective gRNA upon conjugation or recombination with a tracrRNA and/or further components of the gRNA. Therefore, the library comprises library members suitably composed of oligonucleotides of a specific length, but different sequence, each complementary to different genomic sites of the human genome. Such library conveniently comprises at least 100, preferably at least 200 or at least 300 or at least 400, 500 or even at least 1.000 or 2.000, or more library which are oligonucleotides, each capable of hybridizing to different human genomic target sites. Typically, a pair of (complementary) oligonucleotide sequences is targeting a human genomic target site. The library preferably comprises oligonucleotides which are artificial oligonucleotides, e.g. synthesized by suitable methods well-known in the art.

According to a specific embodiment, there is further provided a library of oligonucleotides, which are probes to hybridize with a mutated human genomic target site following DNA break and cellular repair, such as NHEJ. Such library may be used as a tool to determine and select a specific cell line comprising a specific mutation.

The term "mutagenesis" as used in the context of the present invention shall refer to a method of providing mutants of a sequence, e.g. through insertion, deletion and/or substitution of one or more nucleotides or amino acids, so to obtain variants thereof. Mutagenesis may be through random, semi-random or site directed mutation.

Therefore, the invention specifically provides for a mutant somatic human cell line obtainable by a specific production method. The mutant cell line is specifically characterized by the following features: (i) CRISPR knockouts are complete gene knockouts, i.e. the wild-type allele is no longer present in the cell. In contrast, gene trap mutants are partial knockouts whose efficiency depends on the efficiency of the splice acceptor that was used as part of the gene trap and the local chromatin environment; (ii) CRISPR knockouts in haploid human cells can easily and unambiguously be characterized by PCR and Sanger sequencing; (iii) CRISPR knockouts require no further validation at the mRNA level as the Sanger sequencing unambiguously qualifies them as complete knockouts. In contrast, the impact of the gene trap on any given gene needs to be validated by quantitative PCR; (iv) CRISPRs can be designed to target specific genes of interests or isoforms of interest. In contrast, gene traps cannot be steered to integrate in a desirable genomic locus; (v) CRISPRs can be used in combination with a homology template to engineer any genome modification that is desirable, including for instance point mutations or the fusion of tags or reporters. Gene traps have a more limited application profile; (vi) As CRISPRs enable the a priori selection of genes for targeting, their use if compatible with the generation of small custom knockout libraries affecting coherent gene sets, such as the kinases, the G-protein coupled receptors, the druggable genome. Gene traps do not allow the targeting of specific genes and thus, subsets of the human genome may or may not be available, depending on the integration bias of the retrovirus (vii) CRISPRs typically leave no trace, other than the mutation that was introduced. In contrast, gene traps are large cassettes (>2.500 bp) that contain retroviral and other sequences. (viii) In contrast to a gene trap mutant, a CRISPR knockout may be employed for a subsequent genetic screen using gene trap mutagenesis.

According to a specific example, efficient genome editing was performed while only one copy of each gene is present, thus, it is at least 2-fold easier to obtain a knockout as the gene of interest is present at half gene dosage. Yet, the benefit of using haploid human cells is even greater because for gene inactivation, one generally aims at obtaining frameshift mutations and disregards deletion/insertion of 3/6/9 bases that do not disrupt the reading frame. The chance of obtaining a frameshift mutation is ⅔ (66%) for every cleavage event that is inaccurately repaired. So in a haploid human cell line in which cleavage has occurred in 100% of the cells followed by erroneous repair, one obtains a frameshift allele with a 66% chance. In a population of diploid cells in which both alleles are cleaved with an efficiency of 100%, one would obtain frameshift alleles with a ~44% chance (66%×66%) at a maximum. Of course, when a nuclease induces cleavage with a lower efficiency than 100%, the chance of generating 2 frameshift alleles is even less and the advantage of using haploid cells is even greater. In addition, presence of only a single allele prevents gene repair through homologous recombination and thereby further increases the rate of obtaining frameshift alleles.

This is confirmed by the example below, targeting seven genes with established roles in the α-dystroglycan biosynthesis pathway. The human haploid cell line HAP1 was compared to the human cell line 293T, which is the model cell line of choice for genome editing as it is largely diploid. Cells were transfected with expression plasmids for CAS9 and the seven guide RNAs (in parallel) and loss of α-dystroglycan staining was assessed by FACS.

Further, the invention can provide a simple and straightforward protocol that allows the introduction of single nucleotide exchanges at low cost and with high efficiency. To this end, a haploid human cell line referred to HAP2 (herein also referred to as eHAP). These cells are fully haploid somatic cells of human origin, i.e. they possess every human gene in a single gene copy. This is an advantageous configuration for homologous recombination because only one wild-type allele has to be replaced with a mutated allele.

In haploid human cells, every gene is only present in one copy. As a consequence, mutations can be directly visualized, e.g. by PCR amplification and subsequent Sanger sequencing of the PCR product.

In addition, one key advantage of haploid cells is that every resulting clone will carry 100% mutation load, while mutagenesis in diploid cells will often yield cell lines that are heterozygous (50% mutation load). This is particularly beneficial for recessive mutations that, in diploid cells, would be masked by the presence of the second (wild-type) allele.

Specifically, the invention provides invaluable tools, e.g. for the following purposes:

Establish cellular disease models for various diseases caused by somatic or germline mutations (see below).

Assemble panels of mutant cell lines covering mutations isolated from a given cancer of interest (e.g. leukemia, lung cancer, colon cancer, liver cancer, bladder cancer) as reference for research and for diagnostic analysis based on protein, genomic DNA or RNA and derived cDNA by methods of molecular biology, physical measurements of microscopy.

Assemble panels of mutant cell lines covering mutations causing inherited diseases/genetic disorders (e.g. cystic fibrosis, phenylketonuria, polycystic kidney disease, Huntington's disease) as reference for research and for diagnostic analysis based on protein, genomic DNA or RNA and derived cDNA, by methods of molecular biology, physical measurements of microscopy.

Establish cell lines bearing gene sequence variants that can be used a diagnostic standards (e.g. for nucleic acid-based diagnostic kits, used to assess the mutational burden of a given cancer).

Establish cell lines in which endogenous genes are modified to contain a specific sequence tag (myc tag, His tag, HA tag, V5 tag, TAP tag, LAP tag, GFP, RFP, dsRed, mCherry)

Establish highly characterized reference samples by mixtures of cell populations with known composition as reference of patient material. As an example blood—or tumor samples with that contain fractions of cells with a marker, relevant for disease progression or characterization.

Establish cell lines in which particular chromosomal sequences (e.g. exons, genes, splice acceptors, promoters, enhancers) have been deleted.

Specifically, the invention provides invaluable tools, e.g. for establishing cellular disease models or diagnostic standards for various diseases caused by somatic or germline mutations or SNPs. In particular, cell lines can be established in which particular chromosomal sequences (e.g. exons, genes, splice acceptors, promoters, enhancers) have been deleted.

Specific examples are the following:

Introduce a mutation in the active site of an enzyme (kinase, phospholipase, synthetase etc.) to either enhance or diminish its activity Introduce small nucleotide polymorphisms that are naturally found in the human population Introduce mutations isolated from various cancers, to study the function of these mutations in cells Introduce restriction sites that serve as genomic markers Introduce single-nucleotide exchanges in regulatory sequences in the genome to modulate/change the sequence of micro RNAs, splice donor and acceptor sites, promoters, enhancers.

Further, the invention provides for the somatic human diploid cell line obtainable by diploidization of a haploid cell line as described herein. As haploid somatic cells do not naturally occur, results generated in these cells are questioned by the scientific community. As a consequence, a diploid derivative of a haploid cell is considered a valuable asset. This is particularly true in the area of genomic standards for PCR-based diagnostics where the natural genome context and the natural genome copy number are prerequisites for quality control.

As an example, a protocol is described that allows the "conversion" of a haploid cell into a diploid population. To this end, haploid human cells are used for genome engineering to produce a genomic mutation at a GOI (a mutation of interest). Once the mutation has been confirmed by PCR, cells are exposed to stress. Following cellular stress conditions, haploid cells increase their natural tendency to convert to diploid cells. Diploid subclones are then isolated by limiting dilution and quality controlled by propidium iodide staining. As a result of this process, a homogenous population of diploid human cells is produced that are homozygous for the mutation of interest.

Commercial applications of such diploid cell or cell population are e.g. any of the following:
i) Genetic variation between individuals is largely due to single-nucleotide polymorphisms (SNPs). Hence, a cell line in which only one SNP variant is present for every SNP could be useful to study the impact of genetic variation (presence or absence of certain SNPs) on various cellular phenotypes (e.g. gene expression, DNA damage repair, cell proliferation, metabolism, histone modification).
ii) Cellular phenotypes or experimental outcomes that are particularly likely to be affected by SNPs include
   a. EPIGENETICS. Epigenetics is the study of heritable changes that are not caused by the DNA sequence. Mechanisms underlying epigenetic regulation include histone modification (e.g. by methylation or acetylation) and modification of DNA (e.g. by methylation or hydroximethylation). Such modifications have been shown to play a role in repressing or activating transcription from certain loci.
   b. ENHANCERS. Enhancers are regulatory elements in the human genome that regulate the expression of certain genes or gene clusters.
iii) Certain genes are expressed in a parental-specific expression pattern. This means that they are selectively expressed from the maternal or paternal gene copy. A cell line that has two identical copies might represent an interesting model system to study this phenomenon.
iv) The efficiency of homologous recombination (HR) is highly dependent on the presence of SNPs: If a given region of interest displays many heterozygous SNPs, the efficiency of HR is dramatically decreased. If one wants to use a diploid cell line for HR, it would thus be preferred to have access to a cell line in which both gene copies are perfectly identical and thus HR has a higher likelihood of success.

The foregoing description will be more fully understood with reference to the following example. Such example is, however, merely representative of methods of practicing one or more embodiments of the present invention and should not be read as limiting the scope of invention.

EXAMPLES

Example 1: Generation of CRISPR Knockout Clones

HAP1 cells provide a valuable resource, enabling genetic studies in human cells. Herein described is a streamlined protocol that is robust and reliable and thus enables the routine generation of human knockout cell lines. To illustrate the capabilities of the technology, six examples of genes are shown for which HAP1 knockout cell lines were made using CRISPR/Cas technology.

TABLE 1

| Gene | Guide RNA sequence (variable part) | Genomic position |
|---|---|---|
| CHUK | ACAGACGTTCCCGAAGCCGC SEQ ID 98 | chr10: 101989200-101989220 |
| GSK3B | CGGCTTGCAGCTCTCCGCAA SEQ ID 99 | chr3: 119812234-119812254 |
| RIPK2 | CGTCCGCCCGCCACGCAGAC SEQ ID 100 | chr8: 90770386-90770406 |
| CDK4 | TCCCATCAGCACAGTTCGTG SEQ ID 101 | chr12: 58145335-58145355 |
| RIPK1 | AGTACTCCGCTTTCTGTAAA SEQ ID 102 | chr6: 3081216-3081236 |
| EEF2K | TTGACATTCTGGTTCGAGCT SEQ ID 103 | chr16: 22237186-22237206 |

Guide RNAs were cloned into a proprietary expression vector in which guide RNA expression is directed by the U6 promoter. In this expression construct, the variable part of each guide RNA was fused a constant fusion RNA that contains parts of the crRNA and the tracer RNA as depicted in SEQ ID 53 of FIG. 6.

Once each guide RNA expression plasmid had been established and verified by Sanger sequencing, HAP1 cells were transfected with a Cas9 expression plasmid and the guide RNA expression plasmid containing the guide RNA sequences depicted in FIG. 6. For transfection, Turbofectin (Origene) was used according to manufacturer's instructions and a plasmid containing a blasticidin resistance gene was included. 24 hours post transfection, cells were subjected to 20 µg/ml blasticidin for 24 h to eliminate untransfected cells. Then, cells were allowed to recover from the blasticidin treatment for 3-4 days.

Next, single cell clones were established by limiting dilution. To this end, cells were trypsinized and serially diluted to a concentration of 15 cells per ml. 50 µl of this suspension were seeded in each well of a 384 well plate. Individual wells were inspected by microscopy to exclude polyclonal cell lines. Monoclonal cell lines were expanded to 96 well plates. One replicate plate was frozen in freezing medium containing 20% FCS and 10% DMSO. The other replicate plate was used to isolate genomic DNA.

Genomic DNA was isolated using the Direct PCR-Cell Reagent (PeqLab) according to manufacturer's instructions. In brief, cells were washed twice with 100 µl PBS per well. After removal of PBS, 100 µl of Direct PCR-Cell Reagent and 2 µl Proteinase K (20 mg/ml stock) were added to each well. Plates were sealed and incubated at 56° C. for 2 h, followed by the incubation at 80° C. for 45 minutes. The resulting extract was used directly for PCR using GoTaq Polymerase and the following primer pairs:

TABLE 2

| Gene | Forward primers | Reverse primers |
| --- | --- | --- |
| CHUK | TGTAAAACGACGGCCAGTCAA ATACAACTTTGGACACACAGG SEQ ID 104 | TGGGGTTTGGAGAGATCTTATGTTT SEQ ID 105 |
| GSK3B | TGTAAAACGACGGCCAGTAAA GAGAGAAATCAATGGCAGCCT SEQ ID 106 | TATCGTTAACCTAACACCCCAACAT SEQ ID 107 |
| RIPK2 | TGTAAAACGACGGCCAGCTCT AGAAAAGAAGTCAGCTCTGGT SEQ ID 108 | GTCACTGCCATTTGGGCTCTA SEQ ID 109 |
| CDK4 | ATAGGCTGTCTTTTCCCTTTA CTCC SEQ ID 110 | TAGGGTCTCCCTTGATCTGAGAAT SEQ ID 111 |
| RIPK1 | TGTAAAACGACGGCCAGTTCA ACAAGCATTCCAGGTACAATC SEQ ID 112 | TAAAATCACCCAACTTTCTGGAAGC SEQ ID 113 |
| EEF2K | TGTAAAACGACGGCCAGGGTT TCGAATTTAAAATGTGCCTGG SEQ ID 114 | GAAAAACACCCAGTTCCAAGGTAAT SEQ ID 115 |

PCR products were visualized by agarose gel electrophoresis (data not shown) and sent for Sanger sequencing using the following sequencing primers:

TABLE 3

| Gene | Sequencing primers |
| --- | --- |
| CHUK | TGTAAAACGACGGCCAG SEQ ID 116 |
| GSK3B | TGTAAAACGACGGCCAG SEQ ID 116 |
| RIPK2 | TGTAAAACGACGGCCAG SEQ ID 116 |
| CDK4 | TAGGGTCTCCCTTGATCTGAGAAT SEQ ID 117 |
| RIPK1 | TGTAAAACGACGGCCAG SEQ ID 116 |
| EEF2K | TGTAAAACGACGGCCAG SEQ ID 116 |

For each of the six genes under investigation, 24 independent clones were sequenced and at least one clone was recovered that bore a frameshift mutation close to the guide RNA targeting site. Sequencing data for one clone each is provided in FIG. 7 (guide RNA target sequences are underlined):

All clones shown in FIG. 7 were expanded and frozen in several aliquots for storage purposes. In addition, lysates were prepared for Western Blotting using Frackelton buffer (10 mM Tris/HCl pH 7.5, 50 mM NaCl, 30 mM sodium pyrophosphate, 1% Triton X-100, 50 mM NaF and protease inhibitors). Cell extracts were loaded on SDS-PAGEs (7-15% acrylamide, depending on the size of the target protein) and analyzed by immunoblotting using the following antibodies.

TABLE 4

| Antibodies used in this example | | | |
| --- | --- | --- | --- |
| Gene | Protein | Provider | Antibody # |
| CHUK | IKK-α | Cell Signaling Technology | 11930 |
| GSK3B | GSK-3β | Cell Signaling Technology | 9832 |
| RIPK2 | Rip2 | Cell Signaling Technology | 4142 |
| CDK4 | Cdk4 | Santa Cruz | Sc-23896 |
| RIPK1 | Rip1 | Cell Signaling Technology | 3493 |
| EEF2K | eEF2k | Cell Signaling Technology | 3692 |

The result of the Western blotting experiment from six clones is shown in FIG. 8, using the antibodies depicted in Table 4. As shown in FIG. 8, all clones analyzed here show complete loss of gene expression. Furthermore, loss of expression is specific to the gene targeted by the guide RNA and other genes are unaffected. This indicates that the CRISPR/Cas system effectively inactivated the target genes by introducing a frameshift mutation in the coding sequence and highlights the great potential of haploid human cells for CRISPR/Cas-mediated genome editing.

Example 2: Generation of CRISPR Knockout Clones

HAP1 cells provide a valuable resource, enabling genetic studies in human cells. The following example was made according to a streamlined protocol that is robust and reliable and thus enables the routine generation of human knockout cell lines. HAP1 knockout cell lines were made with respect to five examples of genes, using CRISPR/Cas technology.

TABLE 5

| Gene | Guide RNA sequence (variable part) | Genomic position |
|---|---|---|
| OTUB1 | TCGGTCCTGCTGAGCCATGA SEQ ID 118 | chr11: 63755839-63755859 |
| BRDT | CCCAAAGCATTAACGTCAAC SEQ ID 119 | chr1: 92442875-92442895 |
| DDIT4 | GTTTGACCGCTCCACGAGCC SEQ ID 120 | chr10: 74034099-74034119 |
| DDIT4L | TCCTGAACCCAACCTCAACG SEQ ID 121 | chr4: 101109279-101109299 |
| EIF4EBP1 | GGTGCTGAAGAGCGTGCCGC SEQ ID 122 | chr8: 37888206-37888226 |

Guide RNAs were cloned into an expression vector in which guide RNA expression is directed by the U6 promoter. In this expression construct, the variable part of each guide RNA was fused a constant fusion RNA that contains parts of the crRNA and the tracer RNA as depicted in FIG. 6:

Once each guide RNA expression plasmid had been established and verified by Sanger sequencing, HAP1 cells were transfected with a Cas9 expression plasmid and the guide RNA expression plasmid containing the guide RNA sequences depicted above. For transfection, Turbofectin (Origene) was used according to manufacturer's instructions and a plasmid was included containing a blasticidin resistance gene. 24 hours post transfection, cells were subjected to 20 µg/ml blasticidin for 24 h to eliminate untransfected cells. Then, cells were allowed to recover from the blasticidin treatment for 3-4 days.

Next, single cell clones were established by limiting dilution. To this end, cells were trypsinized and serially diluted to a concentration of 15 cells per ml. 50 µl of this suspension were seeded in each well of a 384 well plate. Individual wells were inspected by microscopy to exclude polyclonal cell lines. Monoclonal cell lines were expanded to 96 well plates. One replicate plate was frozen in freezing medium containing 20% FCS and 10% DMSO. The other replicate plate was used to isolate genomic DNA.

Genomic DNA was isolated using the Direct PCR-Cell Reagent (PeqLab) according to manufacturer's instructions. In brief, cells were washed twice with 100 µl PBS per well. After removal of PBS, 100 µl of Direct PCR-Cell Reagent and 2 µl Proteinase K (20 mg/ml stock) were added to each well. Plates were sealed and incubated at 56° C. for 2 h, followed by the incubation at 80° C. for 45 minutes. The resulting extract was used directly for PCR using GoTaq Polymerase and the following primer pairs:

TABLE 6

| Gene | Forward primers | Reverse primers |
|---|---|---|
| OTUB1 | GAATAACTACAAAAGAGCTGGGCTG SEQ ID 123 | TCTAAGCCTGTCTTCCTGACCC SEQ ID 124 |
| BRDT | TTACAAAAGGTGTGAAGAGGAAAGC SEQ ID 125 | CCAGATAGTGTGACTTGGATGATCT SEQ ID 126 |
| DDIT4 | CACTCTGAGTTCATCAGCAAACG SEQ ID 127 | TCACTCACCTTATACTCCAATTCCC SEQ ID 128 |
| DDIT4L | CAATTTCCAAGTTCACGTGCATAAC SEQ ID 129 | GGCAGACATGGTAGATAGAGGTAAC SEQ ID 130 |
| EIF4EBP1 | TGACACCTAACAGAAAGAGGAAACA SEQ ID 131 | AGCGCACAGGAGACCATGT SEQ ID 132 |

PCR products were visualized by agarose gel electrophoresis (data not shown) and sent for Sanger sequencing using the following sequencing primers:

TABLE 7

| Gene | Sequencing primers |
|---|---|
| OTUB1 | GAATAACTACAAAAGAGCTGGGCTG SEQ ID 133 |
| BRDT | TTACAAAAGGTGTGAAGAGGAAAGC SEQ ID 134 |
| DDIT4 | CACTCTGAGTTCATCAGCAAACG SEQ ID 135 |
| DDIT4L | CAATTTCCAAGTTCACGTGCATAAC SEQ ID 136 |
| EIF4EBP1 | TGACACCTAACAGAAAGAGGAAACA SEQ ID 137 |

For each of the five genes under investigation, 24 independent clones were sequenced and at least one clone was recovered that bore a frameshift mutation close to the guide RNA targeting site. Sequencing data for one clone each is provided in FIG. 17 (guide RNA target sequences are underlined).

All clones were expanded and frozen in several aliquots for storage purposes. The results show that (i) frameshift mutants can reliable be obtained from a limited number of clones (here: 12 clones per guide RNA), (ii) deletions are more prominent than insertions and (iii) mutations cluster around the guide RNA target site.

Example 3: Production of a Haploid Clone Expressing Mutant EGFR Protein

The epidermal growth factor receptor (EGFR) regulates a number of cellular signaling pathways that promote cell growth and proliferation. Those include the NF-kB and the MAP/ERK signaling pathway. EGFR is mutated in a number of cancers (e.g. lung cancer and breast cancer) and most of these mutations are activating mutations that lead to elevated EGFR signaling in the resulting cells. One of the most predominant mutations found in non-small cell lung cancer is a single nucleotide exchange at position C2573T4G which leads to a single amino acid change in the kinase domain of the EGFR (Leu858Arg). The resulting mutant EGFR protein is constitutively active and thus promotes tumor growth.

In this example, CRISPR/Cas-mediated homologous recombination is employed in HAP1 cells to engineer the EGFR L858R mutation. Two guide RNAs are selected in the vicinity of the amino acid/site that was to be engineered (FIG. 9).

Homologous recombination needs a homology template that specifies the desired product of the reaction. Therefore, a homology template was designed in which a restriction site was included that was not naturally present. This site could then be used to assess the targeting efficiency by a simple PCR, coupled to a restriction digest (FIG. 10).

The homology template was provided in three "configurations": (i) as a PCR product, obtained from a synthetic 1 kb DNA fragment (gBlock from IDT); (ii) a plasmid containing said PCR product; and (iii) a single stranded DNA oligonucleotide containing the key elements described above. The sequence of said oligonucleotide is specified in FIG. 11.

After assembling the three homology templates, HAP1 cells were transfected with combinations of Cas9, guide RNA and homology template using Turbofectin. A plasmid expressing a blasticidin resistance gene was co-transfected. Untransfected cells were eliminated by treatment of the cells with 20 µg/ml for 24 h.

Pools of transfected cells containing various editing events were harvested a week after transfection. Genomic DNA was isolated using the QIAamp DNA Mini Kit (Qiagen). The EGFR locus under consideration was amplified by PCR using primers that anneal outside of the homology (EGFR fwd TCAGAGAGTCCAAGAAAGCACA (SEQ ID 96), EGFR bwd GAGCCAGTGAAGGGAGAGAA (SEQ ID 97)). This strategy was meant to avoid the amplification of template sequences that might otherwise spoil the outcome of the PCR. PCR products were then subjected to restriction digest with SpeI or Hind III and the products of this reaction were analyzed by gel electrophoresis (FIG. 12).

The agarose gel shows the occurrence of characteristic bands at a molecular weight of ~500 bp, likely arising from cells in which homologous recombination and thus replacement of the wild-type allele had occurred. Of note, this band was only seen in conditions where the restriction enzyme (SpeI or HindIII) had been applied and not in the control conditions. In addition, the band was only detectable in the conditions where PCR products or plasmids were used as homology templates, but not with single-stranded DNA oligonucleotide. This may indicate that HR is more efficiently induced using PCR products or plasmids as homology templates, most likely, because they are double-stranded and the region of homology is longer.

24 clones were isolated, each from the conditions in which the PCR product or the plasmid had been used as templates. These clones were obtained by limiting dilution, plating transfected HAP1 cells at a concentration of ~20 cells/ml. Individual clones were expanded and subject to genomic DNA isolation, using Direct PCR Lysis Reagent (PeqLab). Following genomic DNA isolation, the EGFR locus was amplified with the primer specified above and subjected the PCR products to restriction digest (FIG. 13).

It was surprising that clones were recovered bearing the newly introduced restriction sites in three conditions. In one conditions (guide RNA 1+plasmid donor), 1 out of 23 clones contained the restriction site. In another condition (guide RNA 2+ plasmid donor), 2 out of 24 clones contained the restriction site. In the last condition (guide RNA 2+ PCR product), 1 out of 23 clones contained the restriction site. In all three cases, mutant clones showed no presence of the wild-type allele (as indicated by a residual band that is refractory to SpeI digestion). This shows that the wild-type copy had effectively been replaced with the version introduced via the donor template.

In the last series of experiments, it was confirmed that the Leu858Arg mutation was really present. While this was likely as inferred from the pattern seen in FIG. 13, it could not be formally concluded that the Leu858Arg was retained in addition the SpeI restriction sites. To unequivocally make that statement, the PCR from genomic DNA was repeated and the resulting PCR products were submitted for Sanger sequencing (FIG. 14).

All four clones contained both the newly introduced restriction site (ACTAGT [SEQ ID 138], cleavable by SpeI) and the Leu858Arg mutation (CGG codon highlighted in red). While clone 8-5 was otherwise identical to the sequence expected from the reference genome, additional mutations were noted in the clones. One of them (isolated G highlighted in pink) was seen in three clones. When consulting the SNP database, a small nucleotide polymorphism was noted at that position (dbSNP build 138 rs6970262). So presumably, in some of the clones (e.g. clone 8-5), the homology template was almost completely integrated, while in others (e.g. clones 3-5, 7-12 and 8-10), only parts of it were integrated, leaving the SNP that is naturally present in HAP1 unaffected.

Two additional mutations were noted in clones 3-5 and 7-12, both of which occurred within the guide RNA sequences. These are likely to have arisen from a second Cas9 cleavage event that was subsequently repaired by non-homologous end joining.

In summary, a compelling example is provided to demonstrate that single nucleotide exchanges can be engineered in haploid human cells with unprecedented efficiency and precision.

Discussion

A method is presented that allows the introduction of point mutations into HAP1 cells with surprising efficiency. Clones bearing mutations were recovered at very high frequencies ranging from 1 in 22 (~5%) to 2 in 21 (~10%). This is surprising and non-obvious, given frequencies that were reported previously.

It is noted that some of the clones that were isolated contained additional insertions or deletions (indels) near the guide RNA target site. These additional mutations most likely arose from a second Cas9 cleavage event, followed non-homologous end joining. The resulting indels are problematic at least for some applications of these cells because they may disrupt the open reading frame of the EGFR. In order to prevent re-cleavage of the EGFR locus following insertion of the HR template, a template can be used in which the guide RNA target site has been mutated. The most efficient mutation would lie in the protospacer adjacent motif (PAM) of the corresponding guide RNA(s) because integrity of this motif is strictly required for Cas9 cleavage.

Example 4: Introducing Point Mutations

Cancer is caused by the acquisition of genetic changes that confer a growth advantage for the cells in which they have occurred. In recent years, there has been a large effort to identify recurring cancer mutations through large sequencing projects of tumors and cancer cell lines. The identification of the genes that are mutated in different cancers can help further the understanding of how to detect, diagnose and treat cancers. By modeling these mutations in a cell line, researchers can study the particular effects each mutation has on the cell to underpin the molecular events that contribute to pathogenesis.

As stated in Example 3, a cell line bearing a point mutation in the EGFR that occurs frequently in lung and breast cancers was successfully engineered. In order to extend these results and show that similar results can be obtained for other human genes, it is here demonstrated how CRISPR/Cas9 mediated homologous recombination was used to engineer point mutations in three kinases commonly found mutated in a variety of cancers. The selected point mutations are shown in Table 8.

TABLE 8

Point mutations

| Gene | Amino acid mutation | cDNA mutation |
|---|---|---|
| EGFR | p.T790M | c.2369C > T |
| KIT | p.D816V | c.2447A > T |
| JAK2 | p.V617F | c.1848_1849TG > CT |

To be able to introduce specific mutations by homology-directed repair (HDR), an appropriate homology donor template is needed, along with the Cas9 endonuclease and a suitable guide RNA.

For each mutation, a set of two guide RNAs was designed in relative proximity to the mutation that was to be engineered. A summary of these is shown in Table 9.

TABLE 9

Guide RNA sequences

| Gene and mutation | Guide RNA 1 | Guide RNA 2 |
|---|---|---|
| EGFR T790M | AGCCTACGTGATGGCCAGCGG<br>SEQ ID 139 | CCCAGCAGGCGGCACACGT<br>SEQ ID 140 |
| JAK2 V617F | ACGAGAGTAAGTAAAACTAC<br>SEQ ID 141 | AAAAACAGATGCTCTGAGAA<br>SEQ ID 142 |
| KIT D816V | ATATCCTCCTTACTCATGGTA<br>SEQ ID 143 | GAATCATTCTTGATGTCTC<br>SEQ ID 144 |

The Cas9 endonuclease has two catalytic domains which each cleave one strand of DNA, resulting in a double strand break. Reports from literature have suggested that using a nickase mutant of the Cas9 endonuclease, which has a mutation in one of the two catalytic domains, together with a pair of guide RNAs in close proximity, may increase specificity. To test if this was true in our experimental set-up, the EGFR T790 mutation was engineered using either Cas9 wild-type with a single guide RNA or Cas9 nickase (D10A) with paired guide RNAs.

The donor templates were 1 kb in length, with 500 base pair homology arms on each side of the mutation to be introduced. In addition, several other silent mutations (mutations that do not affect the resulting protein sequence) were included. First, a restriction site that is not naturally present in the genomic sequence was designed for diagnostic purposes. Second, the protospacer adjacent motif (PAM) which is critical for Cas9 cleavage was disrupted in the donor template. This was done to prevent re-cleavage of the locus following insertion of the donor template. The sequences of the three donor templates are included in FIG. 15.

For EGFR T790M, the donor template was provided in two forms (i) as a PCR product, obtained from a synthetic 1 kb DNA fragment (gBlock from IDT) or (ii) a plasmid containing said PCR product. For Jak2 V617F and Kit D816V a PCR product obtained from a synthetic 1 kb DNA fragment (gBlock from IDT) was used as the homology donor template.

To generate the point mutations, HAP1 cells were transfected with Cas9 or Cas9 nickase, guide RNA and donor template using Turbofectin (Origene). A description of the various conditions tested is found in Table 10. A plasmid expressing a blasticidin resistance gene was co-transfected.

24 hours post-transfection, cells were selected with 20 µg/ml blasticidin for 24 hours, in order to eliminate untransfected cells. Then, cells were allowed to recover from the blasticidin treatment for 3-4 days.

TABLE 10

Transfection conditions

| Gene and mutation | Cas9 enzyme | Donor template | Guide RNAs |
|---|---|---|---|
| EGFR T790M | Nickase | PCR product | Guide RNA 1 |
| | | | Guide RNA 2 |
| EGFR T790M | Nickase | Plasmid | Guide RNA 1 |
| | | | Guide RNA 2 |
| JAK2 V617F | Wild-type | PCR product | Guide RNA 1 |
| KIT D816V | Wild-type | PCR product | Guide RNA 2 |

Next, single cell clones were established by limiting dilution. To this end, cells were trypsinized and serially diluted to a concentration of 15 cells per ml. 50 µl of this suspension were seeded in each well of a 384-well plate. Individual wells were inspected by microscopy to exclude polyclonal cell lines. Approximately 24 monoclonal cell lines were expanded to 96-well plates. One replicate plate was frozen in freezing medium containing 20% FCS and 10% DMSO. The other replicate plate was used to isolate genomic DNA.

Genomic DNA was isolated using the Direct PCR-Cell Reagent (PeqLab) according to manufacturer's instructions. In brief, cells were washed twice with 100 µl PBS per well. After removal of PBS, 100 µl of Direct PCR-Cell Reagent and 2 µl Proteinase K (20 mg/ml stock) were added to each well. Plates were sealed and incubated at 56° C. for 2 h, followed by the incubation at 80° C. for 45 minutes.

The edited loci were then amplified by PCR using primers that anneal outside of the homology donor template. This way, residual homology donor template that may contaminate the genomic DNA sample would not confound the sequencing results. The primer sequences used are listed in Table 11.

TABLE 11

Primer sequences for PCR to confirm editing

| Gene and mutation | Forward Primer | Reverse Primer |
|---|---|---|
| EGFR T790M | TGATGTGCAGGGT<br>CAGTCAT<br>SEQ ID 145 | CTCCTTGCACCT<br>CCTCACTG<br>SEQ ID 146 |
| JAK2 V617F | CCCAGGGGTTCTA<br>GTCACAG<br>SEQ ID 147 | GGTGCAATAAAATGA<br>GGCATGC<br>SEQ ID 148 |
| KIT D816V | ACCTTCTTCCGT<br>GTGTCCTT<br>SEQ ID 149 | TGGCAAGGAAAT<br>ACAGCACT<br>SEQ ID 150 |

PCR products were visualized by agarose gel electrophoresis (data not shown) and sent for Sanger sequencing using the sequencing primers shown in Table 12.

TABLE 12

Sequencing Primers

| Gene and mutation | Sequencing Forward Primer | Sequencing Reverse Primer |
|---|---|---|
| EGFR T790M | CCGGACCCCACACAGATT SEQ ID 151 | ATCACCTGGGTCCTCCTG SEQ ID 152 |
| JAK2 V617F | GCAAGTGTTATTTAAAGGC TACATCC SEQ ID 153 | GCATGGGGTACGATTTATACT SEQ ID 154 |
| KIT D816V | GGACATTCAAAGAGATGCA TGC SEQ ID 155 | AGCTCTCCGTGTATTCTAGGA SEQ ID 156 |

Sequencing results were analyzed and showed that every condition yielded at least one clone with the desired mutations. Sequences of all clones bearing the desired point mutation are compiled in FIG. 16.

For EGFR T790M, where the Cas9 nickase together with two guide RNAs was used, both homology donor template conditions (PCR product and plasmid) yielded one positive clone each out of the 24. For JAK2 V617F, one positive clone out of 24 was also obtained. For KIT D816V, the overall efficiency was significantly higher and four positive clones out of 24 were obtained.

In summary, these examples demonstrate that single nucleotide exchanges at a variety of loci can be engineered in haploid human cells with unprecedented efficiency and precision.

Here, the method previously presented in the previous Examples is further expanded to show that point mutations can be engineered in HAP1 cells at several different loci. This further strengthens the conclusion that HAP1 cells are highly amenable to genome engineering and ideally suited for the generation of point mutations. Clones bearing mutations were recovered at very high frequencies ranging from 1 in 24 (~4%) to 4 in 24 (~16%). This is a very high efficiency compared to previously reported results, in particular with the KIT D816V configuration where 16% of correctly edited clones were recovered.

The reason for this high recovery rate may be due to the guide RNA positioning with respect to the introduced point mutation. For KIT D816V the mutation was within the guide RNA sequence, while for Jak2 V617F and EGFR T790M, the guide RNA was located before and after the point mutation, respectively. Based on these results, while it is possible to recover positive clones with all three strategies, it is concluded that having the guide RNA overlap with the introduced mutation may significantly enhance the efficiency of genome editing.

Intriguingly, there were two clones (JAK2_V617F_c778 and KIT_D816V_c769) where some of the additional silent mutations that were present on the homology donor template were not integrated. In both cases these silent mutations were located further away from the cleavage site than the point mutation, which was correctly incorporated. This further highlights the importance of proximity between the engineered mutations and the guide RNA location and suggests an ideal distance between guide RNA and mutation of <80 bp.

In the configuration with EGFR T790M, the use of a Cas9 nickase together with a pair of guide RNAs was tested. With both types of homology donor templates provided, plasmid and PCR product, correctly edited clones recovered. This shows that both the Cas9 nickase and wild-type Cas9 can be used for efficient homology directed repair in HAP1 cells.

Example 5: Advantages of Haploid Cells for Genome Engineering

Although the CRISPR/Cas technology only recently emerged, it has already revolutionized molecular biology research. While generally feasible in diploid cells, many aspects of the technology make it cumbersome and unpredictable in diploid cells:

Unclear Ploidy Status of Cells Complicates Experiments in Commonly used Cell Lines Most of the human cell lines that are commonly used in the molecular biology laboratories are either karyotypically unstable (such as HeLa cells) or they are not diploid (such as A549 that are near-triploid). The notable exception is HCT116, which is known to be stably diploid and has therefore been considered a good substrate for genome engineering in human cells. FIG. 18 shows various human cell lines that are commonly used. As seen in this figure, many of these cell lines are trisomic, tetrasomic or polysomic for many human chromosomes. In the instance where such information is publically available, it can be taken into consideration when planning a genome engineering experiment. However, for many human cell lines, this information is not available or it is unclear whether a particular sub-clone of a cell line has the karyotype described in the literature. Uncertainty about the karyotype is a variable that represents a huge complication for genome editing because the ploidy status is a clear determinant of the success rate as discussed below.

Homozygous Mutants are Hard to Obtain in Diploid or Polyploid Cell Lines

In diploid cells, most genes reveal their loss-of-function phenotype only if both alleles are inactivated in the same cell (homozygous mutation). In contrast, gene function is usually maintained in cells that are heterozygous for a particular mutation because one remaining wild-type allele is usually sufficient to maintain function. To engineer cell lines bearing homozygous mutations is more challenging in diploid than in haploid cells because in haploid cells, a single editing event is sufficient to completely inactivate gene function in these cells. For frameshift mutations that are engineered by Cas9 cleavage, followed by spontaneous non-homologous end joining, the advantage of haploid cells is already considerable. However, the benefit of haploid cells is even more pronounced with regard to genome engineering approaches whose overall efficiency is very low, such as the introduction of point mutations or tagged alleles by the means of homology-directed repair. If, for instance, the chance of obtaining one edited allele is 1%, the chance of obtaining a diploid cell line with two edited alleles corresponds to 1%*1%=0.01%.

Essentiality of Given Genes is Hard to Predict in Diploid or Polyploid Cell Lines A sub-set of the human genome is strictly required for viability of human cells and this gene set is referred to as essential. While some genes are essential in all cells (e.g. ribosomal genes), others are only essential in certain cell types and not in others. Knowledge on essentiality is a key piece of information for genome engineering because essentiality precludes the successful completion of a gene knock-out project. Essentiality of human genes can be predicted from studies in model organisms (such as yeast or mice), but such predictions are not very reliable. There is a unique experimental dataset that lists all genes that are essential in HAP1 or KBM-7 cells. The dataset is based on a large-scale gene trap experiment, in which the fraction of the genome was determined that does not carry active gene traps. This fraction is synonymous with the essential gene set because its inactivation is incompatible with cell growth and proliferation. Such a dataset cannot be gathered in any non-haploid cell type because gene trap mutagenesis will not cause complete gene inactivation.

Genotyping is Complicated in Diploid or Polyploid Cell Lines

CRISPR/Cas allows the targeted introduction of a DNA double-strand break. In diploid cells, both alleles might break, but because the repair is mediated by non-homologous end joining, the two alleles may carry different mutations. In that case, the genotyping of these cell lines (i.e. the determination which mutations are present on each of the two alleles) is very complicated.

To illustrate this, a haploid HAP1 cell clone and a diploid HAP1 cell clone that arose from an experiment in which HAP1 cells were transfected with Cas9, were taken along with a guide RNA targeting the gene OTUD1 (guide RNA sequence: GCTGTCAGCAAGACGGTGTA (SEQ ID 157)). Ploidy of clones 904-8 and 904-10 that were derived from the same experiment was assessed by propidium iodide staining, followed by flow cytometry analysis.

FIG. 18 shows that clone 904-10 shows two peaks at ~200 and ~400, respectively, while clone 904-08 shows two peaks at ~400 and ~800, respectively. Based on controls that are not shown here, it can be concluded that clone 904-10 is haploid, while clone 904-08 is diploid.

To genotype the mutation that had occurred in these clones, the region around the guide RNA target site was amplified by PCR using the following primers:

```
Forward primer:
                                       (SEQ ID 158)
AGCCGGTGATCGTCTCCA Reverse primer:
                                       (SEQ ID 159)
CAAATACAGCATCATAGTGTCCGTT
```

The PCR products obtained from both clones were purified and sent for Sanger sequencing using the reverse primer. The result of the sequencing reaction is shown in FIGS. 18C and 18D. In haploid cells, the sequence of the single edited allele can be clearly inferred from the Sanger sequencing chromatogram. In diploid cells, however, the two alleles seem to carry different mutations. As a consequence, the Sanger sequencing chromatogram can be read up the Cas9-induced breakpoint (marked by the star), but it collapses after this breakpoint because the two sequences from the two alleles cannot be resolved. As a consequence, it is not possible to infer the two mutations from the sequencing chromatogram. To resolve these, one would have to clone PCR products into a vector and sequence individual clones. This is possible, but very cumbersome, especially because this would usually have to be done for multiple clones (at least 10, may be 20 clones).

In contrast, in haploid cells, as illustrated above, there is no ambiguity and the editing event can be clearly traced by a straightforward PCR, coupled to Sanger sequencing.

Example 6: Diploidization of Adherent Somatic Haploid Cells

Haploid human cells have a natural tendency to convert to the diploid state. Haploid cells are thus herein considered a "metastable" state that ultimately converts to the stable diploid state. In this experiment, this conversion is performed in a controlled way and triggered by suboptimal cell culture conditions, e.g. if cells are not passaged and supplied with fresh medium in regular intervals. Cellular stress would promote the diploidization of haploid somatic human cell lines, in particular when applied to adherent cells.

Following exposure to stress as induced by continued passage, e.g. following at least 25 numbers of passaging, single cell clones were isolated by limiting dilutions. To this end, a population of cells containing haploid and diploid subclones were trypsinized and diluted to ~20 cells per milliliter. Cells were then seeded in 384 well plates ("limiting dilution") and were allowed to grow for 14 days. Single wells were visually inspected to make sure that single cell clones were retrieved.

Single clones were expanded from 384 well plates to 6 well plates. Individual clones were stained by propidium iodide staining. To this end, HAP1 cells were harvested by trypsinization and washed twice with PBS. Cells were simultaneously lysed and stained using Nicoletti buffer (0.1% sodium citrate, 0.1% Triton X-100, 0.5 U/ml RNase A, 20 U/ml RNase T1, 50 µg/ml propidium iodide). Haploid and diploid reference cell lines were included as controls. Propidium iodide staining was quantified by flow cytometry.

A representative result is shown in FIG. 19. Clones 1, 3 and 6 are haploid and display a major (1N) peak at a fluorescence intensity of ~190 and a minor (2N) peak at a fluorescence intensity of ~380. The latter arises from haploid cells that duplicated their genome in S phase and are about to undergo mitosis. Clones 2, 4 and 5 are diploid and display a major (2N) peak at a fluorescence intensity of ~380 and a minor (4N) peak at a fluorescence intensity of ~760. So in summary, haploid and diploid clones can be clearly separated and identified by propidium iodide staining and analytical FACS.

To generate a homogenous sub-population of diploid clones and avoid clonal artefacts, several diploid clones were pooled to obtain a polyclonal population of diploid cells. In contrast to the parental population of haploid HAP1 cells, this population is no longer meta-stable, but stably maintains its diploid or near-diploid karyotype. This population can be distinguished from the original haploid population by propidium iodide staining (FIG. 20). Haploid HAP1 and KBM-7 cells (FIGS. 20A and 20B) are nicely haploid with major peaks at a fluorescence intensity of ~220 (1N) and ~440 (2N). In contrast, the peaks for diploid KBM-7 cells and the cell line C665 are shifted by ~2 fold (FIGS. 20C and 20D), indicating that it is diploid or near-diploid.

C665 was also characterized by spectral karyotyping (FIG. 21). Panels A, B and C show various sub-clones that are present in the population of C665. Some clones in the population are perfectly near-diploid, i.e. they have two copies of each chromosome that is present in haploid HAP1 cells in a single copy (FIG. 21C). Other clones contain minor chromosomal aberrations, such as a trisomy of chromosome 8 (FIG. 21B) or a translocation of a portion of chromosome 8 to chromosome 10 (FIG. 21A). Altogether, the spectral karyotyping data show that near-haploid HAP1 cells can be converted to near-diploid cells.

The population of cells derived from such an experiment is unique because it is diploid or near-diploid and contains two identical sets of sister chromosomes. In contrast, naturally-occurring diploid cells contain one chromosome set from the father and one chromosome set from the mother that differ with regards to certain small nucleotide polymorphisms (SNPs). Diploid cells derived from haploid cells are distinct from naturally diploid cells inasmuch as the two genome copies originated from the same haploid copy and thus, there are no heterozygous SNPs.

REFERENCES

[1] Terns M P and Terns R M. CRISPR-Based Adaptive Immune Systems. Curr Opin Microbiol. 2011 June; 14(3): 321-327. doi:10.1016/j.mib.2011.03.005.

[2] Jinek M, Chylinski K, Fonfara I, Hauer M, Doudna J A, Charpentier E. A programmable dual-RNA-guided DNA endonuclease in adaptive bacterial immunity. Science. 2012 Aug. 17; 337(6096):816-21. doi: 10.1126/science.1225829. Epub 2012 Jun. 28.

[3] Mali P, Yang L, Esvelt K M, Aach J, Guell M, DiCarlo J E, Norville J E, Church G M. RNA-guided human genome engineering via Cas9. Science. 2013 Feb. 15; 339(6121): 823-6. doi: 10.1126/science.1232033. Epub 2013 Jan. 3.

[4] Gong L, Ran F A, Cox D, Lin S, Barretto R, Habib N, Hsu P D, Wu X, Jiang W, Marraffini L A, Zhang F. Multiplex genome engineering using CRISPR/Cas systems. Science. 2013 Feb. 15; 339(6121):819-23. doi: 10.1126/science.1231143. Epub 2013 Jan. 3.

[5] Hwang W Y, Fu Y, Reyon D, Maeder M L, Tsai S Q, Sander J D, Peterson R T, Yeh J R, Joung J K. Efficient genome editing in zebrafish using a CRISPR-Cas system. Nat Biotechnol. 2013 March; 31(3):227-9. doi: 10.1038/nbt.2501. Epub 2013 Jan. 29.

[6] Gratz S J, Cummings A M, Nguyen J N, Hamm D C, Donohue L K, Harrison M M, Wildonger J, O'Connor-Giles K M. Genome engineering of Drosophila with the CRISPR RNA-guided Cas9 nuclease. Genetics. 2013 August; 194(4): 1029-35. doi: 10.1534/genetics.113.152710. Epub 2013 May 24.

[7] DiCarlo J E, Norville J E, Mali P, Rios X, Aach J, Church G M. Genome engineering in Saccharomyces cerevisiae using CRISPR-Cas systems. Nucleic Acids Res. 2013 April; 41(7):4336-43. doi: 10.1093/nar/gkt135. Epub 2013 Mar. 4.

[8] Ran F A, Hsu P D, Lin C Y, Gootenberg J S, Konermann S, Trevino A E, Scott D A, Inoue A, Matoba S, Zhang Y, Zhang F. Double nicking by RNA-guided CRISPR Cas9 for enhanced genome editing specificity. Cell. 2013 Sep. 12; 154(6):1380-9. doi: 10.1016/j.cell.2013.08.021. Epub 2013 Aug. 29.

[9] Mali P, Aach J, Stranges P B, Esvelt K M, Moosburner M, Kosuri S, Yang L, Church G M. CAS9 transcriptional activators for target specificity screening and paired nickases for cooperative genome engineering. Nat Biotechnol. 2013 September; 31(9):833-8. doi: 10.1038/nbt.2675. Epub 2013 Aug. 1.

[10] Esvelt K M, Mali P, Braff J L, Moosburner M, Yaung S J, Church G M. Orthogonal Cas9 proteins for RNA-guided gene regulation and editing. Nat Methods. 2013 November; 10(11):1116-21. doi: 10.1038/nmeth.2681. Epub 2013 Sep. 29.

[11] Hou Z, Zhang Y, Propson N E, Howden S E, Chu L F, Sontheimer E J, Thomson J A. Efficient genome engineering in human pluripotent stem cells using Cas9 from Neisseria meningitidis. Proc Natl Acad Sci USA. 2013 Sep. 24; 110(39):15644-9. doi: 10.1073/pnas.1313587110. Epub 2013 Aug. 12.

[12] Burckstummer T, Banning C, Hainzl P, Schobesberger R, Kerzendorfer C, Pauler F M, Chen D, Them N, Schischlik F, Rebsamen M, Smida M, de la Cruz F F, Lapao A, Liszt M, Eizinger B, Guenzl P M, Blomen V A, Konopka T, Gapp B, Parapatics K, Maier B, Stöckl J, Fischl W, Salic S, Taba Casari M R, Knapp S, Bennett K L, Bock C, Colinge J, Kralovics R, Ammerer G, Casari G, Brummelkamp T R, Superti-Furga G, Nijman S M. A reversible gene trap collection empowers haploid genetics in human cells. Nat Methods. 2013 October; 10(10):965-71. doi: 10.1038/nmeth.2609. Epub 2013 Aug. 25.

[13] Jae L T, Raaben M, Riemersma M, van Beusekom E, Blomen V A, Velds A, Kerkhoven R M, Carette J E, Topaloglu H, Meinecke P, Wessels M W, Lefeber D J, Whelan S P, van Bokhoven H, Brummelkamp T R. Deciphering the glycosylome of dystroglycanopathies using haploid screens for lassa virus entry. Science. 2013 Apr. 26; 340(6131):479-83. doi: 10.1126/science.1233675. Epub 2013 Mar. 21.

[14] Carette J E, Raaben M, Wong A C, Herbert A S, Obernosterer G, Mulherkar N, Kuehne A I, Kranzusch P J, Griffin A M, Ruthel G, Dal Cin P, Dye J M, Whelan S P, Chandran K, Brummelkamp T R. Ebola virus entry requires the cholesterol transporter Niemann-Pick C I. Nature. 2011 Aug. 24; 477(7364):340-3. doi: 10.1038/nature10348.

[15] Ran F Ann et al. Nature Protocols 2013, 8(11):2281-2308.

[16] Donner A. Science-Business Exchange 2013, 6(27).

[17] Wei C. et al., J. Genetics Genomics 2013, 40(6):281-289.

[18] Cong, L., Ran, F. A., Cox, D., Lin, S., Barretto, R., Habib, N., et al (2013). Multiplex Genome Engineering Using CRISPR/Cas Systems. Science, 339(6121), 819-823. doi:10.1126/science.1231143.

[19] Inui, M., Miyado, M., Igarashi, M., Tamano, M., Kubo, A., Yamashita, S., et al (2014). Rapid generation of mouse models with defined point mutations by the CRISPR/Cas9 system Scientific Reports, 4, 5396. doi:10.1038/srep05396.

[20] Thompson S L, Compton D A. 2008. Examining the link between chromosomal instability and aneuploidy in human cells. J Cell Biol.; 180(4):665-72.

The invention claimed is:

1. A method of producing a mutant somatic human cell line of cells comprising a genomic mutation of interest (MOI) at a predefined genomic site of interest (GOI) in close proximity to a genomic target site, the method comprising:
   a) providing a guide RNA (gRNA) comprising a tracr-RNA in conjunction with crRNA including an oligonucleotide sequence that hybridizes with the target site;
   b) providing an RNA-guided endonuclease which catalyzes a DNA break at the target site upon hybridizing with the gRNA;
   c) introducing the gRNA into near-haploid or fully haploid cells in the presence of the endonuclease to obtain a repertoire of cells comprising a variety of genomic mutations at the target site;
   d) selecting a cell from said repertoire which comprises the MOI, wherein the selected cell is a near-haploid or fully haploid cell; and
   e) expanding the selected near-haploid or fully haploid cell to obtain the mutant cell line;
   wherein the selected near-haploid or fully haploid cell, the mutant cell line, or both, are adherent.

2. The method of claim 1, wherein the MOI is at least one of
   (i) a mutation knocking out a function of a gene;
   (ii) a mutation introducing at least one of a deletion, substitution, or insertion of one or more nucleotides; or
   (iii) a mutation introducing an exchange sequence of a homology template.

3. The method of claim 1, wherein
   in step c), an expression plasmid incorporating a nucleic acid sequence to express the gRNA is used to transform the cells and to obtain a repertoire of transformant cells comprising the variety of genomic mutations at the target site; and
   in step d), the selected near haploid or fully haploid cell is a transformant cell.

4. The method of claim 1, wherein the selected cell is a fully haploid cell.

5. The method of claim 1, wherein the gRNA comprises a sequence selected from the group consisting of SEQ ID 3, SEQ ID 13, SEQ ID 19, and any of SEQ ID 24-47.

6. The method of claim 1, wherein the endonuclease is selected from the group consisting of CAS9 enzymes originating from any of *Streptococcus pyogenes, Streptococcus thermophiles, Neisseria Meningitis* or *Treponema Denticola*, or Cas9 nickases or artificial enzymes.

7. The method of claim 1, wherein
   A:
   the gRNA comprises a nucleotide sequence chosen from SEQ ID 3, SEQ ID 25, or SEQ ID 26; and
   the endonuclease comprises an amino acid sequence chosen from SEQ ID 1, SEQ ID 5, SEQ ID 7, SEQ ID 8, or SEQ ID 9; or
   B:
   the gRNA comprises a nucleotide sequence chosen from SEQ ID 13, one of SEQ IDs 27-40; and
   the endonuclease comprises an amino acid sequence chosen from SEQ ID 10 or SEQ ID 15; or
   C:
   the gRNA comprises a nucleotide sequence chosen from SEQ ID 19, one of SEQ IDs 41-47; and
   the endonuclease comprises an amino acid sequence chosen from SEQ ID 16 or SEQ ID 21.

8. The method of claim 1, wherein the near-haploid or fully haploid cells of step c) are engineered to express at least one of a Cas9 endonuclease or the gRNA.

9. The method of claim 1, wherein the DNA break is a double strand break or a paired single strand break proximal to a protospacer associated motif (PAM), and the genomic mutation is obtained by homology-directed repair or by non-homologous end-joining.

10. The method of claim 1, wherein the MOI is obtained by cellular repair mechanisms induced by the DNA break.

11. The method of claim 1, wherein the MO1 comprises a mutation introducing an exchange sequence of a homology template, and the homology template is
    a) an oligonucleotide of 20-200 bp length;
    b) a PCR product of 20-5000 bp length; or
    c) any of a) or b) comprised in a donor plasmid.

12. The method of claim 11, wherein the exchange sequence is embedded into a recombining sequence, overlapping with a recombining sequence, or flanked by one or more recombining sequences.

13. The method of claim 11, wherein the exchange sequence has a sequence homology of at least 95% to the GOI.

14. The method of claim 11, wherein the homology template comprises a photospacer associated motif (PAM).

15. The method of claim 1, further comprising cultivating the mutant cell line by asexually replicating the chromosomes within the cells of the mutant cell line, thereby obtaining a population of individual cells, and upon determination of a karyotype of individual cells, selecting a diploid cell, and further expanding the diploid cell to obtain a mutant cell line comprising a diploid karyotype.

16. The method of claim 1, wherein a library of mutant human somatic cell lines of isogenic cells with a variety of genomic mutations at different predefined genomic target sites is produced.

17. The method of claim 4, wherein the selected fully haploid cell is of the HAP2 cell line deposited under DSM ACC3220.

18. The method of claim 9, wherein the DNA break is 3 bp upstream of the PAM.

19. The method of claim 10, wherein the cellular repair mechanisms include introducing at least one of a frameshift mutation, insertion, substitution, or deletion of one or more nucleotides, or a combination thereof.

20. The method of claim 12, wherein the exchange sequence is flanked by recombining sequences at the 5'-end and the 3'-end of the exchange sequence, the recombining sequence being capable of homologous recombination with the GOI.

21. The method of claim 13 wherein the exchange sequence comprises one or more point mutations, or a modified DNA region causing at least one of a different DNA expression or a different phenotype.

22. The method of claim 14, wherein the PAM is mutated to prevent cleavage and repair of the DNA break by non-homologous end joining.

23. A method of producing a mutant somatic human cell line of cells comprising a genomic mutation of interest (MOI) at a predefined genomic site of interest (GOI) in close proximity to a genomic target site, the method comprising:
- providing a guide RNA (gRNA) comprising a sequence selected from the group consisting of SEQ ID 3, SEQ ID 13, SEQ ID 19, SEQ ID 24-47, or a homolog of an aforementioned gRNA sequence having at least 90% degree of homology, that hybridizes with the target site;
- providing an RNA-guided endonuclease which catalyzes a DNA break at the target site upon hybridizing with the gRNA comprising a sequence selected from the group consisting of SEQ ID 1, SEQ ID 5, SEQ ID 7-10, SEQ ID 15, SEQ ID 16, SEQ ID 21, or a homolog of an aforementioned endonuclease sequence having at least 90% degree of homology;
- introducing the gRNA into fully haploid cells in the presence of the endonuclease to obtain a repertoire of cells comprising a variety of genomic mutations at the target site;
- selecting a cell from said repertoire which comprises the MOI, wherein the selected cell is a fully haploid cell; and
- expanding the selected fully haploid cell to obtain the mutant cell line.

* * * * *

SEQUENCE LISTING

<160> NUMBER OF SEQ ID NOS: 159

<210> SEQ ID NO 1
<211> LENGTH: 1368
<212> TYPE: PRT
<213> ORGANISM: Streptococcus pyogenes

<400> SEQUENCE: 1

Met Asp Lys Lys Tyr Ser Ile Gly Leu Asp Ile Gly Thr Asn Ser Val
1               5                   10                  15

```
Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Tyr Thr Arg Arg Lys Asn Arg Ile Cys
65              70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430
```

-continued

```
Leu Lys Asp Asn Arg Glu Lys Ile Glu Lys Ile Leu Thr Phe Arg Ile
            435                 440                 445
Pro Tyr Tyr Val Gly Pro Leu Ala Arg Gly Asn Ser Arg Phe Ala Trp
            450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
                580                 585                 590
Thr Tyr His Asp Leu Leu Lys Ile Ile Lys Asp Lys Asp Phe Leu Asp
            595                 600                 605
Asn Glu Glu Asn Glu Asp Ile Leu Glu Asp Ile Val Leu Thr Leu Thr
            610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
                660                 665                 670
Lys Gln Ser Gly Lys Thr Ile Leu Asp Phe Leu Lys Ser Asp Gly Phe
            675                 680                 685
Ala Asn Arg Asn Phe Met Gln Leu Ile His Asp Asp Ser Leu Thr Phe
            690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
                740                 745                 750
Arg His Lys Pro Glu Asn Ile Val Ile Glu Met Ala Arg Glu Asn Gln
            755                 760                 765
Thr Thr Gln Lys Gly Gln Lys Asn Ser Arg Glu Arg Met Lys Arg Ile
            770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
                820                 825                 830
Leu Ser Asp Tyr Asp Val Asp His Ile Val Pro Gln Ser Phe Leu Lys
            835                 840                 845
Asp Asp Ser Ile Asp Asn Lys Val Leu Thr Arg Ser Asp Lys Asn Arg
```

```
             850                 855                 860
Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Glu Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260
```

| His | Tyr | Leu | Asp | Glu | Ile | Ile | Glu | Gln | Ile | Ser | Glu | Phe | Ser | Lys |
|     | 1265 |     |     |     | 1270 |     |     |     |     | 1275 |     |     |     |     |

| Arg | Val | Ile | Leu | Ala | Asp | Ala | Asn | Leu | Asp | Lys | Val | Leu | Ser | Ala |
|     | 1280 |     |     |     |     | 1285 |     |     |     |     | 1290 |     |     |     |

| Tyr | Asn | Lys | His | Arg | Asp | Lys | Pro | Ile | Arg | Glu | Gln | Ala | Glu | Asn |
|     | 1295 |     |     |     |     | 1300 |     |     |     |     | 1305 |     |     |     |

| Ile | Ile | His | Leu | Phe | Thr | Leu | Thr | Asn | Leu | Gly | Ala | Pro | Ala | Ala |
|     | 1310 |     |     |     |     | 1315 |     |     |     |     | 1320 |     |     |     |

| Phe | Lys | Tyr | Phe | Asp | Thr | Thr | Ile | Asp | Arg | Lys | Arg | Tyr | Thr | Ser |
|     | 1325 |     |     |     |     | 1330 |     |     |     |     | 1335 |     |     |     |

| Thr | Lys | Glu | Val | Leu | Asp | Ala | Thr | Leu | Ile | His | Gln | Ser | Ile | Thr |
|     | 1340 |     |     |     |     | 1345 |     |     |     |     | 1350 |     |     |     |

| Gly | Leu | Tyr | Glu | Thr | Arg | Ile | Asp | Leu | Ser | Gln | Leu | Gly | Gly | Asp |
|     | 1355 |     |     |     |     | 1360 |     |     |     |     | 1365 |     |     |     |

<210> SEQ ID NO 2
<211> LENGTH: 3
<212> TYPE: DNA
<213> ORGANISM: Artificial Sequence
<220> FEATURE:
<223> OTHER INFORMATION: Motif
<220> FEATURE:
<221> NAME/KEY: misc_feature
<222> LOCATION: (1)..(1)
<223> OTHER INFORMATION: wherein N is any of T, C, A or G

<400> SEQUENCE: 2 ngg                                                                   3

<210> SEQ ID NO 3
<211> LENGTH: 96
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the U, C, A or G

<400> SEQUENCE: 3
nnnnnnnnnn nnnnnnnnnn guuuuagagc uagaaauagc aaguuaaaau aaggcuaguc      60
cguuaucaac uugaaaaagu ggcaccgagu cggugc                                96

<210> SEQ ID NO 4
<211> LENGTH: 76
<212> TYPE: RNA
<213> ORGANISM: Artificial Sequence
<220> FEATURE:
<223> OTHER INFORMATION: gRNA

<400> SEQUENCE: 4
guuuuagagc uagaaauagc aaguuaaaau aaggcuaguc cguuaucaac uugaaaaagu      60
ggcaccgagu cggugc                                                      76

<210> SEQ ID NO 5
<211> LENGTH: 1378
<212> TYPE: PRT
<213> ORGANISM: Streptococcus pyogenes

<400> SEQUENCE: 5

Met Pro Lys Lys Lys Arg Lys Val Gly Ser Met Asp Lys Lys Tyr Ser

-continued

```
 1               5                  10                 15
Ile Gly Leu Asp Ile Gly Thr Asn Ser Val Gly Trp Ala Val Ile Thr
                20                 25                 30

Asp Glu Tyr Lys Val Pro Ser Lys Phe Lys Val Leu Gly Asn Thr
                35                 40                 45

Asp Arg His Ser Ile Lys Lys Asn Leu Ile Gly Ala Leu Leu Phe Asp
        50                 55                 60

Ser Gly Glu Thr Ala Glu Ala Thr Arg Leu Lys Arg Thr Ala Arg Arg
 65                 70                 75                 80

Arg Tyr Thr Arg Arg Lys Asn Arg Ile Cys Tyr Leu Gln Glu Ile Phe
                85                 90                 95

Ser Asn Glu Met Ala Lys Val Asp Asp Ser Phe Phe His Arg Leu Glu
                100                105                110

Glu Ser Phe Leu Val Glu Glu Asp Lys Lys His Glu Arg His Pro Ile
                115                120                125

Phe Gly Asn Ile Val Asp Glu Val Ala Tyr His Glu Lys Tyr Pro Thr
        130                135                140

Ile Tyr His Leu Arg Lys Lys Leu Val Asp Ser Thr Asp Lys Ala Asp
145                150                155                160

Leu Arg Leu Ile Tyr Leu Ala Leu Ala His Met Ile Lys Phe Arg Gly
                165                170                175

His Phe Leu Ile Glu Gly Asp Leu Asn Pro Asp Asn Ser Asp Val Asp
                180                185                190

Lys Leu Phe Ile Gln Leu Val Gln Thr Tyr Asn Gln Leu Phe Glu Glu
                195                200                205

Asn Pro Ile Asn Ala Ser Gly Val Asp Ala Lys Ala Ile Leu Ser Ala
        210                215                220

Arg Leu Ser Lys Ser Arg Arg Leu Glu Asn Leu Ile Ala Gln Leu Pro
225                230                235                240

Gly Glu Lys Lys Asn Gly Leu Phe Gly Asn Leu Ile Ala Leu Ser Leu
                245                250                255

Gly Leu Thr Pro Asn Phe Lys Ser Asn Phe Asp Leu Ala Glu Asp Ala
        260                265                270

Lys Leu Gln Leu Ser Lys Asp Thr Tyr Asp Asp Asp Leu Asp Asn Leu
        275                280                285

Leu Ala Gln Ile Gly Asp Gln Tyr Ala Asp Leu Phe Leu Ala Ala Lys
        290                295                300

Asn Leu Ser Asp Ala Ile Leu Leu Ser Asp Ile Leu Arg Val Asn Thr
305                310                315                320

Glu Ile Thr Lys Ala Pro Leu Ser Ala Ser Met Ile Lys Arg Tyr Asp
                325                330                335

Glu His His Gln Asp Leu Thr Leu Leu Lys Ala Leu Val Arg Gln Gln
                340                345                350

Leu Pro Glu Lys Tyr Lys Glu Ile Phe Phe Asp Gln Ser Lys Asn Gly
                355                360                365

Tyr Ala Gly Tyr Ile Asp Gly Gly Ala Ser Gln Glu Glu Phe Tyr Lys
        370                375                380

Phe Ile Lys Pro Ile Leu Glu Lys Met Asp Gly Thr Glu Glu Leu Leu
385                390                395                400

Val Lys Leu Asn Arg Glu Asp Leu Leu Arg Lys Gln Arg Thr Phe Asp
                405                410                415

Asn Gly Ser Ile Pro His Gln Ile His Leu Gly Glu Leu His Ala Ile
                420                425                430
```

-continued

```
Leu Arg Arg Gln Glu Asp Phe Tyr Pro Phe Leu Lys Asp Asn Arg Glu
        435                 440                 445

Lys Ile Glu Lys Ile Leu Thr Phe Arg Ile Pro Tyr Tyr Val Gly Pro
450                 455                 460

Leu Ala Arg Gly Asn Ser Arg Phe Ala Trp Met Thr Arg Lys Ser Glu
465                 470                 475                 480

Glu Thr Ile Thr Pro Trp Asn Phe Glu Val Val Asp Lys Gly Ala
                    485                 490                 495

Ser Ala Gln Ser Phe Ile Glu Arg Met Thr Asn Phe Asp Lys Asn Leu
                500                 505                 510

Pro Asn Glu Lys Val Leu Pro Lys His Ser Leu Leu Tyr Glu Tyr Phe
                515                 520                 525

Thr Val Tyr Asn Glu Leu Thr Lys Val Lys Tyr Val Thr Glu Gly Met
530                 535                 540

Arg Lys Pro Ala Phe Leu Ser Gly Glu Gln Lys Lys Ala Ile Val Asp
545                 550                 555                 560

Leu Leu Phe Lys Thr Asn Arg Lys Val Thr Val Lys Gln Leu Lys Glu
                565                 570                 575

Asp Tyr Phe Lys Lys Ile Glu Cys Phe Asp Ser Val Glu Ile Ser Gly
                580                 585                 590

Val Glu Asp Arg Phe Asn Ala Ser Leu Gly Thr Tyr His Asp Leu Leu
                595                 600                 605

Lys Ile Ile Lys Asp Lys Asp Phe Leu Asp Asn Glu Glu Asn Glu Asp
610                 615                 620

Ile Leu Glu Asp Ile Val Leu Thr Leu Thr Leu Phe Glu Asp Arg Glu
625                 630                 635                 640

Met Ile Glu Glu Arg Leu Lys Thr Tyr Ala His Leu Phe Asp Asp Lys
                645                 650                 655

Val Met Lys Gln Leu Lys Arg Arg Tyr Thr Gly Trp Gly Arg Leu
                660                 665                 670

Ser Arg Lys Leu Ile Asn Gly Ile Arg Asp Lys Gln Ser Gly Lys Thr
                675                 680                 685

Ile Leu Asp Phe Leu Lys Ser Asp Gly Phe Ala Asn Arg Asn Phe Met
                690                 695                 700

Gln Leu Ile His Asp Asp Ser Leu Thr Phe Lys Glu Asp Ile Gln Lys
705                 710                 715                 720

Ala Gln Val Ser Gly Gln Gly Asp Ser Leu His Glu His Ile Ala Asn
                725                 730                 735

Leu Ala Gly Ser Pro Ala Ile Lys Lys Gly Ile Leu Gln Thr Val Lys
                740                 745                 750

Val Val Asp Glu Leu Val Lys Val Met Gly Arg His Lys Pro Glu Asn
                755                 760                 765

Ile Val Ile Glu Met Ala Arg Glu Asn Gln Thr Thr Gln Lys Gly Gln
770                 775                 780

Lys Asn Ser Arg Glu Arg Met Lys Arg Ile Glu Gly Ile Lys Glu
785                 790                 795                 800

Leu Gly Ser Gln Ile Leu Lys Glu His Pro Val Glu Asn Thr Gln Leu
                805                 810                 815

Gln Asn Glu Lys Leu Tyr Leu Tyr Tyr Leu Gln Asn Gly Arg Asp Met
                820                 825                 830

Tyr Val Asp Gln Glu Leu Asp Ile Asn Arg Leu Ser Asp Tyr Asp Val
                835                 840                 845
```

```
Asp His Ile Val Pro Gln Ser Phe Leu Lys Asp Asp Ser Ile Asp Asn
            850                 855                 860

Lys Val Leu Thr Arg Ser Asp Lys Asn Arg Gly Lys Ser Asp Asn Val
865                 870                 875                 880

Pro Ser Glu Glu Val Val Lys Lys Met Lys Asn Tyr Trp Arg Gln Leu
                885                 890                 895

Leu Asn Ala Lys Leu Ile Thr Gln Arg Lys Phe Asp Asn Leu Thr Lys
            900                 905                 910

Ala Glu Arg Gly Gly Leu Ser Glu Leu Asp Lys Ala Gly Phe Ile Lys
            915                 920                 925

Arg Gln Leu Val Glu Thr Arg Gln Ile Thr Lys His Val Ala Gln Ile
930                 935                 940

Leu Asp Ser Arg Met Asn Thr Lys Tyr Asp Glu Asn Asp Lys Leu Ile
945                 950                 955                 960

Arg Glu Val Lys Val Ile Thr Leu Lys Ser Lys Leu Val Ser Asp Phe
                965                 970                 975

Arg Lys Asp Phe Gln Phe Tyr Lys Val Arg Glu Ile Asn Asn Tyr His
            980                 985                 990

His Ala His Asp Ala Tyr Leu Asn Ala Val Val Gly Thr Ala Leu Ile
            995                 1000                1005

Lys Lys Tyr Pro Lys Leu Glu Ser Glu Phe Val Tyr Gly Asp Tyr
        1010                1015                1020

Lys Val Tyr Asp Val Arg Lys Met Ile Ala Lys Ser Glu Gln Glu
        1025                1030                1035

Ile Gly Lys Ala Thr Ala Lys Tyr Phe Phe Tyr Ser Asn Ile Met
        1040                1045                1050

Asn Phe Phe Lys Thr Glu Ile Thr Leu Ala Asn Gly Glu Ile Arg
        1055                1060                1065

Lys Arg Pro Leu Ile Glu Thr Asn Gly Glu Thr Gly Glu Ile Val
        1070                1075                1080

Trp Asp Lys Gly Arg Asp Phe Ala Thr Val Arg Lys Val Leu Ser
        1085                1090                1095

Met Pro Gln Val Asn Ile Val Lys Lys Thr Glu Val Gln Thr Gly
        1100                1105                1110

Gly Phe Ser Lys Glu Ser Ile Leu Pro Lys Arg Asn Ser Asp Lys
        1115                1120                1125

Leu Ile Ala Arg Lys Lys Asp Trp Asp Pro Lys Lys Tyr Gly Gly
        1130                1135                1140

Phe Asp Ser Pro Thr Val Ala Tyr Ser Val Leu Val Val Ala Lys
        1145                1150                1155

Val Glu Lys Gly Lys Ser Lys Lys Leu Lys Ser Val Lys Glu Leu
        1160                1165                1170

Leu Gly Ile Thr Ile Met Glu Arg Ser Ser Phe Glu Lys Asn Pro
        1175                1180                1185

Ile Asp Phe Leu Glu Ala Lys Gly Tyr Lys Glu Val Lys Lys Asp
        1190                1195                1200

Leu Ile Ile Lys Leu Pro Lys Tyr Ser Leu Phe Glu Leu Glu Asn
        1205                1210                1215

Gly Arg Lys Arg Met Leu Ala Ser Ala Gly Glu Leu Gln Lys Gly
        1220                1225                1230

Asn Glu Leu Ala Leu Pro Ser Lys Tyr Val Asn Phe Leu Tyr Leu
        1235                1240                1245

Ala Ser His Tyr Glu Lys Leu Lys Gly Ser Pro Glu Asp Asn Glu
```

```
                    1250                1255                1260
Gln Lys Gln Leu Phe Val Glu Gln His Lys His Tyr Leu Asp Glu
    1265                1270                1275
Ile Ile Glu Gln Ile Ser Glu Phe Ser Lys Arg Val Ile Leu Ala
    1280                1285                1290
Asp Ala Asn Leu Asp Lys Val Leu Ser Ala Tyr Asn Lys His Arg
    1295                1300                1305
Asp Lys Pro Ile Arg Glu Gln Ala Glu Asn Ile Ile His Leu Phe
    1310                1315                1320
Thr Leu Thr Asn Leu Gly Ala Pro Ala Ala Phe Lys Tyr Phe Asp
    1325                1330                1335
Thr Thr Ile Asp Arg Lys Arg Tyr Thr Ser Thr Lys Glu Val Leu
    1340                1345                1350
Asp Ala Thr Leu Ile His Gln Ser Ile Thr Gly Leu Tyr Glu Thr
    1355                1360                1365
Arg Ile Asp Leu Ser Gln Leu Gly Gly Asp
    1370                1375

<210> SEQ ID NO 6
<211> LENGTH: 7
<212> TYPE: PRT
<213> ORGANISM: Artificial Sequence
<220> FEATURE:
<223> OTHER INFORMATION: Signal

<400> SEQUENCE: 6

Pro Lys Lys Lys Arg Lys Val
1               5

<210> SEQ ID NO 7
<211> LENGTH: 1377
<212> TYPE: PRT
<213> ORGANISM: Streptococcus pyogenes

<400> SEQUENCE: 7

Met Asp Lys Lys Tyr Ser Ile Gly Leu Asp Ile Gly Thr Asn Ser Val
1               5                   10                  15
Gly Trp Ala Val Ile Thr Asp Glu Tyr Lys Val Pro Ser Lys Lys Phe
            20                  25                  30
Lys Val Leu Gly Asn Thr Asp Arg His Ser Ile Lys Lys Asn Leu Ile
        35                  40                  45
Gly Ala Leu Leu Phe Asp Ser Gly Glu Thr Ala Glu Ala Thr Arg Leu
    50                  55                  60
Lys Arg Thr Ala Arg Arg Arg Tyr Thr Arg Arg Lys Asn Arg Ile Cys
65                  70                  75                  80
Tyr Leu Gln Glu Ile Phe Ser Asn Glu Met Ala Lys Val Asp Asp Ser
                85                  90                  95
Phe Phe His Arg Leu Glu Glu Ser Phe Leu Val Glu Glu Asp Lys Lys
            100                 105                 110
His Glu Arg His Pro Ile Phe Gly Asn Ile Val Asp Glu Val Ala Tyr
        115                 120                 125
His Glu Lys Tyr Pro Thr Ile Tyr His Leu Arg Lys Lys Leu Val Asp
    130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
```

```
Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
            245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
            325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
            580                 585                 590
```

```
Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
```

```
                    1010                1015                1020
Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Glu Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260

His Tyr Leu Asp Glu Ile Ile Glu Gln Ile Ser Glu Phe Ser Lys
        1265                1270                1275

Arg Val Ile Leu Ala Asp Ala Asn Leu Asp Lys Val Leu Ser Ala
        1280                1285                1290

Tyr Asn Lys His Arg Asp Lys Pro Ile Arg Glu Gln Ala Glu Asn
        1295                1300                1305

Ile Ile His Leu Phe Thr Leu Thr Asn Leu Gly Ala Pro Ala Ala
        1310                1315                1320

Phe Lys Tyr Phe Asp Thr Thr Ile Asp Arg Lys Arg Tyr Thr Ser
        1325                1330                1335

Thr Lys Glu Val Leu Asp Ala Thr Leu Ile His Gln Ser Ile Thr
        1340                1345                1350

Gly Leu Tyr Glu Thr Arg Ile Asp Leu Ser Gln Leu Gly Gly Asp
        1355                1360                1365

Gly Ser Pro Lys Lys Lys Arg Lys Val
        1370                1375

<210> SEQ ID NO 8
<211> LENGTH: 1387
<212> TYPE: PRT
<213> ORGANISM: Streptococcus pyogenes
```

<400> SEQUENCE: 8

Met Pro Lys Lys Arg Lys Val Gly Ser Met Asp Lys Lys Tyr Ser
1               5                   10                  15

Ile Gly Leu Asp Ile Gly Thr Asn Ser Val Gly Trp Ala Val Ile Thr
                20                  25                  30

Asp Glu Tyr Lys Val Pro Ser Lys Lys Phe Lys Val Leu Gly Asn Thr
            35                  40                  45

Asp Arg His Ser Ile Lys Lys Asn Leu Ile Gly Ala Leu Leu Phe Asp
        50                  55                  60

Ser Gly Glu Thr Ala Glu Ala Thr Arg Leu Lys Arg Thr Ala Arg Arg
65                  70                  75                  80

Arg Tyr Thr Arg Arg Lys Asn Arg Ile Cys Tyr Leu Gln Glu Ile Phe
                85                  90                  95

Ser Asn Glu Met Ala Lys Val Asp Asp Ser Phe Phe His Arg Leu Glu
                100                 105                 110

Glu Ser Phe Leu Val Glu Glu Asp Lys Lys His Glu Arg His Pro Ile
            115                 120                 125

Phe Gly Asn Ile Val Asp Glu Val Ala Tyr His Glu Lys Tyr Pro Thr
        130                 135                 140

Ile Tyr His Leu Arg Lys Lys Leu Val Asp Ser Thr Asp Lys Ala Asp
145                 150                 155                 160

Leu Arg Leu Ile Tyr Leu Ala Leu Ala His Met Ile Lys Phe Arg Gly
                165                 170                 175

His Phe Leu Ile Glu Gly Asp Leu Asn Pro Asp Asn Ser Asp Val Asp
                180                 185                 190

Lys Leu Phe Ile Gln Leu Val Gln Thr Tyr Asn Gln Leu Phe Glu Glu
            195                 200                 205

Asn Pro Ile Asn Ala Ser Gly Val Asp Ala Lys Ala Ile Leu Ser Ala
        210                 215                 220

Arg Leu Ser Lys Ser Arg Arg Leu Glu Asn Leu Ile Ala Gln Leu Pro
225                 230                 235                 240

Gly Glu Lys Lys Asn Gly Leu Phe Gly Asn Leu Ile Ala Leu Ser Leu
                245                 250                 255

Gly Leu Thr Pro Asn Phe Lys Ser Asn Phe Asp Leu Ala Glu Asp Ala
                260                 265                 270

Lys Leu Gln Leu Ser Lys Asp Thr Tyr Asp Asp Asp Leu Asp Asn Leu
            275                 280                 285

Leu Ala Gln Ile Gly Asp Gln Tyr Ala Asp Leu Phe Leu Ala Ala Lys
        290                 295                 300

Asn Leu Ser Asp Ala Ile Leu Leu Ser Asp Ile Leu Arg Val Asn Thr
305                 310                 315                 320

Glu Ile Thr Lys Ala Pro Leu Ser Ala Ser Met Ile Lys Arg Tyr Asp
                325                 330                 335

Glu His His Gln Asp Leu Thr Leu Leu Lys Ala Leu Val Arg Gln Gln
                340                 345                 350

Leu Pro Glu Lys Tyr Lys Glu Ile Phe Phe Asp Gln Ser Lys Asn Gly
            355                 360                 365

Tyr Ala Gly Tyr Ile Asp Gly Gly Ala Ser Gln Glu Glu Phe Tyr Lys
        370                 375                 380

Phe Ile Lys Pro Ile Leu Glu Lys Met Asp Gly Thr Glu Glu Leu Leu
385                 390                 395                 400

Val Lys Leu Asn Arg Glu Asp Leu Leu Arg Lys Gln Arg Thr Phe Asp

-continued

```
                405                 410                 415
Asn Gly Ser Ile Pro His Gln Ile His Leu Gly Glu Leu His Ala Ile
            420                 425                 430

Leu Arg Arg Gln Glu Asp Phe Tyr Pro Phe Leu Lys Asp Asn Arg Glu
435                 440                 445

Lys Ile Glu Lys Ile Leu Thr Phe Arg Ile Pro Tyr Tyr Val Gly Pro
    450                 455                 460

Leu Ala Arg Gly Asn Ser Arg Phe Ala Trp Met Thr Arg Lys Ser Glu
465                 470                 475                 480

Glu Thr Ile Thr Pro Trp Asn Phe Glu Glu Val Val Asp Lys Gly Ala
                485                 490                 495

Ser Ala Gln Ser Phe Ile Glu Arg Met Thr Asn Phe Asp Lys Asn Leu
            500                 505                 510

Pro Asn Glu Lys Val Leu Pro Lys His Ser Leu Leu Tyr Glu Tyr Phe
        515                 520                 525

Thr Val Tyr Asn Glu Leu Thr Lys Val Lys Tyr Val Thr Glu Gly Met
    530                 535                 540

Arg Lys Pro Ala Phe Leu Ser Gly Glu Gln Lys Lys Ala Ile Val Asp
545                 550                 555                 560

Leu Leu Phe Lys Thr Asn Arg Lys Val Thr Val Lys Gln Leu Lys Glu
                565                 570                 575

Asp Tyr Phe Lys Lys Ile Glu Cys Phe Asp Ser Val Glu Ile Ser Gly
            580                 585                 590

Val Glu Asp Arg Phe Asn Ala Ser Leu Gly Thr Tyr His Asp Leu Leu
        595                 600                 605

Lys Ile Ile Lys Asp Lys Asp Phe Leu Asp Asn Glu Glu Asn Glu Asp
    610                 615                 620

Ile Leu Glu Asp Ile Val Leu Thr Leu Thr Leu Phe Glu Asp Arg Glu
625                 630                 635                 640

Met Ile Glu Glu Arg Leu Lys Thr Tyr Ala His Leu Phe Asp Asp Lys
                645                 650                 655

Val Met Lys Gln Leu Lys Arg Arg Tyr Thr Gly Trp Gly Arg Leu
            660                 665                 670

Ser Arg Lys Leu Ile Asn Gly Ile Arg Asp Lys Gln Ser Gly Lys Thr
        675                 680                 685

Ile Leu Asp Phe Leu Lys Ser Asp Gly Phe Ala Asn Arg Asn Phe Met
    690                 695                 700

Gln Leu Ile His Asp Asp Ser Leu Thr Phe Lys Glu Asp Ile Gln Lys
705                 710                 715                 720

Ala Gln Val Ser Gly Gln Gly Asp Ser Leu His Glu His Ile Ala Asn
                725                 730                 735

Leu Ala Gly Ser Pro Ala Ile Lys Lys Gly Ile Leu Gln Thr Val Lys
            740                 745                 750

Val Val Asp Glu Leu Val Lys Val Met Gly Arg His Lys Pro Glu Asn
        755                 760                 765

Ile Val Ile Glu Met Ala Arg Glu Asn Gln Thr Thr Gln Lys Gly Gln
    770                 775                 780

Lys Asn Ser Arg Glu Arg Met Lys Arg Ile Glu Glu Gly Ile Lys Glu
785                 790                 795                 800

Leu Gly Ser Gln Ile Leu Lys Glu His Pro Val Glu Asn Thr Gln Leu
                805                 810                 815

Gln Asn Glu Lys Leu Tyr Leu Tyr Tyr Leu Gln Asn Gly Arg Asp Met
            820                 825                 830
```

-continued

Tyr Val Asp Gln Glu Leu Asp Ile Asn Arg Leu Ser Asp Tyr Asp Val
    835                 840                 845

Asp His Ile Val Pro Gln Ser Phe Leu Lys Asp Ser Ile Asp Asn
850                 855                 860

Lys Val Leu Thr Arg Ser Asp Lys Asn Arg Gly Lys Ser Asp Asn Val
865                 870                 875                 880

Pro Ser Glu Glu Val Val Lys Lys Met Lys Asn Tyr Trp Arg Gln Leu
            885                 890                 895

Leu Asn Ala Lys Leu Ile Thr Gln Arg Lys Phe Asp Asn Leu Thr Lys
            900                 905                 910

Ala Glu Arg Gly Gly Leu Ser Glu Leu Asp Lys Ala Gly Phe Ile Lys
            915                 920                 925

Arg Gln Leu Val Glu Thr Arg Gln Ile Thr Lys His Val Ala Gln Ile
            930                 935                 940

Leu Asp Ser Arg Met Asn Thr Lys Tyr Asp Glu Asn Asp Lys Leu Ile
945                 950                 955                 960

Arg Glu Val Lys Val Ile Thr Leu Lys Ser Lys Leu Val Ser Asp Phe
                965                 970                 975

Arg Lys Asp Phe Gln Phe Tyr Lys Val Arg Glu Ile Asn Asn Tyr His
            980                 985                 990

His Ala His Asp Ala Tyr Leu Asn Ala Val Val Gly Thr Ala Leu Ile
            995                 1000                1005

Lys Lys Tyr Pro Lys Leu Glu Ser Glu Phe Val Tyr Gly Asp Tyr
    1010                1015                1020

Lys Val Tyr Asp Val Arg Lys Met Ile Ala Lys Ser Glu Gln Glu
    1025                1030                1035

Ile Gly Lys Ala Thr Ala Lys Tyr Phe Phe Tyr Ser Asn Ile Met
    1040                1045                1050

Asn Phe Phe Lys Thr Glu Ile Thr Leu Ala Asn Gly Glu Ile Arg
    1055                1060                1065

Lys Arg Pro Leu Ile Glu Thr Asn Gly Glu Thr Gly Glu Ile Val
    1070                1075                1080

Trp Asp Lys Gly Arg Asp Phe Ala Thr Val Arg Lys Val Leu Ser
    1085                1090                1095

Met Pro Gln Val Asn Ile Val Lys Lys Thr Glu Val Gln Thr Gly
    1100                1105                1110

Gly Phe Ser Lys Glu Ser Ile Leu Pro Lys Arg Asn Ser Asp Lys
    1115                1120                1125

Leu Ile Ala Arg Lys Lys Asp Trp Asp Pro Lys Lys Tyr Gly Gly
    1130                1135                1140

Phe Asp Ser Pro Thr Val Ala Tyr Ser Val Leu Val Val Ala Lys
    1145                1150                1155

Val Glu Lys Gly Lys Ser Lys Lys Leu Lys Ser Val Lys Glu Leu
    1160                1165                1170

Leu Gly Ile Thr Ile Met Glu Arg Ser Ser Phe Glu Lys Asn Pro
    1175                1180                1185

Ile Asp Phe Leu Glu Ala Lys Gly Tyr Lys Glu Val Lys Lys Asp
    1190                1195                1200

Leu Ile Ile Lys Leu Pro Lys Tyr Ser Leu Phe Glu Leu Glu Asn
    1205                1210                1215

Gly Arg Lys Arg Met Leu Ala Ser Ala Gly Glu Leu Gln Lys Gly
    1220                1225                1230

-continued

Asn Glu Leu Ala Leu Pro Ser Lys Tyr Val Asn Phe Leu Tyr Leu
1235                1240                1245

Ala Ser His Tyr Glu Lys Leu Lys Gly Ser Pro Glu Asp Asn Glu
1250                1255                1260

Gln Lys Gln Leu Phe Val Glu Gln His Lys His Tyr Leu Asp Glu
1265                1270                1275

Ile Ile Glu Gln Ile Ser Glu Phe Ser Lys Arg Val Ile Leu Ala
1280                1285                1290

Asp Ala Asn Leu Asp Lys Val Leu Ser Ala Tyr Asn Lys His Arg
1295                1300                1305

Asp Lys Pro Ile Arg Glu Gln Ala Glu Asn Ile Ile His Leu Phe
1310                1315                1320

Thr Leu Thr Asn Leu Gly Ala Pro Ala Ala Phe Lys Tyr Phe Asp
1325                1330                1335

Thr Thr Ile Asp Arg Lys Arg Tyr Thr Ser Thr Lys Glu Val Leu
1340                1345                1350

Asp Ala Thr Leu Ile His Gln Ser Ile Thr Gly Leu Tyr Glu Thr
1355                1360                1365

Arg Ile Asp Leu Ser Gln Leu Gly Gly Asp Gly Ser Pro Lys Lys
1370                1375                1380

Lys Arg Lys Val
1385

<210> SEQ ID NO 9
<211> LENGTH: 1423
<212> TYPE: PRT
<213> ORGANISM: Streptococcus pyogenes

<400> SEQUENCE: 9

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
                20                  25                  30

Gly Ile His Gly Val Pro Ala Ala Asp Lys Lys Tyr Ser Ile Gly Leu
            35                  40                  45

Asp Ile Gly Thr Asn Ser Val Gly Trp Ala Val Ile Thr Asp Glu Tyr
    50                  55                  60

Lys Val Pro Ser Lys Lys Phe Lys Val Leu Gly Asn Thr Asp Arg His
65                  70                  75                  80

Ser Ile Lys Lys Asn Leu Ile Gly Ala Leu Leu Phe Asp Ser Gly Glu
                85                  90                  95

Thr Ala Glu Ala Thr Arg Leu Lys Arg Thr Ala Arg Arg Arg Tyr Thr
            100                 105                 110

Arg Arg Lys Asn Arg Ile Cys Tyr Leu Gln Glu Ile Phe Ser Asn Glu
        115                 120                 125

Met Ala Lys Val Asp Asp Ser Phe Phe His Arg Leu Glu Glu Ser Phe
    130                 135                 140

Leu Val Glu Glu Asp Lys Lys His Glu Arg His Pro Ile Phe Gly Asn
145                 150                 155                 160

Ile Val Asp Glu Val Ala Tyr His Glu Lys Tyr Pro Thr Ile Tyr His
                165                 170                 175

Leu Arg Lys Lys Leu Val Asp Ser Thr Asp Lys Ala Asp Leu Arg Leu
            180                 185                 190

Ile Tyr Leu Ala Leu Ala His Met Ile Lys Phe Arg Gly His Phe Leu
        195                 200                 205

-continued

```
Ile Glu Gly Asp Leu Asn Pro Asp Asn Ser Asp Val Asp Lys Leu Phe
    210                 215                 220
Ile Gln Leu Val Gln Thr Tyr Asn Gln Leu Phe Glu Glu Asn Pro Ile
225                 230                 235                 240
Asn Ala Ser Gly Val Asp Ala Lys Ala Ile Leu Ser Ala Arg Leu Ser
                245                 250                 255
Lys Ser Arg Arg Leu Glu Asn Leu Ile Ala Gln Leu Pro Gly Glu Lys
            260                 265                 270
Lys Asn Gly Leu Phe Gly Asn Leu Ile Ala Leu Ser Leu Gly Leu Thr
        275                 280                 285
Pro Asn Phe Lys Ser Asn Phe Asp Leu Ala Glu Asp Ala Lys Leu Gln
    290                 295                 300
Leu Ser Lys Asp Thr Tyr Asp Asp Asp Leu Asp Asn Leu Leu Ala Gln
305                 310                 315                 320
Ile Gly Asp Gln Tyr Ala Asp Leu Phe Leu Ala Ala Lys Asn Leu Ser
                325                 330                 335
Asp Ala Ile Leu Leu Ser Asp Ile Leu Arg Val Asn Thr Glu Ile Thr
            340                 345                 350
Lys Ala Pro Leu Ser Ala Ser Met Ile Lys Arg Tyr Asp Glu His His
        355                 360                 365
Gln Asp Leu Thr Leu Leu Lys Ala Leu Val Arg Gln Gln Leu Pro Glu
    370                 375                 380
Lys Tyr Lys Glu Ile Phe Phe Asp Gln Ser Lys Asn Gly Tyr Ala Gly
385                 390                 395                 400
Tyr Ile Asp Gly Gly Ala Ser Gln Glu Glu Phe Tyr Lys Phe Ile Lys
                405                 410                 415
Pro Ile Leu Glu Lys Met Asp Gly Thr Glu Glu Leu Leu Val Lys Leu
            420                 425                 430
Asn Arg Glu Asp Leu Leu Arg Lys Gln Arg Thr Phe Asp Asn Gly Ser
        435                 440                 445
Ile Pro His Gln Ile His Leu Gly Glu Leu His Ala Ile Leu Arg Arg
    450                 455                 460
Gln Glu Asp Phe Tyr Pro Phe Leu Lys Asp Asn Arg Glu Lys Ile Glu
465                 470                 475                 480
Lys Ile Leu Thr Phe Arg Ile Pro Tyr Tyr Val Gly Pro Leu Ala Arg
                485                 490                 495
Gly Asn Ser Arg Phe Ala Trp Met Thr Arg Lys Ser Glu Glu Thr Ile
            500                 505                 510
Thr Pro Trp Asn Phe Glu Glu Val Val Asp Lys Gly Ala Ser Ala Gln
        515                 520                 525
Ser Phe Ile Glu Arg Met Thr Asn Phe Asp Lys Asn Leu Pro Asn Glu
    530                 535                 540
Lys Val Leu Pro Lys His Ser Leu Leu Tyr Glu Tyr Phe Thr Val Tyr
545                 550                 555                 560
Asn Glu Leu Thr Lys Val Lys Tyr Val Thr Glu Gly Met Arg Lys Pro
                565                 570                 575
Ala Phe Leu Ser Gly Glu Gln Lys Lys Ala Ile Val Asp Leu Leu Phe
            580                 585                 590
Lys Thr Asn Arg Lys Val Thr Val Lys Gln Leu Lys Glu Asp Tyr Phe
        595                 600                 605
Lys Lys Ile Glu Cys Phe Asp Ser Val Glu Ile Ser Gly Val Glu Asp
    610                 615                 620
```

-continued

```
Arg Phe Asn Ala Ser Leu Gly Thr Tyr His Asp Leu Leu Lys Ile Ile
625                 630                 635                 640

Lys Asp Lys Asp Phe Leu Asp Asn Glu Glu Asn Glu Asp Ile Leu Glu
            645                 650                 655

Asp Ile Val Leu Thr Leu Thr Leu Phe Glu Asp Arg Glu Met Ile Glu
                660                 665                 670

Glu Arg Leu Lys Thr Tyr Ala His Leu Phe Asp Asp Lys Val Met Lys
            675                 680                 685

Gln Leu Lys Arg Arg Arg Tyr Thr Gly Trp Gly Arg Leu Ser Arg Lys
        690                 695                 700

Leu Ile Asn Gly Ile Arg Asp Lys Gln Ser Gly Lys Thr Ile Leu Asp
705                 710                 715                 720

Phe Leu Lys Ser Asp Gly Phe Ala Asn Arg Asn Phe Met Gln Leu Ile
                725                 730                 735

His Asp Asp Ser Leu Thr Phe Lys Glu Asp Ile Gln Lys Ala Gln Val
            740                 745                 750

Ser Gly Gln Gly Asp Ser Leu His Glu His Ile Ala Asn Leu Ala Gly
        755                 760                 765

Ser Pro Ala Ile Lys Lys Gly Ile Leu Gln Thr Val Lys Val Val Asp
770                 775                 780

Glu Leu Val Lys Val Met Gly Arg His Lys Pro Glu Asn Ile Val Ile
785                 790                 795                 800

Glu Met Ala Arg Glu Asn Gln Thr Thr Gln Lys Gly Gln Lys Asn Ser
                805                 810                 815

Arg Glu Arg Met Lys Arg Ile Glu Glu Gly Ile Lys Glu Leu Gly Ser
            820                 825                 830

Gln Ile Leu Lys Glu His Pro Val Glu Asn Thr Gln Leu Gln Asn Glu
        835                 840                 845

Lys Leu Tyr Leu Tyr Tyr Leu Gln Asn Gly Arg Asp Met Tyr Val Asp
850                 855                 860

Gln Glu Leu Asp Ile Asn Arg Leu Ser Asp Tyr Asp Val Asp His Ile
865                 870                 875                 880

Val Pro Gln Ser Phe Leu Lys Asp Asp Ser Ile Asp Asn Lys Val Leu
                885                 890                 895

Thr Arg Ser Asp Lys Asn Arg Gly Lys Ser Asp Asn Val Pro Ser Glu
            900                 905                 910

Glu Val Val Lys Lys Met Lys Asn Tyr Trp Arg Gln Leu Leu Asn Ala
        915                 920                 925

Lys Leu Ile Thr Gln Arg Lys Phe Asp Asn Leu Thr Lys Ala Glu Arg
930                 935                 940

Gly Gly Leu Ser Glu Leu Asp Lys Ala Gly Phe Ile Lys Arg Gln Leu
945                 950                 955                 960

Val Glu Thr Arg Gln Ile Thr Lys His Val Ala Gln Ile Leu Asp Ser
                965                 970                 975

Arg Met Asn Thr Lys Tyr Asp Glu Asn Asp Lys Leu Ile Arg Glu Val
            980                 985                 990

Lys Val Ile Thr Leu Lys Ser Lys Leu Val Ser Asp Phe Arg Lys Asp
        995                 1000                1005

Phe Gln Phe Tyr Lys Val Arg Glu Ile Asn Asn Tyr His His Ala
        1010                1015                1020

His Asp Ala Tyr Leu Asn Ala Val Val Gly Thr Ala Leu Ile Lys
        1025                1030                1035

Lys Tyr Pro Lys Leu Glu Ser Glu Phe Val Tyr Gly Asp Tyr Lys
```

```
            1040                1045                1050
Val Tyr Asp Val Arg Lys Met Ile Ala Lys Ser Glu Gln Glu Ile
            1055                1060                1065

Gly Lys Ala Thr Ala Lys Tyr Phe Phe Tyr Ser Asn Ile Met Asn
            1070                1075                1080

Phe Phe Lys Thr Glu Ile Thr Leu Ala Asn Gly Glu Ile Arg Lys
            1085                1090                1095

Arg Pro Leu Ile Glu Thr Asn Gly Glu Thr Gly Glu Ile Val Trp
            1100                1105                1110

Asp Lys Gly Arg Asp Phe Ala Thr Val Arg Lys Val Leu Ser Met
            1115                1120                1125

Pro Gln Val Asn Ile Val Lys Lys Thr Glu Val Gln Thr Gly Gly
            1130                1135                1140

Phe Ser Lys Glu Ser Ile Leu Pro Lys Arg Asn Ser Asp Lys Leu
            1145                1150                1155

Ile Ala Arg Lys Lys Asp Trp Asp Pro Lys Lys Tyr Gly Gly Phe
            1160                1165                1170

Asp Ser Pro Thr Val Ala Tyr Ser Val Leu Val Val Ala Lys Val
            1175                1180                1185

Glu Lys Gly Lys Ser Lys Lys Leu Lys Ser Val Lys Glu Leu Leu
            1190                1195                1200

Gly Ile Thr Ile Met Glu Arg Ser Ser Phe Glu Lys Asn Pro Ile
            1205                1210                1215

Asp Phe Leu Glu Ala Lys Gly Tyr Lys Glu Val Lys Lys Asp Leu
            1220                1225                1230

Ile Ile Lys Leu Pro Lys Tyr Ser Leu Phe Glu Leu Glu Asn Gly
            1235                1240                1245

Arg Lys Arg Met Leu Ala Ser Ala Gly Glu Leu Gln Lys Gly Asn
            1250                1255                1260

Glu Leu Ala Leu Pro Ser Lys Tyr Val Asn Phe Leu Tyr Leu Ala
            1265                1270                1275

Ser His Tyr Glu Lys Leu Lys Gly Ser Pro Glu Asp Asn Glu Gln
            1280                1285                1290

Lys Gln Leu Phe Val Glu Gln His Lys His Tyr Leu Asp Glu Ile
            1295                1300                1305

Ile Glu Gln Ile Ser Glu Phe Ser Lys Arg Val Ile Leu Ala Asp
            1310                1315                1320

Ala Asn Leu Asp Lys Val Leu Ser Ala Tyr Asn Lys His Arg Asp
            1325                1330                1335

Lys Pro Ile Arg Glu Gln Ala Glu Asn Ile Ile His Leu Phe Thr
            1340                1345                1350

Leu Thr Asn Leu Gly Ala Pro Ala Ala Phe Lys Tyr Phe Asp Thr
            1355                1360                1365

Thr Ile Asp Arg Lys Arg Tyr Thr Ser Thr Lys Glu Val Leu Asp
            1370                1375                1380

Ala Thr Leu Ile His Gln Ser Ile Thr Gly Leu Tyr Glu Thr Arg
            1385                1390                1395

Ile Asp Leu Ser Gln Leu Gly Gly Asp Lys Arg Pro Ala Ala Thr
            1400                1405                1410

Lys Lys Ala Gly Gln Ala Lys Lys Lys Lys
            1415                1420

<210> SEQ ID NO 10
```

<211> LENGTH: 1121
<212> TYPE: PRT
<213> ORGANISM: Streptococcus thermophilus

<400> SEQUENCE: 10

```
Met Ser Asp Leu Val Leu Gly Leu Asp Ile Gly Ile Gly Ser Val Gly
1               5                   10                  15

Val Gly Ile Leu Asn Lys Val Thr Gly Glu Ile Ile His Lys Asn Ser
            20                  25                  30

Arg Ile Phe Pro Ala Ala Gln Ala Glu Asn Asn Leu Val Arg Arg Thr
        35                  40                  45

Asn Arg Gln Gly Arg Arg Leu Ala Arg Arg Lys Lys His Arg Arg Val
    50                  55                  60

Arg Leu Asn Arg Leu Phe Glu Glu Ser Gly Leu Ile Thr Asp Phe Thr
65                  70                  75                  80

Lys Ile Ser Ile Asn Leu Asn Pro Tyr Gln Leu Arg Val Lys Gly Leu
                85                  90                  95

Thr Asp Glu Leu Ser Asn Glu Glu Leu Phe Ile Ala Leu Lys Asn Met
            100                 105                 110

Val Lys His Arg Gly Ile Ser Tyr Leu Asp Asp Ala Ser Asp Asp Gly
        115                 120                 125

Asn Ser Ser Val Gly Asp Tyr Ala Gln Ile Val Lys Glu Asn Ser Lys
    130                 135                 140

Gln Leu Glu Thr Lys Thr Pro Gly Gln Ile Gln Leu Glu Arg Tyr Gln
145                 150                 155                 160

Thr Tyr Gly Gln Leu Arg Gly Asp Phe Thr Val Glu Lys Asp Gly Lys
                165                 170                 175

Lys His Arg Leu Ile Asn Val Phe Pro Thr Ser Ala Tyr Arg Ser Glu
            180                 185                 190

Ala Leu Arg Ile Leu Gln Thr Gln Gln Glu Phe Asn Pro Gln Ile Thr
        195                 200                 205

Asp Glu Phe Ile Asn Arg Tyr Leu Glu Ile Leu Thr Gly Lys Arg Lys
    210                 215                 220

Tyr Tyr His Gly Pro Gly Asn Glu Lys Ser Arg Thr Asp Tyr Gly Arg
225                 230                 235                 240

Tyr Arg Thr Ser Gly Glu Thr Leu Asp Asn Ile Phe Gly Ile Leu Ile
                245                 250                 255

Gly Lys Cys Thr Phe Tyr Pro Asp Glu Phe Arg Ala Ala Lys Ala Ser
            260                 265                 270

Tyr Thr Ala Gln Glu Phe Asn Leu Leu Asn Asp Leu Asn Asn Leu Thr
        275                 280                 285

Val Pro Thr Glu Thr Lys Lys Leu Ser Lys Glu Gln Lys Asn Gln Ile
    290                 295                 300

Ile Asn Tyr Val Lys Asn Glu Lys Ala Met Gly Pro Ala Lys Leu Phe
305                 310                 315                 320

Lys Tyr Ile Ala Lys Leu Leu Ser Cys Asp Val Ala Asp Ile Lys Gly
                325                 330                 335

Tyr Arg Ile Asp Lys Ser Gly Lys Ala Glu Ile His Thr Phe Glu Ala
            340                 345                 350

Tyr Arg Lys Met Lys Thr Leu Glu Thr Leu Asp Ile Glu Gln Met Asp
        355                 360                 365

Arg Glu Thr Leu Asp Lys Leu Ala Tyr Val Leu Thr Leu Asn Thr Glu
    370                 375                 380

Arg Glu Gly Ile Gln Glu Ala Leu Glu His Glu Phe Ala Asp Gly Ser
```

```
           385                 390                 395                 400
       Phe Ser Gln Lys Gln Val Asp Glu Leu Val Gln Phe Arg Lys Ala Asn
                       405                 410                 415

Ser Ser Ile Phe Gly Lys Gly Trp His Asn Phe Ser Val Lys Leu Met
                       420                 425                 430

Met Glu Leu Ile Pro Glu Leu Tyr Glu Thr Ser Glu Gln Met Thr
                       435                 440                 445

Ile Leu Thr Arg Leu Gly Lys Gln Lys Thr Thr Ser Ser Asn Lys
       450                 455                 460

Thr Lys Tyr Ile Asp Glu Lys Leu Leu Thr Glu Ile Tyr Asn Pro
       465                 470                 475                 480

Val Val Ala Lys Ser Val Arg Gln Ala Ile Lys Ile Val Asn Ala Ala
                       485                 490                 495

Ile Lys Glu Tyr Gly Asp Phe Asp Asn Ile Val Ile Glu Met Ala Arg
                       500                 505                 510

Glu Thr Asn Glu Asp Asp Glu Lys Lys Ala Ile Gln Lys Ile Gln Lys
                       515                 520                 525

Ala Asn Lys Asp Glu Lys Asp Ala Ala Met Leu Lys Ala Ala Asn Gln
       530                 535                 540

Tyr Asn Gly Lys Ala Glu Leu Pro His Ser Val Phe His Gly His Lys
       545                 550                 555                 560

Gln Leu Ala Thr Lys Ile Arg Leu Trp His Gln Gln Gly Glu Arg Cys
                       565                 570                 575

Leu Tyr Thr Gly Lys Thr Ile Ser Ile His Asp Leu Ile Asn Asn Ser
                       580                 585                 590

Asn Gln Phe Glu Val Asp His Ile Leu Pro Leu Ser Ile Thr Phe Asp
                       595                 600                 605

Asp Ser Leu Ala Asn Lys Val Leu Val Tyr Ala Thr Ala Asn Gln Glu
       610                 615                 620

Lys Gly Gln Arg Thr Pro Tyr Gln Ala Leu Asp Ser Met Asp Asp Ala
       625                 630                 635                 640

Trp Ser Phe Arg Glu Leu Lys Ala Phe Val Arg Glu Ser Lys Thr Leu
                       645                 650                 655

Ser Asn Lys Lys Lys Glu Tyr Leu Leu Thr Glu Glu Asp Ile Ser Lys
                       660                 665                 670

Phe Asp Val Arg Lys Lys Phe Ile Glu Arg Asn Leu Val Asp Thr Arg
                       675                 680                 685

Tyr Ala Ser Arg Val Val Leu Asn Ala Leu Gln Glu His Phe Arg Ala
       690                 695                 700

His Lys Ile Asp Thr Lys Val Ser Val Val Arg Gly Gln Phe Thr Ser
       705                 710                 715                 720

Gln Leu Arg Arg His Trp Gly Ile Glu Lys Thr Arg Asp Thr Tyr His
                       725                 730                 735

His His Ala Val Asp Ala Leu Ile Ile Ala Ala Ser Ser Gln Leu Asn
                       740                 745                 750

Leu Trp Lys Lys Gln Lys Asn Thr Leu Val Ser Tyr Ser Glu Asp Gln
                       755                 760                 765

Leu Leu Asp Ile Glu Thr Gly Glu Leu Ile Ser Asp Asp Glu Tyr Lys
       770                 775                 780

Glu Ser Val Phe Lys Ala Pro Tyr Gln His Phe Val Asp Thr Leu Lys
       785                 790                 795                 800

Ser Lys Glu Phe Glu Asp Ser Ile Leu Phe Ser Tyr Gln Val Asp Ser
                       805                 810                 815
```

Lys Phe Asn Arg Lys Ile Ser Asp Ala Thr Ile Tyr Ala Thr Arg Gln
                820                 825                 830

Ala Lys Val Gly Lys Asp Lys Ala Asp Glu Thr Tyr Val Leu Gly Lys
            835                 840                 845

Ile Lys Asp Ile Tyr Thr Gln Asp Gly Tyr Asp Ala Phe Met Lys Ile
850                 855                 860

Tyr Lys Lys Asp Lys Ser Lys Phe Leu Met Tyr Arg His Asp Pro Gln
865                 870                 875                 880

Thr Phe Glu Lys Val Ile Glu Pro Ile Leu Glu Asn Tyr Pro Asn Lys
                885                 890                 895

Gln Ile Asn Asp Lys Gly Lys Glu Val Pro Cys Asn Pro Phe Leu Lys
            900                 905                 910

Tyr Lys Glu Glu His Gly Tyr Ile Arg Lys Tyr Ser Lys Lys Gly Asn
            915                 920                 925

Gly Pro Glu Ile Lys Ser Leu Lys Tyr Tyr Asp Ser Lys Leu Gly Asn
930                 935                 940

His Ile Asp Ile Thr Pro Lys Asp Ser Asn Asn Lys Val Val Leu Gln
945                 950                 955                 960

Ser Val Ser Pro Trp Arg Ala Asp Val Tyr Phe Asn Lys Thr Thr Gly
                965                 970                 975

Lys Tyr Glu Ile Leu Gly Leu Lys Tyr Ala Asp Leu Gln Phe Asp Lys
            980                 985                 990

Gly Thr Gly Thr Tyr Lys Ile Ser  Gln Glu Lys Tyr Asn  Asp Ile Lys
            995                 1000                1005

Lys Lys  Glu Gly Val Asp Ser  Asp Ser Glu Phe Lys  Phe Thr Leu
    1010                1015                1020

Tyr Lys  Asn Asp Leu Leu Leu  Val Lys Asp Thr Glu  Thr Lys Glu
    1025                1030                1035

Gln Gln  Leu Phe Arg Phe Leu  Ser Arg Thr Met Pro  Lys Gln Lys
    1040                1045                1050

His Tyr  Val Glu Leu Lys Pro  Tyr Asp Lys Gln Lys  Phe Glu Gly
    1055                1060                1065

Gly Glu  Ala Leu Ile Lys Val  Leu Gly Asn Val Ala  Asn Ser Gly
    1070                1075                1080

Gln Cys  Lys Lys Gly Leu Gly  Lys Ser Asn Ile Ser  Ile Tyr Lys
    1085                1090                1095

Val Arg  Thr Asp Val Leu Gly  Asn Gln His Ile Ile  Lys Asn Glu
    1100                1105                1110

Gly Asp  Lys Pro Lys Leu Asp  Phe
    1115                1120

<210> SEQ ID NO 11
<211> LENGTH: 6
<212> TYPE: DNA
<213> ORGANISM: Artificial Sequence
<220> FEATURE:
<223> OTHER INFORMATION: Motif
<220> FEATURE:
<221> NAME/KEY: misc_feature
<222> LOCATION: (1)..(2)
<223> OTHER INFORMATION: wherein N is any of the nucleotide T, C, A or G
<220> FEATURE:
<221> NAME/KEY: misc_feature
<222> LOCATION: (3)..(3)
<223> OTHER INFORMATION: wherein N is any of the nucleotide A or G
<220> FEATURE:
<221> NAME/KEY: misc_feature
<222> LOCATION: (5)..(5)

-continued

```
<223> OTHER INFORMATION: wherein N is any of the nucleotide A or G

<400> SEQUENCE: 11 nnngna                                                                    6

<210> SEQ ID NO 12
<211> LENGTH: 7
<212> TYPE: DNA
<213> ORGANISM: Artificial Sequence
<220> FEATURE:
<223> OTHER INFORMATION: Motif
<220> FEATURE:
<221> NAME/KEY: misc_feature
<222> LOCATION: (1)..(2)
<223> OTHER INFORMATION: wherein N is any of the nucleotide T, C, A or G
<220> FEATURE:
<221> NAME/KEY: misc_feature
<222> LOCATION: (7)..(7)
<223> OTHER INFORMATION: wherein N is any of the nucleotide A or T

<400> SEQUENCE: 12 nnagaan                                                                   7

<210> SEQ ID NO 13
<211> LENGTH: 152
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 13
nnnnnnnnnn nnnnnnnnnn guuuuguac ucucaagauu uaaguaacug uacaacgaaa          60
cuuacacagu uacuuaaauc uugcagaagc uacaaagaua aggcuucaug ccgaaaucaa        120
cacccuguca uuuuauggca ggguguuuuu uu                                     152

<210> SEQ ID NO 14
<211> LENGTH: 132
<212> TYPE: RNA
<213> ORGANISM: Artificial Sequence
<220> FEATURE:
<223> OTHER INFORMATION: gRNA

<400> SEQUENCE: 14 guuuuguac ucucaagauu uaaguaacug uacaacgaaa cuuacacagu uacuuaaauc          60
uugcagaagc uacaaagaua aggcuucaug ccgaaaucaa cacccuguca uuuuauggca       120
ggguguuuuu uu                                                            132

<210> SEQ ID NO 15
<211> LENGTH: 1152
<212> TYPE: PRT
<213> ORGANISM: Streptococcus thermophilus

<400> SEQUENCE: 15
```

Met Ser Asp Leu Val Leu Gly Leu Asp Ile Gly Ile Gly Ser Val Gly
1               5                   10                  15

Val Gly Ile Leu Asn Lys Val Thr Gly Glu Ile Ile His Lys Asn Ser
            20                  25                  30

Arg Ile Phe Pro Ala Ala Gln Ala Glu Asn Asn Leu Val Arg Arg Thr
        35                  40                  45

```
Asn Arg Gln Gly Arg Arg Leu Ala Arg Arg Lys Lys His Arg Arg Val
    50                  55                  60

Arg Leu Asn Arg Leu Phe Glu Glu Ser Gly Leu Ile Thr Asp Phe Thr
65                  70                  75                  80

Lys Ile Ser Ile Asn Leu Asn Pro Tyr Gln Leu Arg Val Lys Gly Leu
                85                  90                  95

Thr Asp Glu Leu Ser Asn Glu Glu Leu Phe Ile Ala Leu Lys Asn Met
            100                 105                 110

Val Lys His Arg Gly Ile Ser Tyr Leu Asp Asp Ala Ser Asp Asp Gly
            115                 120                 125

Asn Ser Ser Val Gly Asp Tyr Ala Gln Ile Val Lys Glu Asn Ser Lys
130                 135                 140

Gln Leu Glu Thr Lys Thr Pro Gly Gln Ile Gln Leu Glu Arg Tyr Gln
145                 150                 155                 160

Thr Tyr Gly Gln Leu Arg Gly Asp Phe Thr Val Glu Lys Asp Gly Lys
                165                 170                 175

Lys His Arg Leu Ile Asn Val Phe Pro Thr Ser Ala Tyr Arg Ser Glu
            180                 185                 190

Ala Leu Arg Ile Leu Gln Thr Gln Gln Glu Phe Asn Pro Gln Ile Thr
            195                 200                 205

Asp Glu Phe Ile Asn Arg Tyr Leu Glu Ile Leu Thr Gly Lys Arg Lys
210                 215                 220

Tyr Tyr His Gly Pro Gly Asn Glu Lys Ser Arg Thr Asp Tyr Gly Arg
225                 230                 235                 240

Tyr Arg Thr Ser Gly Glu Thr Leu Asp Asn Ile Phe Gly Ile Leu Ile
                245                 250                 255

Gly Lys Cys Thr Phe Tyr Pro Asp Glu Phe Arg Ala Ala Lys Ala Ser
            260                 265                 270

Tyr Thr Ala Gln Glu Phe Asn Leu Leu Asn Asp Leu Asn Asn Leu Thr
            275                 280                 285

Val Pro Thr Glu Thr Lys Lys Leu Ser Lys Glu Gln Lys Asn Gln Ile
290                 295                 300

Ile Asn Tyr Val Lys Asn Glu Lys Ala Met Gly Pro Ala Lys Leu Phe
305                 310                 315                 320

Lys Tyr Ile Ala Lys Leu Leu Ser Cys Asp Val Ala Asp Ile Lys Gly
                325                 330                 335

Tyr Arg Ile Asp Lys Ser Gly Lys Ala Glu Ile His Thr Phe Glu Ala
            340                 345                 350

Tyr Arg Lys Met Lys Thr Leu Glu Thr Leu Asp Ile Glu Gln Met Asp
            355                 360                 365

Arg Glu Thr Leu Asp Lys Leu Ala Tyr Val Leu Thr Leu Asn Thr Glu
370                 375                 380

Arg Glu Gly Ile Gln Glu Ala Leu Glu His Glu Phe Ala Asp Gly Ser
385                 390                 395                 400

Phe Ser Gln Lys Gln Val Asp Glu Leu Val Gln Phe Arg Lys Ala Asn
                405                 410                 415

Ser Ser Ile Phe Gly Lys Gly Trp His Asn Phe Ser Val Lys Leu Met
            420                 425                 430

Met Glu Leu Ile Pro Glu Leu Tyr Glu Thr Ser Glu Glu Gln Met Thr
            435                 440                 445

Ile Leu Thr Arg Leu Gly Lys Gln Lys Thr Thr Ser Ser Ser Asn Lys
450                 455                 460

Thr Lys Tyr Ile Asp Glu Lys Leu Leu Thr Glu Glu Ile Tyr Asn Pro
```

-continued

```
            465                 470                 475                 480
        Val Val Ala Lys Ser Val Arg Gln Ala Ile Lys Ile Val Asn Ala Ala
                        485                 490                 495
        Ile Lys Glu Tyr Gly Asp Phe Asp Asn Ile Val Ile Glu Met Ala Arg
                        500                 505                 510
        Glu Thr Asn Glu Asp Asp Glu Lys Ala Ile Gln Lys Ile Gln Lys
                        515                 520                 525
        Ala Asn Lys Asp Glu Lys Asp Ala Ala Met Leu Lys Ala Ala Asn Gln
                        530                 535                 540
        Tyr Asn Gly Lys Ala Glu Leu Pro His Ser Val Phe His Gly His Lys
        545                 550                 555                 560
        Gln Leu Ala Thr Lys Ile Arg Leu Trp His Gln Gln Gly Glu Arg Cys
                        565                 570                 575
        Leu Tyr Thr Gly Lys Thr Ile Ser Ile His Asp Leu Ile Asn Asn Ser
                        580                 585                 590
        Asn Gln Phe Glu Val Asp His Ile Leu Pro Leu Ser Ile Thr Phe Asp
                        595                 600                 605
        Asp Ser Leu Ala Asn Lys Val Leu Val Tyr Ala Thr Ala Asn Gln Glu
                        610                 615                 620
        Lys Gly Gln Arg Thr Pro Tyr Gln Ala Leu Asp Ser Met Asp Asp Ala
        625                 630                 635                 640
        Trp Ser Phe Arg Glu Leu Lys Ala Phe Val Arg Glu Ser Lys Thr Leu
                        645                 650                 655
        Ser Asn Lys Lys Lys Glu Tyr Leu Leu Thr Glu Glu Asp Ile Ser Lys
                        660                 665                 670
        Phe Asp Val Arg Lys Lys Phe Ile Glu Arg Asn Leu Val Asp Thr Arg
                        675                 680                 685
        Tyr Ala Ser Arg Val Val Leu Asn Ala Leu Gln Glu His Phe Arg Ala
                        690                 695                 700
        His Lys Ile Asp Thr Lys Val Ser Val Val Arg Gly Gln Phe Thr Ser
        705                 710                 715                 720
        Gln Leu Arg Arg His Trp Gly Ile Glu Lys Thr Arg Asp Thr Tyr His
                        725                 730                 735
        His His Ala Val Asp Ala Leu Ile Ile Ala Ala Ser Ser Gln Leu Asn
                        740                 745                 750
        Leu Trp Lys Lys Gln Lys Asn Thr Leu Val Ser Tyr Ser Glu Asp Gln
                        755                 760                 765
        Leu Leu Asp Ile Glu Thr Gly Glu Leu Ile Ser Asp Asp Glu Tyr Lys
                        770                 775                 780
        Glu Ser Val Phe Lys Ala Pro Tyr Gln His Phe Val Asp Thr Leu Lys
        785                 790                 795                 800
        Ser Lys Glu Phe Glu Asp Ser Ile Leu Phe Ser Tyr Gln Val Asp Ser
                        805                 810                 815
        Lys Phe Asn Arg Lys Ile Ser Asp Ala Thr Ile Tyr Ala Thr Arg Gln
                        820                 825                 830
        Ala Lys Val Gly Lys Asp Lys Ala Asp Glu Thr Tyr Val Leu Gly Lys
                        835                 840                 845
        Ile Lys Asp Ile Tyr Thr Gln Asp Gly Tyr Asp Ala Phe Met Lys Ile
                        850                 855                 860
        Tyr Lys Lys Asp Lys Ser Lys Phe Leu Met Tyr Arg His Asp Pro Gln
        865                 870                 875                 880
        Thr Phe Glu Lys Val Ile Glu Pro Ile Leu Glu Asn Tyr Pro Asn Lys
                        885                 890                 895
```

-continued

```
Gln Ile Asn Asp Lys Gly Lys Glu Val Pro Cys Asn Pro Phe Leu Lys
            900                 905                 910
Tyr Lys Glu Glu His Gly Tyr Ile Arg Lys Tyr Ser Lys Lys Gly Asn
            915                 920                 925
Gly Pro Glu Ile Lys Ser Leu Lys Tyr Tyr Asp Ser Lys Leu Gly Asn
            930                 935                 940
His Ile Asp Ile Thr Pro Lys Asp Ser Asn Asn Lys Val Val Leu Gln
945                 950                 955                 960
Ser Val Ser Pro Trp Arg Ala Asp Val Tyr Phe Asn Lys Thr Thr Gly
                965                 970                 975
Lys Tyr Glu Ile Leu Gly Leu Lys Tyr Ala Asp Leu Gln Phe Asp Lys
            980                 985                 990
Gly Thr Gly Thr Tyr Lys Ile Ser Gln Glu Lys Tyr Asn Asp Ile Lys
            995                 1000                1005
Lys Lys Glu Gly Val Asp Ser Asp Ser Glu Phe Lys Phe Thr Leu
            1010                1015                1020
Tyr Lys Asn Asp Leu Leu Leu Val Lys Asp Thr Glu Thr Lys Glu
            1025                1030                1035
Gln Gln Leu Phe Arg Phe Leu Ser Arg Thr Met Pro Lys Gln Lys
            1040                1045                1050
His Tyr Val Glu Leu Lys Pro Tyr Asp Lys Gln Lys Phe Glu Gly
            1055                1060                1065
Gly Glu Ala Leu Ile Lys Val Leu Gly Asn Val Ala Asn Ser Gly
            1070                1075                1080
Gln Cys Lys Lys Gly Leu Gly Lys Ser Asn Ile Ser Ile Tyr Lys
            1085                1090                1095
Val Arg Thr Asp Val Leu Gly Asn Gln His Ile Ile Lys Asn Glu
            1100                1105                1110
Gly Asp Lys Pro Lys Leu Asp Phe Ala Ala Ala Asp Pro Lys Lys
            1115                1120                1125
Lys Arg Lys Val Asp Pro Lys Lys Lys Arg Lys Val Asp Pro Lys
            1130                1135                1140
Lys Lys Arg Lys Val Asp Thr Ala Ala
            1145                1150

<210> SEQ ID NO 16
<211> LENGTH: 1081
<212> TYPE: PRT
<213> ORGANISM: Neisseria meningitidis

<400> SEQUENCE: 16

Met Ala Ala Phe Lys Pro Asn Pro Ile Asn Tyr Ile Leu Gly Leu Asp
1               5                   10                  15
Ile Gly Ile Ala Ser Val Gly Trp Ala Met Val Glu Ile Asp Glu Asp
                20                  25                  30
Glu Asn Pro Ile Cys Leu Ile Asp Leu Gly Val Arg Val Phe Glu Arg
            35                  40                  45
Ala Glu Val Pro Lys Thr Gly Asp Ser Leu Ala Met Ala Arg Arg Leu
        50                  55                  60
Ala Arg Ser Val Arg Arg Leu Thr Arg Arg Arg Ala His Arg Leu Leu
65                  70                  75                  80
Arg Ala Arg Arg Leu Leu Lys Arg Glu Gly Val Leu Gln Ala Ala Asp
                85                  90                  95
Phe Asp Glu Asn Gly Leu Ile Lys Ser Leu Pro Asn Thr Pro Trp Gln
```

-continued

```
               100                 105                 110
Leu Arg Ala Ala Ala Leu Asp Arg Lys Leu Thr Pro Leu Glu Trp Ser
            115                 120                 125

Ala Val Leu Leu His Leu Ile Lys His Arg Gly Tyr Leu Ser Gln Arg
        130                 135                 140

Lys Asn Glu Gly Glu Thr Ala Asp Lys Glu Leu Gly Ala Leu Leu Lys
145                 150                 155                 160

Gly Val Ala Asp Asn Ala His Ala Leu Gln Thr Gly Asp Phe Arg Thr
                165                 170                 175

Pro Ala Glu Leu Ala Leu Asn Lys Phe Glu Lys Glu Ser Gly His Ile
            180                 185                 190

Arg Asn Gln Arg Gly Asp Tyr Ser His Thr Phe Ser Arg Lys Asp Leu
        195                 200                 205

Gln Ala Glu Leu Ile Leu Leu Phe Glu Lys Gln Lys Glu Phe Gly Asn
    210                 215                 220

Pro His Val Ser Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
                245                 250                 255

His Cys Thr Phe Glu Pro Ala Glu Pro Lys Ala Ala Lys Asn Thr Tyr
            260                 265                 270

Thr Ala Glu Arg Phe Ile Trp Leu Thr Lys Leu Asn Asn Leu Arg Ile
        275                 280                 285

Leu Glu Gln Gly Ser Glu Arg Pro Leu Thr Asp Thr Glu Arg Ala Thr
    290                 295                 300

Leu Met Asp Glu Pro Tyr Arg Lys Ser Lys Leu Thr Tyr Ala Gln Ala
305                 310                 315                 320

Arg Lys Leu Leu Gly Leu Glu Asp Thr Ala Phe Phe Lys Gly Leu Arg
                325                 330                 335

Tyr Gly Lys Asp Asn Ala Glu Ala Ser Thr Leu Met Glu Met Lys Ala
            340                 345                 350

Tyr His Ala Ile Ser Arg Ala Leu Glu Lys Glu Gly Leu Lys Asp Lys
        355                 360                 365

Lys Ser Pro Leu Asn Leu Ser Pro Glu Leu Gln Asp Glu Ile Gly Thr
    370                 375                 380

Ala Phe Ser Leu Phe Lys Thr Asp Glu Asp Ile Thr Gly Arg Leu Lys
385                 390                 395                 400

Asp Arg Ile Gln Pro Glu Ile Leu Glu Ala Leu Leu Lys His Ile Ser
                405                 410                 415

Phe Asp Lys Phe Val Gln Ile Ser Leu Lys Ala Leu Arg Arg Ile Val
            420                 425                 430

Pro Leu Met Glu Gln Gly Lys Arg Tyr Asp Glu Ala Cys Ala Glu Ile
        435                 440                 445

Tyr Gly Asp His Tyr Gly Lys Lys Asn Thr Glu Glu Lys Ile Tyr Leu
    450                 455                 460

Pro Pro Ile Pro Ala Asp Glu Ile Arg Asn Pro Val Val Leu Arg Ala
465                 470                 475                 480

Leu Ser Gln Ala Arg Lys Val Ile Asn Gly Val Val Arg Arg Tyr Gly
                485                 490                 495

Ser Pro Ala Arg Ile His Ile Glu Thr Ala Arg Glu Val Gly Lys Ser
            500                 505                 510

Phe Lys Asp Arg Lys Glu Ile Glu Lys Arg Gln Glu Glu Asn Arg Lys
        515                 520                 525
```

```
Asp Arg Glu Lys Ala Ala Lys Phe Arg Glu Tyr Phe Pro Asn Phe
            530                 535                 540

Val Gly Glu Pro Lys Ser Lys Asp Ile Leu Lys Leu Arg Leu Tyr Glu
545                 550                 555                 560

Gln Gln His Gly Lys Cys Leu Tyr Ser Gly Lys Glu Ile Asn Leu Gly
                565                 570                 575

Arg Leu Asn Glu Lys Gly Tyr Val Glu Ile Asp His Ala Leu Pro Phe
            580                 585                 590

Ser Arg Thr Trp Asp Asp Ser Phe Asn Asn Lys Val Leu Val Leu Gly
            595                 600                 605

Ser Glu Asn Gln Asn Lys Gly Asn Gln Thr Pro Tyr Glu Tyr Phe Asn
610                 615                 620

Gly Lys Asp Asn Ser Arg Glu Trp Gln Glu Phe Lys Ala Arg Val Glu
625                 630                 635                 640

Thr Ser Arg Phe Pro Arg Ser Lys Lys Gln Arg Ile Leu Leu Gln Lys
            645                 650                 655

Phe Asp Glu Asp Gly Phe Lys Glu Arg Asn Leu Asn Asp Thr Arg Tyr
            660                 665                 670

Val Asn Arg Phe Leu Cys Phe Val Ala Asp Arg Met Arg Leu Thr Gly
            675                 680                 685

Lys Gly Lys Lys Arg Val Phe Ala Ser Asn Gly Gln Ile Thr Asn Leu
690                 695                 700

Leu Arg Gly Phe Trp Gly Leu Arg Lys Val Arg Ala Glu Asn Asp Arg
705                 710                 715                 720

His His Ala Leu Asp Ala Val Val Val Ala Cys Ser Thr Val Ala Met
            725                 730                 735

Gln Gln Lys Ile Thr Arg Phe Val Arg Tyr Lys Glu Met Asn Ala Phe
            740                 745                 750

Asp Gly Lys Thr Ile Asp Lys Glu Thr Gly Glu Val Leu His Gln Lys
            755                 760                 765

Thr His Phe Pro Gln Pro Trp Glu Phe Phe Ala Gln Glu Val Met Ile
    770                 775                 780

Arg Val Phe Gly Lys Pro Asp Gly Lys Pro Glu Phe Glu Glu Ala Asp
785                 790                 795                 800

Thr Pro Glu Lys Leu Arg Thr Leu Leu Ala Glu Lys Leu Ser Ser Arg
            805                 810                 815

Pro Glu Ala Val His Glu Tyr Val Thr Pro Leu Phe Val Ser Arg Ala
            820                 825                 830

Pro Asn Arg Lys Met Ser Gly Gln Gly His Met Glu Thr Val Lys Ser
            835                 840                 845

Ala Lys Arg Leu Asp Glu Gly Val Ser Val Leu Arg Val Pro Leu Thr
850                 855                 860

Gln Leu Lys Leu Lys Asp Leu Glu Lys Met Val Asn Arg Glu Arg Glu
865                 870                 875                 880

Pro Lys Leu Tyr Glu Ala Leu Lys Ala Arg Leu Glu Ala His Lys Asp
            885                 890                 895

Asp Pro Ala Lys Ala Phe Ala Glu Pro Phe Tyr Lys Tyr Asp Lys Ala
            900                 905                 910

Gly Asn Arg Thr Gln Gln Val Lys Ala Val Arg Val Glu Gln Val Gln
            915                 920                 925

Lys Thr Gly Val Trp Val Arg Asn His Asn Gly Ile Ala Asp Asn Ala
930                 935                 940
```

-continued

```
Thr Met Val Arg Val Asp Val Phe Glu Lys Gly Asp Lys Tyr Tyr Leu
945                 950                 955                 960

Val Pro Ile Tyr Ser Trp Gln Val Ala Lys Gly Ile Leu Pro Asp Arg
            965                 970                 975

Ala Val Val Gln Gly Lys Asp Glu Asp Trp Gln Leu Ile Asp Asp
        980                 985                 990

Ser Phe Asn Phe Lys Phe Ser Leu His Pro Asn Asp Leu Val Glu Val
        995                 1000                1005

Ile Thr Lys Lys Ala Arg Met Phe Gly Tyr Phe Ala Ser Cys His
    1010                1015                1020

Arg Gly Thr Gly Asn Ile Asn Ile Arg Ile His Asp Leu Asp His
    1025                1030                1035

Lys Ile Gly Lys Asn Gly Ile Leu Glu Gly Ile Gly Val Lys Thr
    1040                1045                1050

Ala Leu Ser Phe Gln Lys Tyr Gln Ile Asp Glu Leu Gly Lys Glu
    1055                1060                1065

Ile Arg Pro Cys Arg Leu Lys Lys Arg Pro Pro Val Arg
    1070                1075                1080

<210> SEQ ID NO 17
<211> LENGTH: 8
<212> TYPE: DNA
<213> ORGANISM: Artificial Sequence
<220> FEATURE:
<223> OTHER INFORMATION: Motif
<220> FEATURE:
<221> NAME/KEY: misc_feature
<222> LOCATION: (1)..(4)
<223> OTHER INFORMATION: wherein N is any of the nucleotide T, C, A or G
<220> FEATURE:
<221> NAME/KEY: misc_feature
<222> LOCATION: (7)..(8)
<223> OTHER INFORMATION: wherein N is any of the nucleotide T, C, A or G

<400> SEQUENCE: 17 nnnngann                                                              8

<210> SEQ ID NO 18
<211> LENGTH: 8
<212> TYPE: DNA
<213> ORGANISM: Artificial Sequence
<220> FEATURE:
<223> OTHER INFORMATION: Motif
<220> FEATURE:
<221> NAME/KEY: misc_feature
<222> LOCATION: (1)..(4)
<223> OTHER INFORMATION: wherein N is any of the nucleotide T, C, A or G

<400> SEQUENCE: 18 nnnngatt                                                              8

<210> SEQ ID NO 19
<211> LENGTH: 145
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(24)
<223> OTHER INFORMATION: wherein N is any of the nucleotide U, C, A or G

<400> SEQUENCE: 19
nnnnnnnnnn nnnnnnnnnn nnnnguugua gcucccuuuc ucauuuggga aacgaaauga    60
```

```
gaaccguugc uacaauaagg ccgucugaaa agaugugccg caacgcucug ccccuuaaag      120
cuucugcuuu aagggggcauc guuua                                          145
```

<210> SEQ ID NO 20
<211> LENGTH: 121
<212> TYPE: RNA
<213> ORGANISM: Artificial Sequence
<220> FEATURE:
<223> OTHER INFORMATION: gRNA

<400> SEQUENCE: 20

```
guuguagcuc ccuuucucau uugggaaacg aaaugagaac cguugcuaca auaaggccgu      60
cugaaaagau gugccgcaac gcucugcccc uuaaagcuuc ugcuuuaagg ggcaucguuu     120
a                                                                    121
```

<210> SEQ ID NO 21
<211> LENGTH: 1113
<212> TYPE: PRT
<213> ORGANISM: Neisseria meningitidis

<400> SEQUENCE: 21

```
Met Ala Ala Phe Lys Pro Asn Pro Ile Asn Tyr Ile Leu Gly Leu Asp
1               5                   10                  15

Ile Gly Ile Ala Ser Val Gly Trp Ala Met Val Glu Ile Asp Glu Asp
            20                  25                  30

Glu Asn Pro Ile Cys Leu Ile Asp Leu Gly Val Arg Val Phe Glu Arg
        35                  40                  45

Ala Glu Val Pro Lys Thr Gly Asp Ser Leu Ala Met Ala Arg Arg Leu
    50                  55                  60

Ala Arg Ser Val Arg Arg Leu Thr Arg Arg Ala His Arg Leu Leu
65                  70                  75                  80

Arg Ala Arg Arg Leu Leu Lys Arg Glu Gly Val Leu Gln Ala Ala Asp
                85                  90                  95

Phe Asp Glu Asn Gly Leu Ile Lys Ser Leu Pro Asn Thr Pro Trp Gln
            100                 105                 110

Leu Arg Ala Ala Ala Leu Asp Arg Lys Leu Thr Pro Leu Glu Trp Ser
        115                 120                 125

Ala Val Leu Leu His Leu Ile Lys His Arg Gly Tyr Leu Ser Gln Arg
    130                 135                 140

Lys Asn Glu Gly Glu Thr Ala Asp Lys Glu Leu Gly Ala Leu Leu Lys
145                 150                 155                 160

Gly Val Ala Asp Asn Ala His Ala Leu Gln Thr Gly Asp Phe Arg Thr
                165                 170                 175

Pro Ala Glu Leu Ala Leu Asn Lys Phe Glu Lys Glu Ser Gly His Ile
            180                 185                 190

Arg Asn Gln Arg Gly Asp Tyr Ser His Thr Phe Ser Arg Lys Asp Leu
        195                 200                 205

Gln Ala Glu Leu Ile Leu Leu Phe Glu Lys Gln Lys Glu Phe Gly Asn
    210                 215                 220

Pro His Val Ser Gly Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
                245                 250                 255

His Cys Thr Phe Glu Pro Ala Glu Pro Lys Ala Ala Lys Asn Thr Tyr
            260                 265                 270
```

Thr Ala Glu Arg Phe Ile Trp Leu Thr Lys Leu Asn Asn Leu Arg Ile
            275                 280                 285

Leu Glu Gln Gly Ser Glu Arg Pro Leu Thr Asp Thr Glu Arg Ala Thr
        290                 295                 300

Leu Met Asp Glu Pro Tyr Arg Lys Ser Lys Leu Thr Tyr Ala Gln Ala
305                 310                 315                 320

Arg Lys Leu Leu Gly Leu Glu Asp Thr Ala Phe Phe Lys Gly Leu Arg
                325                 330                 335

Tyr Gly Lys Asp Asn Ala Glu Ala Ser Thr Leu Met Glu Met Lys Ala
            340                 345                 350

Tyr His Ala Ile Ser Arg Ala Leu Glu Lys Glu Gly Leu Lys Asp Lys
        355                 360                 365

Lys Ser Pro Leu Asn Leu Ser Pro Glu Leu Gln Asp Glu Ile Gly Thr
    370                 375                 380

Ala Phe Ser Leu Phe Lys Thr Asp Glu Asp Ile Thr Gly Arg Leu Lys
385                 390                 395                 400

Asp Arg Ile Gln Pro Glu Ile Leu Glu Ala Leu Leu Lys His Ile Ser
                405                 410                 415

Phe Asp Lys Phe Val Gln Ile Ser Leu Lys Ala Leu Arg Arg Ile Val
            420                 425                 430

Pro Leu Met Glu Gln Gly Lys Arg Tyr Asp Glu Ala Cys Ala Glu Ile
        435                 440                 445

Tyr Gly Asp His Tyr Gly Lys Lys Asn Thr Glu Glu Lys Ile Tyr Leu
    450                 455                 460

Pro Pro Ile Pro Ala Asp Glu Ile Arg Asn Pro Val Val Leu Arg Ala
465                 470                 475                 480

Leu Ser Gln Ala Arg Lys Val Ile Asn Gly Val Val Arg Arg Tyr Gly
                485                 490                 495

Ser Pro Ala Arg Ile His Ile Glu Thr Ala Arg Glu Val Gly Lys Ser
            500                 505                 510

Phe Lys Asp Arg Lys Glu Ile Glu Lys Arg Gln Glu Glu Asn Arg Lys
        515                 520                 525

Asp Arg Glu Lys Ala Ala Ala Lys Phe Arg Glu Tyr Phe Pro Asn Phe
    530                 535                 540

Val Gly Glu Pro Lys Ser Lys Asp Ile Leu Lys Leu Arg Leu Tyr Glu
545                 550                 555                 560

Gln Gln His Gly Lys Cys Leu Tyr Ser Gly Lys Glu Ile Asn Leu Gly
                565                 570                 575

Arg Leu Asn Glu Lys Gly Tyr Val Glu Ile Asp His Ala Leu Pro Phe
            580                 585                 590

Ser Arg Thr Trp Asp Asp Ser Phe Asn Asn Lys Val Leu Val Leu Gly
        595                 600                 605

Ser Glu Asn Gln Asn Lys Gly Asn Gln Thr Pro Tyr Glu Tyr Phe Asn
    610                 615                 620

Gly Lys Asp Asn Ser Arg Glu Trp Gln Glu Phe Lys Ala Arg Val Glu
625                 630                 635                 640

Thr Ser Arg Phe Pro Arg Ser Lys Lys Gln Arg Ile Leu Leu Gln Lys
                645                 650                 655

Phe Asp Glu Asp Gly Phe Lys Glu Arg Asn Leu Asn Asp Thr Arg Tyr
            660                 665                 670

Val Asn Arg Phe Leu Cys Gln Phe Val Ala Asp Arg Met Arg Leu Thr
        675                 680                 685

Gly Lys Gly Lys Lys Arg Val Phe Ala Ser Asn Gly Gln Ile Thr Asn

```
                690             695              700
Leu Leu Arg Gly Phe Trp Gly Leu Arg Lys Val Arg Ala Glu Asn Asp
705             710              715             720

Arg His His Ala Leu Asp Ala Val Val Ala Cys Ser Thr Val Ala
                725             730              735

Met Gln Gln Lys Ile Thr Arg Phe Val Arg Tyr Lys Glu Met Asn Ala
                740             745              750

Phe Asp Gly Lys Thr Ile Asp Lys Glu Thr Gly Glu Val Leu His Gln
                755             760              765

Lys Thr His Phe Pro Gln Pro Trp Glu Phe Phe Ala Gln Glu Val Met
770             775              780

Ile Arg Val Phe Gly Lys Pro Asp Gly Lys Pro Glu Phe Glu Glu Ala
785             790              795             800

Asp Thr Pro Glu Lys Leu Arg Thr Leu Leu Ala Glu Lys Leu Ser Ser
                805             810              815

Arg Pro Glu Ala Val His Glu Tyr Val Thr Pro Leu Phe Val Ser Arg
                820             825              830

Ala Pro Asn Arg Lys Met Ser Gly Gln Gly His Met Glu Thr Val Lys
                835             840              845

Ser Ala Lys Arg Leu Asp Glu Gly Val Ser Val Leu Arg Val Pro Leu
                850             855              860

Thr Gln Leu Lys Leu Lys Asp Leu Glu Lys Met Val Asn Arg Glu Arg
865             870              875             880

Glu Pro Lys Leu Tyr Glu Ala Leu Lys Ala Arg Leu Glu Ala His Lys
                885             890              895

Asp Asp Pro Ala Lys Ala Phe Ala Glu Pro Phe Tyr Lys Tyr Asp Lys
                900             905              910

Ala Gly Asn Arg Thr Gln Gln Val Lys Ala Val Arg Val Glu Gln Val
                915             920              925

Gln Lys Thr Gly Val Trp Val Arg Asn His Asn Gly Ile Ala Asp Asn
                930             935              940

Ala Thr Met Val Arg Val Asp Val Phe Glu Lys Gly Asp Lys Tyr Tyr
945             950              955             960

Leu Val Pro Ile Tyr Ser Trp Gln Val Ala Lys Gly Ile Leu Pro Asp
                965             970              975

Arg Ala Val Val Gln Gly Lys Asp Glu Glu Asp Trp Gln Leu Ile Asp
                980             985              990

Asp Ser Phe Asn Phe Lys Phe Ser Leu His Pro Asn Asp Leu Val Glu
                995             1000             1005

Val Ile Thr Lys Lys Ala Arg Met Phe Gly Tyr Phe Ala Ser Cys
     1010            1015             1020

His Arg Gly Thr Gly Asn Ile Asn Ile Arg Ile His Asp Leu Asp
     1025            1030             1035

His Lys Ile Gly Lys Asn Gly Ile Leu Glu Gly Ile Gly Val Lys
     1040            1045             1050

Thr Ala Leu Ser Phe Gln Lys Tyr Gln Ile Asp Glu Leu Gly Lys
     1055            1060             1065

Glu Ile Arg Pro Cys Arg Leu Lys Lys Arg Pro Val Arg Ala
     1070            1075             1080

Ala Ala Asp Pro Lys Lys Lys Arg Lys Val Asp Pro Lys Lys Lys
     1085            1090             1095

Arg Lys Val Asp Pro Lys Lys Lys Arg Lys Val Asp Thr Ala Ala
     1100            1105             1110
```

<210> SEQ ID NO 22
<211> LENGTH: 1395
<212> TYPE: PRT
<213> ORGANISM: Treponema denticola

<400> SEQUENCE: 22

```
Met Lys Lys Glu Ile Lys Asp Tyr Phe Leu Gly Leu Asp Val Gly Thr
1               5                   10                  15

Gly Ser Val Gly Trp Ala Val Thr Asp Thr Asp Tyr Lys Leu Leu Lys
            20                  25                  30

Ala Asn Arg Lys Asp Leu Trp Gly Met Arg Cys Phe Glu Thr Ala Glu
        35                  40                  45

Thr Ala Glu Val Arg Arg Leu His Arg Gly Ala Arg Arg Ile Glu
    50                  55                  60

Arg Arg Lys Lys Arg Ile Lys Leu Leu Gln Glu Leu Phe Ser Gln Glu
65                  70                  75                  80

Ile Ala Lys Thr Asp Glu Gly Phe Phe Gln Arg Met Lys Glu Ser Pro
                85                  90                  95

Phe Tyr Ala Glu Asp Lys Thr Ile Leu Gln Glu Asn Thr Leu Phe Asn
            100                 105                 110

Asp Lys Asp Phe Ala Asp Lys Thr Tyr His Lys Ala Tyr Pro Thr Ile
        115                 120                 125

Asn His Leu Ile Lys Ala Trp Ile Glu Asn Lys Val Lys Pro Asp Pro
    130                 135                 140

Arg Leu Leu Tyr Leu Ala Cys His Asn Ile Ile Lys Lys Arg Gly His
145                 150                 155                 160

Phe Leu Phe Glu Gly Asp Phe Asp Ser Glu Asn Gln Phe Asp Thr Ser
                165                 170                 175

Ile Gln Ala Leu Phe Glu Tyr Leu Arg Glu Asp Met Glu Val Asp Ile
            180                 185                 190

Asp Ala Asp Ser Gln Lys Val Lys Glu Ile Leu Lys Asp Ser Ser Leu
        195                 200                 205

Lys Asn Ser Glu Lys Gln Ser Arg Leu Asn Lys Ile Leu Gly Leu Lys
    210                 215                 220

Pro Ser Asp Lys Gln Lys Lys Ala Ile Thr Asn Leu Ile Ser Gly Asn
225                 230                 235                 240

Lys Ile Asn Phe Ala Asp Leu Tyr Asp Asn Pro Asp Leu Lys Asp Ala
                245                 250                 255

Glu Lys Asn Ser Ile Ser Phe Ser Lys Asp Phe Asp Ala Leu Ser
            260                 265                 270

Asp Asp Leu Ala Ser Ile Leu Gly Asp Ser Phe Glu Leu Leu Leu Lys
        275                 280                 285

Ala Lys Ala Val Tyr Asn Cys Ser Val Leu Ser Lys Val Ile Gly Asp
    290                 295                 300

Glu Gln Tyr Leu Ser Phe Ala Lys Val Lys Ile Tyr Glu Lys His Lys
305                 310                 315                 320

Thr Asp Leu Thr Lys Leu Lys Asn Val Ile Lys Lys His Phe Pro Lys
                325                 330                 335

Asp Tyr Lys Lys Val Phe Gly Tyr Asn Lys Asn Glu Lys Asn Asn Asn
            340                 345                 350

Asn Tyr Ser Gly Tyr Val Gly Val Cys Lys Thr Lys Ser Lys Lys Leu
        355                 360                 365

Ile Ile Asn Asn Ser Val Asn Gln Glu Asp Phe Tyr Lys Phe Leu Lys
```

```
            370                 375                 380
Thr Ile Leu Ser Ala Lys Ser Glu Ile Lys Glu Val Asn Asp Ile Leu
385                 390                 395                 400

Thr Glu Ile Glu Thr Gly Thr Phe Leu Pro Lys Gln Ile Ser Lys Ser
                405                 410                 415

Asn Ala Glu Ile Pro Tyr Gln Leu Arg Lys Met Glu Leu Glu Lys Ile
                420                 425                 430

Leu Ser Asn Ala Glu Lys His Phe Ser Phe Leu Lys Gln Lys Asp Glu
                435                 440                 445

Lys Gly Leu Ser His Ser Glu Lys Ile Ile Met Leu Leu Thr Phe Lys
450                 455                 460

Ile Pro Tyr Tyr Ile Gly Pro Ile Asn Asp Asn His Lys Lys Phe Phe
465                 470                 475                 480

Pro Asp Arg Cys Trp Val Val Lys Lys Glu Lys Ser Pro Ser Gly Lys
                485                 490                 495

Thr Thr Pro Trp Asn Phe Phe Asp His Ile Asp Lys Glu Lys Thr Ala
                500                 505                 510

Glu Ala Phe Ile Thr Ser Arg Thr Asn Phe Cys Thr Tyr Leu Val Gly
                515                 520                 525

Glu Ser Val Leu Pro Lys Ser Ser Leu Leu Tyr Ser Glu Tyr Thr Val
530                 535                 540

Leu Asn Glu Ile Asn Asn Leu Gln Ile Ile Ile Asp Gly Lys Asn Ile
545                 550                 555                 560

Cys Asp Ile Lys Leu Lys Gln Lys Ile Tyr Glu Asp Leu Phe Lys Lys
                565                 570                 575

Tyr Lys Lys Ile Thr Gln Lys Gln Ile Ser Thr Phe Ile Lys His Glu
                580                 585                 590

Gly Ile Cys Asn Lys Thr Asp Glu Val Ile Ile Leu Gly Ile Asp Lys
                595                 600                 605

Glu Cys Thr Ser Ser Leu Lys Ser Tyr Ile Glu Leu Lys Asn Ile Phe
                610                 615                 620

Gly Lys Gln Val Asp Glu Ile Ser Thr Lys Asn Met Leu Glu Glu Ile
625                 630                 635                 640

Ile Arg Trp Ala Thr Ile Tyr Asp Glu Gly Glu Gly Lys Thr Ile Leu
                645                 650                 655

Lys Thr Lys Ile Lys Ala Glu Tyr Gly Lys Tyr Cys Ser Asp Glu Gln
                660                 665                 670

Ile Lys Lys Ile Leu Asn Leu Lys Phe Ser Gly Trp Gly Arg Leu Ser
                675                 680                 685

Arg Lys Phe Leu Glu Thr Val Thr Ser Glu Met Pro Gly Phe Ser Glu
                690                 695                 700

Pro Val Asn Ile Ile Thr Ala Met Arg Glu Thr Gln Asn Asn Leu Met
705                 710                 715                 720

Glu Leu Leu Ser Ser Glu Phe Thr Phe Thr Glu Asn Ile Lys Lys Ile
                725                 730                 735

Asn Ser Gly Phe Glu Asp Ala Glu Lys Gln Phe Ser Tyr Asp Gly Leu
                740                 745                 750

Val Lys Pro Leu Phe Leu Ser Pro Ser Val Lys Met Leu Trp Gln
                755                 760                 765

Thr Leu Lys Leu Val Lys Glu Ile Ser His Ile Thr Gln Ala Pro Pro
                770                 775                 780

Lys Lys Ile Phe Ile Glu Met Ala Lys Gly Ala Glu Leu Glu Pro Ala
785                 790                 795                 800
```

```
Arg Thr Lys Thr Arg Leu Lys Ile Leu Gln Asp Leu Tyr Asn Asn Cys
            805                 810                 815

Lys Asn Asp Ala Asp Ala Phe Ser Ser Glu Ile Lys Asp Leu Ser Gly
            820                 825                 830

Lys Ile Glu Asn Glu Asp Asn Leu Arg Leu Arg Ser Asp Lys Leu Tyr
            835                 840                 845

Leu Tyr Tyr Thr Gln Leu Gly Lys Cys Met Tyr Cys Gly Lys Pro Ile
            850                 855                 860

Glu Ile Gly His Val Phe Asp Thr Ser Asn Tyr Asp Ile Asp His Ile
865                 870                 875                 880

Tyr Pro Gln Ser Lys Ile Lys Asp Asp Ser Ile Ser Asn Arg Val Leu
            885                 890                 895

Val Cys Ser Ser Cys Asn Lys Asn Lys Glu Asp Lys Tyr Pro Leu Lys
            900                 905                 910

Ser Glu Ile Gln Ser Lys Gln Arg Gly Phe Trp Asn Phe Leu Gln Arg
            915                 920                 925

Asn Asn Phe Ile Ser Leu Glu Lys Leu Asn Arg Leu Thr Arg Ala Thr
            930                 935                 940

Pro Ile Ser Asp Asp Glu Thr Ala Lys Phe Ile Ala Arg Gln Leu Val
945                 950                 955                 960

Glu Thr Arg Gln Ala Thr Lys Val Ala Ala Lys Val Leu Glu Lys Met
            965                 970                 975

Phe Pro Glu Thr Lys Ile Val Tyr Ser Lys Ala Glu Thr Val Ser Met
            980                 985                 990

Phe Arg Asn Lys Phe Asp Ile Val Lys Cys Arg Glu Ile Asn Asp Phe
            995                1000                1005

His His Ala His Asp Ala Tyr Leu Asn Ile Val Val Gly Asn Val
            1010                1015                1020

Tyr Asn Thr Lys Phe Thr Asn Pro Trp Asn Phe Ile Lys Glu
            1025                1030                1035

Lys Arg Asp Asn Pro Lys Ile Ala Asp Thr Tyr Asn Tyr Tyr Lys
            1040                1045                1050

Val Phe Asp Tyr Asp Val Lys Arg Asn Asn Ile Thr Ala Trp Glu
            1055                1060                1065

Lys Gly Lys Thr Ile Ile Thr Val Lys Asp Met Leu Lys Arg Asn
            1070                1075                1080

Thr Pro Ile Tyr Thr Arg Gln Ala Ala Cys Lys Lys Gly Glu Leu
            1085                1090                1095

Phe Asn Gln Thr Ile Met Lys Lys Gly Leu Gly Gln His Pro Leu
            1100                1105                1110

Lys Lys Glu Gly Pro Phe Ser Asn Ile Ser Lys Tyr Gly Gly Tyr
            1115                1120                1125

Asn Lys Val Ser Ala Ala Tyr Tyr Thr Leu Ile Glu Tyr Glu Glu
            1130                1135                1140

Lys Gly Asn Lys Ile Arg Ser Leu Glu Thr Ile Pro Leu Tyr Leu
            1145                1150                1155

Val Lys Asp Ile Gln Lys Asp Gln Asp Val Leu Lys Ser Tyr Leu
            1160                1165                1170

Thr Asp Leu Leu Gly Lys Lys Glu Phe Lys Ile Leu Val Pro Lys
            1175                1180                1185

Ile Lys Ile Asn Ser Leu Leu Lys Ile Asn Gly Phe Pro Cys His
            1190                1195                1200
```

-continued

```
Ile Thr Gly Lys Thr Asn Asp Ser Phe Leu Leu Arg Pro Ala Val
    1205                1210                1215

Gln Phe Cys Cys Ser Asn Asn Glu Val Leu Tyr Phe Lys Lys Ile
    1220                1225                1230

Ile Arg Phe Ser Glu Ile Arg Ser Gln Arg Glu Lys Ile Gly Lys
    1235                1240                1245

Thr Ile Ser Pro Tyr Glu Asp Leu Ser Phe Arg Ser Tyr Ile Lys
    1250                1255                1260

Glu Asn Leu Trp Lys Lys Thr Lys Asn Asp Glu Ile Gly Glu Lys
    1265                1270                1275

Glu Phe Tyr Asp Leu Leu Gln Lys Lys Asn Leu Glu Ile Tyr Asp
    1280                1285                1290

Met Leu Leu Thr Lys His Lys Asp Thr Ile Tyr Lys Lys Arg Pro
    1295                1300                1305

Asn Ser Ala Thr Ile Asp Ile Leu Val Lys Gly Lys Glu Lys Phe
    1310                1315                1320

Lys Ser Leu Ile Ile Glu Asn Gln Phe Glu Val Ile Leu Glu Ile
    1325                1330                1335

Leu Lys Leu Phe Ser Ala Thr Arg Asn Val Ser Asp Leu Gln His
    1340                1345                1350

Ile Gly Gly Ser Lys Tyr Ser Gly Val Ala Lys Ile Gly Asn Lys
    1355                1360                1365

Ile Ser Ser Leu Asp Asn Cys Ile Leu Ile Tyr Gln Ser Ile Thr
    1370                1375                1380

Gly Ile Phe Glu Lys Arg Ile Asp Leu Leu Lys Val
    1385                1390                1395

<210> SEQ ID NO 23
<211> LENGTH: 6
<212> TYPE: DNA
<213> ORGANISM: Artificial Sequence
<220> FEATURE:
<223> OTHER INFORMATION: Motif
<220> FEATURE:
<221> NAME/KEY: misc_feature
<222> LOCATION: (1)..(1)
<223> OTHER INFORMATION: wherein N is any of the nucleotide T, C, A or G
<220> FEATURE:
<221> NAME/KEY: misc_feature
<222> LOCATION: (6)..(6)
<223> OTHER INFORMATION: wherein N is any of the nucleotide T, C, A or G

<400> SEQUENCE: 23 naaaan                                                                  6

<210> SEQ ID NO 24
<211> LENGTH: 1426
<212> TYPE: PRT
<213> ORGANISM: Treponema denticola

<400> SEQUENCE: 24

Met Lys Lys Glu Ile Lys Asp Tyr Phe Leu Gly Leu Asp Val Gly Thr
  1               5                  10                  15

Gly Ser Val Gly Trp Ala Val Thr Asp Thr Asp Tyr Lys Leu Leu Lys
             20                  25                  30

Ala Asn Arg Lys Asp Leu Trp Gly Met Arg Cys Phe Glu Thr Ala Glu
         35                  40                  45

Thr Ala Glu Val Arg Arg Leu His Arg Gly Ala Arg Arg Arg Ile Glu
     50                  55                  60
```

```
Arg Arg Lys Lys Arg Ile Lys Leu Leu Gln Glu Leu Phe Ser Gln Glu
 65              70                  75                  80

Ile Ala Lys Thr Asp Glu Gly Phe Phe Gln Arg Met Lys Glu Ser Pro
             85                  90                  95

Phe Tyr Ala Glu Asp Lys Thr Ile Leu Gln Glu Asn Thr Leu Phe Asn
            100                 105                 110

Asp Lys Asp Phe Ala Asp Lys Thr Tyr His Lys Ala Tyr Pro Thr Ile
        115                 120                 125

Asn His Leu Ile Lys Ala Trp Ile Glu Asn Lys Val Lys Pro Asp Pro
    130                 135                 140

Arg Leu Leu Tyr Leu Ala Cys His Asn Ile Ile Lys Lys Arg Gly His
145                 150                 155                 160

Phe Leu Phe Glu Gly Asp Phe Asp Ser Glu Asn Gln Phe Asp Thr Ser
                165                 170                 175

Ile Gln Ala Leu Phe Glu Tyr Leu Arg Glu Asp Met Glu Val Asp Ile
            180                 185                 190

Asp Ala Asp Ser Gln Lys Val Lys Glu Ile Leu Lys Asp Ser Ser Leu
        195                 200                 205

Lys Asn Ser Glu Lys Gln Ser Arg Leu Asn Lys Ile Leu Gly Leu Lys
    210                 215                 220

Pro Ser Asp Lys Gln Lys Lys Ala Ile Thr Asn Leu Ile Ser Gly Asn
225                 230                 235                 240

Lys Ile Asn Phe Ala Asp Leu Tyr Asp Asn Pro Asp Leu Lys Asp Ala
                245                 250                 255

Glu Lys Asn Ser Ile Ser Phe Ser Lys Asp Asp Phe Asp Ala Leu Ser
            260                 265                 270

Asp Asp Leu Ala Ser Ile Leu Gly Asp Ser Phe Glu Leu Leu Leu Lys
        275                 280                 285

Ala Lys Ala Val Tyr Asn Cys Ser Val Leu Ser Lys Val Ile Gly Asp
    290                 295                 300

Glu Gln Tyr Leu Ser Phe Ala Lys Val Lys Ile Tyr Glu Lys His Lys
305                 310                 315                 320

Thr Asp Leu Thr Lys Leu Lys Asn Val Ile Lys Lys His Phe Pro Lys
                325                 330                 335

Asp Tyr Lys Lys Val Phe Gly Tyr Asn Lys Asn Glu Lys Asn Asn Asn
            340                 345                 350

Asn Tyr Ser Gly Tyr Val Gly Val Cys Lys Thr Lys Ser Lys Lys Leu
        355                 360                 365

Ile Ile Asn Asn Ser Val Asn Gln Glu Asp Phe Tyr Lys Phe Leu Lys
    370                 375                 380

Thr Ile Leu Ser Ala Lys Ser Glu Ile Lys Glu Val Asn Asp Ile Leu
385                 390                 395                 400

Thr Glu Ile Glu Thr Gly Thr Phe Leu Pro Lys Gln Ile Ser Lys Ser
                405                 410                 415

Asn Ala Glu Ile Pro Tyr Gln Leu Arg Lys Met Glu Leu Glu Lys Ile
            420                 425                 430

Leu Ser Asn Ala Glu Lys His Phe Ser Phe Leu Lys Gln Lys Asp Glu
        435                 440                 445

Lys Gly Leu Ser His Ser Glu Lys Ile Ile Met Leu Leu Thr Phe Lys
    450                 455                 460

Ile Pro Tyr Tyr Ile Gly Pro Ile Asn Asp Asn His Lys Lys Phe Phe
465                 470                 475                 480

Pro Asp Arg Cys Trp Val Val Lys Lys Glu Lys Ser Pro Ser Gly Lys
```

```
                485                 490                 495
Thr Thr Pro Trp Asn Phe Phe Asp His Ile Asp Lys Glu Lys Thr Ala
            500                 505                 510
Glu Ala Phe Ile Thr Ser Arg Thr Asn Phe Cys Thr Tyr Leu Val Gly
            515                 520                 525
Glu Ser Val Leu Pro Lys Ser Ser Leu Leu Tyr Ser Glu Tyr Thr Val
            530                 535                 540
Leu Asn Glu Ile Asn Asn Leu Gln Ile Ile Asp Gly Lys Asn Ile
545                 550                 555                 560
Cys Asp Ile Lys Leu Lys Gln Lys Ile Tyr Glu Asp Leu Phe Lys Lys
            565                 570                 575
Tyr Lys Lys Ile Thr Gln Lys Gln Ile Ser Thr Phe Ile Lys His Glu
            580                 585                 590
Gly Ile Cys Asn Lys Thr Asp Glu Val Ile Ile Leu Gly Ile Asp Lys
            595                 600                 605
Glu Cys Thr Ser Ser Leu Lys Ser Tyr Ile Glu Leu Lys Asn Ile Phe
            610                 615                 620
Gly Lys Gln Val Asp Glu Ile Ser Thr Lys Asn Met Leu Glu Glu Ile
625                 630                 635                 640
Ile Arg Trp Ala Thr Ile Tyr Asp Glu Gly Glu Lys Thr Ile Leu
            645                 650                 655
Lys Thr Lys Ile Lys Ala Glu Tyr Gly Lys Tyr Cys Ser Asp Glu Gln
            660                 665                 670
Ile Lys Lys Ile Leu Asn Leu Lys Phe Ser Gly Trp Gly Arg Leu Ser
            675                 680                 685
Arg Lys Phe Leu Glu Thr Val Thr Ser Glu Met Pro Gly Phe Ser Glu
            690                 695                 700
Pro Val Asn Ile Ile Thr Ala Met Arg Glu Thr Gln Asn Asn Leu Met
705                 710                 715                 720
Glu Leu Leu Ser Ser Glu Phe Thr Phe Thr Glu Asn Ile Lys Lys Ile
            725                 730                 735
Asn Ser Gly Phe Glu Asp Ala Glu Lys Gln Phe Ser Tyr Asp Gly Leu
            740                 745                 750
Val Lys Pro Leu Phe Leu Ser Pro Ser Val Lys Lys Met Leu Trp Gln
            755                 760                 765
Thr Leu Lys Leu Val Lys Glu Ile Ser His Ile Thr Gln Ala Pro Pro
            770                 775                 780
Lys Lys Ile Phe Ile Glu Met Ala Lys Gly Ala Glu Leu Glu Pro Ala
785                 790                 795                 800
Arg Thr Lys Thr Arg Leu Lys Ile Leu Gln Asp Leu Tyr Asn Asn Cys
            805                 810                 815
Lys Asn Asp Ala Asp Ala Phe Ser Glu Ile Lys Asp Leu Ser Gly
            820                 825                 830
Lys Ile Glu Asn Glu Asp Asn Leu Arg Leu Arg Ser Asp Lys Leu Tyr
            835                 840                 845
Leu Tyr Tyr Thr Gln Leu Gly Lys Cys Met Tyr Cys Gly Lys Pro Ile
            850                 855                 860
Glu Ile Gly His Val Phe Asp Thr Ser Asn Tyr Asp Ile Asp His Ile
865                 870                 875                 880
Tyr Pro Gln Ser Lys Ile Lys Asp Asp Ser Ile Ser Asn Arg Val Leu
            885                 890                 895
Val Cys Ser Ser Cys Asn Lys Asn Lys Glu Asp Lys Tyr Pro Leu Lys
            900                 905                 910
```

```
Ser Glu Ile Gln Ser Lys Gln Arg Gly Phe Trp Asn Phe Leu Gln Arg
        915                 920                 925

Asn Asn Phe Ile Ser Leu Glu Lys Leu Asn Arg Leu Thr Arg Ala Thr
        930                 935                 940

Pro Ile Ser Asp Asp Glu Thr Ala Lys Phe Ile Ala Arg Gln Leu Val
945                 950                 955                 960

Glu Thr Arg Gln Ala Thr Lys Val Ala Ala Lys Val Leu Glu Lys Met
                965                 970                 975

Phe Pro Glu Thr Lys Ile Val Tyr Ser Lys Ala Glu Thr Val Ser Met
                980                 985                 990

Phe Arg Asn Lys Phe Asp Ile Val Lys Cys Arg Glu Ile Asn Asp Phe
                995                1000                1005

His His Ala His Asp Ala Tyr Leu Asn Ile Val Val Gly Asn Val
        1010                1015                1020

Tyr Asn Thr Lys Phe Thr Asn Asn Pro Trp Asn Phe Ile Lys Glu
        1025                1030                1035

Lys Arg Asp Asn Pro Lys Ile Ala Asp Thr Tyr Asn Tyr Tyr Lys
        1040                1045                1050

Val Phe Asp Tyr Asp Val Lys Arg Asn Asn Ile Thr Ala Trp Glu
        1055                1060                1065

Lys Gly Lys Thr Ile Ile Thr Val Lys Asp Met Leu Lys Arg Asn
        1070                1075                1080

Thr Pro Ile Tyr Thr Arg Gln Ala Ala Cys Lys Lys Gly Glu Leu
        1085                1090                1095

Phe Asn Gln Thr Ile Met Lys Lys Gly Leu Gly Gln His Pro Leu
        1100                1105                1110

Lys Lys Glu Gly Pro Phe Ser Asn Ile Ser Lys Tyr Gly Gly Tyr
        1115                1120                1125

Asn Lys Val Ser Ala Ala Tyr Tyr Thr Leu Ile Glu Tyr Glu Glu
        1130                1135                1140

Lys Gly Asn Lys Ile Arg Ser Leu Glu Thr Ile Pro Leu Tyr Leu
        1145                1150                1155

Val Lys Asp Ile Gln Lys Asp Gln Asp Val Leu Lys Ser Tyr Leu
        1160                1165                1170

Thr Asp Leu Leu Gly Lys Lys Glu Phe Lys Ile Leu Val Pro Lys
        1175                1180                1185

Ile Lys Ile Asn Ser Leu Leu Lys Ile Asn Gly Phe Pro Cys His
        1190                1195                1200

Ile Thr Gly Lys Thr Asn Asp Ser Phe Leu Leu Arg Pro Ala Val
        1205                1210                1215

Gln Phe Cys Cys Ser Asn Asn Glu Val Leu Tyr Phe Lys Lys Ile
        1220                1225                1230

Ile Arg Phe Ser Glu Ile Arg Ser Gln Arg Glu Lys Ile Gly Lys
        1235                1240                1245

Thr Ile Ser Pro Tyr Glu Asp Leu Ser Phe Arg Ser Tyr Ile Lys
        1250                1255                1260

Glu Asn Leu Trp Lys Lys Thr Lys Asn Asp Glu Ile Gly Glu Lys
        1265                1270                1275

Glu Phe Tyr Asp Leu Leu Gln Lys Lys Asn Leu Glu Ile Tyr Asp
        1280                1285                1290

Met Leu Leu Thr Lys His Lys Asp Thr Ile Tyr Lys Lys Arg Pro
        1295                1300                1305
```

-continued

```
Asn Ser Ala Thr Ile Asp Ile Leu Val Lys Gly Lys Glu Lys Phe
    1310                1315                1320

Lys Ser Leu Ile Ile Glu Asn Gln Phe Glu Val Ile Leu Glu Ile
    1325                1330                1335

Leu Lys Leu Phe Ser Ala Thr Arg Asn Val Ser Asp Leu Gln His
    1340                1345                1350

Ile Gly Gly Ser Lys Tyr Ser Gly Val Ala Lys Ile Gly Asn Lys
    1355                1360                1365

Ile Ser Ser Leu Asp Asn Cys Ile Leu Ile Tyr Gln Ser Ile Thr
    1370                1375                1380

Gly Ile Phe Glu Lys Arg Ile Asp Leu Leu Lys Val Ala Ala Ala
    1385                1390                1395

Asp Pro Lys Lys Lys Arg Lys Val Asp Pro Lys Lys Lys Arg Lys
    1400                1405                1410

Val Asp Pro Lys Lys Lys Arg Lys Val Asp Thr Ala Ala
    1415                1420                1425

<210> SEQ ID NO 25
<211> LENGTH: 102
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 25
nnnnnnnnnn nnnnnnnnnn guuuuagagc uagaaauagc aaguuaaaau aaggcuaguc     60
cguuaucaac uugaaaaagu ggcaccgagu cggugcuuuu uu                      102

<210> SEQ ID NO 26
<211> LENGTH: 150
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 26
nnnnnnnnnn nnnnnnnnnn guuuuagagc uaugcuguuu ugaauggucc caaaacgaaa     60
uuguuggaac cauucaaaac agcauagcaa guuaaaauaa ggcuaguccg uuaucaacuu    120
gaaaaagugg caccgagucg gugcuuuuuu                                    150

<210> SEQ ID NO 27
<211> LENGTH: 105
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 27
nnnnnnnnnn nnnnnnnnnn guuuuguac ucucagaaau gcagaagcua caaagauaag     60
gcuucaugcc gaaaucaaca cccugucauu uuauggcagg guguu                   105
```

<210> SEQ ID NO 28
<211> LENGTH: 147
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 28
nnnnnnnnnn nnnnnnnnnn guuuuguac ucucaagauu uaaguaacug uacaacgaaa    60
cuuacacagu uacuuaaauc uugcagaagc uacaaagaua aggcuucaug ccgaaaucaa   120
cacccuguca uuuuauggca gggguguu                                     147

<210> SEQ ID NO 29
<211> LENGTH: 110
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 29
nnnnnnnnnn nnnnnnnnnn guuuuuguac ucucagaaau gcagaagcua caaagauaag    60
gcuucaugcc gaaaucaaca cccugucauu uuauggcagg guguuuuuu               110

<210> SEQ ID NO 30
<211> LENGTH: 110
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 30
nnnnnnnnnn nnnnnnnnnn guuuuaguac ucucagaaau gcagaagcuu caaagauaag    60
gcuucaugcc gaaaucaaca cccugucauu uuauggcagg guguuuuuu               110

<210> SEQ ID NO 31
<211> LENGTH: 110
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 31
nnnnnnnnnn nnnnnnnnnn guuuguguac ucucagaaau gcagaagcua caaagauaag    60
gcuucaugcc gaaaucaaca cccugucauu uuauggcagg guguuuuuu               110

<210> SEQ ID NO 32
<211> LENGTH: 110
<212> TYPE: RNA

<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 32
nnnnnnnnnn nnnnnnnnnn guuuauguac ucucagaaau gcagaagcua caaagauaag      60
gcuucaugcc gaaaucaaca cccugucauu uuauggcagg guguuuuuu               110

<210> SEQ ID NO 33
<211> LENGTH: 105
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 33
nnnnnnnnnn nnnnnnnnnn guuuuuguac ucugaaaaga agcuacaaag auaaggcuuc      60
augccgaaau caacacccug ucauuuuaug gcaggguguu uuuuu                     105

<210> SEQ ID NO 34
<211> LENGTH: 105
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 34
nnnnnnnnnn nnnnnnnnnn guuuaguac ucugaaaaga agcuucaaag auaaggcuuc       60
augccgaaau caacacccug ucauuuuaug gcaggguguu uuuuu                     105

<210> SEQ ID NO 35
<211> LENGTH: 105
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 35
nnnnnnnnnn nnnnnnnnnn guuuuguac ucugaaaaga agcuacaaag auaaggcuuc       60
augccgaaau caacacccug ucauuuuaug gcaggguguu uuuuu                     105

<210> SEQ ID NO 36
<211> LENGTH: 105
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 36
nnnnnnnnnn nnnnnnnnnn guuuauguac ucugaaaaga agcuacaaag auaaggcuuc    60
augccgaaau caacacccug ucauuuuaug gcaggguguu uuuuu    105

<210> SEQ ID NO 37
<211> LENGTH: 152
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 37
nnnnnnnnnn nnnnnnnnnn guuuuguac ucucaagauu uaaguaacug uacaacgaaa    60
cuuacacagu uacuuaaauc uugcagaagc uacaaagaua aggcuucaug ccgaaaucaa    120
cacccuguca uuuuauggca ggguguuuuu uu    152

<210> SEQ ID NO 38
<211> LENGTH: 152
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 38
nnnnnnnnnn nnnnnnnnnn guuuaguac ucucaagauu uaaguaacug uacaacgaaa    60
cuuacacagu uacuuaaauc uugcagaagc uucaaagaua aggcuucaug ccgaaaucaa    120
cacccuguca uuuuauggca ggguguuuuu uu    152

<210> SEQ ID NO 39
<211> LENGTH: 152
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 39
nnnnnnnnnn nnnnnnnnnn guuuguguac ucucaagauu uaaguaacug uacaacgaaa    60
cuuacacagu uacuuaaauc uugcagaagc uacaaagaua aggcuucaug ccgaaaucaa    120
cacccuguca uuuuauggca ggguguuuuu uu    152

<210> SEQ ID NO 40
<211> LENGTH: 152
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

```
<400> SEQUENCE: 40
nnnnnnnnnn nnnnnnnnnn guuuauguac ucucaagauu uaaguaacug uacaacgaaa        60
cuuacacagu uacuuaaauc uugcagaagc uacaaagaua aggcuucaug ccgaaaucaa       120
cacccuguca uuuuauggca ggguguuuuu uu                                    152

<210> SEQ ID NO 41
<211> LENGTH: 121
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 41
nnnnnnnnnn nnnnnnnnnn guuguagcuc ccuuucucga aagagaaccg uugcuacaau        60
aaggccgucu gaaaagaugu gccgcaacgc ucugccccuu aaagcuucug cuuuaagggg      120
c                                                                      121

<210> SEQ ID NO 42
<211> LENGTH: 157
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein X is any of the nucleotide U, C, A or G
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 42
nnnnnnnnnn nnnnnnnnnn guuguagcuc ccuuucucau uucgcagugc uacaaugaaa        60
auugucgcac ugcgaaauga gaaccguugc uacaauaagg ccgucugaaa agaugugccg      120
caacgcucug ccccuuaaag cuucugcuuu aagggc                                157

<210> SEQ ID NO 43
<211> LENGTH: 128
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 43
nnnnnnnnnn nnnnnnnnnn guuguagcuc ccuuucucga aagagaaccg uugcuacaau        60
aaggccgucu gaaaagaugu gccgcaacgc ucugccccuu aaagcuucug cuuuaacggg      120
cuuuuuuu                                                               128

<210> SEQ ID NO 44
<211> LENGTH: 124
<212> TYPE: RNA
<213> ORGANISM: Artificial Sequence
<220> FEATURE:
<223> OTHER INFORMATION: gRNA
```

<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 44
nnnnnnnnnn nnnnnnnnnn guuguagcuc ccuuucgaaa gaaccguugc uacaauaagg      60
ccgucugaaa agaugugccg caacgcucug ccccuuaaag cuucugcuuu aacgggcuuu     120
uuuu                                                                 124

<210> SEQ ID NO 45
<211> LENGTH: 116
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 45
nnnnnnnnnn nnnnnnnnnn guuguagcuc ccgaaacguu gcuacaauaa ggccgucuga      60
aaagaugugc cgcaacgcuc ugccccuuaa agcuucugcu uuaacgggcu uuuuu          116

<210> SEQ ID NO 46
<211> LENGTH: 164
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 46
nnnnnnnnnn nnnnnnnnnn guuguagcuc ccuuucucau uucgcagugc uacaaugaaa      60
auugucgcac ugcgaaauga gaaccguugc uacaauaagg ccgucugaaa agaugugccg     120
caacgcucug ccccuuaaag cuucugcuuu aaggggcuuu uuuu                     164

<210> SEQ ID NO 47
<211> LENGTH: 141
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 47
nnnnnnnnnn nnnnnnnnnn guuguagcuc ccuuucucau uucggaaacg aaaugagaac      60
cguugcuaca auaaggccgu cugaaaagau gugccgcaac gcucugcccc uuaaagcuuc     120
ugcuuuaagg ggcaucguuu a                                              141

<210> SEQ ID NO 48
<211> LENGTH: 4
<212> TYPE: RNA
<213> ORGANISM: Artificial Sequence
<220> FEATURE:
<223> OTHER INFORMATION: Linker

```
<400> SEQUENCE: 48 gaaa                                                                      4

<210> SEQ ID NO 49
<211> LENGTH: 16
<212> TYPE: PRT
<213> ORGANISM: Artificial Sequence
<220> FEATURE:
<223> OTHER INFORMATION: Signal

<400> SEQUENCE: 49

Lys Arg Pro Ala Ala Thr Lys Lys Ala Gly Gln Ala Lys Lys Lys Lys
1               5                   10                  15

<210> SEQ ID NO 50
<211> LENGTH: 9
<212> TYPE: PRT
<213> ORGANISM: Artificial Sequence
<220> FEATURE:
<223> OTHER INFORMATION: Signal

<400> SEQUENCE: 50

Pro Ala Ala Lys Arg Val Lys Leu Asp
1               5

<210> SEQ ID NO 51
<211> LENGTH: 9
<212> TYPE: PRT
<213> ORGANISM: Artificial Sequence
<220> FEATURE:
<223> OTHER INFORMATION: Signal

<400> SEQUENCE: 51

Pro Pro Arg Lys Lys Arg Thr Val Val
1               5

<210> SEQ ID NO 52
<211> LENGTH: 11
<212> TYPE: PRT
<213> ORGANISM: Artificial Sequence
<220> FEATURE:
<223> OTHER INFORMATION: Signal

<400> SEQUENCE: 52

Pro Arg Pro Pro Lys Met Ala Arg Tyr Asp Asn
1               5                   10

<210> SEQ ID NO 53
<211> LENGTH: 102
<212> TYPE: RNA
<213> ORGANISM: Streptococcus pyogenes
<220> FEATURE:
<221> NAME/KEY: misc_feature
<222> LOCATION: (1)..(20)
<223> OTHER INFORMATION: wherein N is any of U, C, A, or G

<400> SEQUENCE: 53
nnnnnnnnnn nnnnnnnnnn guuuuagagc uagaaauagc aaguuaaaau aaggcuaguc    60
cguuaucaac uugaaaaagu ggcaccgagu cggugcuuuu uu                      102

<210> SEQ ID NO 54
<211> LENGTH: 12
<212> TYPE: RNA
<213> ORGANISM: Artificial Sequence
<220> FEATURE:
<223> OTHER INFORMATION: Linker
```

<400> SEQUENCE: 54
guuuuagagc ua                                                                                      12

<210> SEQ ID NO 55
<211> LENGTH: 952
<212> TYPE: DNA
<213> ORGANISM: Artificial Sequence
<220> FEATURE:
<223> OTHER INFORMATION: Motif

<400> SEQUENCE: 55

```
tggcttaaaa accctgaacg acattccttt gcaccagctt ggtgaggagg gcatggtccc    60
cgccacccccc cacccccact ttgcagataa accacatgca ggaaggtcag cctggcaagt   120
ccagtaagtt caagcccagg tctcaactgg gcagcagagc tcctgctctt ctttgtcctc   180
atatacgagc acctctggac ttaaaacttg aggaactgga tggagaaaag ttaatggtca   240
gcagcgggtt acatcttctt tcatgcgcct ttccattctt tggatcagta gtcactaacg   300
ttcgccagcc ataagtcctc gacgtggaga ggctcagagc ctggcatgaa catgaccctg   360
aattcggatg cagagcttct tcccatgatg atctgtccct cacagcaggg tcttctctgt   420
ttcagggcat gaactacttg gaggaccgtc gcttggtgca ccgcgacctg gcagccagga   480
acgtactggt gaaaacaccg cagcatgtca agatcacaga ttttgggctg ccaaaactgc   540
tgggtgcgga agagaaagaa taccatgcag aaggaggcaa agtaaggagg tggctttagg   600
tcagccagca ttttcctgac accagggacc aggctgcctt cccactagct gtattgttta   660
acacatgcag gggaggatgc tctccagaca ttctgggtga gctcgcagca gctgctgctg   720
gcagctgggt ccagccaggg tctcctggta gtgtgagcca gagctgcttt gggaacagta   780
cttgctggga cagtgaatga ggatgttatc cccaggtgat cattagcaaa tgttaggttt   840
cagtctctcc ctgcaggata tataagtccc cttcaatagc gcaattggga aaggtcacag   900
ctgccttggt ggtccactgc tgtcaaggac acctaaggaa caggaaaggc cc           952
```

<210> SEQ ID NO 56
<211> LENGTH: 952
<212> TYPE: DNA
<213> ORGANISM: Artificial Sequence
<220> FEATURE:
<223> OTHER INFORMATION: Motif

<400> SEQUENCE: 56

```
tggcttaaaa accctgaacg acattccttt gcaccagctt ggtgaggagg gcatggtccc    60
cgccacccccc cacccccact ttgcagataa accacatgca ggaaggtcag cctggcaagt   120
ccagtaagtt caagcccagg tctcaactgg gcagcagagc tcctgctctt ctttgtcctc   180
atatacgagc acctctggac ttaaaacttg aggaactgga tggagaaaag ttaatggtca   240
gcagcgggtt acatcttctt tcatgcgcct ttccattctt tggatcagta gtcactaacg   300
ttcgccagcc ataagtcctc gacgtggaga ggctcagagc ctggcatgaa catgaccctg   360
aattcggatg cagagcttct tcccatgatg atctgtccct cacagcaggg tcttctctgt   420
ttcagggcat gaactacttg gaggaccgtc gcttggtgca ccgcgacctg gcagccagga   480
acgtactagt gaaaacaccg cagcatgtca agatcacaga ttttgggcgg ccaaaactgc   540
tgggtgcgga agagaaagaa taccatgcag aaggaggcaa agtaaggagg tggctttagg   600
tcagccagca ttttcctgac accagggacc aggctgcctt cccactagct gtattgttta   660
```

| acacatgcag | gggaggatgc | tctccagaca | ttctgggtga | gctcgcagca | gctgctgctg | 720 |
| gcagctgggt | ccagccaggg | tctcctggta | gtgtgagcca | gagctgcttt | gggaacagta | 780 |
| cttgctggga | cagtgaatga | ggatgttatc | cccaggtgat | cattagcaaa | tgttaggttt | 840 |
| cagtctctcc | ctgcaggata | tataagtccc | cttcaatagc | gcaattggga | aaggtcacag | 900 |
| ctgccttggt | ggtccactgc | tgtcaaggac | acctaaggaa | caggaaaggc | cc | 952 |

```
<210> SEQ ID NO 57
<211> LENGTH: 93
<212> TYPE: DNA
<213> ORGANISM: Artificial Sequence
<220> FEATURE:
<223> OTHER INFORMATION: Motif

<400> SEQUENCE: 57
```

| gtactggtga | aaacaccgca | gcatgtcaag | atcacagatt | ttgggcgggc | caagcttctg | 60 |
| ggtgcggaag | agaaagaata | ccatgcagaa | gga | | | 93 |

```
<210> SEQ ID NO 58
<211> LENGTH: 810
<212> TYPE: DNA
<213> ORGANISM: Artificial Sequence
<220> FEATURE:
<223> OTHER INFORMATION: Motif
<220> FEATURE:
<221> NAME/KEY: misc_feature
<222> LOCATION: (712)..(712)
<223> OTHER INFORMATION: n is a, c, g, or t
<220> FEATURE:
<221> NAME/KEY: misc_feature
<222> LOCATION: (716)..(717)
<223> OTHER INFORMATION: n is a, c, g, or t
<220> FEATURE:
<221> NAME/KEY: misc_feature
<222> LOCATION: (730)..(731)
<223> OTHER INFORMATION: n is a, c, g, or t

<400> SEQUENCE: 58
```

| ctcgacgtgg | agaggctcag | agcctggcat | gaacatgacc | ctgaattcgg | atgcagagct | 60 |
| tcttcccatg | atgatctgtc | cctcacagca | gggtcttctc | tgtttcaggg | catgaactac | 120 |
| ttggaggacc | gtcacgcttg | gtgcaccgcg | acctggcagc | caggaacgta | ctagtgaaaa | 180 |
| caccgcagca | tgtcaagatc | acagattttg | ggcgggccaa | actgctgggt | gcggaagaga | 240 |
| aagaatacca | tgcagaagga | ggcaaagtaa | ggaggtggct | ttaggtcagc | cagcattttc | 300 |
| ctgacaccag | ggaccaggct | gccttcccac | tagctgtatt | gtttaacaca | tgcaggggag | 360 |
| gatgctctcc | agacattctg | ggtgagctcg | cagcagctgc | tgctggcagc | tgggtccagc | 420 |
| cagggtctcc | tggtagtgtg | agccagagct | gctttgggaa | cggtacttgc | tgggacagtg | 480 |
| aatgaggatg | ttatccccag | gtgatcatta | gcaaatgtta | ggtttcagtc | tctccctgca | 540 |
| ggatatataa | gtccccttca | atagcgcaat | tgggaaaggt | cacagctgcc | ttggtggtcc | 600 |
| actgctgtca | aggacaccta | aggaacagga | aaggccccat | gcggacccga | gctcccaggg | 660 |
| ctgtctgtgg | ctcgtggctg | ggacaggcag | caatggagtc | cttctctcca | cncccnnggc | 720 |
| tcacatgaan | nagatgtaac | ccgctgctga | ccattaactt | tttctccatc | cagttcctca | 780 |
| agttttaagt | ccagaggtgc | tcgtatatga | | | | 810 |

```
<210> SEQ ID NO 59
<211> LENGTH: 706
<212> TYPE: DNA
<213> ORGANISM: Artificial Sequence
```

-continued

```
<220> FEATURE:
<223> OTHER INFORMATION: Motif
<220> FEATURE:
<221> NAME/KEY: misc_feature
<222> LOCATION: (706)..(706)
<223> OTHER INFORMATION: n is a, c, g, or t

<400> SEQUENCE: 59
gtggagaggc tcagagcctg gcatgaacat gaccctgaat tcggatgcag agcttcttcc      60
catgatgatc tgtccctcac agcagggtct tctctgtttc agggcatgaa ctacttggag     120
gaccgtcgct tggtgcaccg cgacctggca gccaggaaac gtactagtga aaacaccgca     180
gcatgtcaag atcacagatt ttgggcgggc caaactgctg ggtgcggaag agaaagaata     240
ccatgcagaa ggaggcaaag taaggaggtg gctttaggtc agccagcatt ttcctgacac     300
cagggaccag gctgccttcc cactagctgt attgtttaac acatgcaggg gaggatgctc     360
tccagacatt ctgggtgagc tcgcagcagc tgctgctggc agctgggtcc agccagggtc     420
tcctggtagt gtgagccaga gctgctttgg gaacggtact tgctgggaca gtgaatgagg     480
atgttatccc caggtgatca ttagcaaatg ttaggtttca gtctctccct gcaggatata     540
taagtcccct tcaatagcgc aattgggaaa ggtcacagct gccttggtgg tccactgctg     600
tcaaggacac ctaaggaaca ggaaaggccc catgcggacc cgagctccca gggctgtctg     660
tggctcgtgg ctgggacagg cagcaatgga gtccttctct ccctcn                    706

<210> SEQ ID NO 60
<211> LENGTH: 8
<212> TYPE: DNA
<213> ORGANISM: Artificial Sequence
<220> FEATURE:
<223> OTHER INFORMATION: Motif
<220> FEATURE:
<221> NAME/KEY: misc_feature
<222> LOCATION: (1)..(4)
<223> OTHER INFORMATION: wherein N is any of the nucleotide T, C, A or G
<220> FEATURE:
<221> NAME/KEY: misc_feature
<222> LOCATION: (8)..(8)
<223> OTHER INFORMATION: wherein N is any of the nucleotide T, C, A or G

<400> SEQUENCE: 60 nnnngttn                                                                8

<210> SEQ ID NO 61
<211> LENGTH: 8
<212> TYPE: DNA
<213> ORGANISM: Artificial Sequence
<220> FEATURE:
<223> OTHER INFORMATION: Motif
<220> FEATURE:
<221> NAME/KEY: misc_feature
<222> LOCATION: (1)..(4)
<223> OTHER INFORMATION: wherein N is any of the nucleotide T, C, A or G
<220> FEATURE:
<221> NAME/KEY: misc_feature
<222> LOCATION: (6)..(7)
<223> OTHER INFORMATION: wherein N is any of the nucleotide T, C, A or G

<400> SEQUENCE: 61 nnnngnnt                                                                8

<210> SEQ ID NO 62
<211> LENGTH: 787
<212> TYPE: DNA
<213> ORGANISM: Artificial Sequence
<220> FEATURE:
```

<223> OTHER INFORMATION: Motif
<220> FEATURE:
<221> NAME/KEY: misc_feature
<222> LOCATION: (702)..(703)
<223> OTHER INFORMATION: n is a, c, g, or t
<220> FEATURE:
<221> NAME/KEY: misc_feature
<222> LOCATION: (706)..(708)
<223> OTHER INFORMATION: n is a, c, g, or t
<220> FEATURE:
<221> NAME/KEY: misc_feature
<222> LOCATION: (710)..(710)
<223> OTHER INFORMATION: n is a, c, g, or t
<220> FEATURE:
<221> NAME/KEY: misc_feature
<222> LOCATION: (722)..(722)
<223> OTHER INFORMATION: n is a, c, g, or t
<220> FEATURE:
<221> NAME/KEY: misc_feature
<222> LOCATION: (726)..(726)
<223> OTHER INFORMATION: n is a, c, g, or t
<220> FEATURE:
<221> NAME/KEY: misc_feature
<222> LOCATION: (737)..(737)
<223> OTHER INFORMATION: n is a, c, g, or t
<220> FEATURE:
<221> NAME/KEY: misc_feature
<222> LOCATION: (747)..(747)
<223> OTHER INFORMATION: n is a, c, g, or t

<400> SEQUENCE: 62

| | | | | | |
|---|---|---|---|---|---|
| tggagaggct | cagagcctgg | catgaacatg | accctgaatt | cggatgcaga | gcttcttccc | 60 |
| atgatgatct | gtccctcaca | gcagggtctt | ctctgtttca | gggcatgaac | tacttggagg | 120 |
| accgtcgctt | ggtgcaccgc | gacctggcag | ccaggaacgt | actagtgaaa | acaccgcagc | 180 |
| atgtcaagat | cacagatttt | gggcgggcca | aactgctggg | tgcggaagag | aaagaatacc | 240 |
| atgcagaagg | aggcaaagta | aggaggtggc | tttaggtcag | ccagcatttt | cctgacacca | 300 |
| gggaccaggc | tgccttccca | ctagctgtat | tgtttaacac | atgcagggga | ggatgctctc | 360 |
| cagacattct | gggtgagctc | gcagcagctg | ctgctggcag | ctgggtccag | ccagggtctc | 420 |
| ctggtagtgt | gagccagagc | tgctttggga | acagtacttg | ctgggacagt | gaatgaggat | 480 |
| gttatcccca | ggtgatcatt | agcaaatgtt | aggtttcagt | ctctccctgc | aggatatata | 540 |
| agtccccttc | aatagcgcaa | ttgggaaagg | tcacagctgc | cttggtggtc | cactgctgtc | 600 |
| aaggacacct | aaggaacagg | aaaggcccca | tgcggacccg | agctcccagg | gctgtctgtg | 660 |
| gctcgtggct | gggacaggca | gcaatggagt | ccttctctcc | anncnnngn | cttcaatgaa | 720 |
| anaaanatgt | aaccccnctg | ctgaccntta | acttttttctc | catccagttc | ctcaagtttt | 780 |
| aagtcca | | | | | | 787 |

<210> SEQ ID NO 63
<211> LENGTH: 789
<212> TYPE: DNA
<213> ORGANISM: Artificial Sequence
<220> FEATURE:
<223> OTHER INFORMATION: Motif
<220> FEATURE:
<221> NAME/KEY: misc_feature
<222> LOCATION: (705)..(707)
<223> OTHER INFORMATION: n is a, c, g, or t

<400> SEQUENCE: 63

| | | | | | |
|---|---|---|---|---|---|
| gtggagaggc | tcagagcctg | gcatgaacat | gaccctgaat | tcggatgcag | agcttcttcc | 60 |
| catgatgatc | tgtccctcac | agcagggtct | tctctgtttc | agggcatgaa | ctacttggag | 120 |
| gaccgtcgct | tggtgcaccg | cgacctggca | gccaggaacg | tactagtgaa | aacaccgcag | 180 |

```
catgtcaaga tcacagattt tgggcgggcc aaactgctgg gtgcggaaga gaaagaatac      240
catgcagaag gaggcaaagt aaggaggtgg ctttaggtca gccagcattt tcctgacacc      300
agggaccagg ctgccttccc actagctgta ttgtttaaca catgcagggg aggatgctct      360
ccagacattc tgggtgagct cgcagcagct gctgctggca gctgggtcca gccagggtct      420
cctggtagtg tgagccagag ctgctttggg aacggtactt gctgggacag tgaatgagga      480
tgttatcccc aggtgatcat tagcaaatgt taggtttcag tctctccctg caggatatat      540 aagtccccctt caatagcgca attgggaaag gtcacagctg ccttggtggt ccactgctgt     600
caaggacacc taaggaacag gaaaggcccc atgcggaccc gagctcccag ggctgtctgt      660
ggctcgtggc tgggacaggc agcaatggag tccttctctc ccacnnnctg ggcttcacat      720
gaaagaagat gtaacccgct gctgaccatt aactttctc catccagttc ctcaagtttt       780
aagtccaga                                                             789

<210> SEQ ID NO 64
<211> LENGTH: 1000
<212> TYPE: DNA
<213> ORGANISM: Artificial Sequence
<220> FEATURE:
<223> OTHER INFORMATION: Motif

<400> SEQUENCE: 64
ccggacccca cacagattcc tacaggccct catgatattt taaaacacag catcctcaac      60
cttgaggcgg aggtcttcat aacaaagata ctatcagttc ccaaactcag agatcaggtg      120
actccgactc ctcctttatc caatgtgctc ctcatggcca ctgttgcctg gcctctctg      180 tcatggggaa tccccagatg cacccaggag ggccctctc ccactgcatc tgtcacttca      240
cagccctgcg taaacgtccc tgtgctaggt cttttgcagg cacagctttt cctccatgag     300
tacgtatttt gaaactcaag atcgcattca tgcgtcttca cctggaaggg gtccatgtgc     360
ccctccttct ggccaccatg cgaagccaca ctgacgtgcc tctccctccc tccaggaagc   420
ctacgtgatg gccagcgtag acaaccctca cgtgtgccgc ctgctgggca tatgcctcac    480
ctccaccgtg cagctcatca tgcagctcat gcccttcggc tgcctcctgg actatgtccg    540
ggaacacaaa gacaatattg ctcccagta cctgctcaac tggtgtgtgc agatcgcaaa     600
ggtaatcagg gaagggagat acggggaggg gagataagga gccaggatcc tcacatgcgg   660
tctgcgctcc tgggatagca agagtttgcc atggggatat gtgtgtgcgt gcatgcagca    720
cacacacatt cctttatttt ggattcaatc aagttgatct tcttgtgcac aaatcagtgc    780
ctgtcccatc tgcatgtgga aactctcatc aatcagctac ctttgaagaa ttttctcttt    840
attgagtgct cagtgtggtc tgatgtctct gttcttattt ctctggaatt ctttgtgaat   900
actgtggtga tttgtagtgg agaaggaata ttgcttcccc cattcaggac ttgataacaa     960
ggtaagcaag ccaggccaag gccaggagga cccaggtgat                         1000

<210> SEQ ID NO 65
<211> LENGTH: 1000
<212> TYPE: DNA
<213> ORGANISM: Artificial Sequence
<220> FEATURE:
<223> OTHER INFORMATION: Motif

<400> SEQUENCE: 65
tatcctgaca cagatgtcgt gatattttat ctgcacattc ttaattcttt agcaagtgtt      60
```

-continued

| | |
|---|---|
| atttaaaggc tacatccatc tacctcagtt tcctatatct atctctgaca tctacctcta | 120 |
| gttgtacttc tgtcctctat ttcaggtgtt atgggtcaag cctgtttgac tggcattatt | 180 |
| catgattcct gtaccactct tgctctctct cactttgatc tccatattcc aggcttacac | 240 |
| aggggtttcc tcagaacgtt gatggcagtt gcaggtccat ataaagggac caaagcacat | 300 |
| tgtatcctca tctatagtca tgctgaaagt aggagaaagt gcatctttat tatggcagag | 360 |
| agaattttct gaactattta tggacaacag tcaaacaaca attctttgta cttttttttt | 420 |
| tccttagtct ttctttgaag cagcaagtat gatgagcaag ctttctcaca agcatttggt | 480 |
| tttaaattat ggagtatgtt tctgtggaga cgagagtaag taaaactaca gactttctaa | 540 |
| tgcttttctc agagcatctg tttttgttta tatagagaat tcagtttcag gatcacagct | 600 |
| aggtgtcagt gtaaactata atttaacagg agttaagtat ttttgaaact gaaaacactg | 660 |
| taggactatt cagttatatc ttgtgaaaaa ggaaagcaat gaagttaaaa gtagaaggtt | 720 |
| acaatgccca aacaatagag tattatagta aacaaatgtc tataaaacat tttgtgttca | 780 |
| tgatagcaaa agagattatg gcaggttcaa cataacattg gaataactgg ccttttcagt | 840 |
| acaaacttat ctggaattat gaagacaaag catataaatg atacacttaa tttttaatgg | 900 |
| aactgacaga aatgattatg ttgatatgat actagatata ttttttggct aaatttaggt | 960 |
| gttcacagaa actactaaaa gtataaatcg taccccatgc | 1000 |

<210> SEQ ID NO 66
<211> LENGTH: 924
<212> TYPE: DNA
<213> ORGANISM: Artificial Sequence
<220> FEATURE:
<223> OTHER INFORMATION: Motif

<400> SEQUENCE: 66

| | |
|---|---|
| aaggacattc aaagagatgc atgcaaaatg aattttcagt ttaaacaata tgatatgact | 60 |
| atttcttatg tatttcccta tgaatgaaag cagtcctgag aagaaaacag catttattag | 120 |
| aattgctttt aaagagagatt ataataatta gactcttgat tatgtgaaca tcattcaagg | 180 |
| cgtacttttg attttttattt ttggtgtact gaatacttta aaacaaaagt attggatttt | 240 |
| ttataatata agcaacacta tagtattaaa aagttagttt tcactcttta caagttaaaa | 300 |
| tgaatttaaa tggttttctt ttctcctcca acctaatagt gtattcacag agacttggca | 360 |
| gccagaaata tcctccttac tcatggtcga atcacaaaga tctgtgattt tggtctagca | 420 |
| agagtcatca agaatgattc taattatgtg gttaaaggaa acgtgagtac ccattctctg | 480 |
| cttgacagtc ctgcaaagga ttttagtttt caactttcga taaaaattgt ttcctgtgat | 540 |
| tttcataatg taaatcctgt ctagggatat cacacatttt agcagtcaaa ttaagtatac | 600 |
| ttcagcaaaa tttgcatggt atgctgaaca ttactacaac taacattcaa taatagaagt | 660 |
| cctaattcta attgtgtaat tttggggcat gtgaaggaaa cagaaatagc cttaattttc | 720 |
| attatagcct gagaatagca atgaacttga ttttgctcaa gtgtaacaaa tgtaggtcat | 780 |
| tgaaggtcac agcaggagaa attttggggg gattggcatg ccgtgtgaaa aatattaaaa | 840 |
| tctaagatca tattcagagt tagccatata gaatgttgga tcctagaata cacggagagc | 900 |
| tattaaatag gttcataagt aata | 924 |

<210> SEQ ID NO 67
<211> LENGTH: 917
<212> TYPE: DNA
<213> ORGANISM: Artificial Sequence
<220> FEATURE:
<223> OTHER INFORMATION: Motif
<220> FEATURE:
<221> NAME/KEY: misc_feature
<222> LOCATION: (11)..(11)
<223> OTHER INFORMATION: n is a, c, g, or t

<400> SEQUENCE: 67

| | | | | | |
|---|---|---|---|---|---|
| ctatctctga | natctacctc | tagttgtact | tctgtcctct | atttcaggtg | ttatgggtca | 60 |
| agcctgtttg | actggcatta | ttcatgattc | ctgtaccact | cttgctctct | ctcactttga | 120 |
| tctccatatt | ccaggcttac | acaggggttt | cctcagaacg | ttgatggcag | ttgcaggtcc | 180 |
| atataaaggg | accaaagcac | attgtatcct | catctatagt | catgctgaaa | gtaggagaaa | 240 |
| gtgcatcttt | attatggcag | agagaatttt | ctgaactatt | tatggacaac | agtcaaacaa | 300 |
| caattctttg | tacttttttt | tttccttagt | ctttctttga | agcagcaagt | atgatgagca | 360 |
| agctttctca | caagcatttg | gttttaaatt | atggagtatg | tttctgtgga | gacgagagta | 420 |
| agtaaaacta | cagactttct | aatgcttttc | tcaragcatc | tgttttgtt | tatatagaaa | 480 |
| attcagtttc | aggatcacag | ctaggtgtca | gtgtaaacta | taatttaaca | ggagttaagt | 540 |
| attttgaaa | ctgaaaacac | tgtaggacta | ttcagttata | tcttgtgaaa | aggaaagca | 600 |
| atgaagttaa | aagtagaagg | ttacaatgcc | caaacaatag | agtattatag | taaacaaatg | 660 |
| tctataaaac | attttgtgtt | catgatagca | aaagagatta | tggcaggttc | aacataacat | 720 |
| tggaataact | ggccttttca | gtacaaactt | atctggaatt | atgaagacaa | agcatataaa | 780 |
| tgatacactt | aattttaat | ggaactgaca | gaaatgatta | tgttgatatg | atactagata | 840 |
| tattttttgg | ctaaatttag | gtgttcacag | aaactactaa | aagtataaat | cgtaccccat | 900 |
| gctttaatac | tatacag | | | | | 917 |

<210> SEQ ID NO 68
<211> LENGTH: 720
<212> TYPE: DNA
<213> ORGANISM: Artificial Sequence
<220> FEATURE:
<223> OTHER INFORMATION: Motif
<220> FEATURE:
<221> NAME/KEY: misc_feature
<222> LOCATION: (635)..(635)
<223> OTHER INFORMATION: n is a, c, g, or t

<400> SEQUENCE: 68

| | | | | | |
|---|---|---|---|---|---|
| ctgagaagaa | aacagcattt | attagaattg | cttttaaaag | agattataat | aattagactc | 60 |
| ttgattatgt | gaacatcatt | caaggcgtac | ttttgatttt | tatttttggt | gtactgaata | 120 |
| ctttaaaaca | aaagtattgg | attttttata | atataagcaa | cactatagta | ttaaaaagtt | 180 |
| agttttcact | ctttacragt | taaaatgaat | ttaaatggtt | ttcttttctc | ctccaaccta | 240 |
| rtagtgtatt | cacagagact | tggcagccag | aaatatcctc | cttactcatg | gtcgaatcac | 300 |
| aragatctgt | gattttggtc | tagcaagagt | catcaagaat | gattctaatt | atgtggttaa | 360 |
| aggaaacgtg | agtacccatt | ctctgcttga | cagtcctgca | aaggatttt | agtttcaact | 420 |
| ttcgataaaa | attgtttcct | gtgattttca | taatgtaaat | cctgtctagg | gatatcacac | 480 |
| attttagcag | tcaattaag | tatacttcag | caaaatttgc | atggtatgct | gaacattact | 540 |
| acaactaaca | ttcaataata | gaagtcctaa | ttctaattgt | gtaattttgg | ggcatgtgaa | 600 |
| ggaaacagaa | atagccttaa | ttttcattat | agccntgaga | atagcaatga | actttgattt | 660 |
| ttgctcaaag | tgtaacaaaa | tgtaaggtca | tttgaaaggt | cacaagcagg | gagaaaattk | 720 |

<210> SEQ ID NO 69
<211> LENGTH: 715
<212> TYPE: DNA
<213> ORGANISM: Artificial Sequence
<220> FEATURE:
<223> OTHER INFORMATION: Motif
<220> FEATURE:
<221> NAME/KEY: misc_feature
<222> LOCATION: (311)..(311)
<223> OTHER INFORMATION: n is a, c, g, or t

<400> SEQUENCE: 69

```
aaagcagtcc tgagaagaaa acagcattta ttagaattgc ttttaaaaga gattataata      60
attagactct tgattatgtg aacatcattc aaggcgtact tttgattttt attttttggtg    120 tactgaatac tttaaaacaa aagtattgga ttttktataa tataagcaac actatagtat    180
taaaaagtta gttttcactc tttacragtt aaaatgaatt taaatggttt tcttttctcc    240
tccaacctar tagtgtattc acagagactt ggcagccaga aatatcctcc ttactcatgg    300
tcgaatcaca nagatctgtg attttggtct agcaagagtc atcaagaatg attctaatta    360
tgtggttaaa ggaaacgtga gtacccattc tctgcttgac agtcctgcaa aggattttta    420
gtttcaactt tcgataaaaa ttgtttcctg tgattttcat aatgtaaatc ctgtctaggg    480
atatcacaca ttttagcagt caaattaagt atacttcagc aaaatttgca tggtatgctg    540
aacattacta caactaacat tcaataatag aagtcctaat tctaattgtg taattttggg    600
gcatgtgaag gaaacagaaa tagccttaat tttcattata gcctgagaat agcaatgaac    660 ttgattttg ctcaagtgta acaaatgtag gtcatttgaa ggtcacagca gggag          715
```

<210> SEQ ID NO 70
<211> LENGTH: 825
<212> TYPE: DNA
<213> ORGANISM: Artificial Sequence
<220> FEATURE:
<223> OTHER INFORMATION: Motif

<400> SEQUENCE: 70

```
gcatgcaaaa tgaatttcag tttaaacaat atgatatgac tattcttatg tatttcccta      60
tgaatgaaag cagtcctgag aagaaaacag catttattag aattgctttt aaagagatt     120 ataataatta gactcttgat tatgtgaaca tcattcaagg cgtacttttg attttttattt    180 ttggtgtact gaatacttta aaacaaaagt attggatttt ttataatata agcaacacta    240
tagtattaaa aagttagttt tcactctttta caagttaaaa tgaatttaaa tggttttctt    300
ttctcctcca acctaatagt gtattcacag agacttggca gccagaaata tcctccttac    360
tcatggtcga atcacaaaga tctgtgattt tggtctagca agagtcatca agaatgattc    420
taattatgtg gttaaaggaa acgtgagtac ccattctctg cttgacagtc ctgcaaagga    480 ttttagttt caactttcga taaaaattgt ttcctgtgat tttcataatg taaatcctgt    540
ctagggatat cacacatttt agcagtcaaa ttaagtatac ttcagcaaaa tttgcatggt    600
atgctgaaca ttactacaac taacattcaa taatagaagt cctaattcta attgtgtaat    660 tttgggcat gtgaaggaaa cagaaatagc cttaattttc attatagcct gagaatagca    720
atgaacttga ttttgctcaa gtgtaacaaa tgtaggtcat gaaggtcac agcaggagaa    780 attttggggg gattggcatg ccgtgtgaaa aatattaaaa tctaa                    825
```

<210> SEQ ID NO 71
<211> LENGTH: 716

<212> TYPE: DNA
<213> ORGANISM: Artificial Sequence
<220> FEATURE:
<223> OTHER INFORMATION: Motif

<400> SEQUENCE: 71

```
aagaaaacag catttattag aattgctttt aaaagagatt ataataatta gactcttgat      60
tatgtgaaca tcattcaagg cgtacttttg atttttattt ttggtgtact gaatacttta     120
aaacaaaagt attggatttt ttataatata agcaacacta tagtattaaa aagttagttt     180
tcactcttta caagttaaaa tgaatttaaa tggttttctt ttctcctcca acctartagt     240
gtattcacag agacttggca gccagaaata tcctccttac tcatggtcgg atcacaraga    300
tttgtgattt tggtctagca agagtcatca agaatgattc taattatgtg gttaaaggaa    360
acgtgagtac ccattctctg cttgacagtc ctgcaaagga tttttagttt caactttcga   420
taaaaattgt ttcctgtgat tttcataatg taaatcctgt ctagggatat cacacatttt   480
agcagtcaaa ttaagtatac ttcagcaaaa tttgcatggt atgctgaaca ttactacaac   540
taacattcaa taatagaagt cctaattcta attgtgtaat tttggggcat gtgaaggaaa   600
cagaaatagc cttaattttc attatagcct gagaatagca atgaacttga ttttgctcaa   660
gtgtaacaaa tgtaggtcat tgaaggtcac agcaggagaa attttggggg gattgg       716
```

<210> SEQ ID NO 72
<211> LENGTH: 769
<212> TYPE: DNA
<213> ORGANISM: Artificial Sequence
<220> FEATURE:
<223> OTHER INFORMATION: Motif

<400> SEQUENCE: 72

```
ccgactcctc ctttatccaa tgtgctcctc atggccactg ttgcctgggc ctctctgtca      60
tggggaatcc ccagatgcac ccaggagggg cccccctccca ctgcatctgt cacttcacag   120
ccctgcgtaa acgtccctgt gctaggtctt ttgcaggcac agcttttcct ccatgagtac    180
gtattttgaa actcaagatc gcattcatgc gtcttcacct ggaagggtc catgtgcccc    240
tccttctggc caccatgcga agccacactg acgtgcctct ccctccctcc aggaagccta    300
cgtgatggcc agcgtagaca accctcacgt gtgccgcctg ctgggcatat gcctcacctc    360
caccgtgcag ctcatcatgc agctcatgcc cttcggctgc ctcctggact atgtccggga    420
acacaaagac aatattggct cccagtacct gctcaactgg tgtgtgcaga tcgcaaaggt    480
aatcagggaa gggagatacg gggaggggag ataaggagcc aggatcctca catgcggtct    540
gcgctcctgg gatagcaaga gtttgccatg gggatatgtg tgtgcgtgca tgcagcacac   600
acacattcct ttattttgga ttcaatcaag ttgatcttct tgtgcacaaa tcagtgcctg    660
tcccatctgc atgtggaaac tctcatcaat cagctacctt tgaagaattt tctctttatt    720
gagtgctcag tgtggtctga tgtctctgtt cttatttctc tggaattct                769
```

<210> SEQ ID NO 73
<211> LENGTH: 767
<212> TYPE: DNA
<213> ORGANISM: Artificial Sequence
<220> FEATURE:
<223> OTHER INFORMATION: Motif
<220> FEATURE:
<221> NAME/KEY: misc_feature
<222> LOCATION: (748)..(748)
<223> OTHER INFORMATION: n is a, c, g, or t

<400> SEQUENCE: 73

```
gactcctcct ttatccaatg tgctcctcat ggccactgtt gcctgggcct ctctgtcatg    60
gggaatcccc agatgcaccc aggaggggcc ctctcccact gcatctgtca cttcacagcc   120
ctgcgtaaac gtccctgtgc taggtctttt gcaggcacag cttttcctcc atgagtacgt   180
attttgaaac tcaagatcgc atkcatgcgt cttcacctgg aaggggtcca tgtgcccctc   240
cttctggcca ccatgcgaag ccacactgac gtgcctctcc ctcccaccag gaagcctacg   300
tgatggccag cgtagacaac cctcacgtgt gccgcctgct gggcatatgc ctcacctcca   360
ccgtgcagct catcatgcag ctcatgccct tcggctgcct cctggactat gtccgggaac   420
acaaagacaa tattggctcc cagtacctgc tcaactgggg tgtgcagatc gcaaaggtaa   480
tcagggaagg gagatacggg gaggggagat aaggagccag gatcctcaca tgcggtctgc   540
gctcctggga tagcaagagt ttgccatggg gatatgtgtg tgcgtgcatg cagcacacac   600
acattccttt attttggatt caatcaagtt gatcttcttg tgcacaaatc agtgcctgtc   660
ccatctgcat gtggaaactc tcatcaatca gctacctttg aagaattttc tctttattga   720
gtgctcagtg tggtctgatg tctctgtnct atttctctgg aattctt                 767
```

<210> SEQ ID NO 74
<211> LENGTH: 89
<212> TYPE: DNA
<213> ORGANISM: Artificial Sequence
<220> FEATURE:
<223> OTHER INFORMATION: Wild type segment

<400> SEQUENCE: 74

```
ctgcggccgg gcgcgggcgg gccctgggag atgcgggagc ggctgggcac cggcggcttc    60
gggaacgtct gtctgtacca gcatcgggt                                      89
```

<210> SEQ ID NO 75
<211> LENGTH: 63
<212> TYPE: DNA
<213> ORGANISM: Artificial Sequence
<220> FEATURE:
<223> OTHER INFORMATION: Clone sequence segment

<400> SEQUENCE: 75

```
ctgcggccgg gcgcgggcgg gccctgggag atgcgggaac gtctgtctgt accagcatcg    60
ggt                                                                   63
```

<210> SEQ ID NO 76
<211> LENGTH: 88
<212> TYPE: DNA
<213> ORGANISM: Artificial Sequence
<220> FEATURE:
<223> OTHER INFORMATION: Wild type sequence

<400> SEQUENCE: 76

```
ggtgattcgc gaagagagtg atcatgtcag ggcggcccag aaccacctcc tttgcggaga    60
gctgcaagcc ggtgcagcag ccttcagc                                       88
```

<210> SEQ ID NO 77
<211> LENGTH: 80
<212> TYPE: DNA
<213> ORGANISM: Artificial Sequence
<220> FEATURE:
<223> OTHER INFORMATION: Clone sequence segment

<400> SEQUENCE: 77
```

```
ggtgattcgc gaagagagtg atcatgtcag ggcggcccag aaccacctcc tttgcggaag    60
ccggtgcagc agccttcagc                                                80

<210> SEQ ID NO 78
<211> LENGTH: 86
<212> TYPE: DNA
<213> ORGANISM: Artificial Sequence
<220> FEATURE:
<223> OTHER INFORMATION: Wild type sequence

<400> SEQUENCE: 78
tgcgctacct gagccgcggc gcctctggca ctgtgtcgtc cgcccgccac gcagactggc    60
gcgtccaggt ggccgtgaag cacctg                                         86

<210> SEQ ID NO 79
<211> LENGTH: 81
<212> TYPE: DNA
<213> ORGANISM: Artificial Sequence
<220> FEATURE:
<223> OTHER INFORMATION: Clone sequence segment

<400> SEQUENCE: 79
tgcgctacct gagccgcggc gcctctggca ctgtgtcgtc cgcccgccac gcagcgcgtc    60
caggtggccg tgaagcacct g                                              81

<210> SEQ ID NO 80
<211> LENGTH: 90
<212> TYPE: DNA
<213> ORGANISM: Artificial Sequence
<220> FEATURE:
<223> OTHER INFORMATION: Wild type sequence

<400> SEQUENCE: 80
gtggccctca agagtgtgag agtccccaat ggaggaggag gtggaggagg ccttcccatc    60
agcacagttc gtgaggtggc tttactgagg                                     90

<210> SEQ ID NO 81
<211> LENGTH: 86
<212> TYPE: DNA
<213> ORGANISM: Artificial Sequence
<220> FEATURE:
<223> OTHER INFORMATION: Clone sequence segment

<400> SEQUENCE: 81
gtggccctca agagtgtgag agtccccaat ggaggaggag gtggaggagg ccttcccatc    60
agcacagtga ggtggcttta ctgagg                                         86

<210> SEQ ID NO 82
<211> LENGTH: 88
<212> TYPE: DNA
<213> ORGANISM: Artificial Sequence
<220> FEATURE:
<223> OTHER INFORMATION: Wild type sequence

<400> SEQUENCE: 82
catagactta atatcacttg ttttagatga gtactccgct ttctgtaaaa ggaaggataa    60
ttttggaaat cattgaagga atgtgcta                                       88

<210> SEQ ID NO 83
<211> LENGTH: 74
<212> TYPE: DNA
```

<213> ORGANISM: Artificial Sequence
<220> FEATURE:
<223> OTHER INFORMATION: Clone sequence segment
<220> FEATURE:
<221> NAME/KEY: misc_feature
<222> LOCATION: (26)..(26)
<223> OTHER INFORMATION: n is a, c, g, or t

<400> SEQUENCE: 83
catagactta atatcacttg ttttanatga gtactccgct ttctgttttt ggaaatcatt    60
gaaggaatgt gcta    74

<210> SEQ ID NO 84
<211> LENGTH: 89
<212> TYPE: DNA
<213> ORGANISM: Artificial Sequence
<220> FEATURE:
<223> OTHER INFORMATION: Wild type sequence

<400> SEQUENCE: 84
ggttacttca tctgccccat cacggatgac ccaagctcga accagaatgt caattccaag    60
gttaataagt actacagcaa cctaacaaa    89

<210> SEQ ID NO 85
<211> LENGTH: 78
<212> TYPE: DNA
<213> ORGANISM: Artificial Sequence
<220> FEATURE:
<223> OTHER INFORMATION: Clone sequence segment

<400> SEQUENCE: 85
ggttacttca tctgccccat cacggatgaa ccagaatgtc aattccaagg ttaataagta    60
ctacagcaac ctaacaaa    78

<210> SEQ ID NO 86
<211> LENGTH: 88
<212> TYPE: DNA
<213> ORGANISM: Artificial Sequence
<220> FEATURE:
<223> OTHER INFORMATION: Wild type sequence

<400> SEQUENCE: 86
tgttaactgt ctggcctatg atgaagccat catggctcag caggaccgaa ttcagcaaga    60
ggtgaggggc tgcagtgggc gagggagg    88

<210> SEQ ID NO 87
<211> LENGTH: 81
<212> TYPE: DNA
<213> ORGANISM: Artificial Sequence
<220> FEATURE:
<223> OTHER INFORMATION: Clone sequence segment

<400> SEQUENCE: 87
tgttaactgt ctggcctatg atgaagccat cagcaggacc gaattcagca agaggtgagg    60
ggctgcagtg ggcgagggag g    81

<210> SEQ ID NO 88
<211> LENGTH: 79
<212> TYPE: DNA
<213> ORGANISM: Artificial Sequence
<220> FEATURE:
<223> OTHER INFORMATION: Wild type sequence

<400> SEQUENCE: 88

```
gcatggccct tttataatcc tgttgacgtt aatgctttgg gactccataa ctactatgac    60
gttgtcaaaa atccgatgg                                                 79
```

<210> SEQ ID NO 89
<211> LENGTH: 77
<212> TYPE: DNA
<213> ORGANISM: Artificial Sequence
<220> FEATURE:
<223> OTHER INFORMATION: Clone sequence segment
<220> FEATURE:
<221> NAME/KEY: misc_feature
<222> LOCATION: (3)..(3)
<223> OTHER INFORMATION: n is a, c, g, or t

<400> SEQUENCE: 89

```
gcntggccct tttataatcc tggacgttaa tgctttggga ctccataact actatgacgt    60
tgtcaaaaat ccgatgg                                                   77
```

<210> SEQ ID NO 90
<211> LENGTH: 86
<212> TYPE: DNA
<213> ORGANISM: Artificial Sequence
<220> FEATURE:
<223> OTHER INFORMATION: Wild type sequence

<400> SEQUENCE: 90

```
cctggggtc ggcgacccgg gaggaggggt tgaccgctc cacgagcctg gagagctcgg      60
actgcgagtc cctggacagc agcaac                                         86
```

<210> SEQ ID NO 91
<211> LENGTH: 79
<212> TYPE: DNA
<213> ORGANISM: Artificial Sequence
<220> FEATURE:
<223> OTHER INFORMATION: Clone sequence segment

<400> SEQUENCE: 91

```
cctggggtc ggcgacccgg gaggaggggt tgaccgctc cacgagagct cggactgcga      60
gtccctggac agcagcaac                                                 79
```

<210> SEQ ID NO 92
<211> LENGTH: 88
<212> TYPE: DNA
<213> ORGANISM: Artificial Sequence
<220> FEATURE:
<223> OTHER INFORMATION: Wild type sequence

<400> SEQUENCE: 92

```
aaaaagaaaa ctccatttct tacagatttt gactactggg attatgttgt tcctgaaccc    60
aacctcaacg aggtaatatt tgaggaat                                       88
```

<210> SEQ ID NO 93
<211> LENGTH: 78
<212> TYPE: DNA
<213> ORGANISM: Artificial Sequence
<220> FEATURE:
<223> OTHER INFORMATION: Clone sequence segment

<400> SEQUENCE: 93

```
aaaaagaaaa ctccatttct tacagatttt gactactggg attatgttgt tcctgaaacg    60
aggtaatatt tgaggaat                                                  78
```

<210> SEQ ID NO 94
<211> LENGTH: 89
<212> TYPE: DNA
<213> ORGANISM: Artificial Sequence
<220> FEATURE:
<223> OTHER INFORMATION: Wild type sequence

<400> SEQUENCE: 94
ctcccgcccg gggactacag cacgacccccc ggcggcacgc tcttcagcac cacccccggga     60 ggtaggcgcg ggcttggcga cgccgcttg                                          89

<210> SEQ ID NO 95
<211> LENGTH: 75
<212> TYPE: DNA
<213> ORGANISM: Artificial Sequence
<220> FEATURE:
<223> OTHER INFORMATION: Clone sequence segment

<400> SEQUENCE: 95
ctcccgcccg gggactacag cacgactctt cagcaccacc ccgggaggta ggcgcgggct     60
tggcgacgcc gcttg                                                         75

<210> SEQ ID NO 96
<211> LENGTH: 22
<212> TYPE: DNA
<213> ORGANISM: Artificial Sequence
<220> FEATURE:
<223> OTHER INFORMATION: EGFR fwd

<400> SEQUENCE: 96
tcagagagtc caagaaagca ca                                                 22

<210> SEQ ID NO 97
<211> LENGTH: 20
<212> TYPE: DNA
<213> ORGANISM: Artificial Sequence
<220> FEATURE:
<223> OTHER INFORMATION: EGFR bwd

<400> SEQUENCE: 97
gagccagtga agggagagaa                                                    20

<210> SEQ ID NO 98
<211> LENGTH: 20
<212> TYPE: DNA
<213> ORGANISM: Artificial Sequence
<220> FEATURE:
<223> OTHER INFORMATION: gRNA

<400> SEQUENCE: 98
acagacgttc ccgaagccgc                                                    20

<210> SEQ ID NO 99
<211> LENGTH: 20
<212> TYPE: DNA
<213> ORGANISM: Artificial Sequence
<220> FEATURE:
<223> OTHER INFORMATION: gRNA

<400> SEQUENCE: 99
cggcttgcag ctctccgcaa                                                    20

<210> SEQ ID NO 100
<211> LENGTH: 20

```
<212> TYPE: DNA
<213> ORGANISM: Artificial Sequence
<220> FEATURE:
<223> OTHER INFORMATION: gRNA

<400> SEQUENCE: 100
cgtccgcccg ccacgcagac                                                 20

<210> SEQ ID NO 101
<211> LENGTH: 20
<212> TYPE: DNA
<213> ORGANISM: Artificial Sequence
<220> FEATURE:
<223> OTHER INFORMATION: gRNA

<400> SEQUENCE: 101
tcccatcagc acagttcgtg                                                 20

<210> SEQ ID NO 102
<211> LENGTH: 20
<212> TYPE: DNA
<213> ORGANISM: Artificial Sequence
<220> FEATURE:
<223> OTHER INFORMATION: gRNA

<400> SEQUENCE: 102
agtactccgc tttctgtaaa                                                 20

<210> SEQ ID NO 103
<211> LENGTH: 20
<212> TYPE: DNA
<213> ORGANISM: Artificial Sequence
<220> FEATURE:
<223> OTHER INFORMATION: gRNA

<400> SEQUENCE: 103
ttgacattct ggttcgagct                                                 20

<210> SEQ ID NO 104
<211> LENGTH: 42
<212> TYPE: DNA
<213> ORGANISM: Artificial Sequence
<220> FEATURE:
<223> OTHER INFORMATION: Forward primer

<400> SEQUENCE: 104
tgtaaaacga cggccagtca aatacaactt tggacacaca gg                        42

<210> SEQ ID NO 105
<211> LENGTH: 25
<212> TYPE: DNA
<213> ORGANISM: Artificial Sequence
<220> FEATURE:
<223> OTHER INFORMATION: Reverse primer

<400> SEQUENCE: 105
tggggtttgg agagatctta tgttt                                           25

<210> SEQ ID NO 106
<211> LENGTH: 42
<212> TYPE: DNA
<213> ORGANISM: Artificial Sequence
<220> FEATURE:
<223> OTHER INFORMATION: Forward primer

<400> SEQUENCE: 106
```
tgtaaaacga cggccagtaa agagagaaat caatggcagc ct    42

<210> SEQ ID NO 107
<211> LENGTH: 25
<212> TYPE: DNA
<213> ORGANISM: Artificial Sequence
<220> FEATURE:
<223> OTHER INFORMATION: Reverse primer

<400> SEQUENCE: 107
tatcgttaac ctaacacccc aacat    25

<210> SEQ ID NO 108
<211> LENGTH: 42
<212> TYPE: DNA
<213> ORGANISM: Artificial Sequence
<220> FEATURE:
<223> OTHER INFORMATION: Forward primer

<400> SEQUENCE: 108
tgtaaaacga cggccagctc tagaaaagaa gtcagctctg gt    42

<210> SEQ ID NO 109
<211> LENGTH: 21
<212> TYPE: DNA
<213> ORGANISM: Artificial Sequence
<220> FEATURE:
<223> OTHER INFORMATION: Reverse primer

<400> SEQUENCE: 109
gtcactgcca tttgggctct a    21

<210> SEQ ID NO 110
<211> LENGTH: 25
<212> TYPE: DNA
<213> ORGANISM: Artificial Sequence
<220> FEATURE:
<223> OTHER INFORMATION: Forward primer

<400> SEQUENCE: 110
ataggctgtc ttttcccttt actcc    25

<210> SEQ ID NO 111
<211> LENGTH: 24
<212> TYPE: DNA
<213> ORGANISM: Artificial Sequence
<220> FEATURE:
<223> OTHER INFORMATION: Reverse primer

<400> SEQUENCE: 111
tagggtctcc cttgatctga gaat    24

<210> SEQ ID NO 112
<211> LENGTH: 42
<212> TYPE: DNA
<213> ORGANISM: Artificial Sequence
<220> FEATURE:
<223> OTHER INFORMATION: Forward primer

<400> SEQUENCE: 112
tgtaaaacga cggccagttc aacaagcatt ccaggtacaa tc    42

<210> SEQ ID NO 113
<211> LENGTH: 25
<212> TYPE: DNA
<213> ORGANISM: Artificial Sequence

```
<220> FEATURE:
<223> OTHER INFORMATION: Reverse primer

<400> SEQUENCE: 113
taaaatcacc caactttctg gaagc                                              25

<210> SEQ ID NO 114
<211> LENGTH: 42
<212> TYPE: DNA
<213> ORGANISM: Artificial Sequence
<220> FEATURE:
<223> OTHER INFORMATION: Forward primer

<400> SEQUENCE: 114
tgtaaaacga cggccagggt ttcgaattta aaatgtgcct gg                           42

<210> SEQ ID NO 115
<211> LENGTH: 25
<212> TYPE: DNA
<213> ORGANISM: Artificial Sequence
<220> FEATURE:
<223> OTHER INFORMATION: Reverse primer

<400> SEQUENCE: 115
gaaaaacacc cagttccaag gtaat                                              25

<210> SEQ ID NO 116
<211> LENGTH: 17
<212> TYPE: DNA
<213> ORGANISM: Artificial Sequence
<220> FEATURE:
<223> OTHER INFORMATION: Primer

<400> SEQUENCE: 116
tgtaaaacga cggccag                                                       17

<210> SEQ ID NO 117
<211> LENGTH: 24
<212> TYPE: DNA
<213> ORGANISM: Artificial Sequence
<220> FEATURE:
<223> OTHER INFORMATION: Primer

<400> SEQUENCE: 117
tagggtctcc cttgatctga gaat                                               24

<210> SEQ ID NO 118
<211> LENGTH: 20
<212> TYPE: DNA
<213> ORGANISM: Artificial Sequence
<220> FEATURE:
<223> OTHER INFORMATION: gRNA

<400> SEQUENCE: 118
tcggtcctgc tgagccatga                                                    20

<210> SEQ ID NO 119
<211> LENGTH: 20
<212> TYPE: DNA
<213> ORGANISM: Artificial Sequence
<220> FEATURE:
<223> OTHER INFORMATION: gRNA

<400> SEQUENCE: 119
cccaaagcat taacgtcaac                                                    20
```

<210> SEQ ID NO 120
<211> LENGTH: 20
<212> TYPE: DNA
<213> ORGANISM: Artificial Sequence
<220> FEATURE:
<223> OTHER INFORMATION: gRNA

<400> SEQUENCE: 120
gtttgaccgc tccacgagcc                                           20

<210> SEQ ID NO 121
<211> LENGTH: 20
<212> TYPE: DNA
<213> ORGANISM: Artificial Sequence
<220> FEATURE:
<223> OTHER INFORMATION: gRNA

<400> SEQUENCE: 121
tcctgaaccc aacctcaacg                                           20

<210> SEQ ID NO 122
<211> LENGTH: 20
<212> TYPE: DNA
<213> ORGANISM: Artificial Sequence
<220> FEATURE:
<223> OTHER INFORMATION: gRNA

<400> SEQUENCE: 122
ggtgctgaag agcgtgccgc                                           20

<210> SEQ ID NO 123
<211> LENGTH: 25
<212> TYPE: DNA
<213> ORGANISM: Artificial Sequence
<220> FEATURE:
<223> OTHER INFORMATION: Forward primer

<400> SEQUENCE: 123
gaataactac aaaagagctg ggctg                                     25

<210> SEQ ID NO 124
<211> LENGTH: 22
<212> TYPE: DNA
<213> ORGANISM: Artificial Sequence
<220> FEATURE:
<223> OTHER INFORMATION: Reverse primer

<400> SEQUENCE: 124
tctaagcctg tcttcctgac cc                                        22

<210> SEQ ID NO 125
<211> LENGTH: 25
<212> TYPE: DNA
<213> ORGANISM: Artificial Sequence
<220> FEATURE:
<223> OTHER INFORMATION: Forward primer

<400> SEQUENCE: 125
ttacaaaagg tgtgaagagg aaagc                                     25

<210> SEQ ID NO 126
<211> LENGTH: 25
<212> TYPE: DNA
<213> ORGANISM: Artificial Sequence
<220> FEATURE:
<223> OTHER INFORMATION: Reverse primer

```
<400> SEQUENCE: 126
ccagatagtg tgacttggat gatct                                          25

<210> SEQ ID NO 127
<211> LENGTH: 23
<212> TYPE: DNA
<213> ORGANISM: Artificial Sequence
<220> FEATURE:
<223> OTHER INFORMATION: Forward primer

<400> SEQUENCE: 127
cactctgagt tcatcagcaa acg                                            23

<210> SEQ ID NO 128
<211> LENGTH: 25
<212> TYPE: DNA
<213> ORGANISM: Artificial Sequence
<220> FEATURE:
<223> OTHER INFORMATION: Reverse primer

<400> SEQUENCE: 128
tcactcacct tatactccaa ttccc                                          25

<210> SEQ ID NO 129
<211> LENGTH: 25
<212> TYPE: DNA
<213> ORGANISM: Artificial Sequence
<220> FEATURE:
<223> OTHER INFORMATION: Forward primer

<400> SEQUENCE: 129
caatttccaa gttcacgtgc ataac                                          25

<210> SEQ ID NO 130
<211> LENGTH: 25
<212> TYPE: DNA
<213> ORGANISM: Artificial Sequence
<220> FEATURE:
<223> OTHER INFORMATION: Reverseprimer

<400> SEQUENCE: 130
ggcagacatg gtagatagag gtaac                                          25

<210> SEQ ID NO 131
<211> LENGTH: 25
<212> TYPE: DNA
<213> ORGANISM: Artificial Sequence
<220> FEATURE:
<223> OTHER INFORMATION: Forward primer

<400> SEQUENCE: 131
tgacacctaa cagaaagagg aaaca                                          25

<210> SEQ ID NO 132
<211> LENGTH: 19
<212> TYPE: DNA
<213> ORGANISM: Artificial Sequence
<220> FEATURE:
<223> OTHER INFORMATION: Reverse primer

<400> SEQUENCE: 132
agcgcacagg agaccatgt                                                 19

<210> SEQ ID NO 133
```

```
<211> LENGTH: 25
<212> TYPE: DNA
<213> ORGANISM: Artificial Sequence
<220> FEATURE:
<223> OTHER INFORMATION: Primer

<400> SEQUENCE: 133
gaataactac aaaagagctg ggctg                                            25

<210> SEQ ID NO 134
<211> LENGTH: 25
<212> TYPE: DNA
<213> ORGANISM: Artificial Sequence
<220> FEATURE:
<223> OTHER INFORMATION: Primer

<400> SEQUENCE: 134
ttacaaaagg tgtgaagagg aaagc                                            25

<210> SEQ ID NO 135
<211> LENGTH: 23
<212> TYPE: DNA
<213> ORGANISM: Artificial Sequence
<220> FEATURE:
<223> OTHER INFORMATION: Primer

<400> SEQUENCE: 135
cactctgagt tcatcagcaa acg                                              23

<210> SEQ ID NO 136
<211> LENGTH: 25
<212> TYPE: DNA
<213> ORGANISM: Artificial Sequence
<220> FEATURE:
<223> OTHER INFORMATION: Primer

<400> SEQUENCE: 136
caatttccaa gttcacgtgc ataac                                            25

<210> SEQ ID NO 137
<211> LENGTH: 25
<212> TYPE: DNA
<213> ORGANISM: Artificial Sequence
<220> FEATURE:
<223> OTHER INFORMATION: Primer

<400> SEQUENCE: 137
tgacacctaa cagaaagagg aaaca                                            25

<210> SEQ ID NO 138
<211> LENGTH: 6
<212> TYPE: DNA
<213> ORGANISM: Artificial Sequence
<220> FEATURE:
<223> OTHER INFORMATION: gRNA

<400> SEQUENCE: 138 actagt                                                                  6

<210> SEQ ID NO 139
<211> LENGTH: 20
<212> TYPE: DNA
<213> ORGANISM: Artificial Sequence
<220> FEATURE:
<223> OTHER INFORMATION: gRNA

<400> SEQUENCE: 139
```

| | |
|---|---|
| agcctacgtg atggccagcg | 20 |

<210> SEQ ID NO 140
<211> LENGTH: 20
<212> TYPE: DNA
<213> ORGANISM: Artificial Sequence
<220> FEATURE:
<223> OTHER INFORMATION: gRNA

<400> SEQUENCE: 140

| | |
|---|---|
| gcccagcagg cggcacacgt | 20 |

<210> SEQ ID NO 141
<211> LENGTH: 20
<212> TYPE: DNA
<213> ORGANISM: Artificial Sequence
<220> FEATURE:
<223> OTHER INFORMATION: gRNA

<400> SEQUENCE: 141

| | |
|---|---|
| acgagagtaa gtaaaactac | 20 |

<210> SEQ ID NO 142
<211> LENGTH: 20
<212> TYPE: DNA
<213> ORGANISM: Artificial Sequence
<220> FEATURE:
<223> OTHER INFORMATION: gRNA

<400> SEQUENCE: 142

| | |
|---|---|
| aaaaacagat gctctgagaa | 20 |

<210> SEQ ID NO 143
<211> LENGTH: 20
<212> TYPE: DNA
<213> ORGANISM: Artificial Sequence
<220> FEATURE:
<223> OTHER INFORMATION: gRNA

<400> SEQUENCE: 143

| | |
|---|---|
| atatcctcct tactcatggt | 20 |

<210> SEQ ID NO 144
<211> LENGTH: 20
<212> TYPE: DNA
<213> ORGANISM: Artificial Sequence
<220> FEATURE:
<223> OTHER INFORMATION: gRNA

<400> SEQUENCE: 144

| | |
|---|---|
| agaatcattc ttgatgtctc | 20 |

<210> SEQ ID NO 145
<211> LENGTH: 20
<212> TYPE: DNA
<213> ORGANISM: Artificial Sequence
<220> FEATURE:
<223> OTHER INFORMATION: Forward primer

<400> SEQUENCE: 145

| | |
|---|---|
| tgatgtgcag ggtcagtcat | 20 |

<210> SEQ ID NO 146
<211> LENGTH: 20
<212> TYPE: DNA

```
<213> ORGANISM: Artificial Sequence
<220> FEATURE:
<223> OTHER INFORMATION: Reverse Primer

<400> SEQUENCE: 146
ctccttgcac ctcctcactg                                                  20

<210> SEQ ID NO 147
<211> LENGTH: 20
<212> TYPE: DNA
<213> ORGANISM: Artificial Sequence
<220> FEATURE:
<223> OTHER INFORMATION: Forward Primer

<400> SEQUENCE: 147
cccaggggtt ctagtcacag                                                  20

<210> SEQ ID NO 148
<211> LENGTH: 22
<212> TYPE: DNA
<213> ORGANISM: Artificial Sequence
<220> FEATURE:
<223> OTHER INFORMATION: Reverse primer

<400> SEQUENCE: 148
ggtgcaataa aatgaggcat gc                                               22

<210> SEQ ID NO 149
<211> LENGTH: 20
<212> TYPE: DNA
<213> ORGANISM: Artificial Sequence
<220> FEATURE:
<223> OTHER INFORMATION: Forward primer

<400> SEQUENCE: 149
accttcttcc gtgtgtcctt                                                  20

<210> SEQ ID NO 150
<211> LENGTH: 20
<212> TYPE: DNA
<213> ORGANISM: Artificial Sequence
<220> FEATURE:
<223> OTHER INFORMATION: Reverse primer

<400> SEQUENCE: 150
tggcaaggaa atacagcact                                                  20

<210> SEQ ID NO 151
<211> LENGTH: 18
<212> TYPE: DNA
<213> ORGANISM: Artificial Sequence
<220> FEATURE:
<223> OTHER INFORMATION: Forward primer

<400> SEQUENCE: 151
ccggacccca cacagatt                                                    18

<210> SEQ ID NO 152
<211> LENGTH: 18
<212> TYPE: DNA
<213> ORGANISM: Artificial Sequence
<220> FEATURE:
<223> OTHER INFORMATION: Reverse primer

<400> SEQUENCE: 152
atcacctggg tcctcctg                                                    18
```

<210> SEQ ID NO 153
<211> LENGTH: 26
<212> TYPE: DNA
<213> ORGANISM: Artificial Sequence
<220> FEATURE:
<223> OTHER INFORMATION: Forward primer

<400> SEQUENCE: 153
gcaagtgtta tttaaaggct acatcc                                         26

<210> SEQ ID NO 154
<211> LENGTH: 21
<212> TYPE: DNA
<213> ORGANISM: Artificial Sequence
<220> FEATURE:
<223> OTHER INFORMATION: Reverse primer

<400> SEQUENCE: 154
gcatggggta cgatttatac t                                              21

<210> SEQ ID NO 155
<211> LENGTH: 22
<212> TYPE: DNA
<213> ORGANISM: Artificial Sequence
<220> FEATURE:
<223> OTHER INFORMATION: Forward primer

<400> SEQUENCE: 155
ggacattcaa agagatgcat gc                                             22

<210> SEQ ID NO 156
<211> LENGTH: 21
<212> TYPE: DNA
<213> ORGANISM: Artificial Sequence
<220> FEATURE:
<223> OTHER INFORMATION: Reverse primer

<400> SEQUENCE: 156
agctctccgt gtattctagg a                                              21

<210> SEQ ID NO 157
<211> LENGTH: 20
<212> TYPE: DNA
<213> ORGANISM: Artificial Sequence
<220> FEATURE:
<223> OTHER INFORMATION: gRNA

<400> SEQUENCE: 157
gctgtcagca agacggtgta                                                20

<210> SEQ ID NO 158
<211> LENGTH: 18
<212> TYPE: DNA
<213> ORGANISM: Artificial Sequence
<220> FEATURE:
<223> OTHER INFORMATION: Forward primer

<400> SEQUENCE: 158
agccggtgat cgtctcca                                                  18

<210> SEQ ID NO 159
<211> LENGTH: 25
<212> TYPE: DNA
<213> ORGANISM: Artificial Sequence
<220> FEATURE:

```
<223> OTHER INFORMATION: Reverse primer

<400> SEQUENCE: 159
caaatacagc atcatagtgt ccgtt                                           25
```